US012677592B2

(12) United States Patent
Hong et al.

(10) Patent No.: US 12,677,592 B2
(45) **Date of Patent: *Jul. 7, 2026**

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Jin-Ri Hong, Gyeonggi-do (KR); Hyo-Soon Park, Gyeonggi-do (KR); Hyo-Jung Lee, Gyeonggi-do (KR); Hyun-Ju Kang, Gyeonggi-do (KR)

(73) Assignee: DuPont Specialty Materials Korea Ltd. (KR)

( * ) Notice: Subject to any disclaimer, the term of this patent is extended or adjusted under 35 U.S.C. 154(b) by 987 days.

This patent is subject to a terminal disclaimer.

(21) Appl. No.: 17/290,181

(22) PCT Filed: Oct. 31, 2019

(86) PCT No.: PCT/KR2019/014568

§ 371 (c)(1),
(2) Date: Apr. 29, 2021

(87) PCT Pub. No.: WO2020/091446

PCT Pub. Date: May 7, 2020

(65) Prior Publication Data

US 2022/0045281 A1 Feb. 10, 2022

(30) Foreign Application Priority Data

Oct. 31, 2018 (KR) ........................ 10-2018-0131609
Oct. 29, 2019 (KR) ........................ 10-2019-0135292

(51) Int. Cl.
*H10K 85/60* (2023.01)
*C07D 209/94* (2006.01)
*C07D 403/10* (2006.01)
*C09K 11/06* (2006.01)
*H10K 50/11* (2023.01)
*H10K 101/10* (2023.01)

(52) U.S. Cl.
CPC ....... *H10K 85/6572* (2023.02); *C07D 209/94* (2013.01); *C07D 403/10* (2013.01); *C09K 11/06* (2013.01); *H10K 85/636* (2023.02); *H10K 85/654* (2023.02); *C09K 2211/1018* (2013.01); *H10K 50/11* (2023.02); *H10K 2101/10* (2023.02)

(58) Field of Classification Search
CPC .................................................. H10K 85/6572
See application file for complete search history.

(56) References Cited

U.S. PATENT DOCUMENTS

| | | | |
|---|---|---|---|
| 2016/0163998 A1 | 6/2016 | Saito et al. | |
| 2018/0175306 A1 | 6/2018 | Dyatkin et al. | |
| 2018/0351108 A1 | 12/2018 | Moon et al. | |
| 2020/0013965 A1 | 1/2020 | Yang et al. | |

FOREIGN PATENT DOCUMENTS

| | | | |
|---|---|---|---|
| KR | 20150121337 A * | 10/2015 | C07D 209/56 |
| WO | 2018021841 A1 | 2/2018 | |
| WO | 2018159964 A1 | 9/2018 | |

OTHER PUBLICATIONS

Dopper "Synthesis and Properties of Some Heterocirculenes." J. Org. Chem., vol. 40, No. 13, 1975 1957-1966.*
Yamamoto "Synthesis and molecular structure of [7]circulene." Journal of the American Chemical Society, 110(11), 3578-84, 1988.*
Karaush-Karmazin "Impact of heteroatoms (S, Se, and Te) on the aromaticity of heterocirculenes" New J. Chem., 2019, 43, 12178-12190; First published Jul. 2, 2019.*
Upadhyay, G. M. et al., "Synthesis and photophysical properties of aza[n]helicenes", Journal of organic chemistry, 2016, vol. 81, No. 17, pp. 7751-7759.
Search Report from China National Intellectual Property Administration for China Patent application No. 201980071338.7; Application Date: Oct. 31, 2019.
Request for the Submission of an Opinion from Korea Intellectual Property Office for Korea patent application No. 10-2019-0135292; Application Date: Oct. 29, 2019.
Search Report from China National Intellectual Property Administration, Application No. 201980071338.7, Filing Date: Oct. 31, 2019.

* cited by examiner

*Primary Examiner* — David K O'Dell
(74) *Attorney, Agent, or Firm* — G. Creston Campbell

(57) ABSTRACT

The present disclosure relates to an organic electroluminescent compound and an organic electroluminescent device comprising the same. By comprising the organic electroluminescent compound according to the present disclosure, an organic electroluminescent device having a low driving voltage and/or a high luminous efficiency and/or a long lifespan can be provided.

7 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

An electroluminescent device (EL device) is a self-light-emitting display device which has advantages in that it provides a wider viewing angle, a greater contrast ratio, and a faster response time. The first organic EL device was developed by Eastman Kodak in 1987, by using small aromatic diamine molecules and aluminum complexes as materials for forming a light-emitting layer [see Appl. Phys. Lett. 51, 913, 1987].

An organic EL device (OLED) changes electric energy into light by applying electricity to an organic electroluminescent material, and commonly comprises an anode, a cathode, and an organic layer formed between the two electrodes. The organic layer of the organic EL device may comprise a hole injection layer, a hole transport layer, a hole auxiliary layer, a light-emitting auxiliary layer, an electron blocking layer, a light-emitting layer (containing host and dopant materials), an electron buffer layer, a hole blocking layer, an electron transport layer, an electron injection layer, etc. The materials used in the organic layer can be classified into a hole injection material, a hole transport material, a hole auxiliary material, a light-emitting auxiliary material, an electron blocking material, a light-emitting material, an electron buffer material, a hole blocking material, an electron transport material, an electron injection material, etc., depending on their functions. In the organic EL device, holes from the anode and electrons from the cathode are injected into a light-emitting layer by the application of electric voltage, and excitons having high energy are produced by the recombination of the holes and electrons. The organic light-emitting compound moves into an excited state by the energy and emits light from the energy when the organic light-emitting compound returns to the ground state from the excited state.

The important factor determining luminous efficiency in an organic EL device is light-emitting materials. The light-emitting materials are required to have the following features: high quantum efficiency, high movement degree of an electron and a hole, and uniformity and stability of the formed light-emitting material layer. The light-emitting materials are classified into blue, green, and red light-emitting materials according to the light-emitting color, and further include yellow or orange light-emitting materials. In addition, the light-emitting materials are classified into a host material and a dopant material in a functional aspect. Recently, an urgent task is the development of an organic EL device having high efficiency and long lifespan. In particular, the development of highly excellent light-emitting material over conventional materials is urgently required, considering the EL properties necessary for medium- and large-sized OLED panels. For this, the desirable properties of the host material, which acts as a solvent and the sole energy transporter in the solid state, should be high purity and have a suitable molecular weight to enable vacuum deposition. Furthermore, a host material is required to have high glass transition temperature and pyrolysis temperature to achieve thermal stability, high electrochemical stability to achieve long lifespan, easy formability of an amorphous thin film, good adhesion with adjacent layers, and no movement between layers.

In addition, development of materials having good thermal stability in a hole transport layer, a buffer layer, an electron transport layer, etc., and capable of improving the performance of an organic electroluminescent device, such as driving voltage, luminescent efficiency, and lifespan, is required.

DISCLOSURE OF INVENTION

Technical Problem

The object of the present disclosure is to provide an organic electroluminescent compound capable of firstly producing an organic electroluminescent device having low driving voltage and/or high luminous efficiency and/or long lifespan, and secondly, to provide the organic electroluminescent device comprising the organic electroluminescent compound.

Solution to Problem

As a result of intensive studies to solve the technical problem above, the present inventors found that the aforementioned objective can be achieved by the organic electroluminescent compound represented by the following formula 1, so that the present invention was completed.

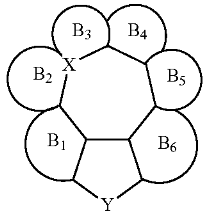

(1)

In formula 1, $B_1$ to $B_6$ are each independently absent or each independently represent a substituted or unsubstituted (C5-C10)aromatic ring, whose at least one carbon atom in the aromatic ring may be replaced with at least one heteroatom selected from nitrogen, oxygen, and sulfur; provided that at least five of $B_1$ to $B_6$ are present and adjacent rings of $B_1$ to $B_6$ may be fused to each other;

X represents C or N.

Y represents —N-$L_1$-$Ar_1$, —O—, —S—, or —$CR_1R_2$;

$L_1$ represents a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene;

$Ar_1$ represents a substituted or unsubstituted (C6-C30) aryl, a substituted or unsubstituted (3- to 30-membered) heteroaryl, or —$NR_3R_4$; and $R_1$ to $R_4$ each independently represent hydrogen, deuterium, halogen, cyano, a substituted or unsubstituted (C1-C30)alkyl, a substituted or unsubstituted (C6-C30) aryl, a substituted or unsubstituted (3- to 30-membered) heteroaryl, or a substituted or unsubstituted (C3-C30)

cycloalkyl; or may be linked to an adjacent substituent to form a substituted or unsubstituted ring.

Advantageous Effects of Invention

The organic electroluminescent device having low driving voltage and/or high luminous efficiency and/or long lifespan can be prepared, by comprising an organic electroluminescent compound according to the present disclosure.

MODE FOR THE INVENTION

Hereinafter, the present disclosure will be described in detail. However, the following description is intended to explain the invention, and is not meant in any way to restrict the scope of the invention.

The present disclosure relates to an organic electroluminescent compound represented by formula 1, an organic electroluminescent material comprising the organic electroluminescent compound, and an organic electroluminescent device comprising the organic electroluminescent compound.

The term "an organic electroluminescent compound" in the present disclosure means a compound that may be used in an organic electroluminescent device, and may be comprised in any layers constituting an organic electroluminescent device, if necessary.

The term "an organic electroluminescent material" in the present disclosure means a material that may be used in an organic electroluminescent device, and may comprise at least one compound. If necessary, the organic electroluminescent material may be comprised in any layers constituting an organic electroluminescent device. For example, the organic electroluminescent material may be a hole injection material, a hole transport material, a hole auxiliary material, a light-emitting auxiliary material, an electron blocking material, a light-emitting material (containing host and dopant materials), an electron buffer material, a hole blocking material, an electron transport material, an electron injection material, etc.

Herein, "(C1-C30)alkyl" is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, isopropyl, n-butyl, isobutyl, tert-butyl, etc. "(C3-C30)cycloalkyl" is a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, etc. "(C6-C30)aryl(ene)" is a monocyclic or fused ring radical derived from an aromatic hydrocarbon having 6 to 30 ring backbone carbon atoms, in which the number of the ring backbone carbon atoms is preferably 6 to 20, more preferably 6 to 15, may be partially saturated, and may comprise a spiro structure. Examples of the aryl specifically include phenyl, biphenyl, terphenyl, quaterphenyl, naphthyl, binaphthyl, phenylnaphthyl, naphthylphenyl, fluorenyl, phenylfluorenyl, dimethylfluorenyl, diphenylfluorenyl, benzofluorenyl, diphenylbenzofluorenyl, dibenzofluorenyl, phenanthrenyl, benzophenanthrenyl, phenylphenanthrenyl, anthracenyl, benzanthracenyl, indenyl, triphenylenyl, pyrenyl, tetracenyl, perylenyl, chrysenyl, benzochrysenyl, naphthacenyl, fluoranthenyl, benzofluoranthenyl, toyly, xylyl, mesityl, cumenyl, spiro[fluorene-fluorene]yl, spiro[fluorene-benzofluorene]yl, azulenyl, etc. More specifically, the aryl may be o-tolyl, m-tolyl, p-tolyl, 2,3-xylyl, 3,4-xylyl, 2,5-xylyl, mesityl, o-cumenyl, m-cumenyl, p-cumenyl, p-t-butylphenyl, p-(2-phenylpropyl)phenyl, 4'-methylbiphenyl, 4"-t-butyl-p-terphenyl-4-yl, o-biphenyl, m-biphenyl, p-biphenyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 1-naphthyl, 2-naphthyl, 1-fluorenyl, 2-fluorenyl, 3-fluorenyl, 4-fluorenyl, 9-fluorenyl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, 1-anthryl, 2-anthryl, 9-anthryl, 1-phenanthryl, 2-phenanthryl, 3-phenanthryl, 4-phenanthryl, 9-phenanthryl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 3-fluoranthenyl, 4-fluoranthenyl, 8-fluoranthenyl, 9-fluoranthenyl, and benzofluoranthenyl, etc. "(3- to 30-membered)heteroaryl(ene)" is an aryl group having at least one heteroatom selected from the group consisting of B, N, O, S, Si, P, and Ge and 3 to 30 ring backbone atoms, in which the number of ring backbone atoms is preferably 5 to 25; having preferably 1 to 4 heteroatoms, and may be a monocyclic ring, or a fused ring condensed with at least one benzene ring; may be partially saturated. The heteroatom may be linked to at least one substituents selected from the group consisting of hydrogen, deuterium, halogen, cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl (C6-30)arylamino. Further, the heteroaryl may be one formed by linking at least one heteroaryl or aryl group to a heteroaryl group via a single bond(s); examples of the heteroaryl specifically include a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, imidazopyridinyl, isoindolyl, indolyl, benzoindolyl, indazolyl, benzothiadiazolyl, quinolyl, isoquinolyl, cinnolinyl, quinazolinyl, quinoxalinyl, carbazolyl, azacarbazolyl, benzocarbazolyl, dibenzocarbazolyl, phenoxazinyl, phenanthridinyl, benzodioxolyl, indolizidinyl, acrylidinyl, silafluorenyl, germafluorenyl, etc. More specifically, the heteroaryl may be 1-pyrrolyl, 2-pyrrolyl, 3-pyrrolyl, 2-pyridinyl, 3-pyridinyl, 4-pyridinyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolizidinyl, 2-indolizidinyl, 3-indolizidinyl, 5-indolizidinyl, 6-indolizidinyl, 7-indolizidinyl, 8-indolizidinyl, 2-imidazopyridinyl, 3-imidazopyridinyl, 5-imidazopyridinyl, 6-imidazopyridinyl, 7-imidazopyridinyl, 8-imidazopyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazole-1-yl, azacarbazole-2-yl, azacarbazole-3-yl, azacarbazole-4-yl, azacarbazole-5-yl, azacarbazole-6-yl, azacarbazole-7-yl, azacarbazole-8-yl, azacarbazole-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acrylidinyl, 2-acrylidinyl, 3-acrylidinyl, 4-acrylidinyl, 9-acrylidinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrole-1-yl, 2-methylpyrrole-3-yl, 2-methylpyrrole-4-yl, 2-methylpyrrole-5-yl, 3-methylpyrrole-1-yl 3-methylpyrrole-2-yl, 3-methylpyrrole-4-yl, 3-methylpyrrole-5-yl, 2-t-buthylpyrrole-4-yl, 3-(2-phenylpropyl)pyrrole-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-silafluorenyl, 2-silafluorenyl, 3-silafluorenyl, 4-silafluorenyl, 1-germafluorenyl, 2-germafluorenyl, 3-germafluorenyl, and 4-germafluorenyl. "Halogen" includes F, Cl, Br, and I.

In addition, "ortho (o)," "meta (m)," and "para (p)" are meant to signify the substitution position of all substituents. Ortho position is a compound with substituents, which are adjacent between each other, e.g., at the 1 and 2 positions on benzene. Meta position is the next substitution position of the immediately adjacent substitution position, e.g., a compound with substituents at the 1 and 3 positions on benzene. Para position is the next substitution position of the meta position, e.g., a compound with substituents at the 1 and 4 positions on benzene.

Herein, "aromatic ring" is meant to be a mono- or polycyclic, unsaturated hydrocarbon, and any cyclic moiety exhibiting some aromatic characters or π-bond, wherein at least one carbon atom in the aromatic ring may be replaced with at least one heteroatom selected from nitrogen, oxygen, and sulfur. For example, the aromatic ring contains (C5-C30)aryl, (5- to 30-membered)heteroaryl, or the ring(s) in which they are fused. The aromatic ring according to the embodiment, e.g., may be (C5-C25)aryl or (5- to 25-membered)heteroaryl, e.g., (C5-C18)aryl, (5- to 18-membered) heteroaryl, or the combination thereof.

Herein, "a substituted or unsubstituted ring formed in linking to an adjacent substituent" means a substituted or unsubstituted (3- to 30-membered) mono- or polycyclic, alicyclic, aromatic ring, or a combination thereof, formed by linking or fusing two or more adjacent substituents; preferably, may be a substituted or unsubstituted (3- to 26-membered) mono- or polycyclic, alicyclic, aromatic ring, or a combination thereof. In addition, the formed ring may contain at least a heteroatom selected from the group consisting of B, N, O, S, Si, and P, preferably, N, O, and S. According to one embodiment, the formed ring has (5- to 20-membered) ring backbone atoms, and according to another embodiment, the formed ring has (5- to 15-membered) ring backbone atoms.

In addition, "substituted" in the expression "substituted or unsubstituted" means that a hydrogen atom in a certain functional group is replaced with another atom or functional group, i.e., a substituent. The substituents of the substituted (C1-C30)alkyl(ene), the substituted (C6-C30)aryl(ene), the substituted (3- to 30-membered)heteroaryl(ene), the substituted (C3-C30)cycloalkyl(ene), the substituted (C1-C30) alkoxy, the substituted tri(C1-C30)alkylsilyl, the substituted di(C1-C30)alkyl(C6-C30)arylsilyl, the substituted (C1-C30) alkyldi(C6-C30)arylsilyl, the substituted tri(C6-C30)arylsilyl, the substituted mono- or di-(C1-C30)alkylamino, the substituted mono- or di-(C6-C30)arylamino, the substituted (C1-C30)alkyl(C6-30)arylamino, and the substituted ring in $Ar_1$, $L_1$, $R_1$ to $R_4$, and $R_3$, each independently represent at least one selected from the group consisting of deuterium, halogen, cyano, carboxyl, nitro, hydroxyl, (C1-C30)alkyl, halo(C1-C30)alkyl, (C2-C30)alkenyl, (C2-C30)alkynyl, (C1-C30)alkoxy, (C1-C30)alkylthio, (C3-C30)cycloalkyl, (C3-C30)cycloalkenyl, (3- to 7-membered)heterocycloalkyl, (C6-C30)aryloxy, (C6-C30)arylthio, (C6-C30)aryl-substituted or unsubstituted (5- to 30-membered)heteroaryl, (5- to 30-membered)heteroaryl-substituted or unsubstituted (C6-C30)aryl, tri(C1-C30)alkylsilyl, tri(C6-C30)arylsilyl, di(C1-C30)alkyl(C6-C30)arylsilyl, (C1-C30)alkyldi(C6-C30)arylsilyl, amino, mono- or di-(C1-C30)alkylamino, (C1-C30)alkyl-substituted or unsubstituted mono- or di-(C6-C30)arylamino, (C1-C30)alkyl(C6-C30)arylamino, (C1-C30)alkylcarbonyl, (C1-C30)alkoxycarbonyl, (C6-C30)arylcarbonyl, di(C6-C30)arylboronyl, di(C1-C30)alkylboronyl, (C1-C30)alkyl(C6-C30)arylboronyl, (C6-C30) ar(C1-C30)alkyl, and (C1-C30)alkyl(C6-C30)aryl. For example, the substituents may be a substituted or unsubstituted methyl, a substituted or unsubstituted phenyl, a substituted or unsubstituted m-biphenyl, a substituted or unsubstituted p-biphenyl, a substituted or unsubstituted naphthyl, a substituted or unsubstituted fluorenyl, a substituted or unsubstituted pyridinyl, a substituted or unsubstituted carbazolyl, a substituted or unsubstituted dibenzofuranyl, a substituted or unsubstituted dibenzothiophenyl, or a substituted or unsubstituted benzoxazolyl, etc.

Hereinafter, the organic electroluminescent compound according to one embodiment will be described.

The organic electroluminescent compound according to one embodiment is represented by the following formula 1.

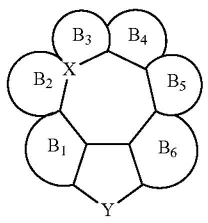

(1)

In formula 1, $B_1$ to $B_6$ are each independently absent or each independently represent a substituted or unsubstituted (C5-C10) aromatic ring, whose at least one carbon atom in the aromatic ring may be replaced with at least one heteroatom selected from nitrogen, oxygen, and sulfur;

provided that at least five of $B_1$ to $B_6$ are present and adjacent rings of $B_1$ to $B_6$ may be fused to each other;

X represents C or N;

Y represents —N-$L_1$-$Ar_1$, —O—, —S—, or —$CR_1R_2$;

$L_1$ represents a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene;

$Ar_1$ represents a substituted or unsubstituted (C6-C30) aryl, a substituted or unsubstituted (3- to 30-membered) heteroaryl, or —$NR_3R_4$;

$R_1$ to $R_4$ each independently represent hydrogen, deuterium, halogen, cyano, a substituted or unsubstituted (C1-C30)alkyl, a substituted or unsubstituted (C6-C30) aryl, a substituted or unsubstituted (3- to 30-membered) heteroaryl, or a substituted or unsubstituted (C3-C30) cycloalkyl; or may be linked to an adjacent substituent to form a substituted or unsubstituted ring.

In one embodiment, $B_1$ to $B_6$ are each independently absent, or each independently represent a substituted or unsubstituted (C5-C10) aromatic ring, whose at least one carbon atom in the aromatic ring may be replaced with at least one heteroatom selected from nitrogen, oxygen, and sulfur; provided that at least five of $B_1$ to $B_6$ are present, and adjacent rings of $B_1$ to $B_6$ may be present in fusion with each other. Wherein, the fusing of each other with adjacent rings of $B_1$ to $B_6$ means that $B_1$ ring and $B_2$ ring, $B_2$ ring and $B_3$ ring, $B_3$ ring and $B_4$ ring, $B_4$ ring and $B_5$ ring, or $B_5$ ring and $B_6$ ring are fused with each other. Specifically, $B_1$ to $B_6$ each independently represent a substituted or unsubstituted (C5-C10) aromatic ring, e.g., a substituted or unsubstituted (C5-C10)aryl, or a substituted or unsubstituted (C5-C10) heteroaryl.

In one embodiment, Y represents —N-$L_1$-$Ar_1$, —O—, —S—, or —$CR_1R_2$.

In one embodiment, $L_1$ represents a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene, preferably, may be a single bond, a substituted or unsubstituted (C6-C30)arylene, or a substituted or unsubstituted (3- to 30-membered)heteroarylene, more preferably, may be a single bond, a substituted or unsubstituted (C6-C25)arylarylene, or a substituted or unsubstituted (5- to 25-membered)heteroarylene. For example, $L_1$ may be a single bond or a substituted or unsubstituted phenylene, a substituted or unsubstituted biphenylene, a substituted or unsubstituted pyridinylene, a substituted or unsubstituted isoquinolinylene, a substituted or unsubstituted quinoxalinylene, a substituted or unsubstituted benzoquinoxalinylene, a substituted or unsubstituted quinazolinylene, a substituted or unsubstituted benzoquinazolinylene, a substituted or unsubstituted benzofuropyrimidinylene, or a substituted or unsubstituted naphthyridinylene.

In one embodiment, $Ar_1$ presents a substituted or unsubstituted (C6-C30)aryl, a substituted or unsubstituted (3- to 30-membered)heteroaryl, or —$NR_3R_4$, preferably, may be a substituted or unsubstituted (C6-C25)aryl, a substituted or unsubstituted (5- to 25-membered)heteroaryl, or —$NR_3R_4$, more preferably, may be a substituted or unsubstituted (C6-C18)aryl, a substituted or unsubstituted (5- to 18-membered)heteroaryl, or —$NR_3R_4$. Wherein, $R_3$ and $R_4$ each independently represent hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, or a substituted or unsubstituted (C3-C30)cycloalkyl; or may be linked to an adjacent substituent to form a substituted or unsubstituted ring, preferably, may be a substituted or unsubstituted (C6-C25)aryl, more preferably, may be a substituted or unsubstituted (C6-C18)aryl.

For example, $Ar_1$ may be a substituted or unsubstituted phenyl, a substituted or unsubstituted m-biphenyl, a substituted or unsubstituted p-biphenyl, a substituted or unsubstituted fluorenyl, a substituted or unsubstituted pyrimidinyl, a substituted or unsubstituted triazinyl, a substituted or unsubstituted quinolinyl, a substituted or unsubstituted isoquinolinyl, a substituted or unsubstituted quinoxalinyl, a substituted or unsubstituted benzoquinoxalinyl, a substituted or unsubstituted quinazolinyl, a substituted or unsubstituted benzoquinazolinyl, a substituted or unsubstituted naphthyridinyl, a substituted or unsubstituted benzofuropyrimidinyl, a substituted or unsubstituted dibenzofuranyl, a substituted or unsubstituted dibenzothiophenyl, a substituted or unsubstituted carbazolyl, or diphenylamino.

In one embodiment, $R_1$ and $R_2$ each independently represent hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, or a substituted or unsubstituted (C3-C30) cycloalkyl; or may be linked to an adjacent substituent to form a substituted or unsubstituted ring, preferably, may be a substituted or unsubstituted (C1-C30)alkyl or a substituted or unsubstituted (C6-C30)aryl, more preferably, may be a substituted or unsubstituted (C1-C10)alkyl or a substituted or unsubstituted (C6-C18)aryl. For example, $R_1$ and $R_2$ each independently may be methyl or phenyl.

In one embodiment, X may be C or N, preferably, when X is C, the formula 1 may be represented by the following formula 1-1, and when X is N, the formula 1 may be represented by the following formula 1-2.

(1-1)

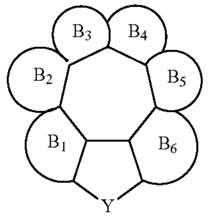

(1-2)

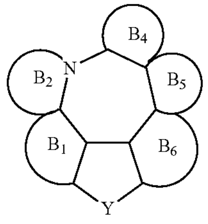

In formulae 1-1 and 1-2.

$B_1$ to $B_6$ and Y are as defined in formula 1.

The organic electroluminescent compound of formula 1 according to one embodiment in which X represents C; $B_1$ to $B_6$ are each independently absent, or each independently represent a substituted or unsubstituted benzene ring, a substituted or unsubstituted naphthalene ring, a substituted or unsubstituted pyrrole ring, a substituted or unsubstituted furan ring, or a substituted or unsubstituted thiophene ring.

The organic electroluminescent compound of formula 1 according to one embodiment in which X represents N; $B_2$ or $B_3$ is absent, or may be fused with X to form a substituted or unsubstituted pyridine ring or a substituted or unsubstituted indole ring. In one embodiment, the formula 1 may be the organic electroluminescent compound in which X represents N; $B_2$ is absent; and $B_3$ is fused with X to form a substituted or unsubstituted pyridine ring or a substituted or unsubstituted indole ring. In one embodiment, the formula 1 may be the organic electroluminescent compound in which X represents N; $B_3$ is absent; and $B_2$ is fused with X to form a substituted or unsubstituted pyridine ring or a substituted or unsubstituted indole ring.

The organic electroluminescent compound of formula 1 according to one embodiment may be re resented by any one of the following formulae 2 to 7.

(2)

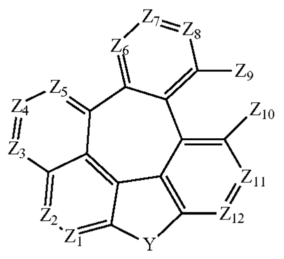

(3)

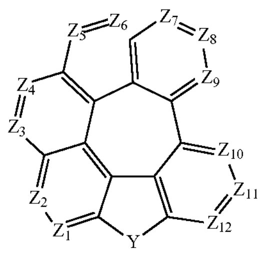

(4)

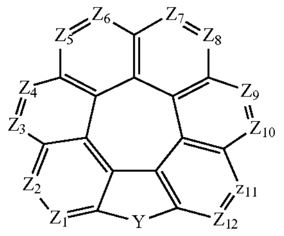

(5)

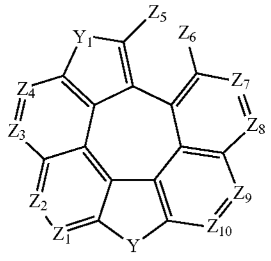

-continued (6)

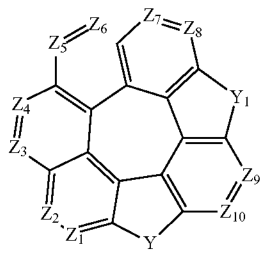

(7)

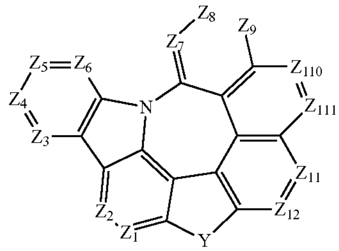

In formulae 2 to 7, $Y_1$ is as defined as Y;

$Z_1$ to $Z_{13}$ each independently represent N or $CR_a$;

$R_a$ each independently represent hydrogen, deuterium, halogen, cyano, a substituted or unsubstituted (C1-C33)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a Substituted or unsubstituted tri(C6-C30)arylsilyl, a substituted or unsubstituted mono- or di-(C1-C30)alkylamino, a substituted or unsubstituted mono- or di-(C6-C30)arylamino, a substituted or unsubstituted (C1-C30)alkyl (C6-30)arylamino, a substituted or unsubstituted mono- or di-(3- to 30-membered)heteroarylamino, or a substituted or unsubstituted (C6-C30)aryl(3- to 30-membered)heteroarylamino; or may be fused with each other to form a ring.

In one embodiment, $R_a$ each independently may be a substituted or unsubstituted (C6-C30)aryl, a substituted or unsubstituted mono- or di-(C6-C30)arylamino, a substituted or unsubstituted (C6-C30)aryl(3- to 30-membered)heteroarylamino, preferably, a substituted or unsubstituted (C6-C25)aryl, a substituted or unsubstituted di(C6-C25)arylamino, a substituted or unsubstituted (C6-C25)aryl(5- to 25-membered)heteroarylamino, more preferably, a substituted or unsubstituted (C6-C18)aryl, a substituted or unsubstituted di(C6-C18)arylamino, or a substituted or unsubstituted (C6-C18)aryl(5- to 18-membered)heteroarylamino. For example, $R_a$ may be selected from any of the substituents listed below.

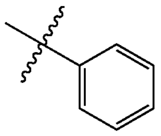

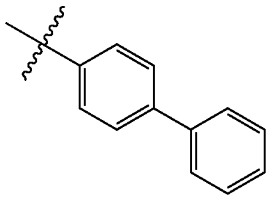

-continued
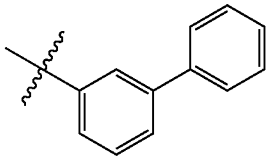
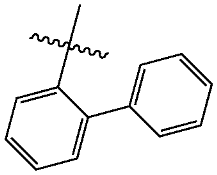
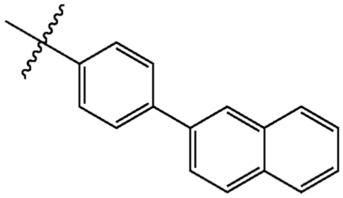
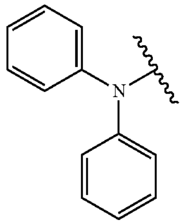
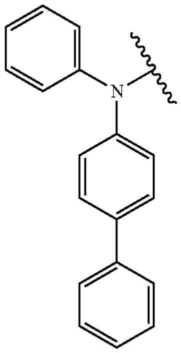
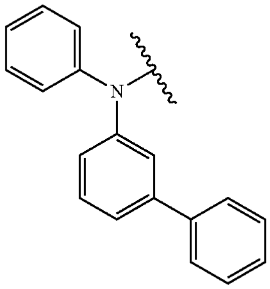
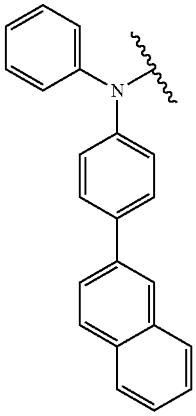
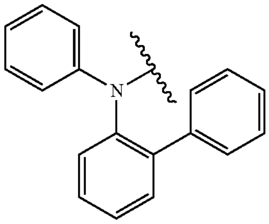
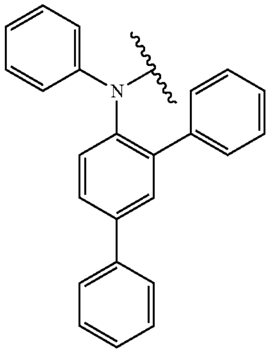
-continued
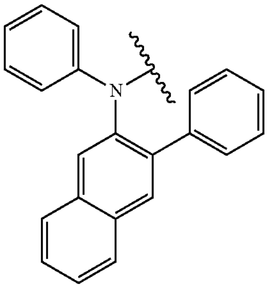
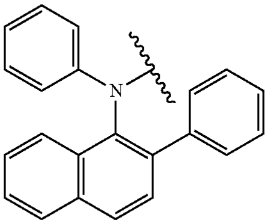
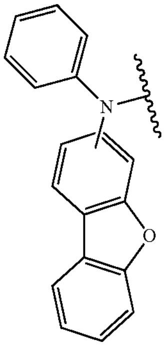
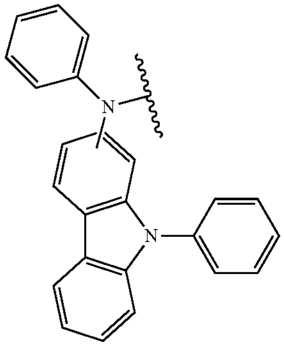
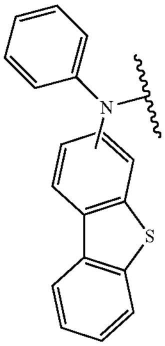
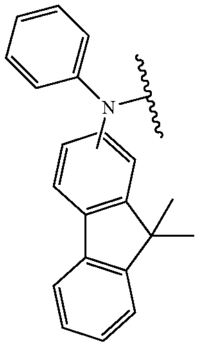
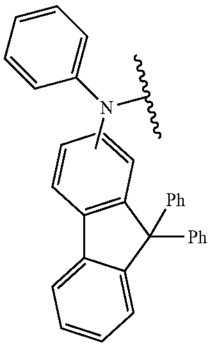
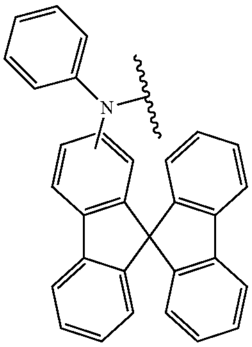

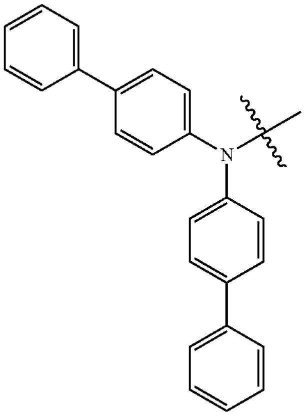
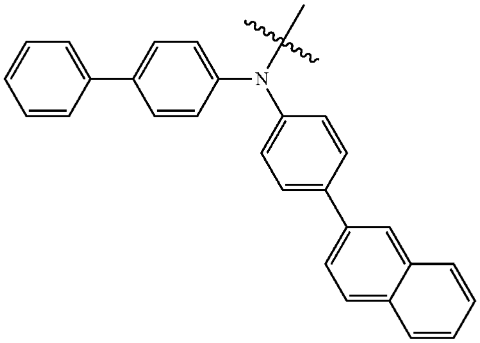
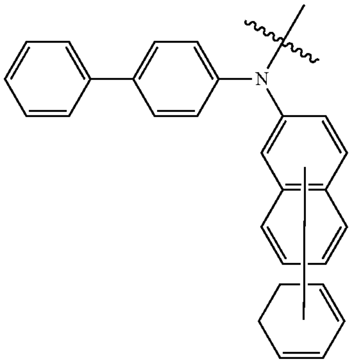
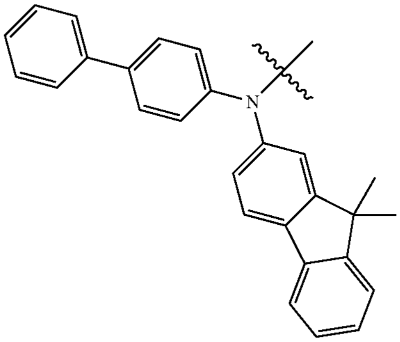
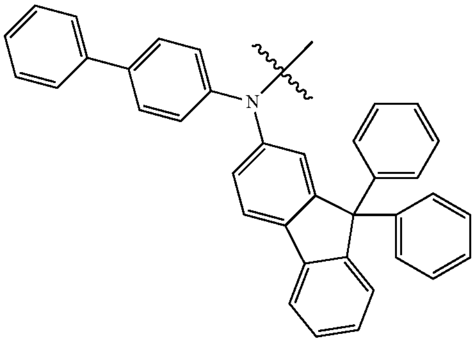
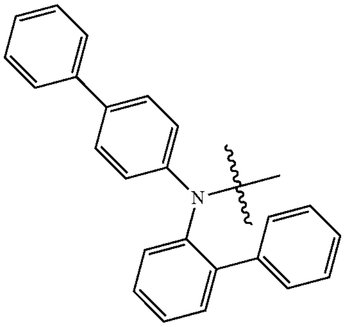
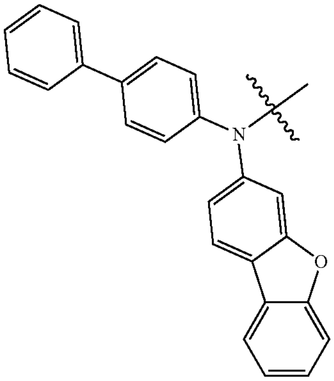
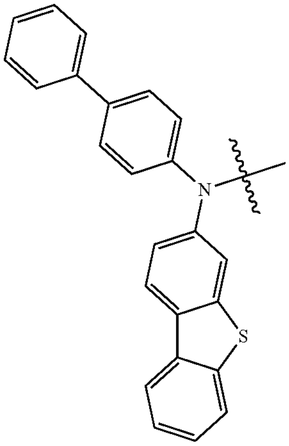

-continued

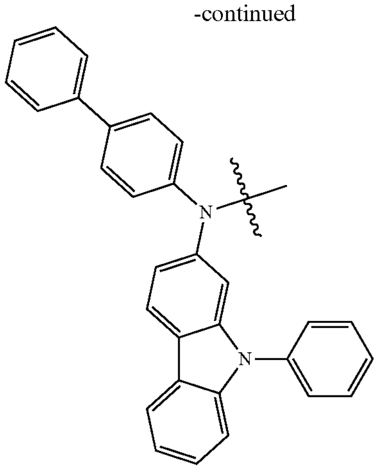

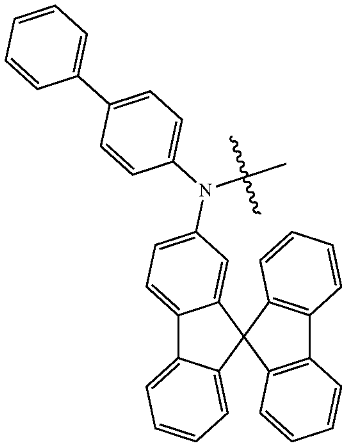 [SMILES: *N(c1ccc(-c2ccccc2)cc1)c1ccc2c(c1)C1(c3ccccc3-c3ccccc31)c1ccccc1-2]

-continued

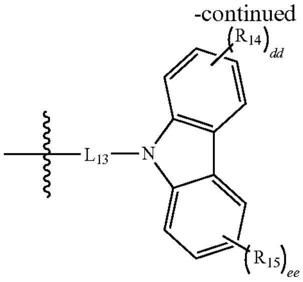

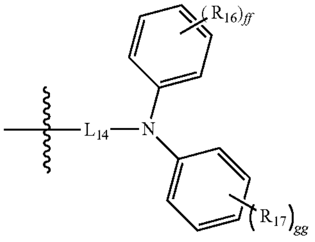

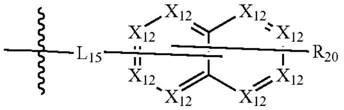

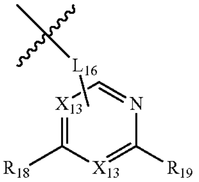

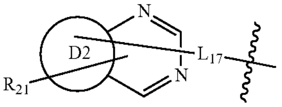

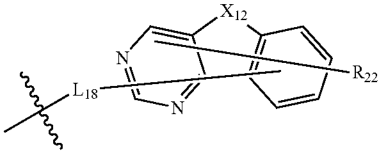

$Ar_1$, $R_1$ to $R_4$, and $R_a$ according to one embodiment each independently may be selected from any of the substituents listed in Group 1 below.

[Group 1]

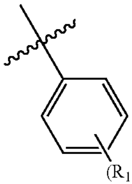

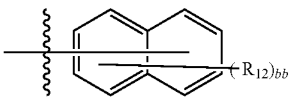

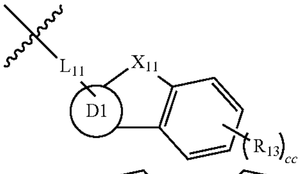

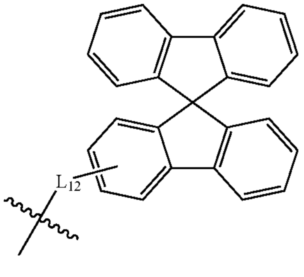

In Group 1,

D1 and D2 each independently represent a benzene ring or a naphthalene ring;

$X_{11}$ represents O, S, $NR_{11}$, or $CR_{12}R_{13}$;

$X_{12}$ each independently represent $CR_{31}$ or N; provided that at least one $X_{12}$ is N;

$X_{13}$ each independently represent $CR_{32}$ or N;

$L_{11}$ to $L_{18}$ each independently represent a single bond, a substituted or unsubstituted (C6-C30)arylene, or a substituted or unsubstituted (3- to 30-membered)heteroarylene;

$R_{11}$ to $R_{22}$, $R_{31}$, and $R_{32}$ each independently represent hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, or a substituted or unsubstituted (C3-C30)cycloalkyl; or may be linked to an adjacent substituent to form a substituted or unsubstituted ring;

aa, ff, and gg each independently represent an integer of 1 to 5, bb represents an integer of 1 to 7, cc to ee each independently represent an integer of 1 to 4; and when aa to gg are 2 or more, each of $R_{11}$ to $R_{17}$ may be the same or different.

$Ar_1$, $R_1$ to $R_4$, and $R_a$ according to one embodiment each independently may be selected from any of the substituents listed in Group 2 below.
[Group 2]
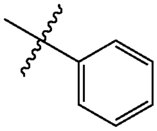
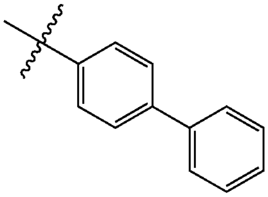
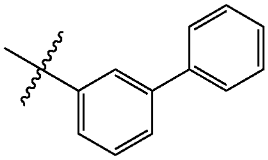
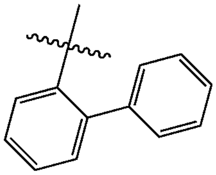
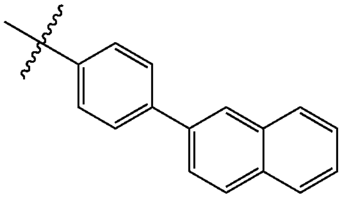
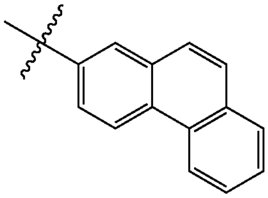
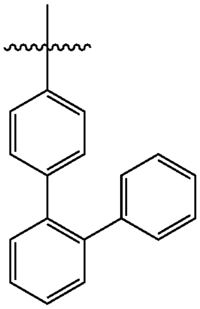
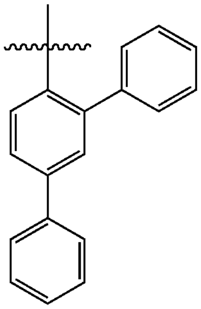
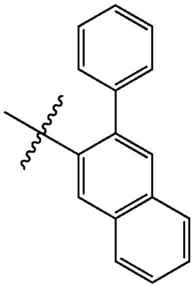
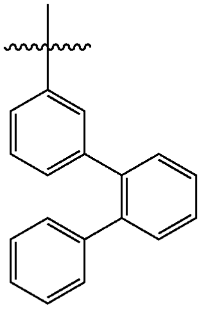
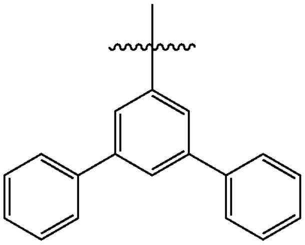
-continued
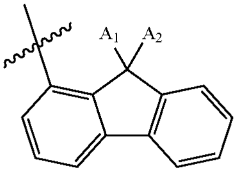
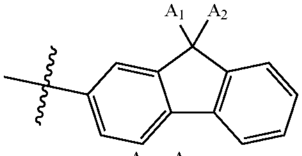
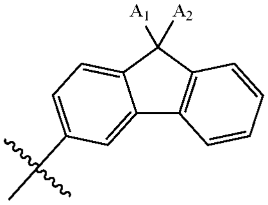
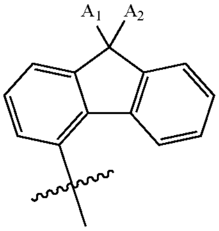
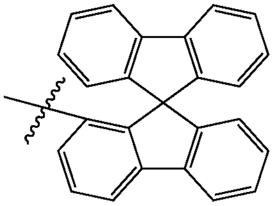
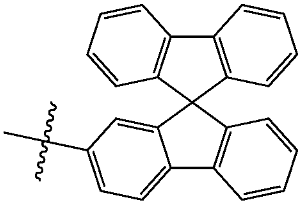
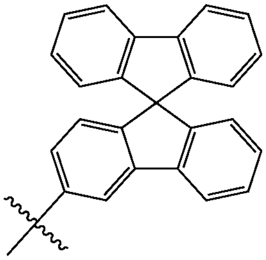
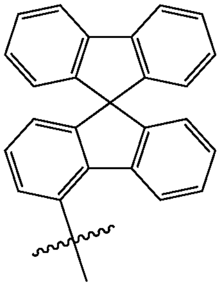
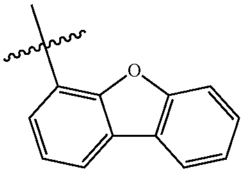
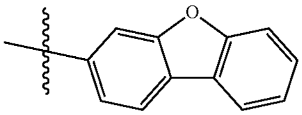
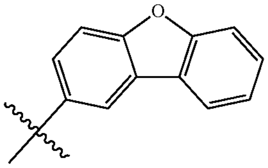
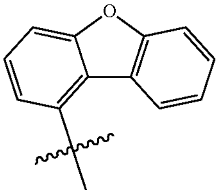

-continued
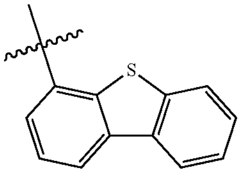
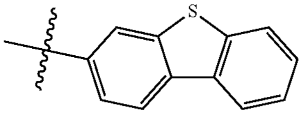
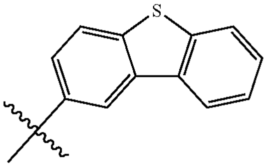
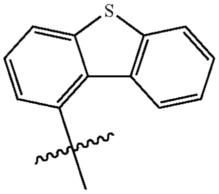
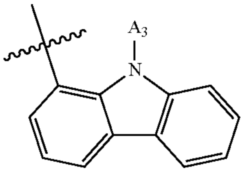
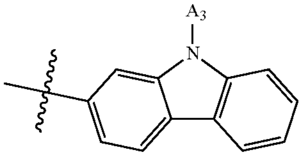
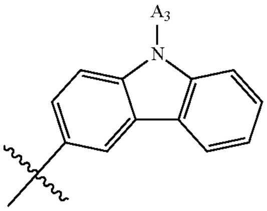
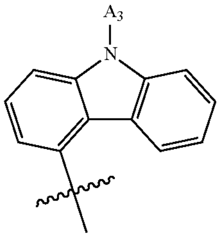
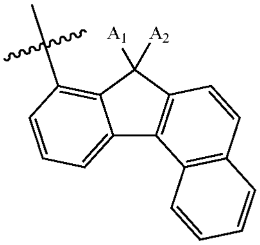
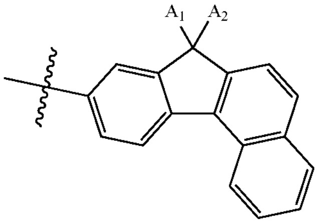
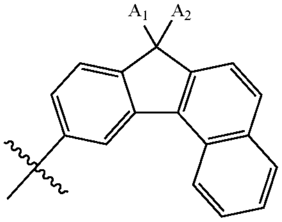
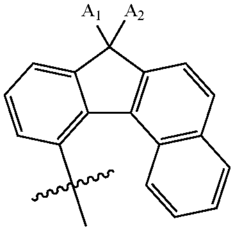
-continued
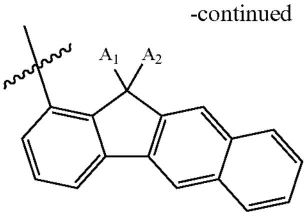
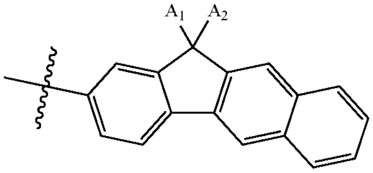
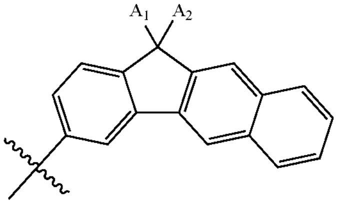
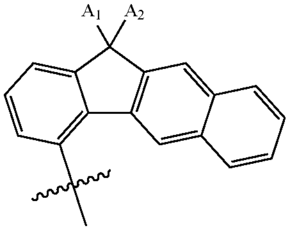
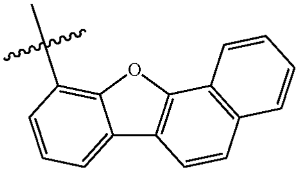
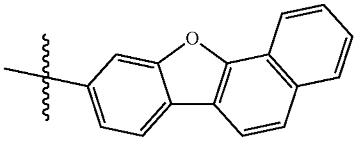
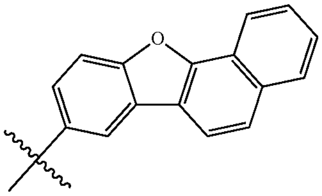
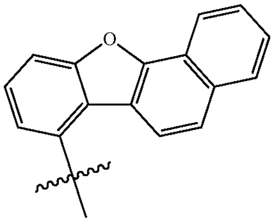
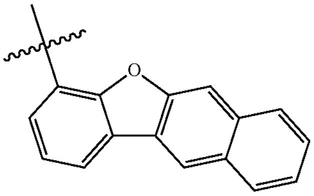

-continued
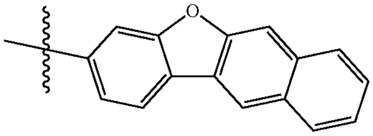
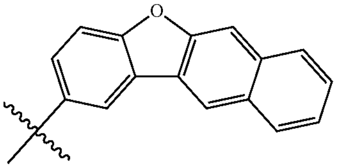
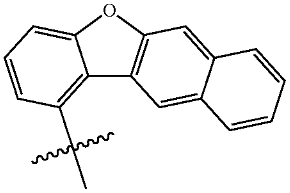
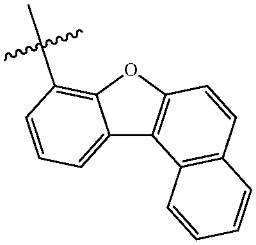
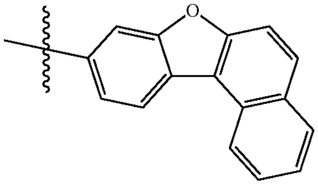
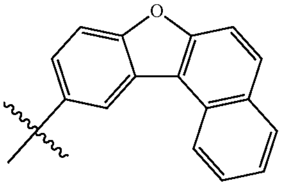
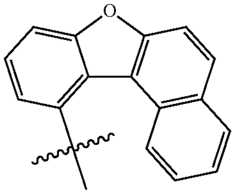
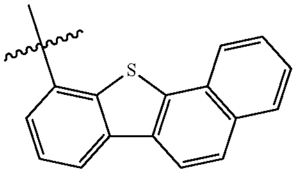
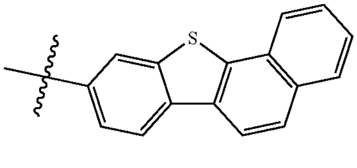
-continued
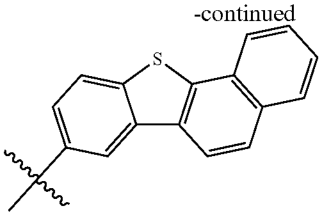
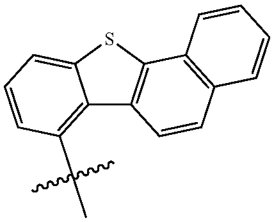
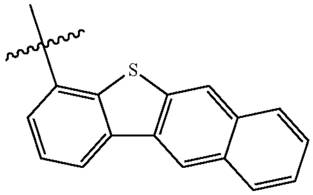
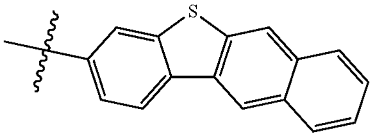
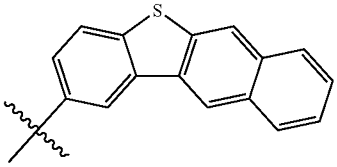
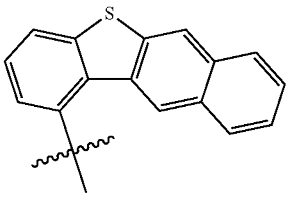
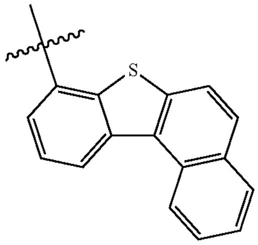
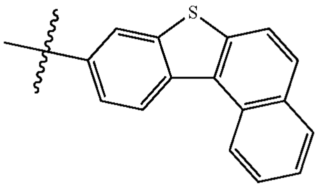
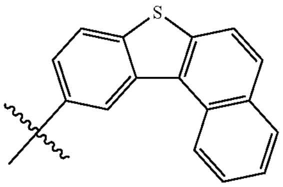
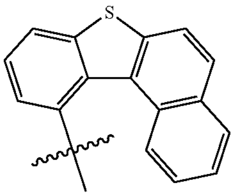

-continued
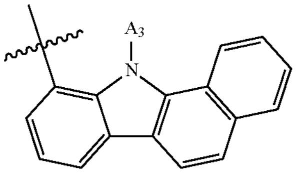
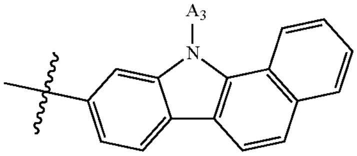
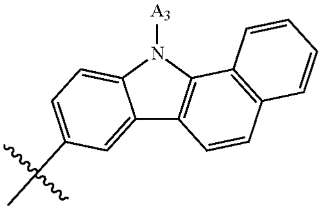
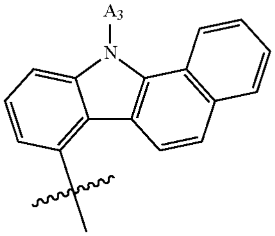
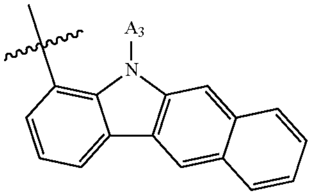
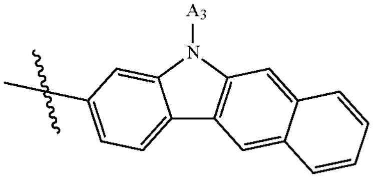
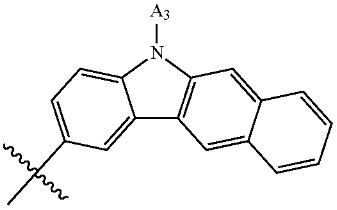
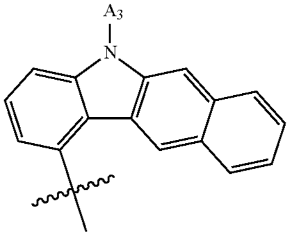
-continued
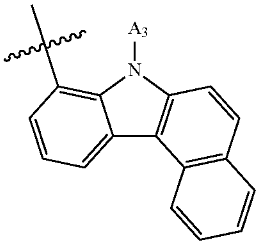
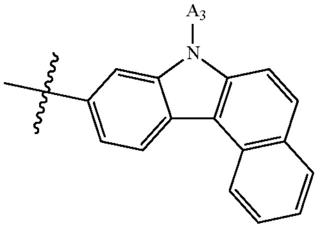
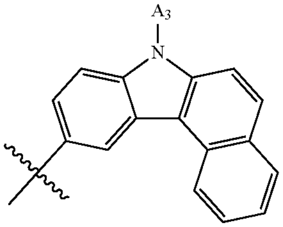
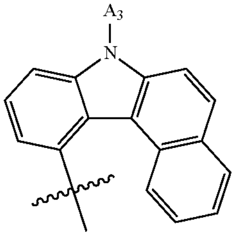
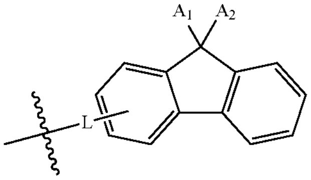
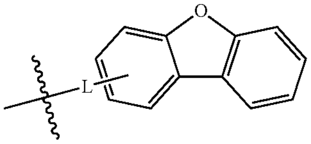
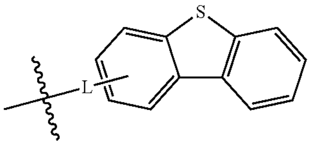
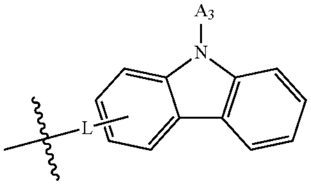
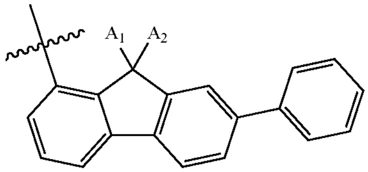
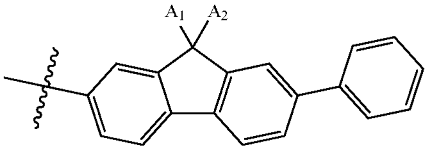

-continued
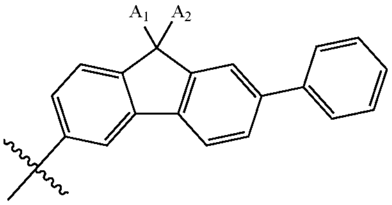
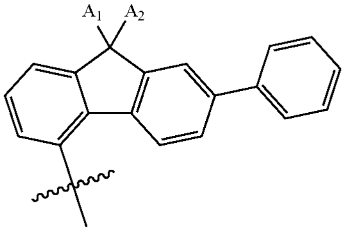
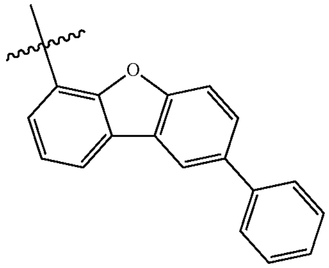
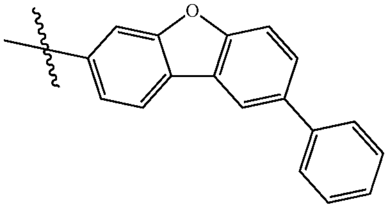
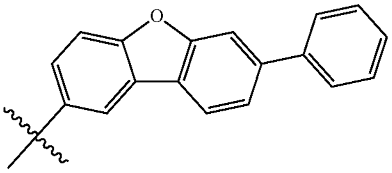
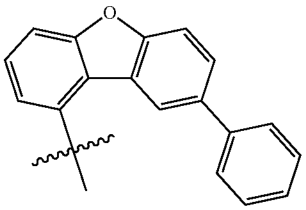
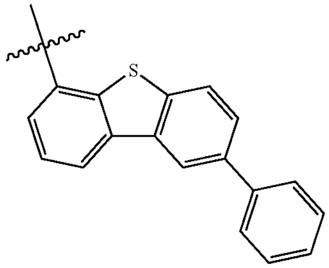
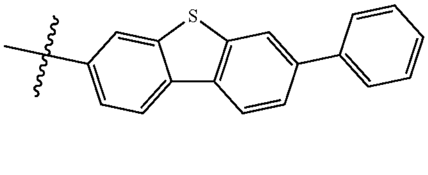
-continued
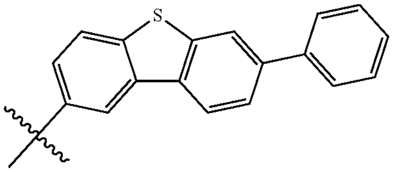
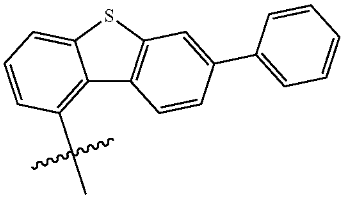
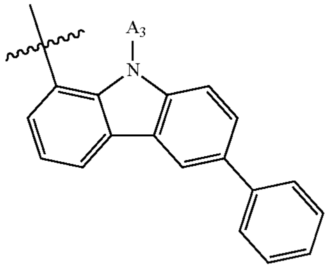
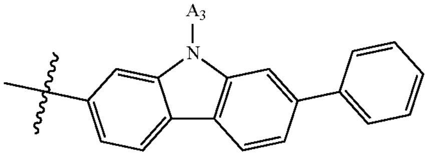
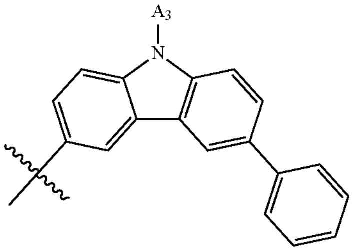
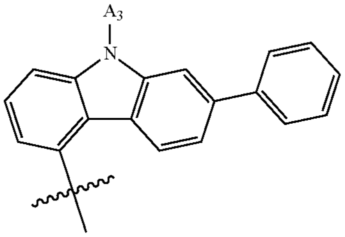
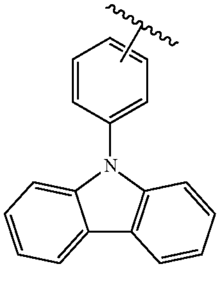
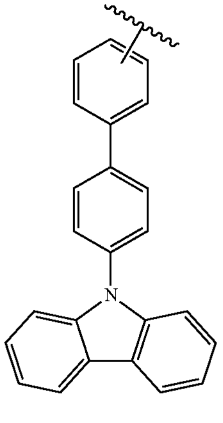

-continued
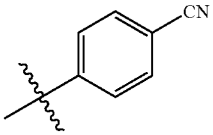
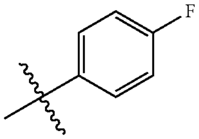
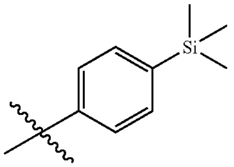
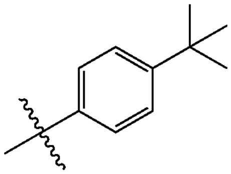
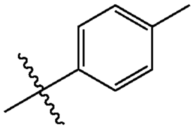
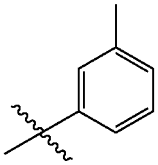
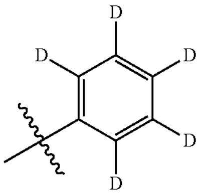
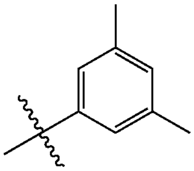
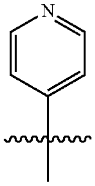
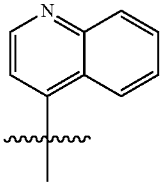
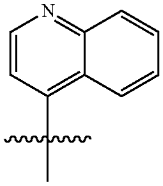
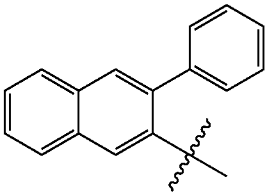
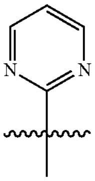
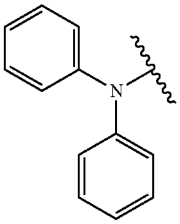
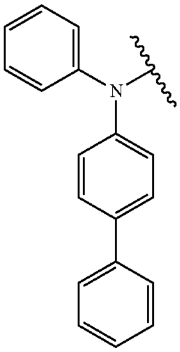
-continued
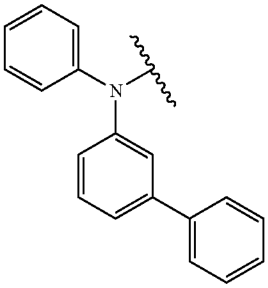
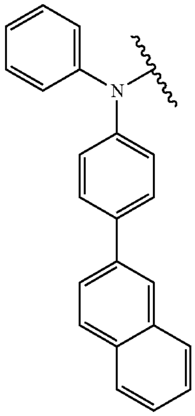
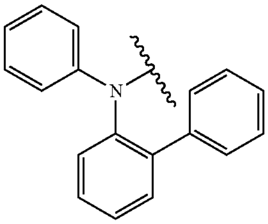
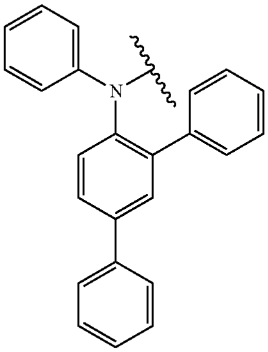
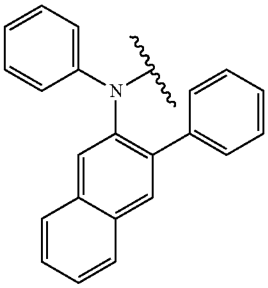
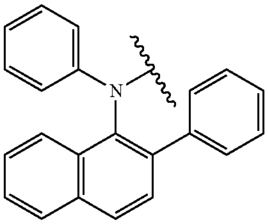
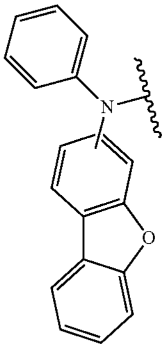

-continued
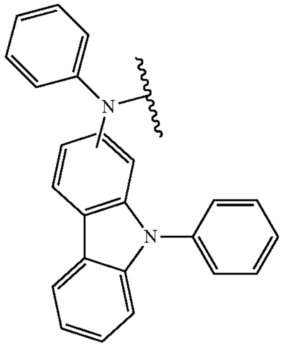
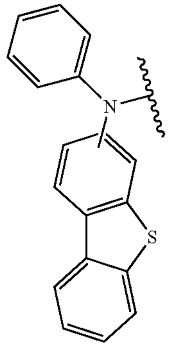
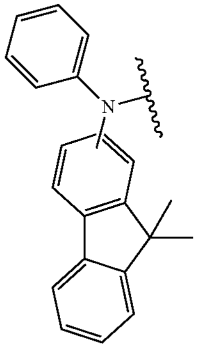
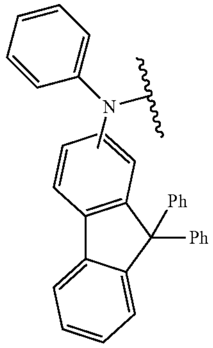
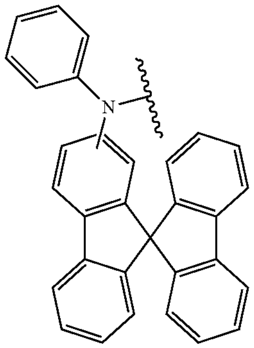
In Group 2,
L is as defined as $L_1$ in formula 1; and
$A_1$ to $A_3$ each independently represent a substituted or unsubstituted (C1-C30)alkyl or a substituted or unsubstituted (C6-C30)aryl.
$Ar_1$, $R_1$ to $R_4$, and $R_a$ according to another embodiment each independently may be selected from any of the substituents listed in Group 3 below.
[Group 3]
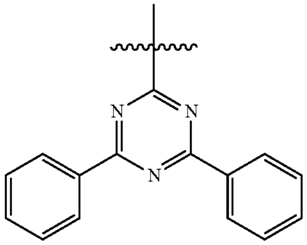
-continued
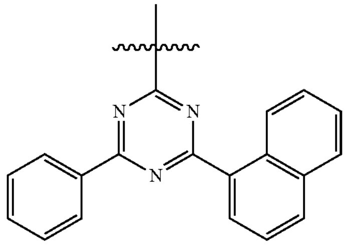
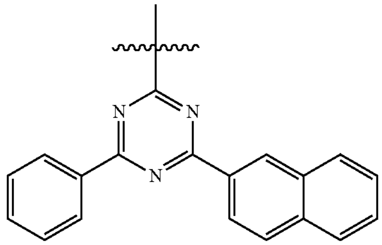
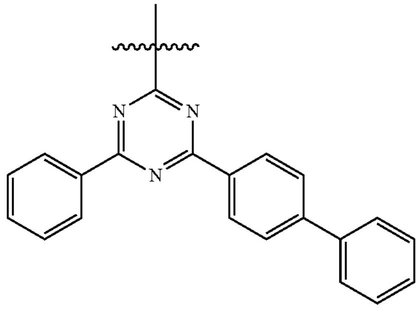
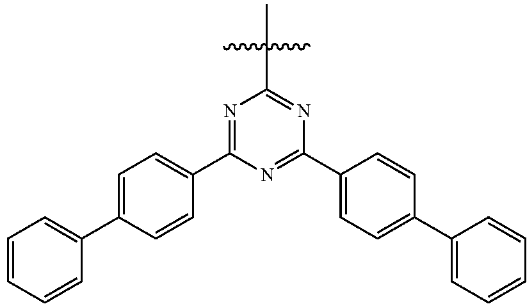
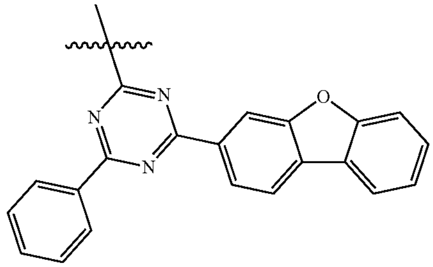
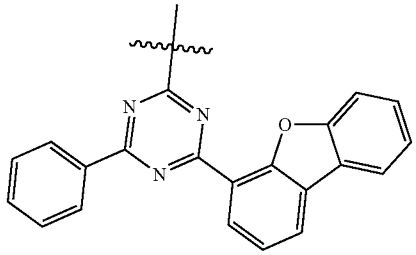

-continued
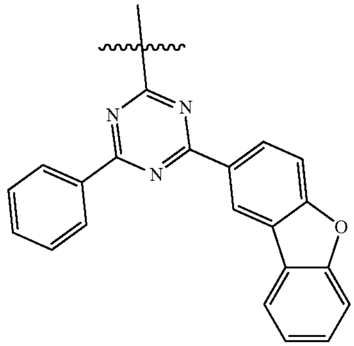
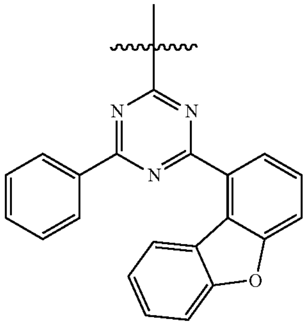
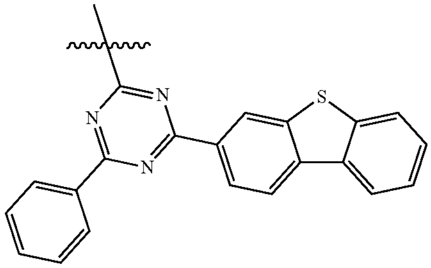
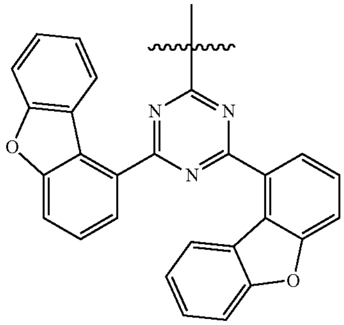
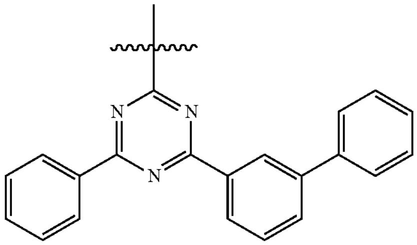
-continued
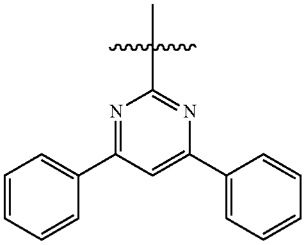
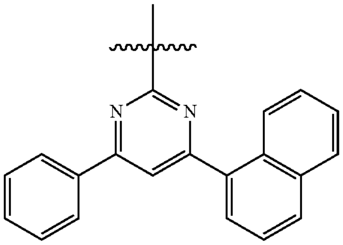
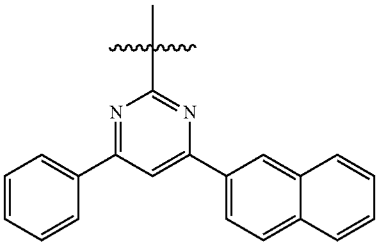
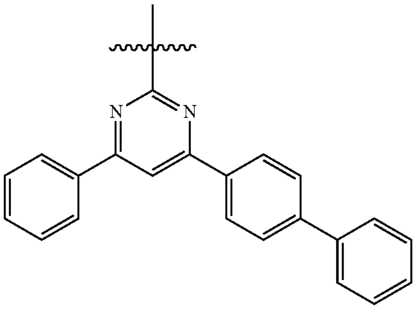
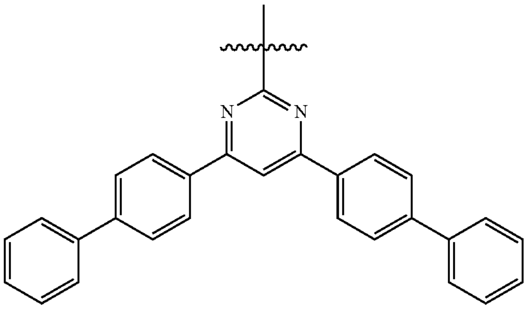
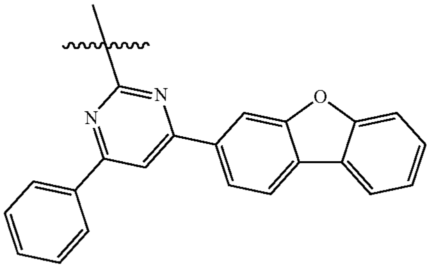

-continued
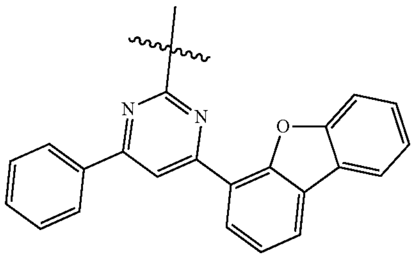
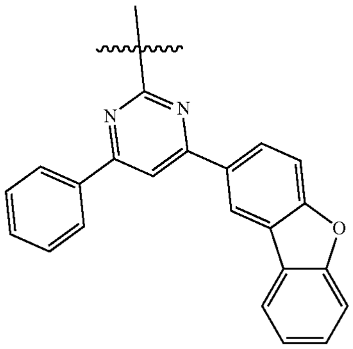
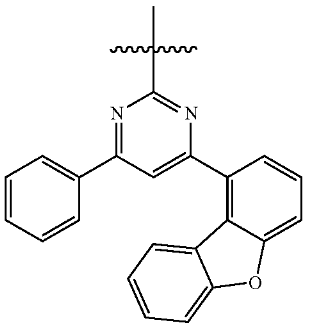
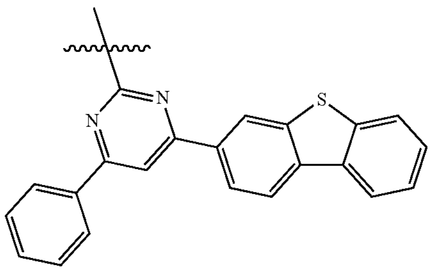
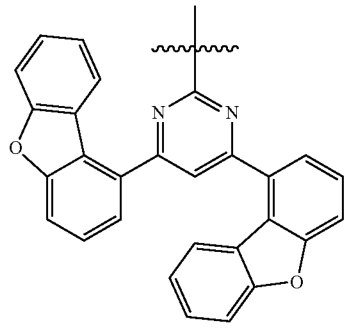
-continued
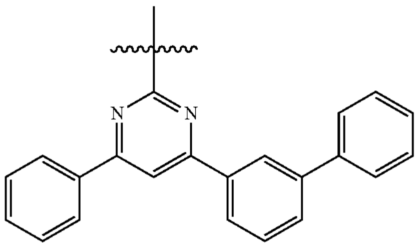
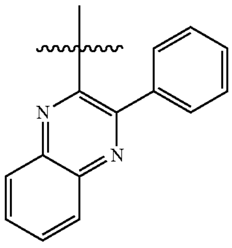
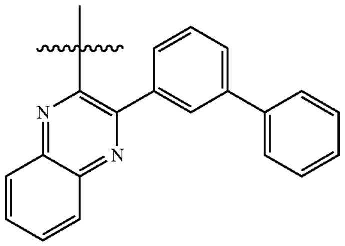
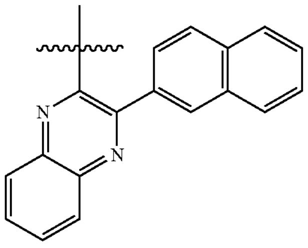
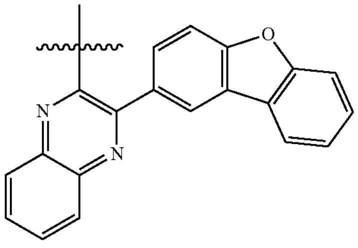
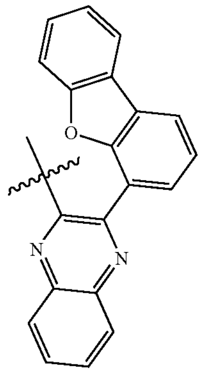

-continued
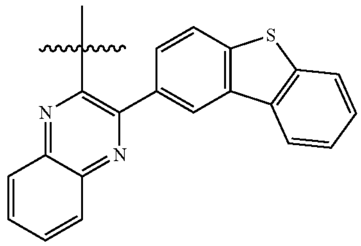
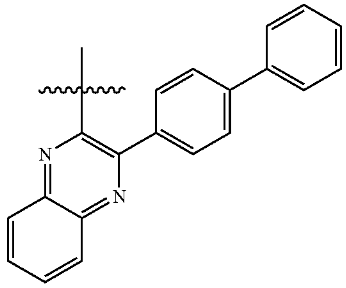
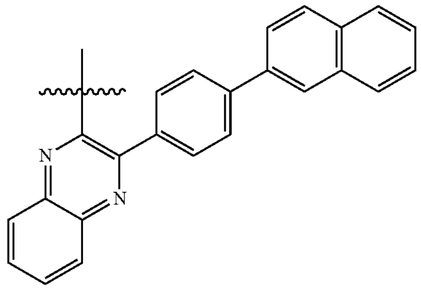
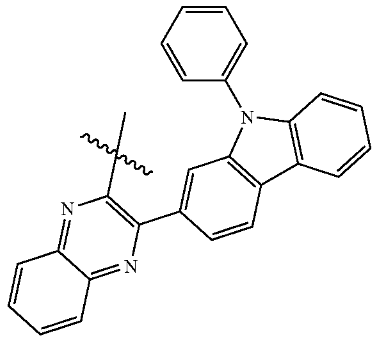
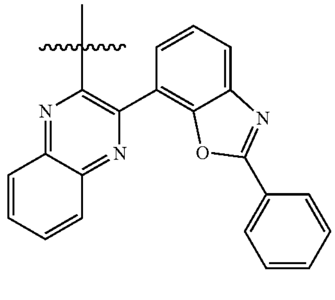
-continued
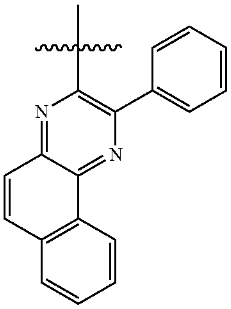
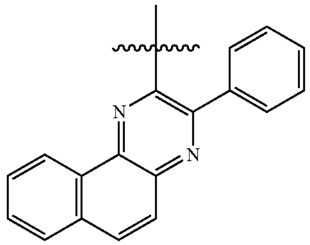
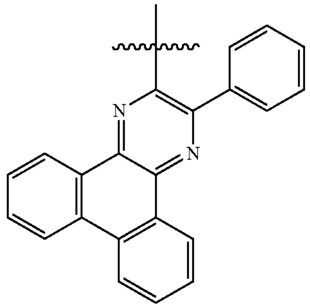
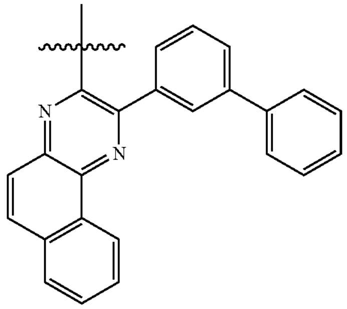
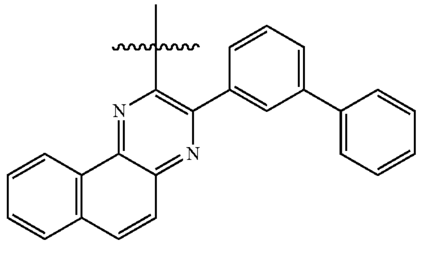

-continued
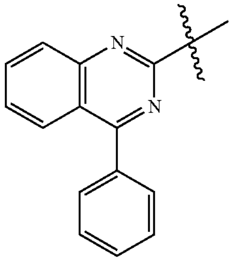
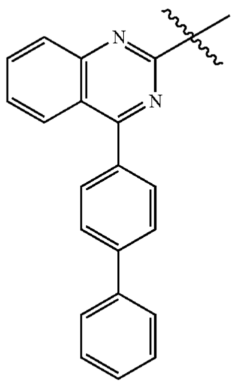
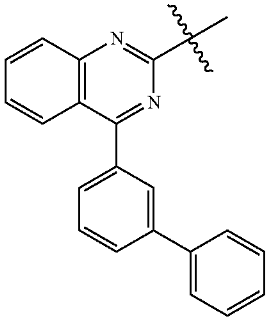
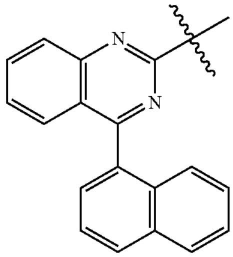
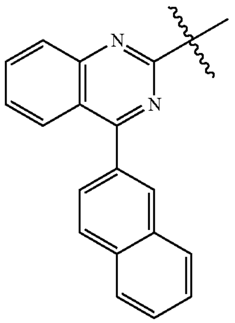
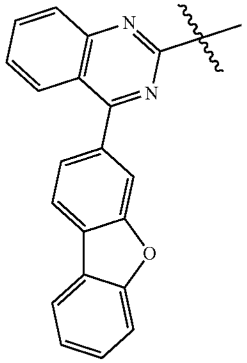
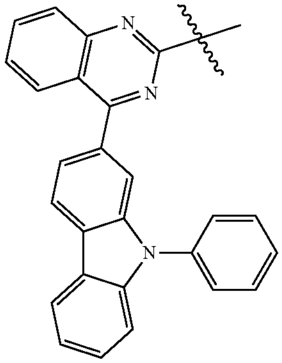
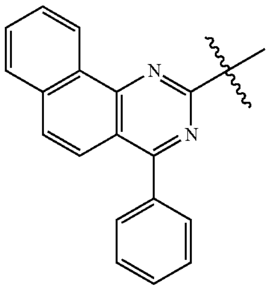
-continued
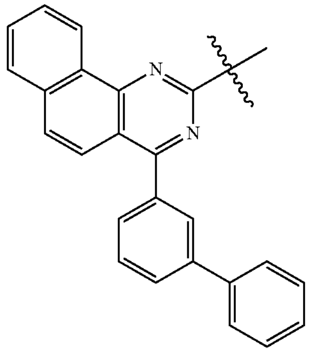
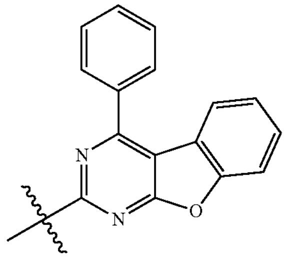
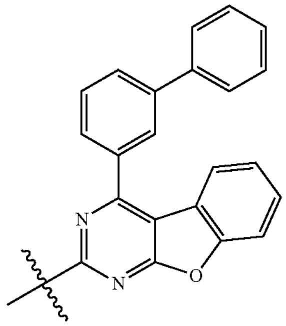
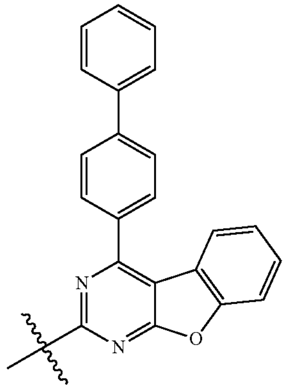
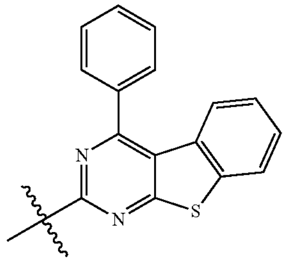

-continued
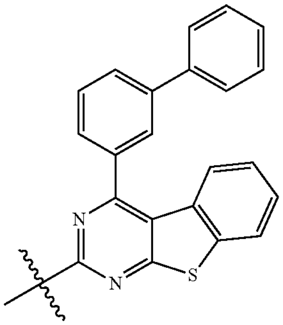
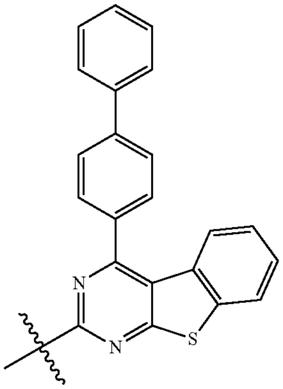
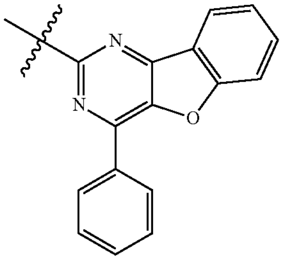
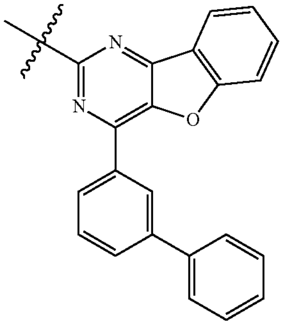
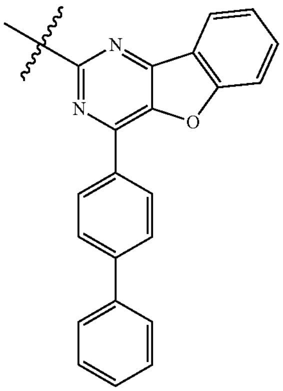
-continued
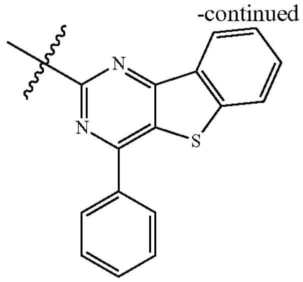
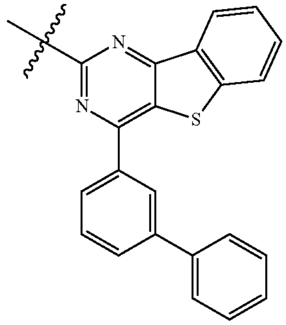
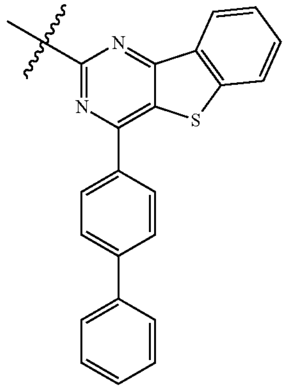
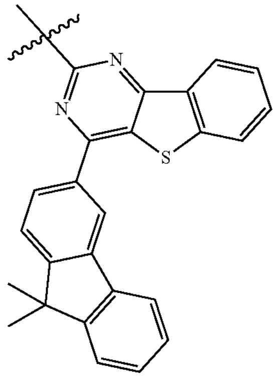
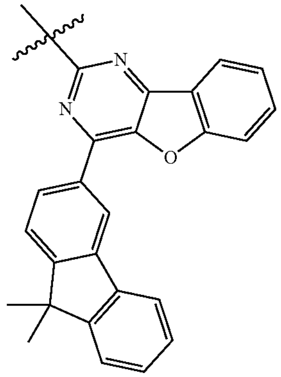

-continued

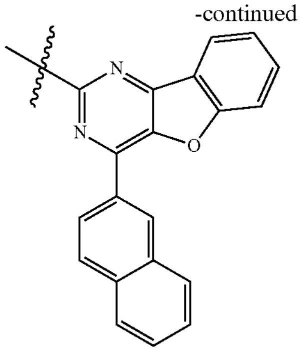

In one embodiment, in $Ar_1$, $L_1$, $R_1$ to $R_4$, and $R_a$, the substituents of the substituted (C1-C30)alkyl(ene), the substituted (C6-C30)aryl(ene), the substituted (3- to 30-membered)heteroaryl(ene), the substituted (C3-C30)cycloalkyl (ene), the substituted (C1-C30)alkoxy, the substituted tri (C1-C30)alkylsilyl, the substituted di(C1-C30)alkyl(C6-C30)arylsilyl, the substituted (C1-C30)alkyldi(C6-C30) arylsilyl, the substituted tri(C6-C30)arylsilyl, the substituted mono- or di-(C1-C30)alkylamino, the substituted mono- or di-(C6-C30)arylamino, the substituted (C1-C30)alkyl(C6-30)arylamino, and the substituted ring each independently represent at least one selected from the group consisting of deuterium, halogen, cyano, carboxyl, nitro, hydroxyl, (C1-C30)alkyl, halo(C1-C30)alkyl, (C2-C30)alkenyl, (C2-C30) alkynyl, (C1-C30)alkoxy, (C1-C30)alkylthio, (C3-C30)cycloalkyl, (C3-C30)cycloalkenyl, (3- to 7-membered) heterocycloalkyl, (C6-C30)aryloxy, (C6-C30)arylthio, (C6-C30)aryl-substituted or unsubstituted (3- to 30-membered) heteroaryl, (3- to 30-membered)heteroaryl-substituted or unsubstituted (C6-C30)aryl, tri(C1-C30)alkylsilyl, tri(C6-C30)arylsilyl, di(C1-C30)alkyl(C6-C30)arylsilyl, (C1-C30) alkyldi(C6-C30)arylsilyl, amino, mono- or di-(C1-C30)alkylamino, (C1-C30)alkyl-substituted or unsubstituted mono- or di-(C6-C30)arylamino, (C1-C30)alkyl(C6-C30) arylamino, (C1-C30)alkylcarbonyl, (C1-C30)alkoxycarbonyl, (C6-C30)arylcarbonyl, di(C6-C30)arylboronyl, di(C1-C30)alkylboronyl, (C1-C30)alkyl(C6-C30)arylboronyl, (C6-C30)ar(C1-C30)alkyl, and (C1-C30)alkyl(C6-C30) aryl. Preferably, the substituents may be (C1-C30)alkyl, (C6-C30)aryl, or (3- to 30-membered)heteroaryl, more preferably (C1-C10)alkyl, (C6-C25)aryl, or (5- to 25-membered)heteroaryl. For example, the substituents may be methyl, phenyl, m-biphenyl, p-biphenyl, naphthyl, fluorenyl, pyridinyl, dibenzofuranyl, dibenzothiophenyl, carbazolyl, or benzoxazolyl, etc.

According to one embodiment, the organic electroluminescent compound represented by the formula 1 may be illustrated by the following compounds, but is not limited thereto.

1

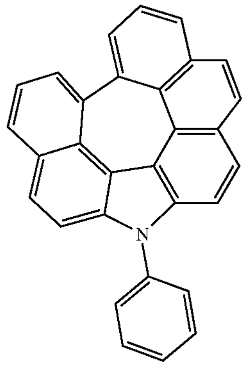

2

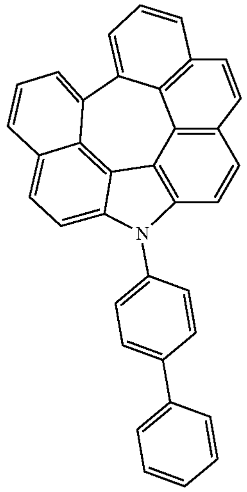

3

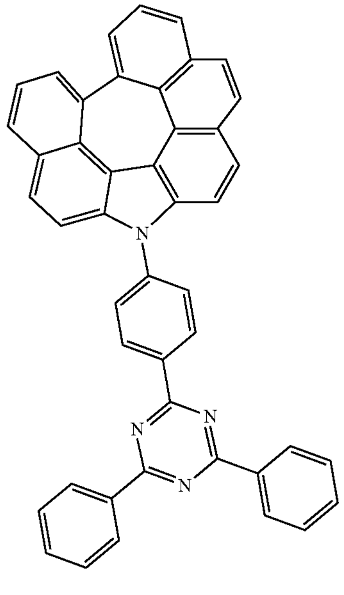

-continued
4
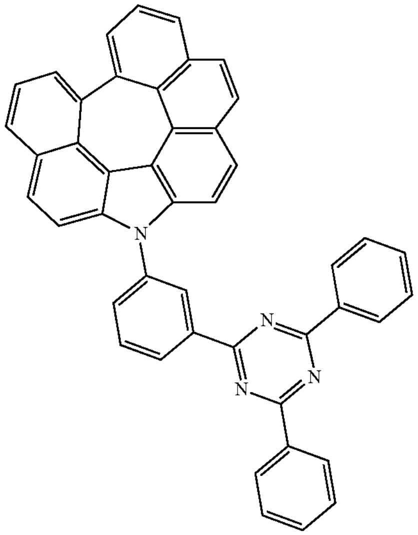
5
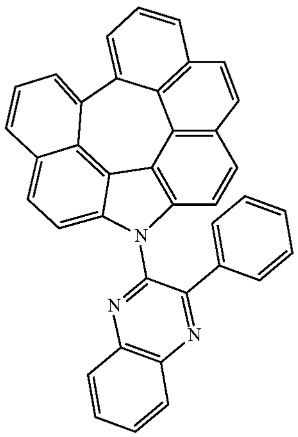
6
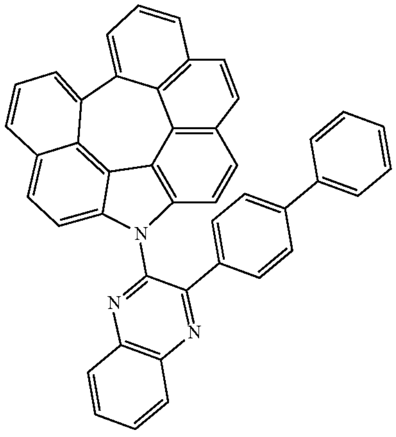
-continued
7
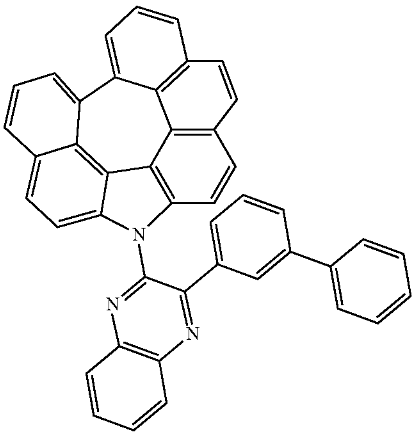
8
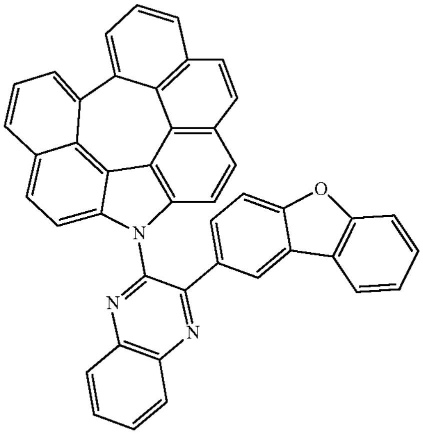
9
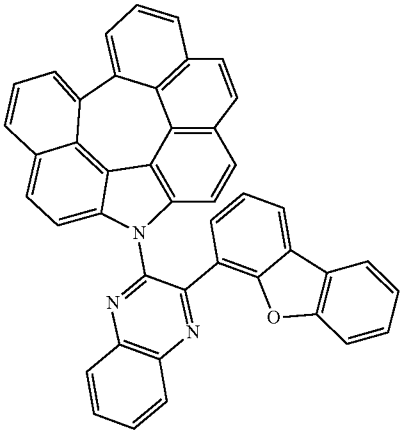

-continued
10
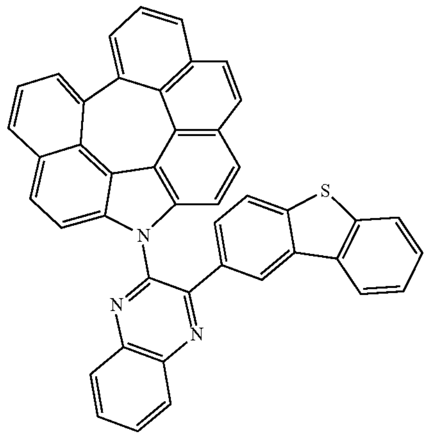
11
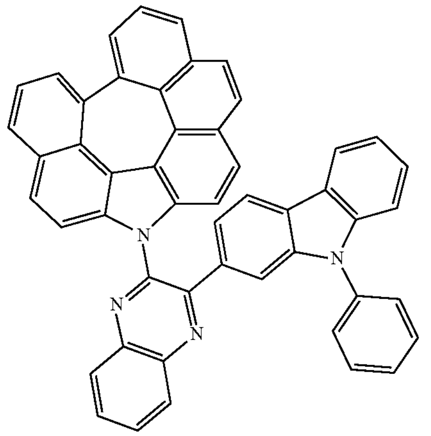
12
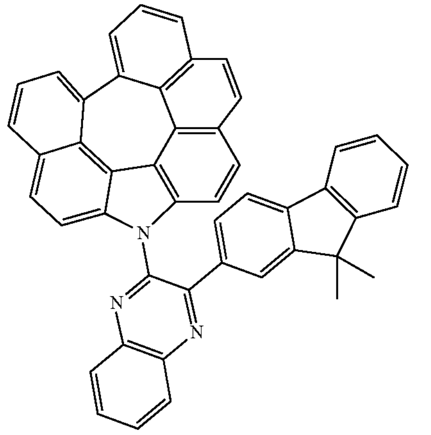
-continued
13
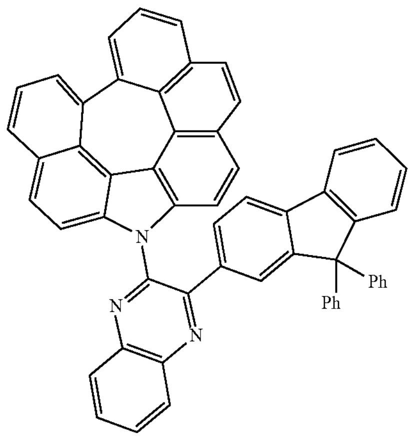
14
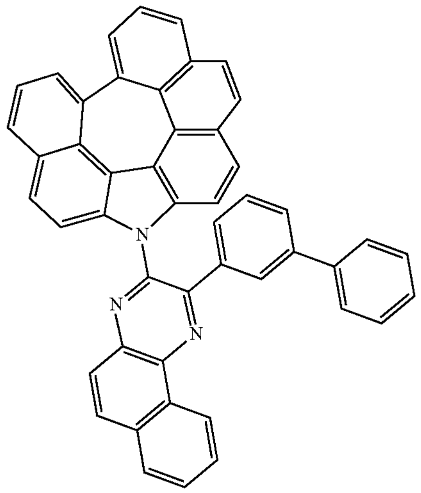
15
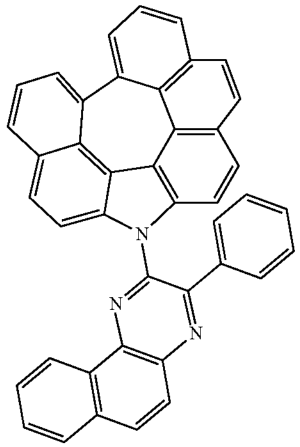

-continued
16
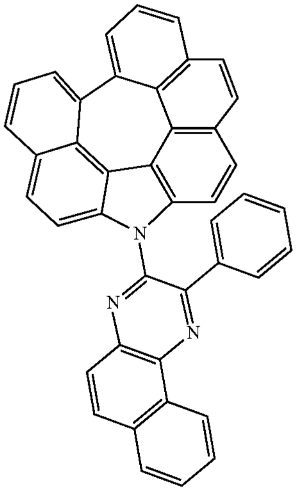
17
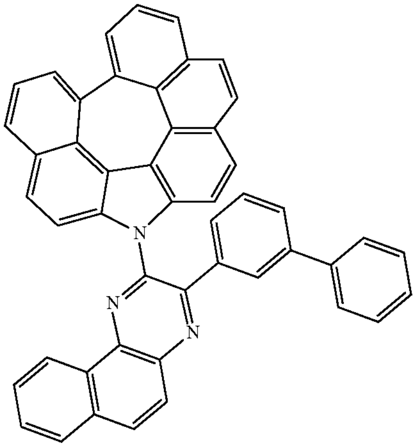
18
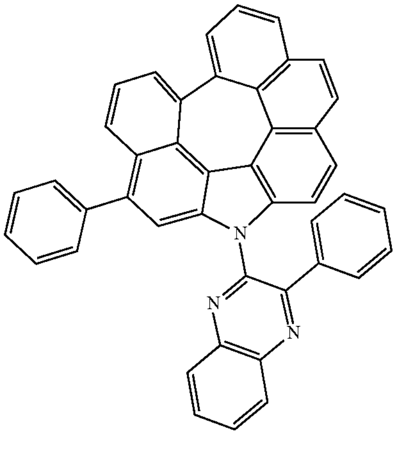
-continued
19
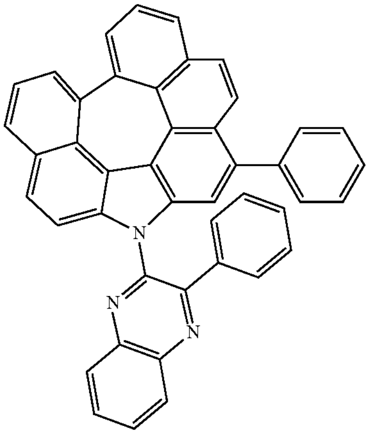
20
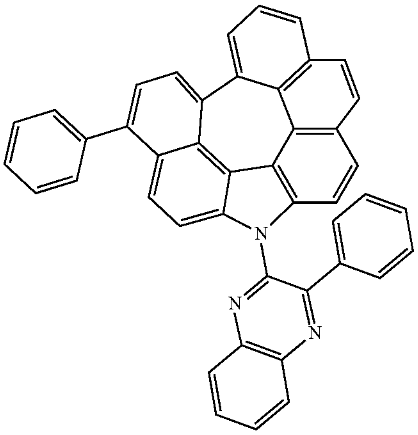
21
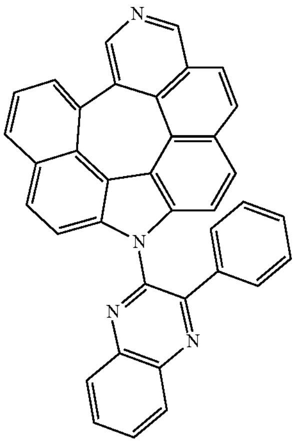

-continued
22
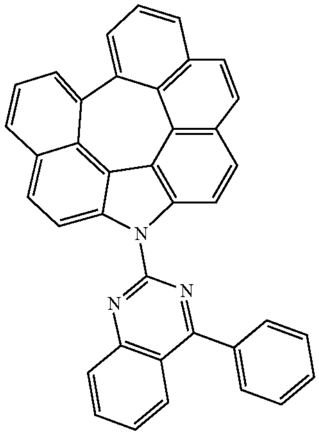
23
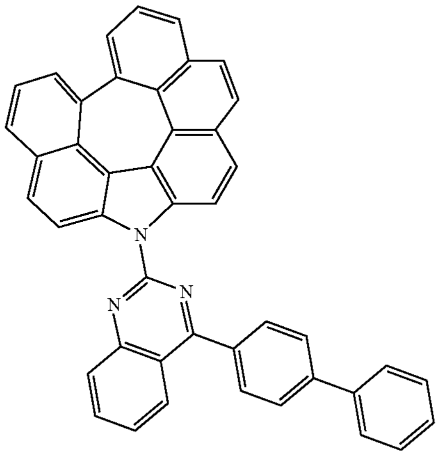
24
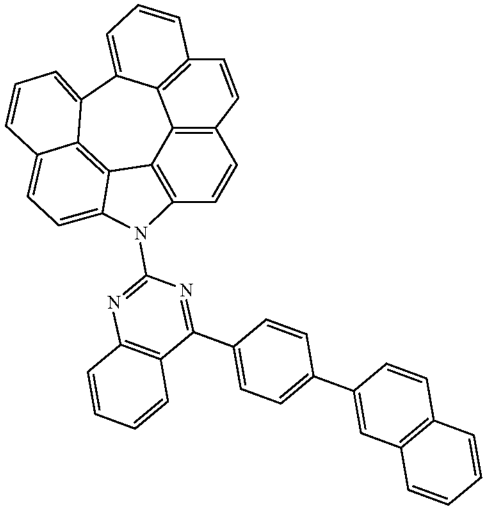
-continued
25
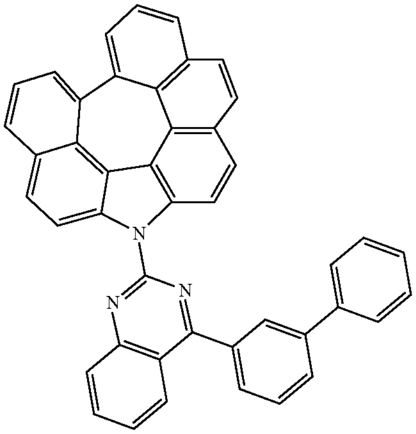
26
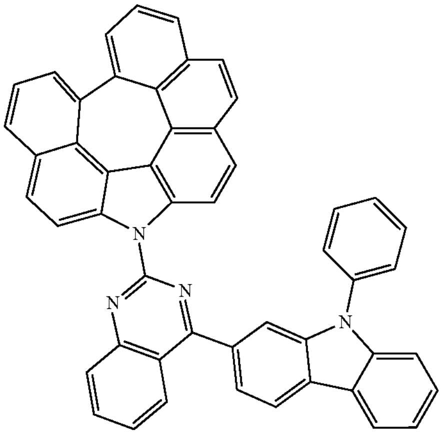
27
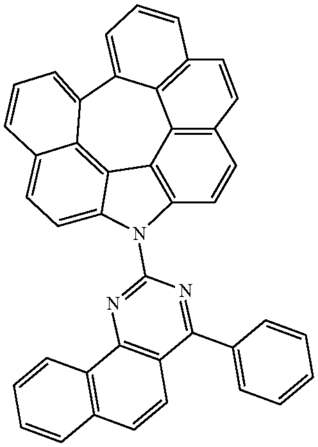

-continued
28
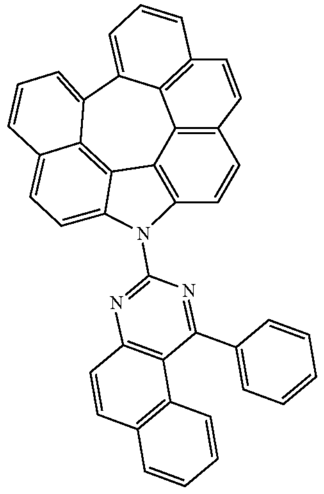
29
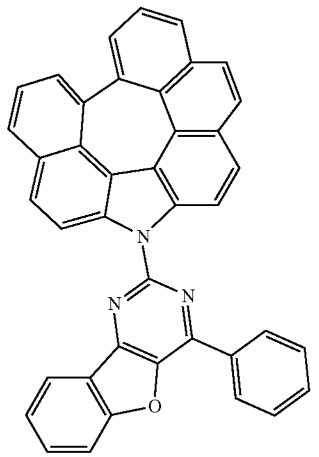
30
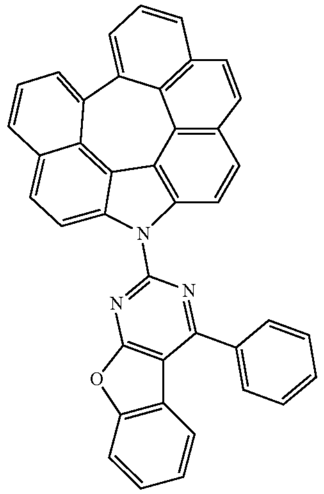
-continued
31
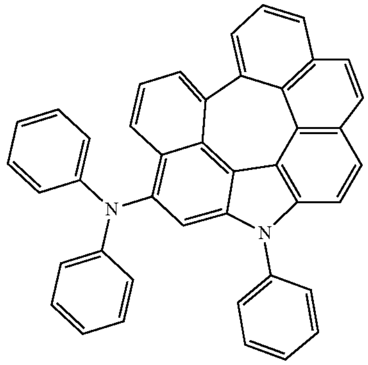
32
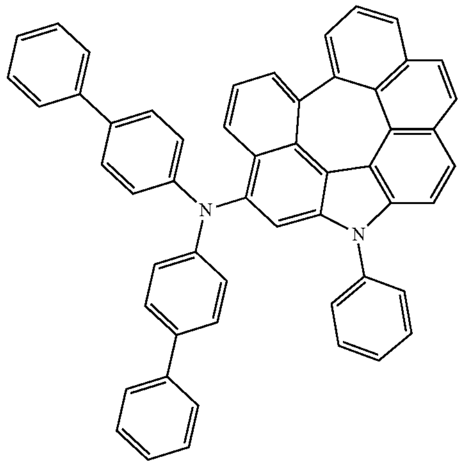
33
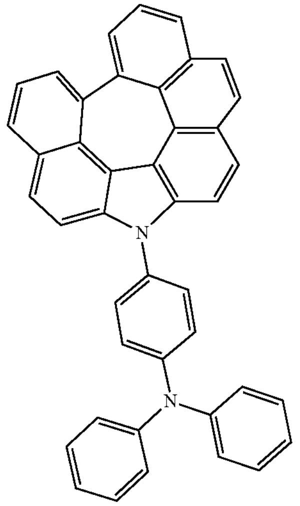

-continued
34
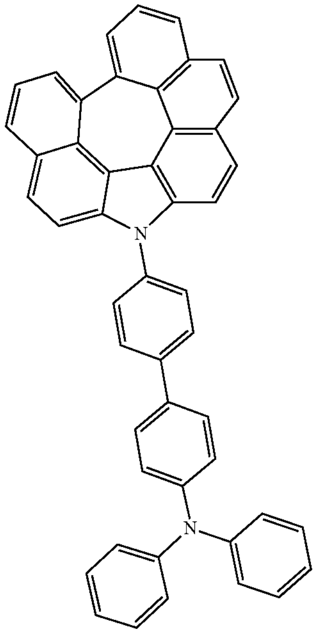
35
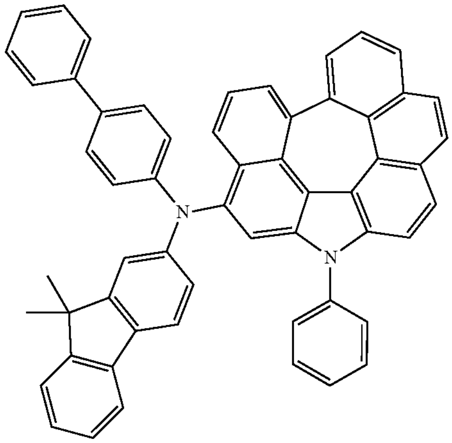
36
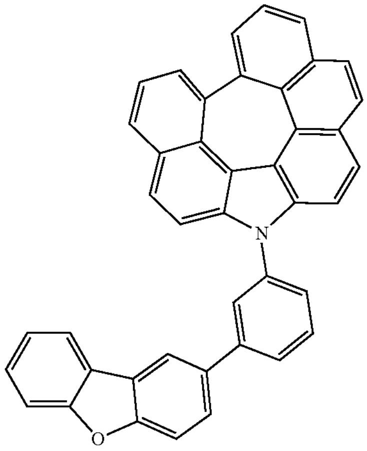
-continued
37
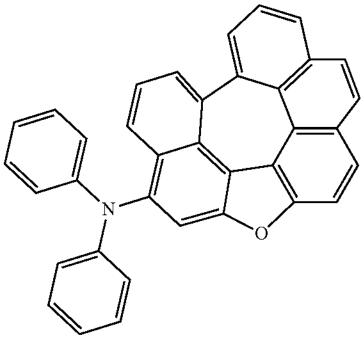
38
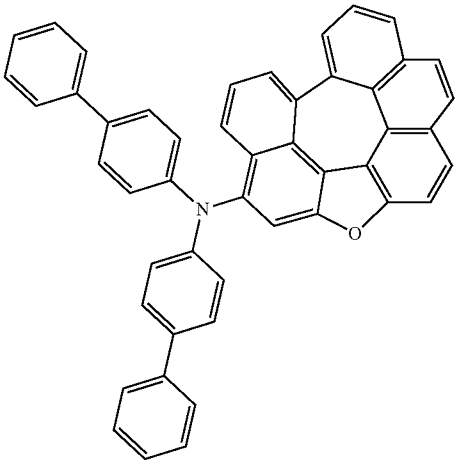
39
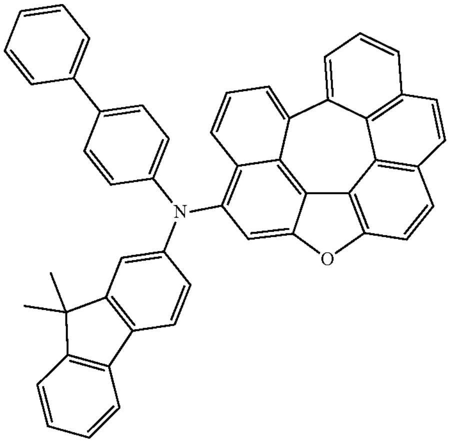
40
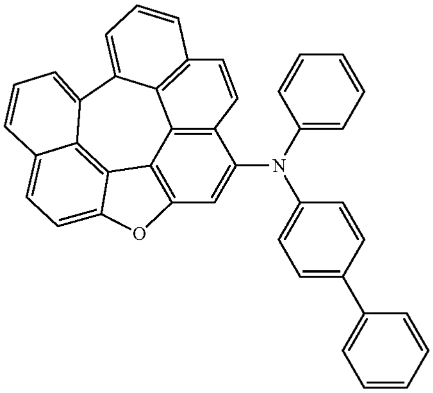

-continued
41
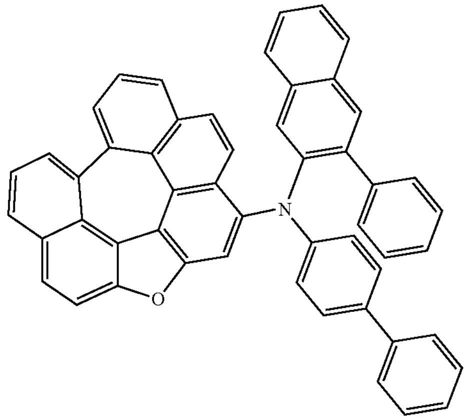
42
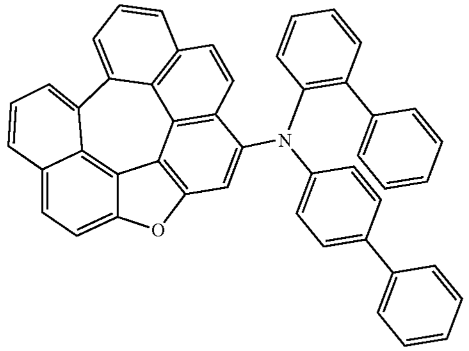
43
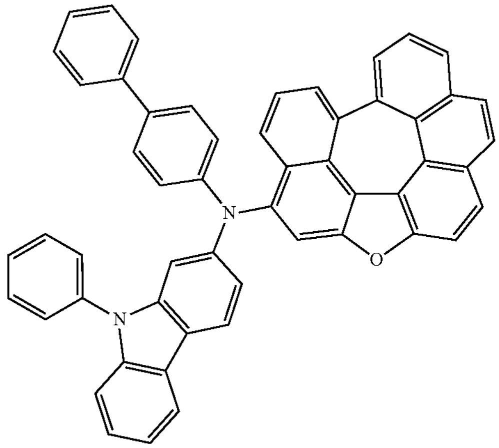
-continued
44
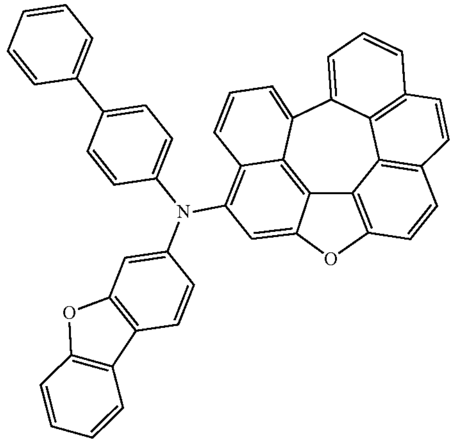
45
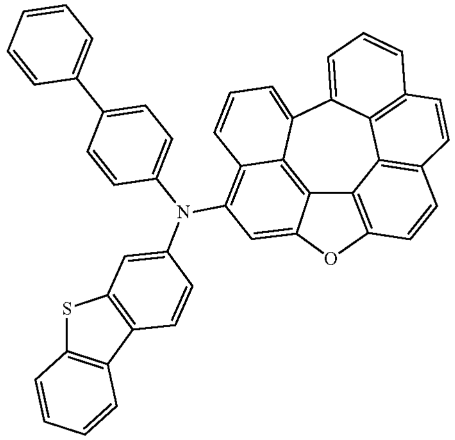
46
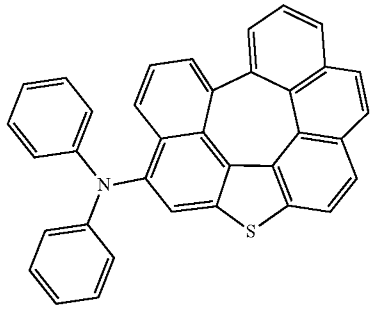
47
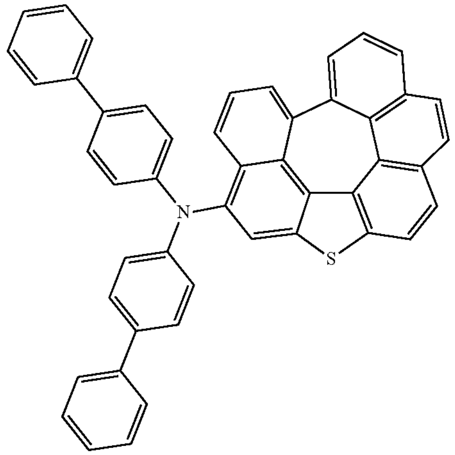

-continued
48
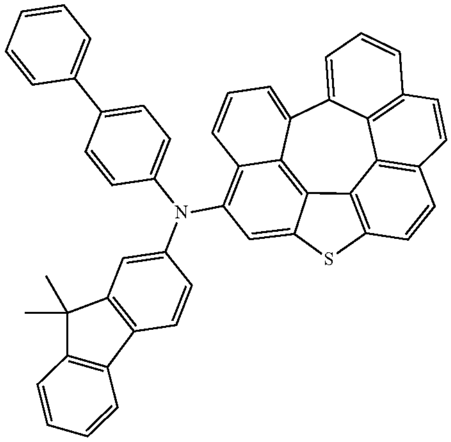
49
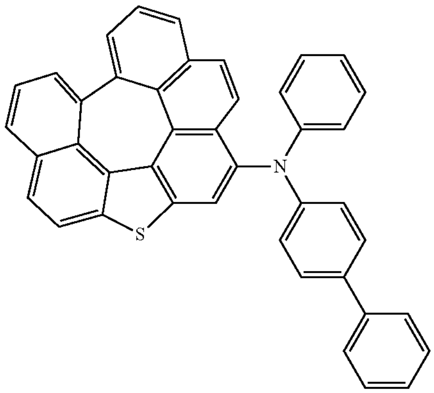
50
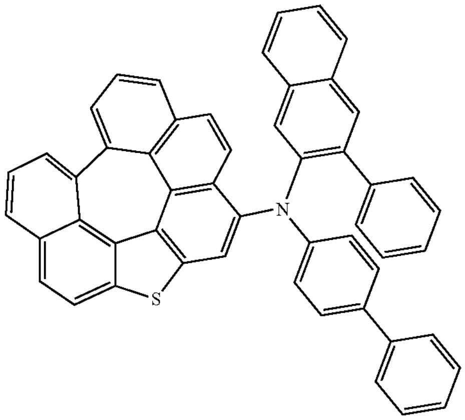
51
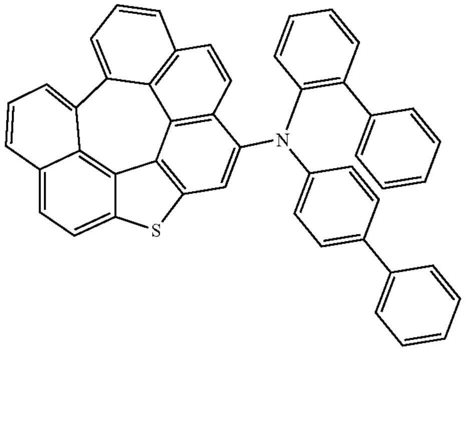
-continued
52
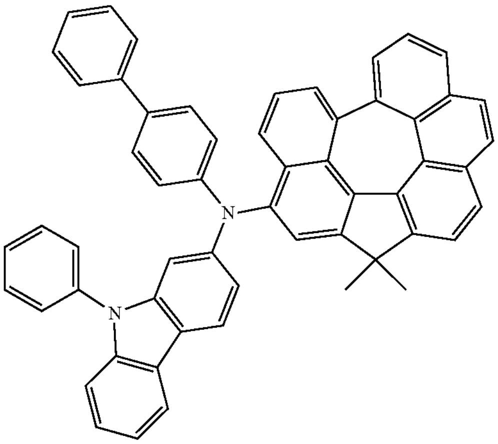
53
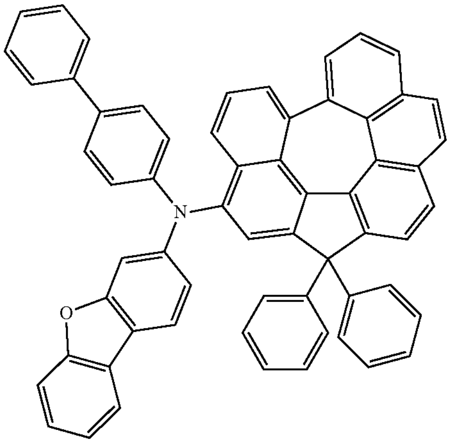
54
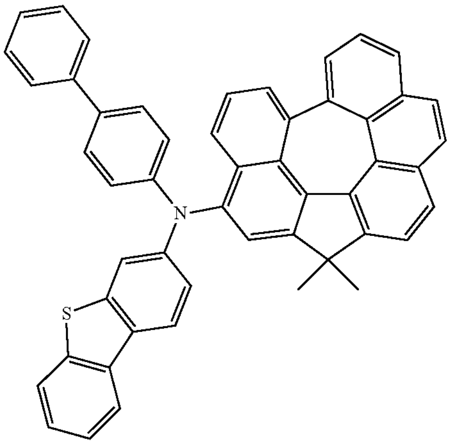

-continued
55
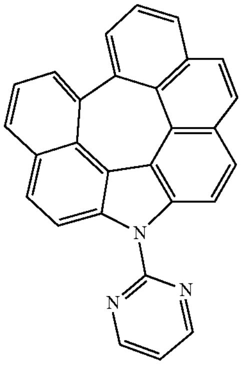
56
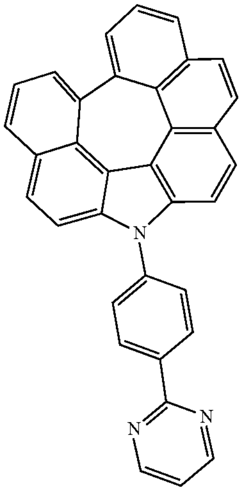
57
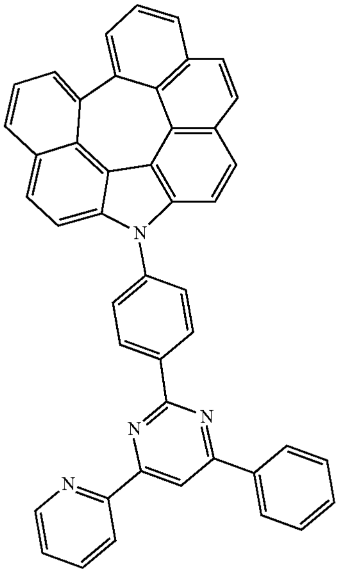
-continued
58
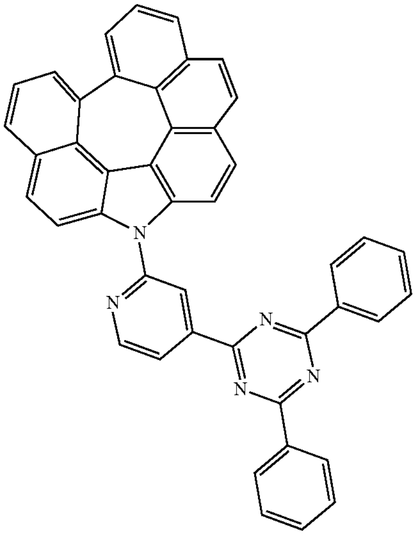
59
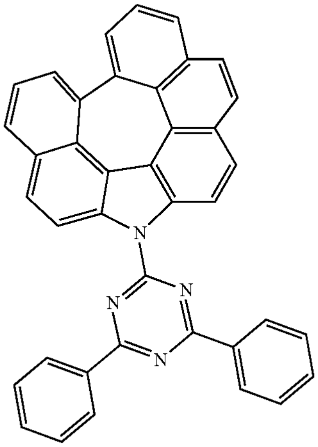
60
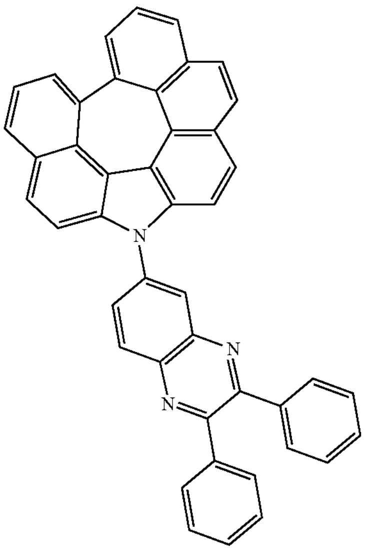

-continued
61
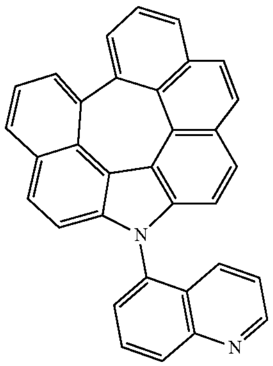
62
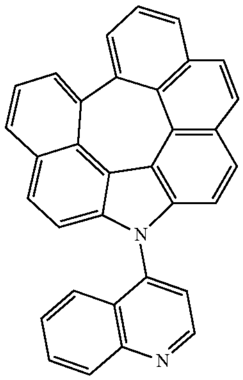
63
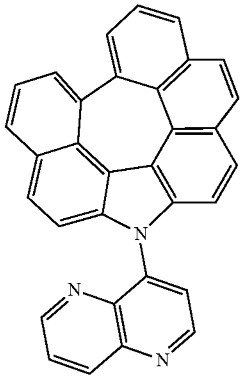
-continued
64
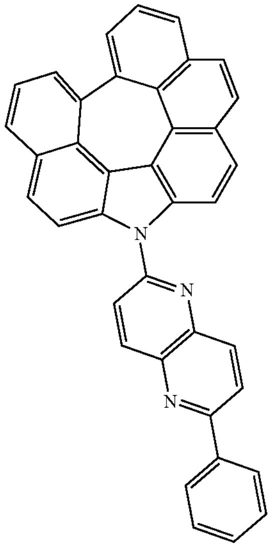
65
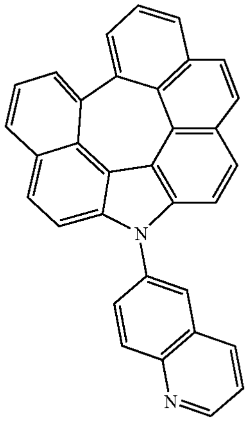
66
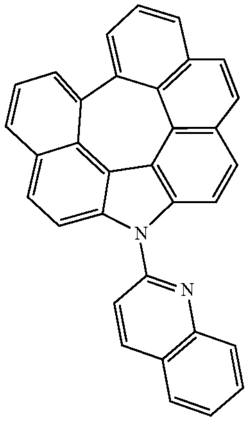

-continued
67
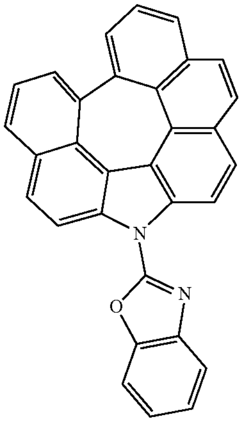
68
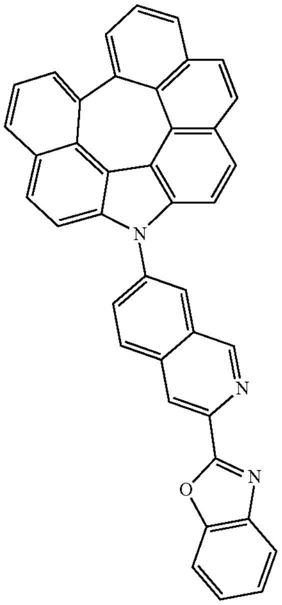
69
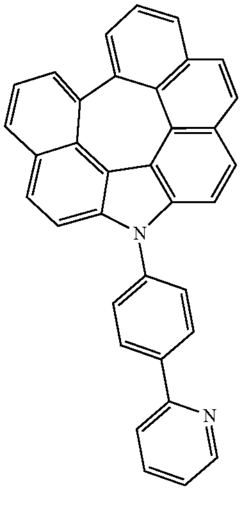
-continued
70
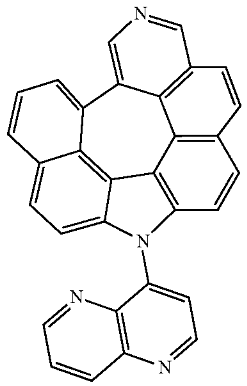
71
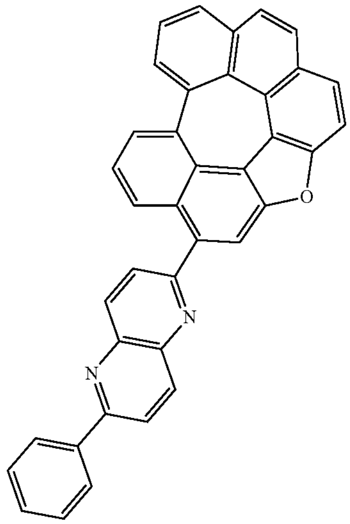
72
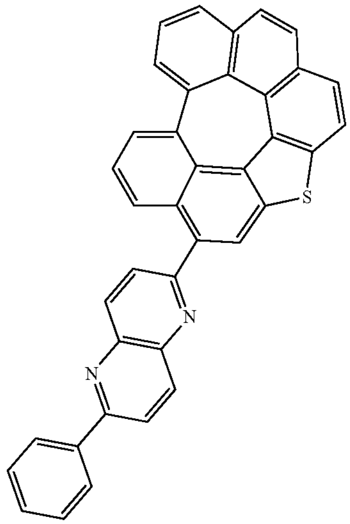

-continued
73
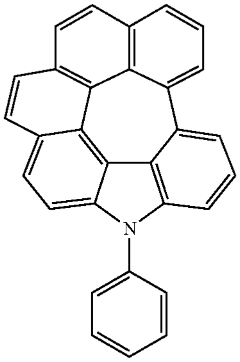
74
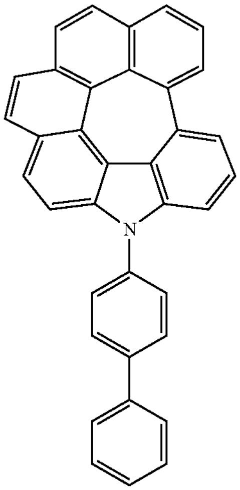
75
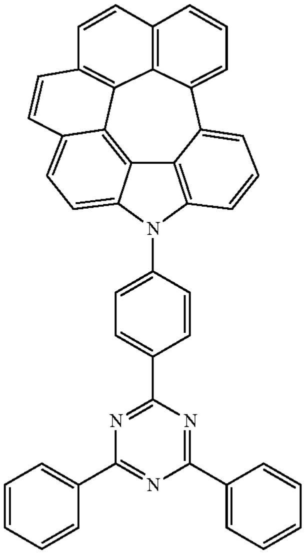
-continued
76
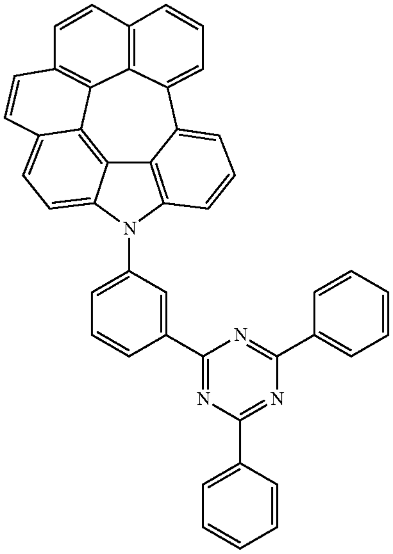
77
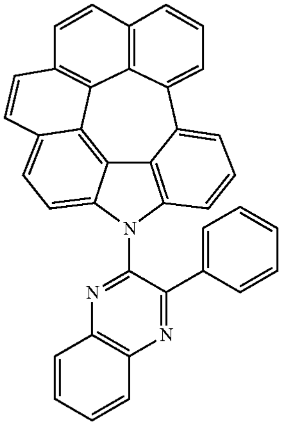
78
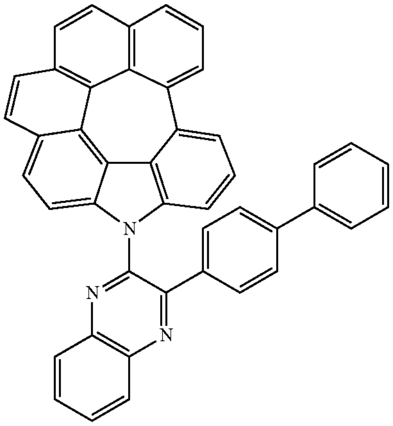

-continued
79
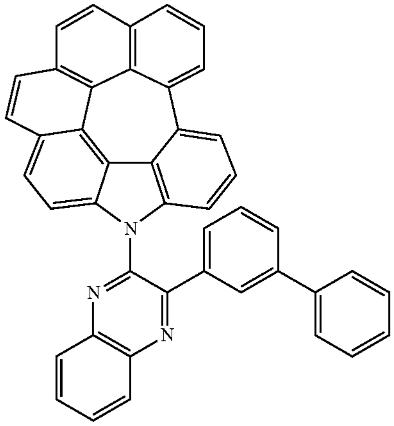
80
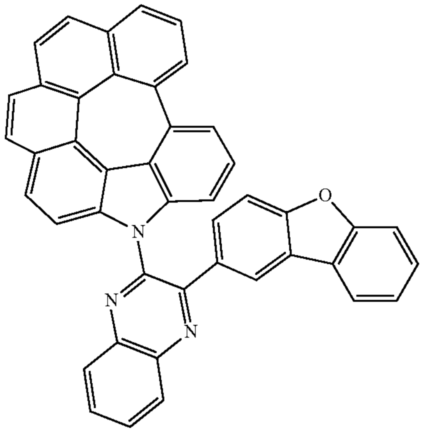
81
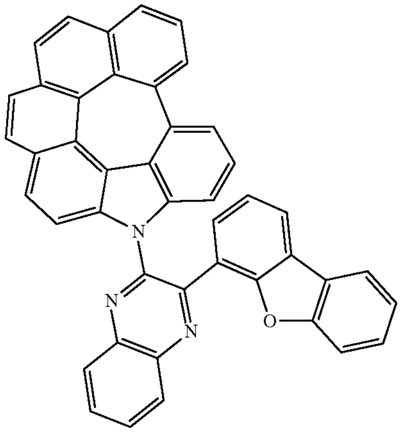
-continued
82
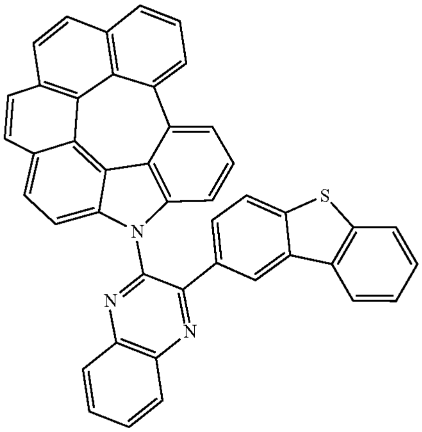
83
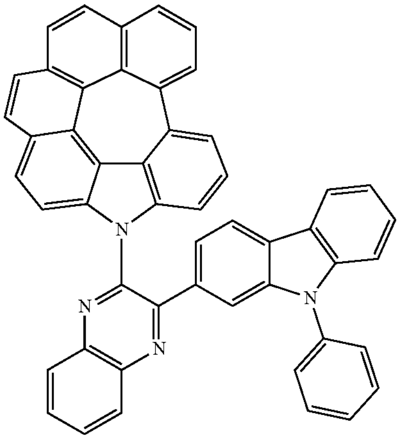
84
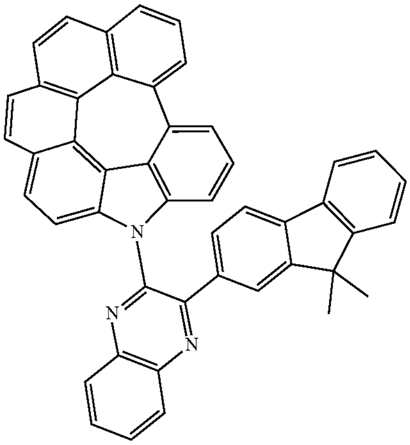

-continued
85
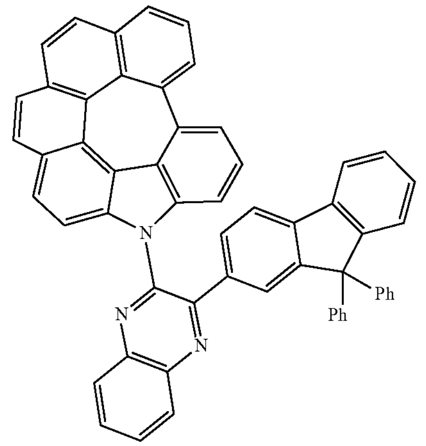
86
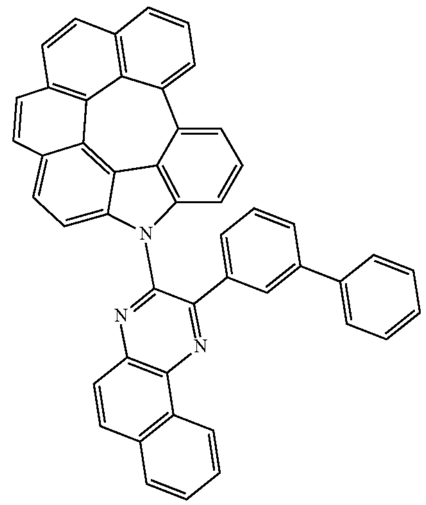
87
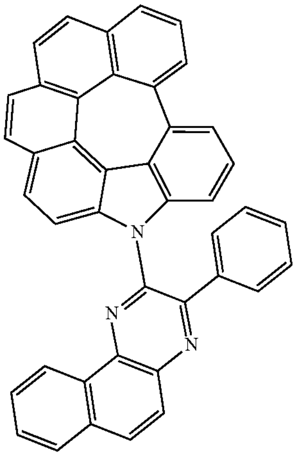
-continued
88
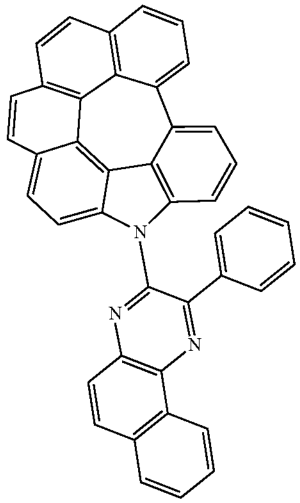
89
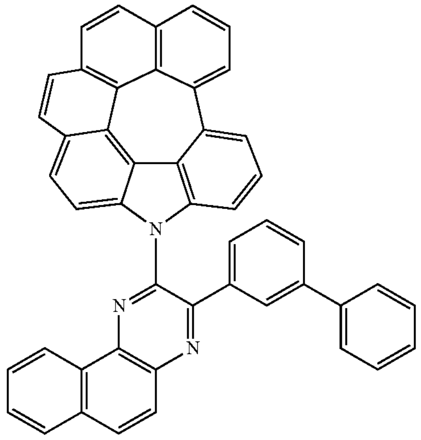
90
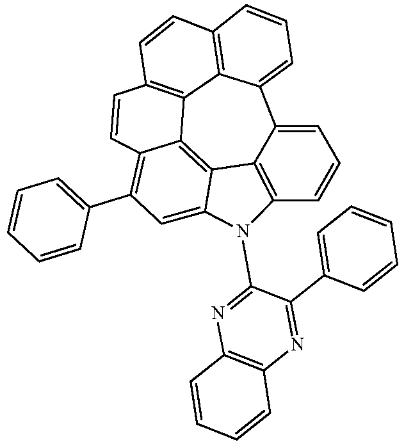

-continued
91
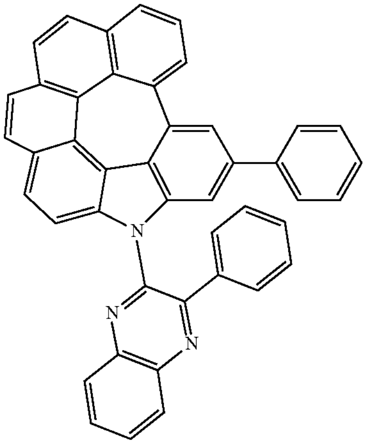
92
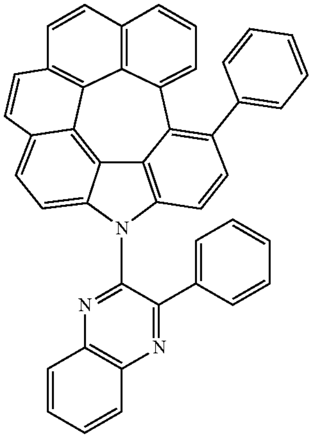
93
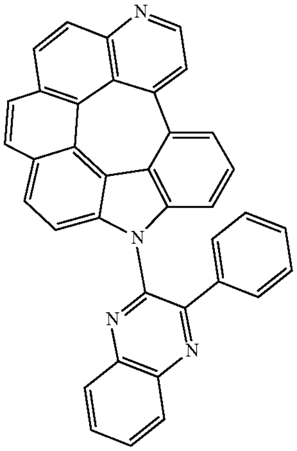
-continued
94
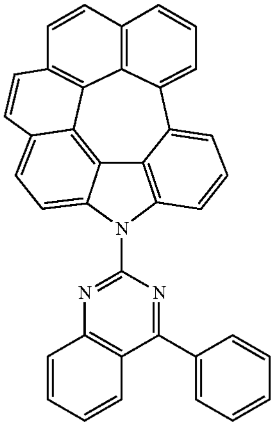
95
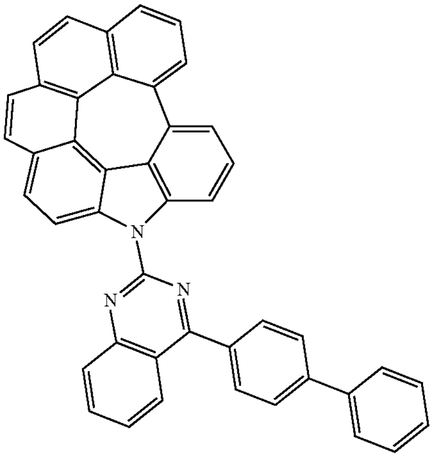
96
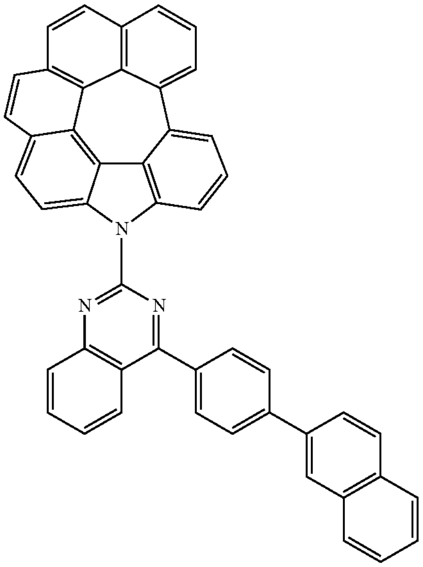

-continued
97
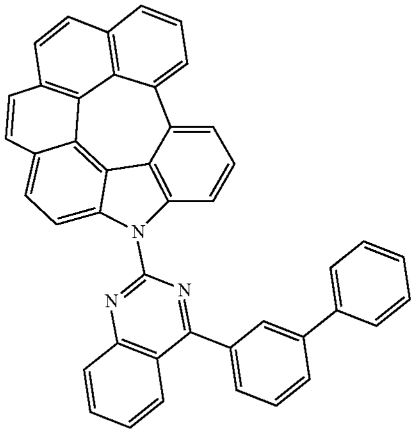
98
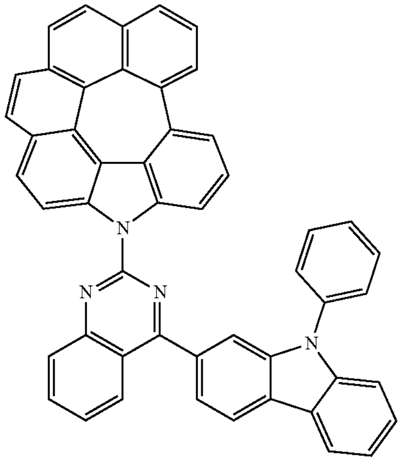
99
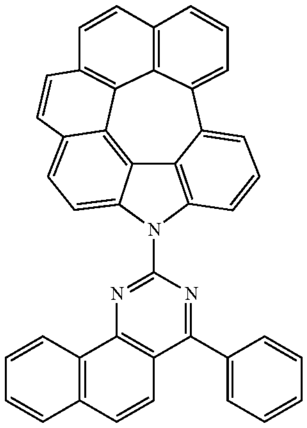
-continued
100
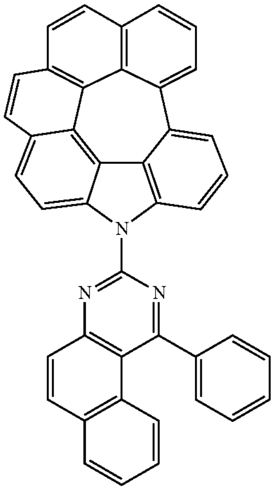
101
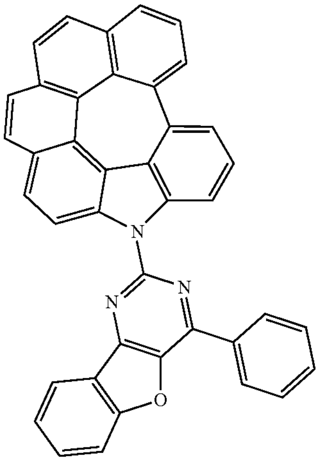
102
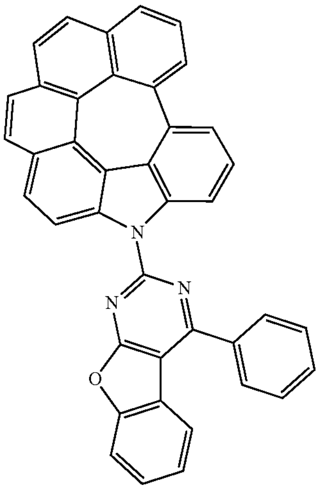

-continued
103
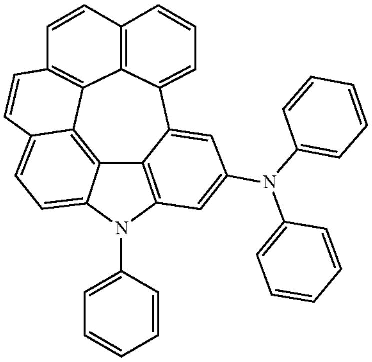
104
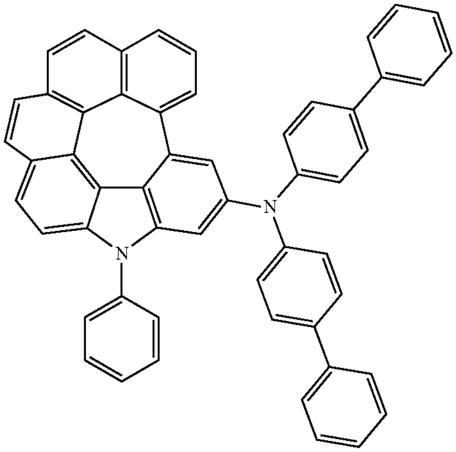
105
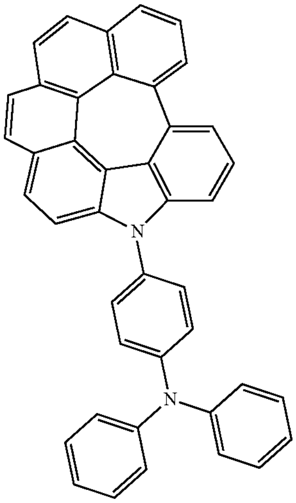
-continued
106
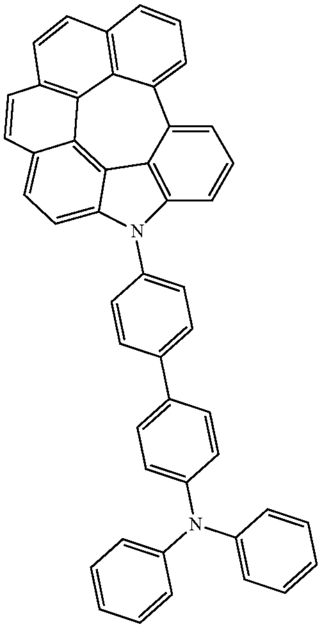
107
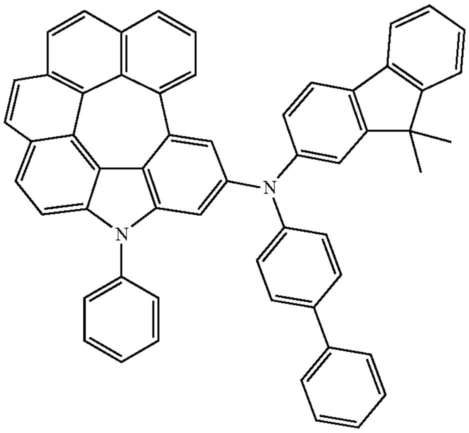
108
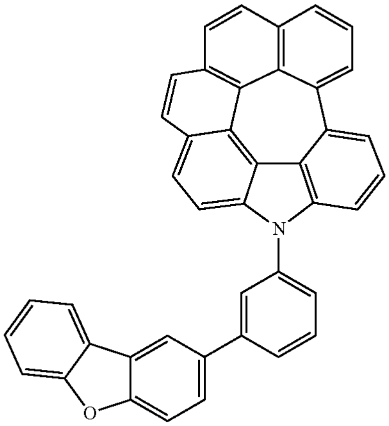

-continued
109
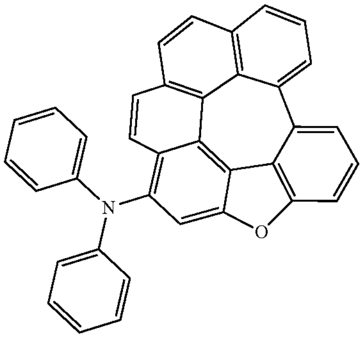
110
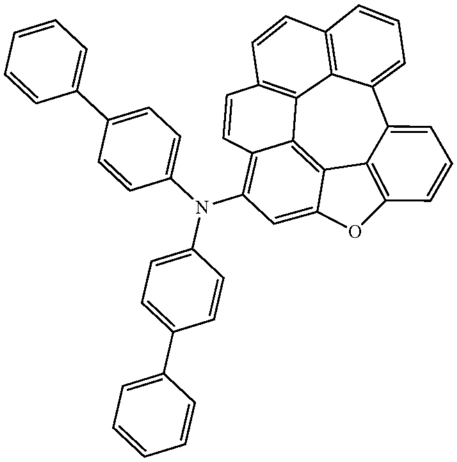
111
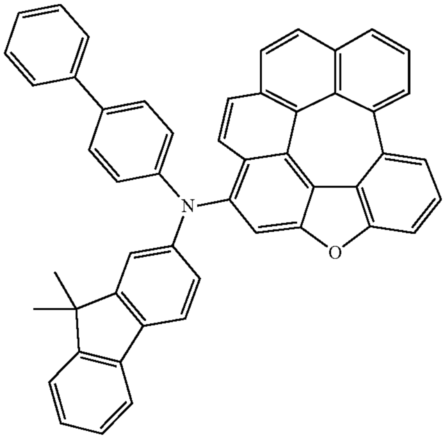
112
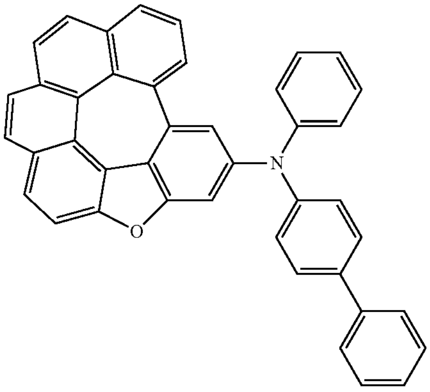
-continued
113
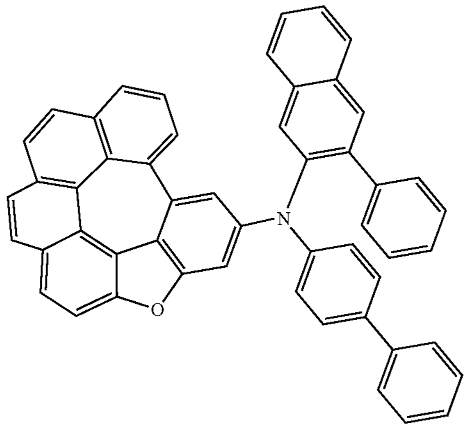
114
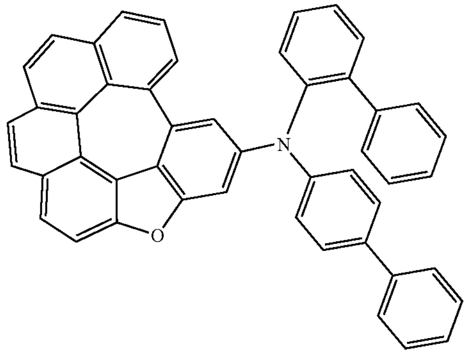
115
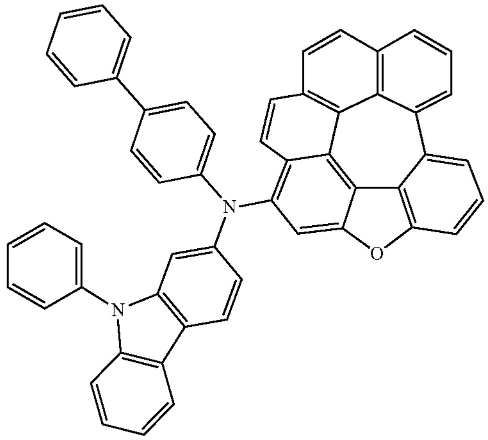

-continued
116
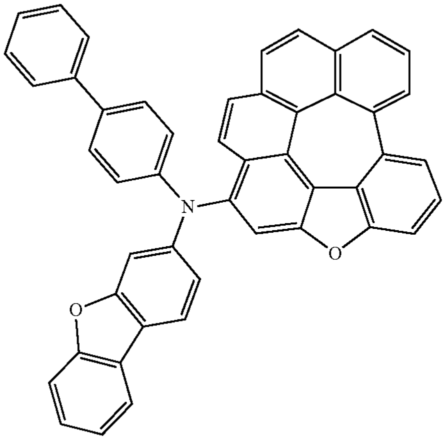
117
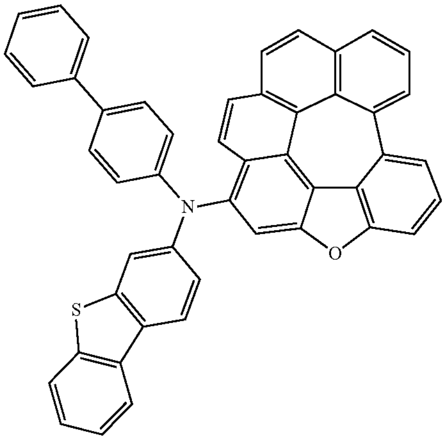
118
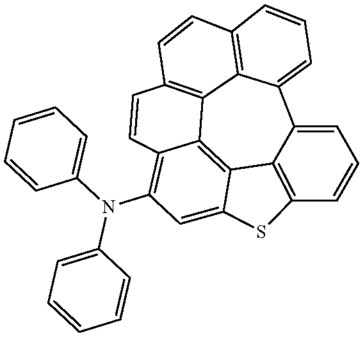
-continued
119
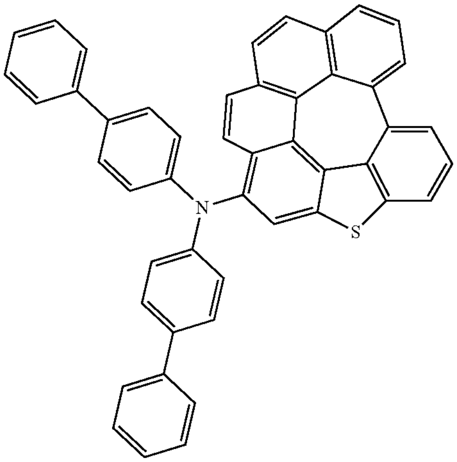
120
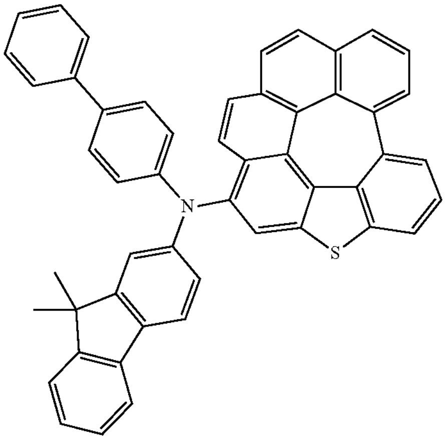
121
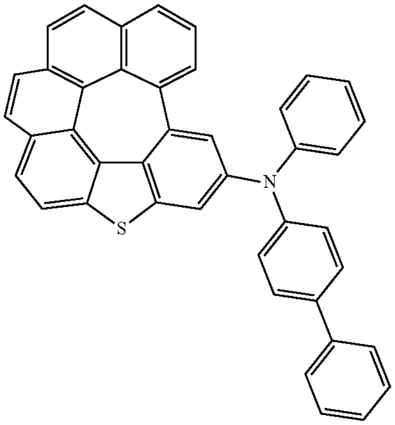

-continued
122
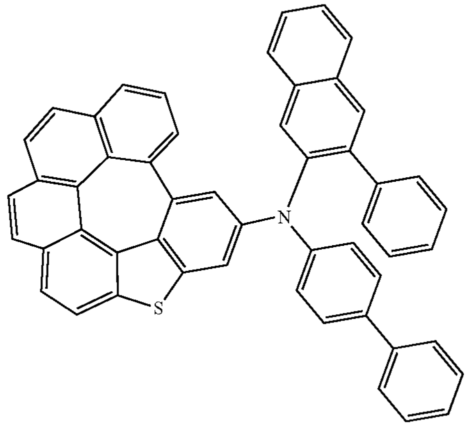
123
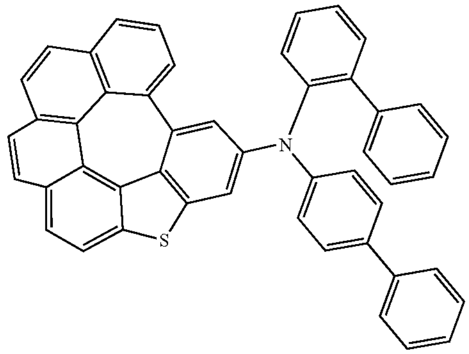
124
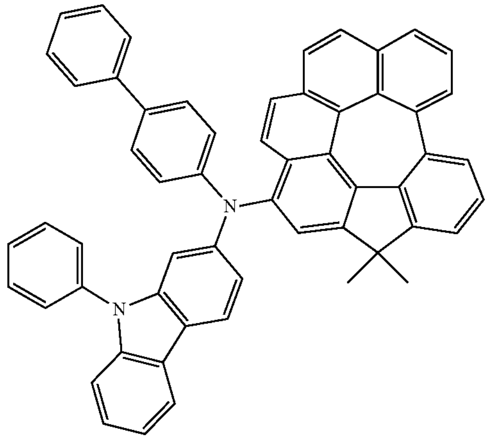
-continued
125
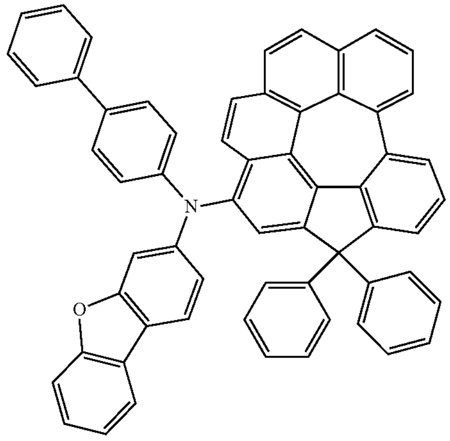
126
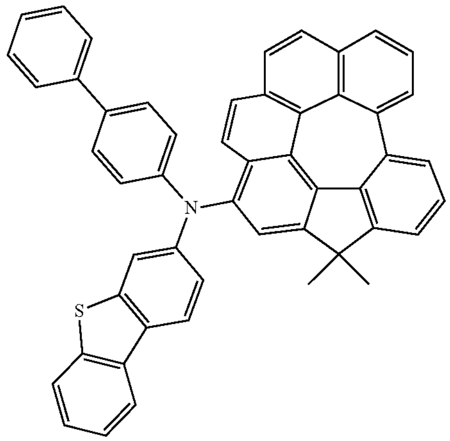
127
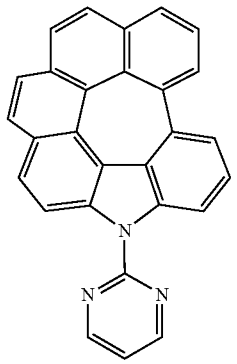

-continued
128
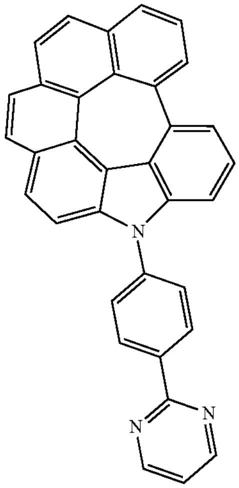
129
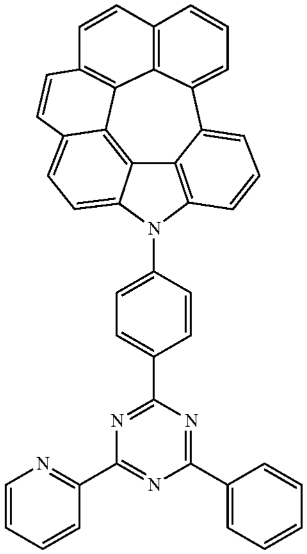
130
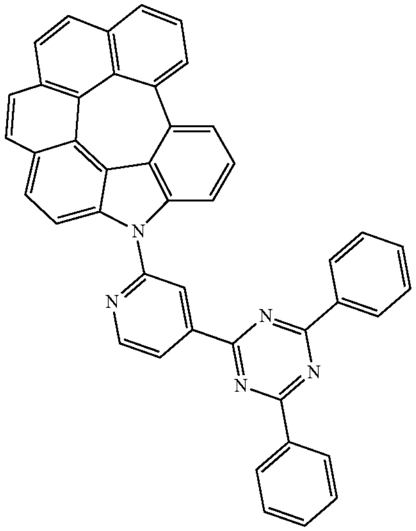
-continued
131
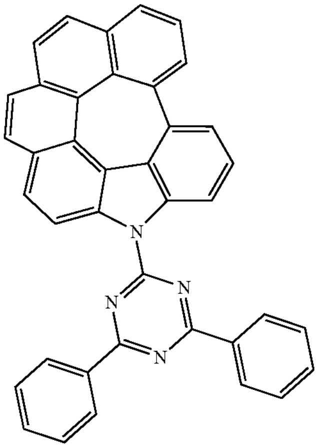
132
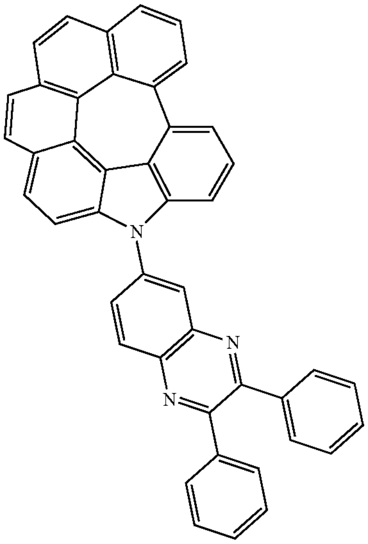
133
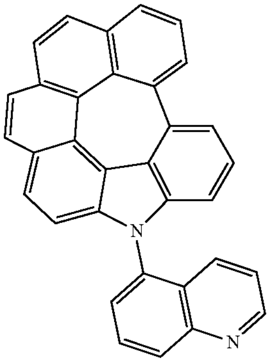

-continued
134
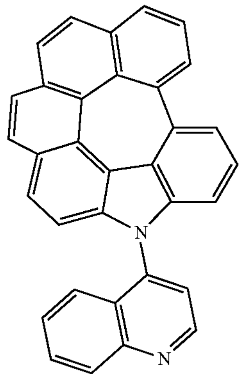
135
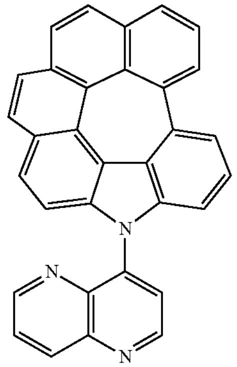
136
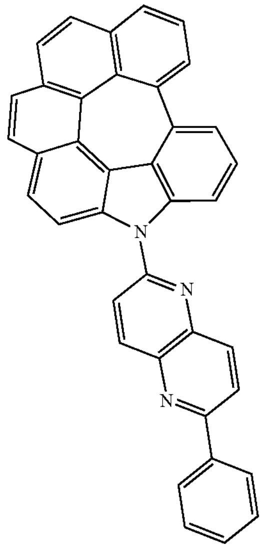
-continued
137
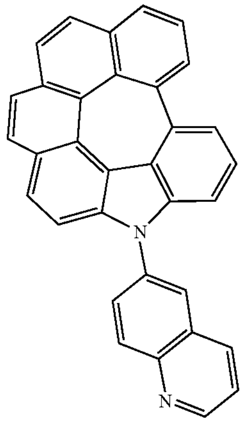
138
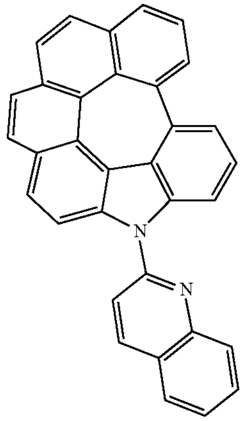
139
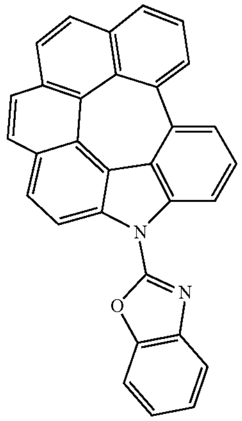

-continued
140
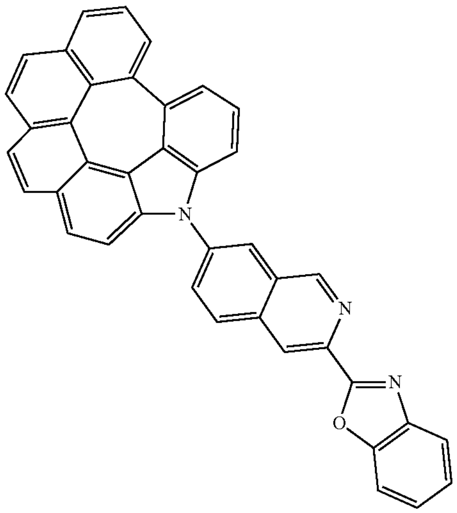
141
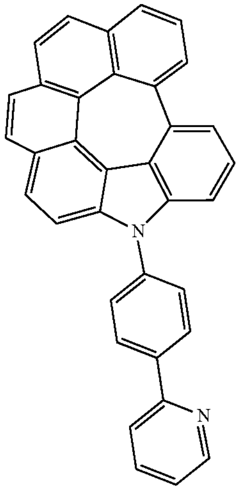
142
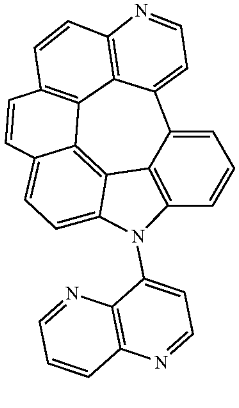
-continued
143
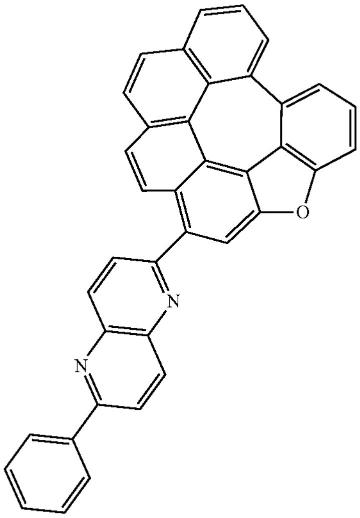
144
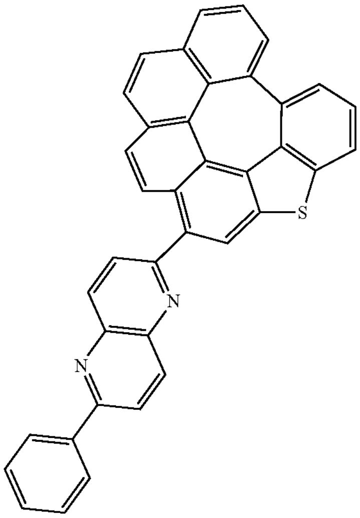
145
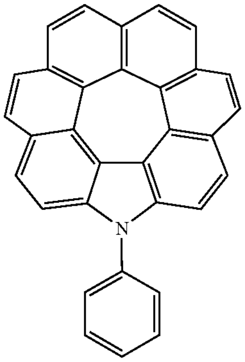

-continued
146
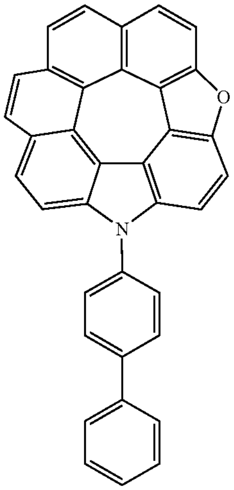
147
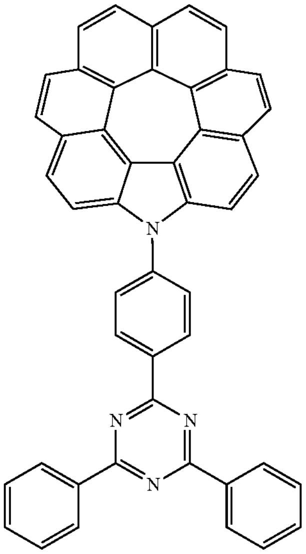
148
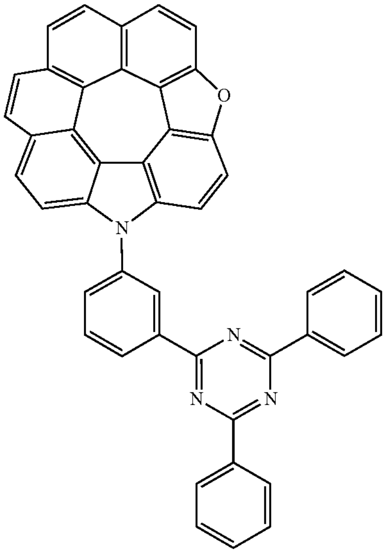
-continued
149
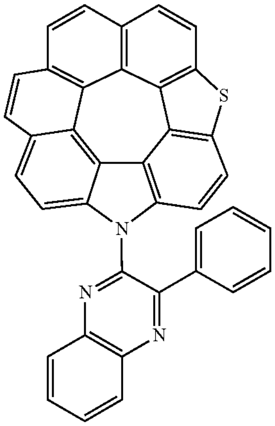
150
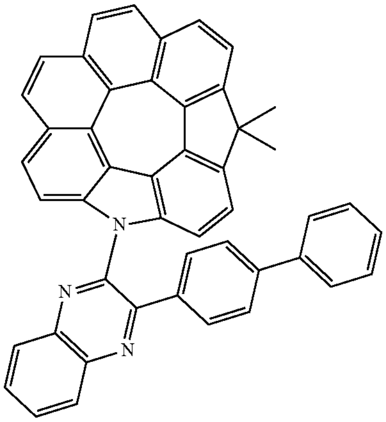
151
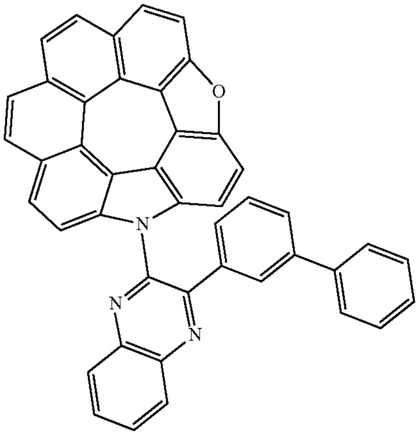

-continued
152
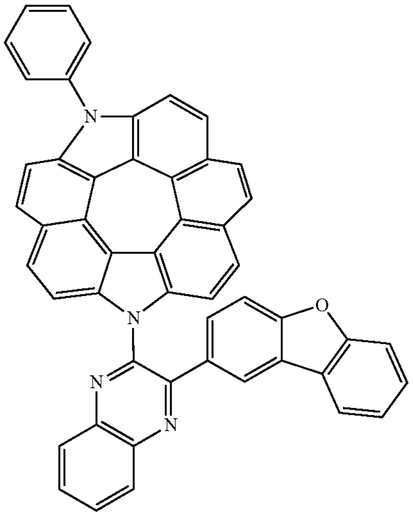
153
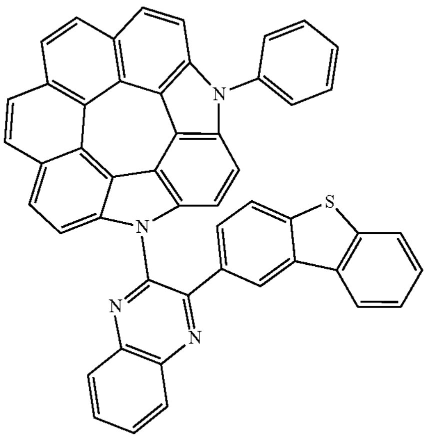
154
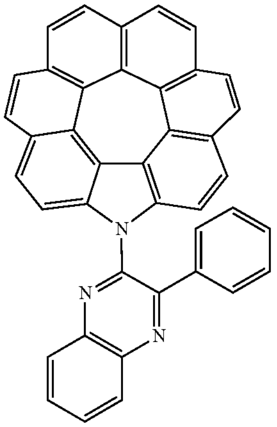
-continued
155
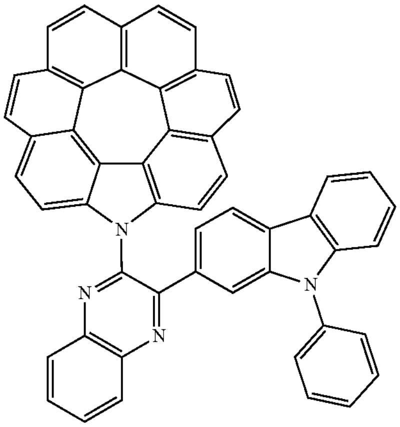
156
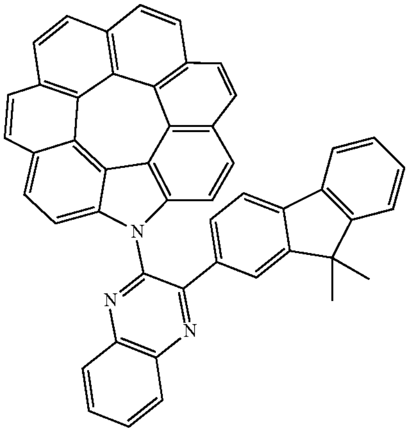
157
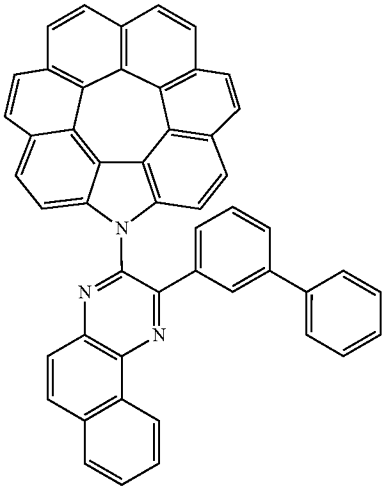

-continued
158
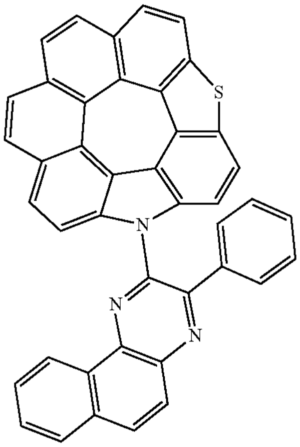
159
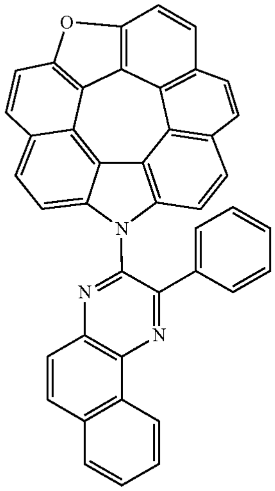
160
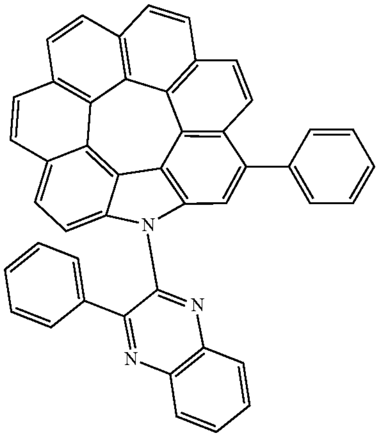
-continued
161
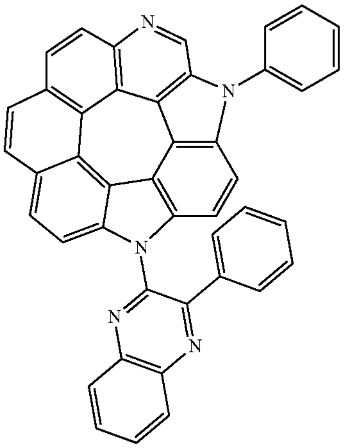
162
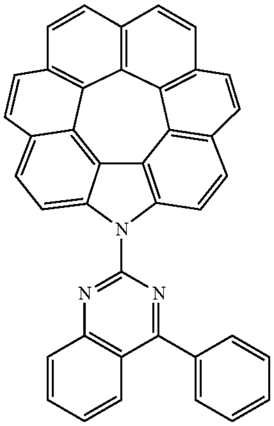
163
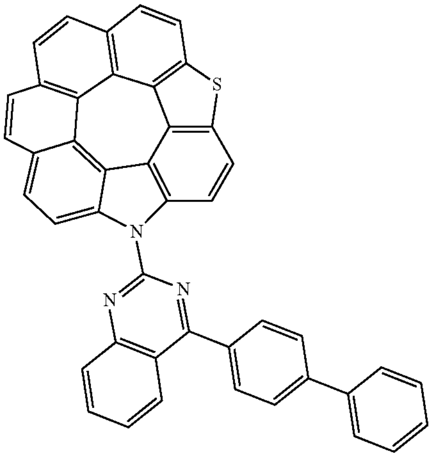

-continued
164
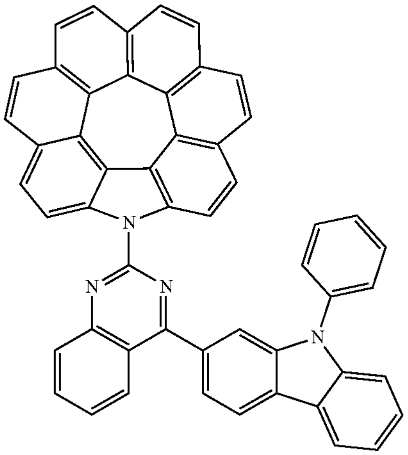
165
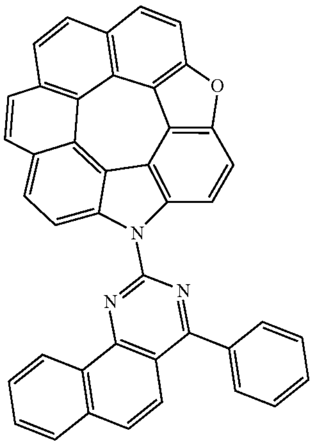
166
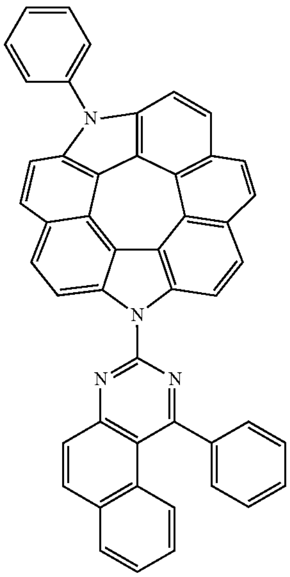
-continued
167
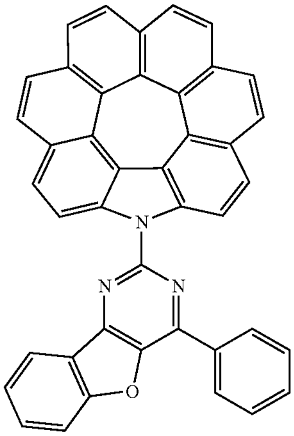
168
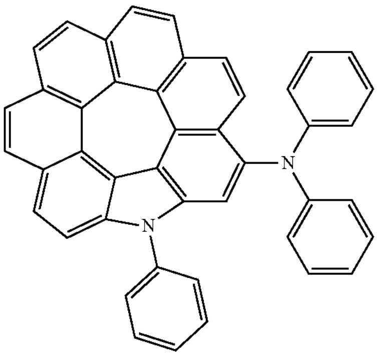
169
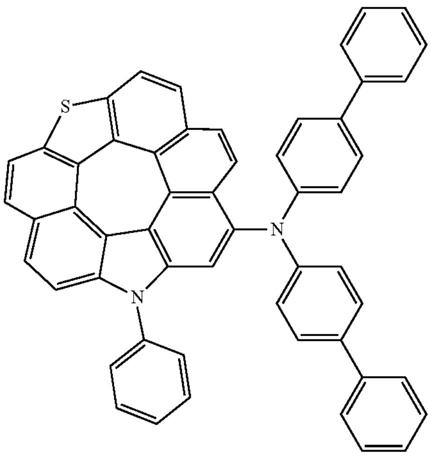

170
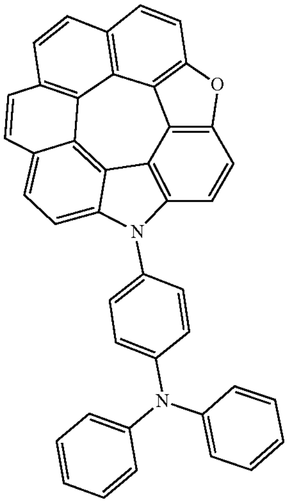
171
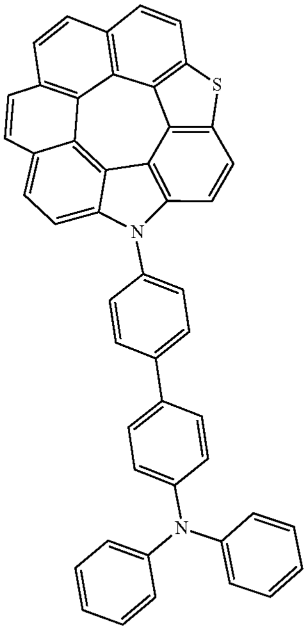
172
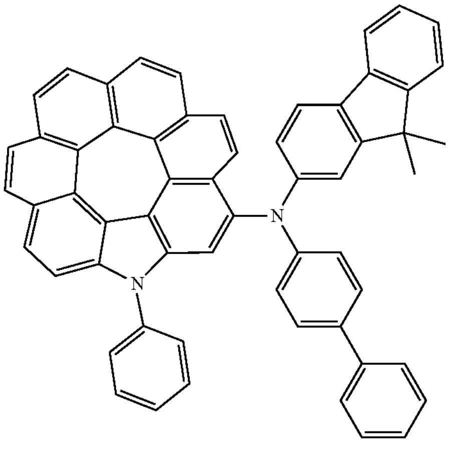
173
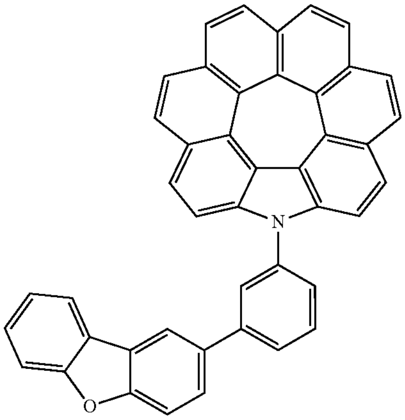
174
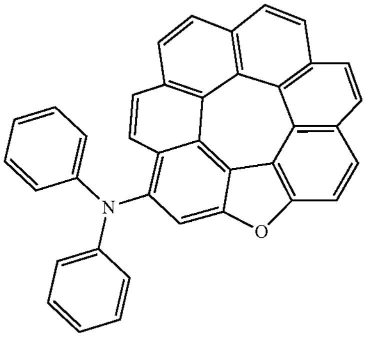
175
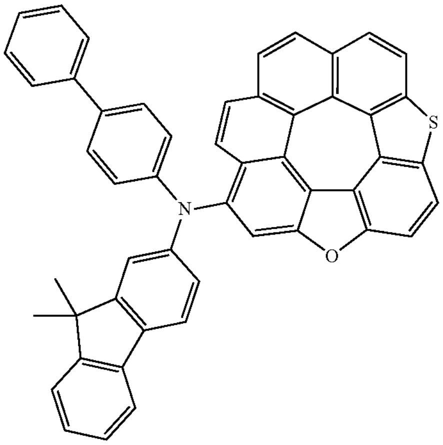
176
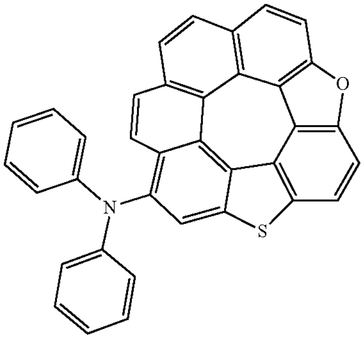

-continued
177
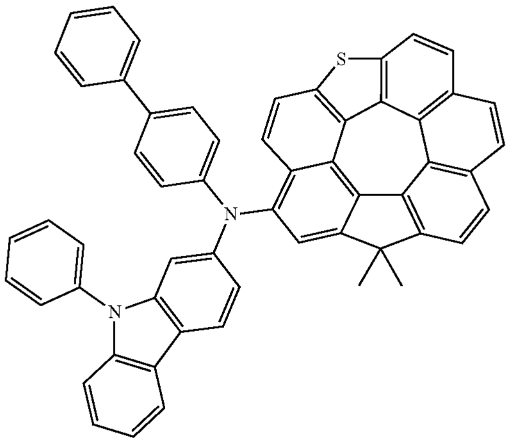
178
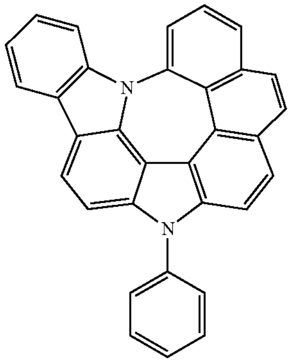
179
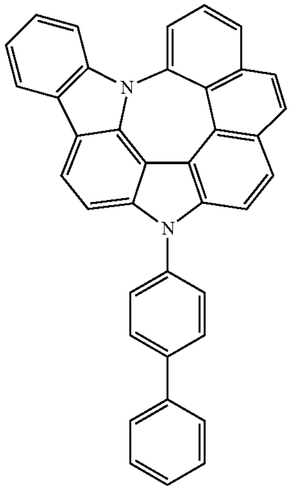
-continued
180
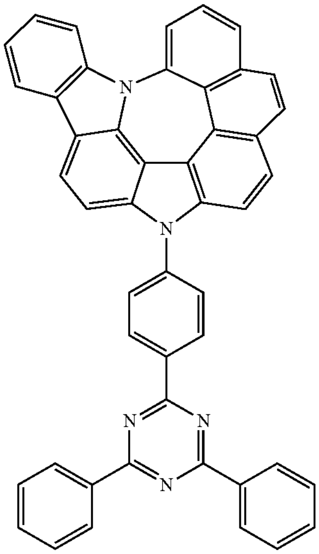
181
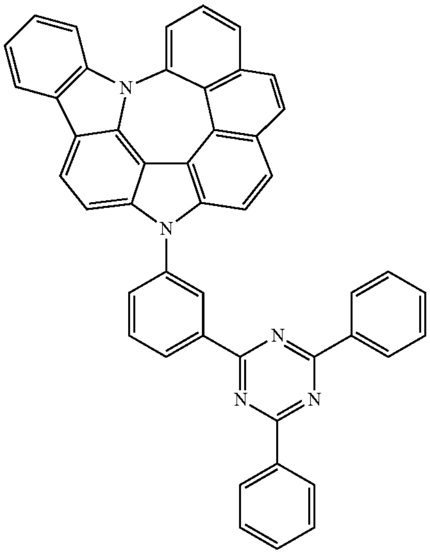
182
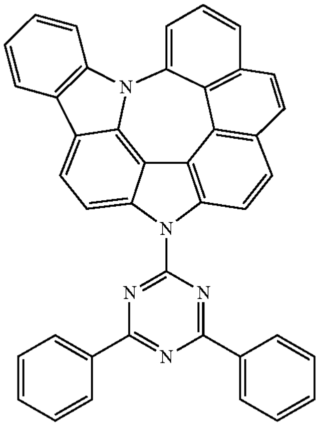

-continued
183
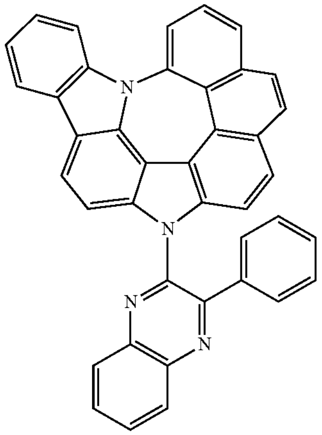
184
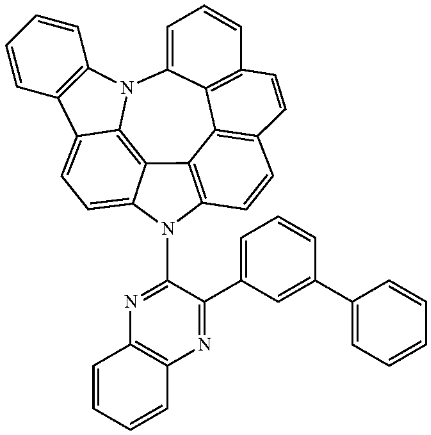
185
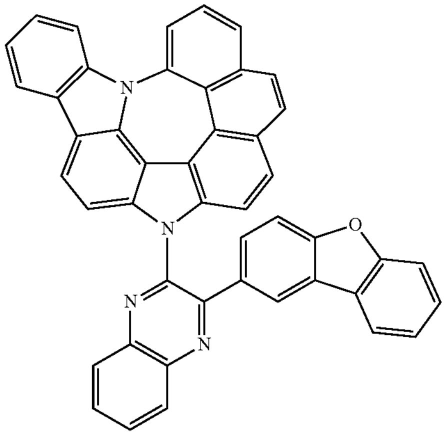
-continued
186
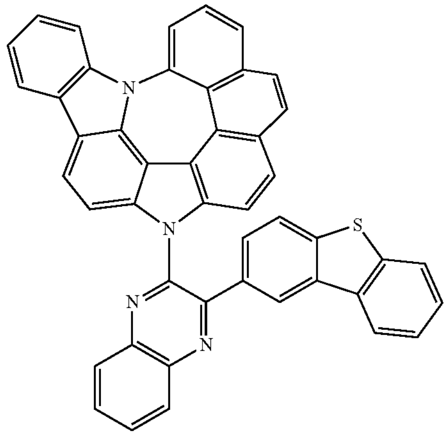
187
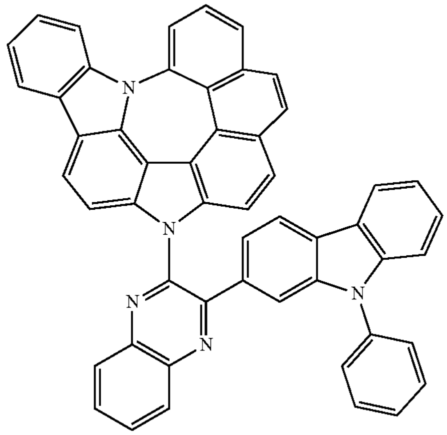
188
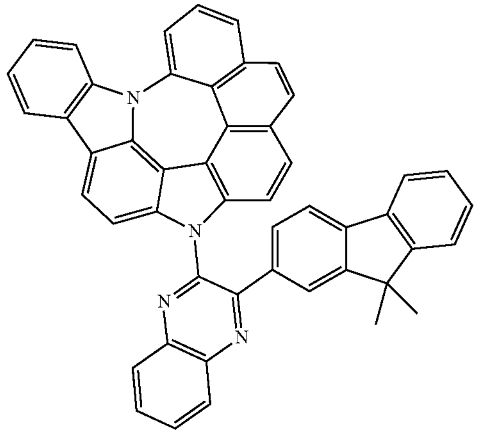

-continued
189
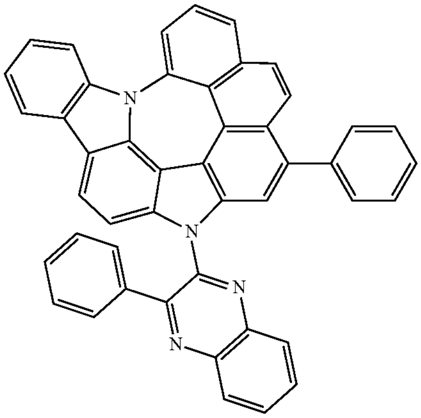
190
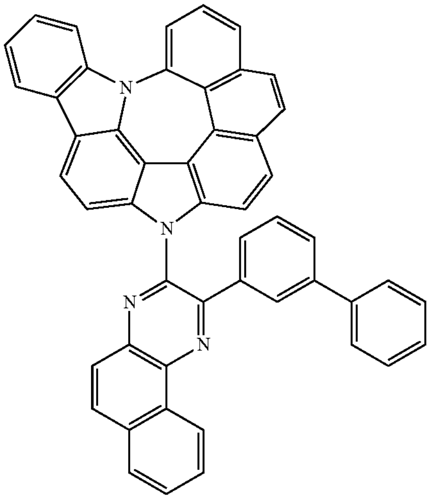
191
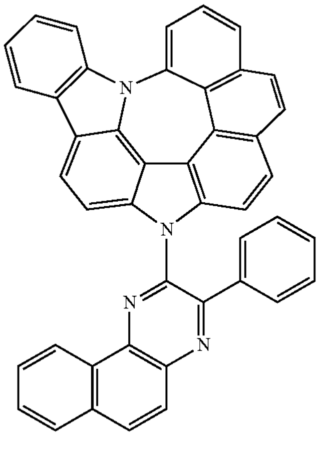
-continued
192
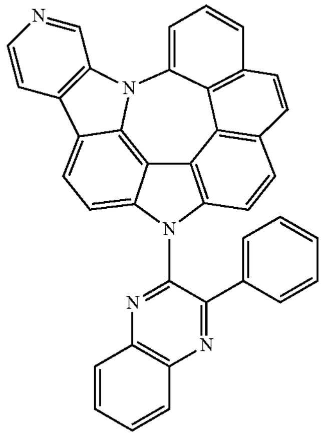
193
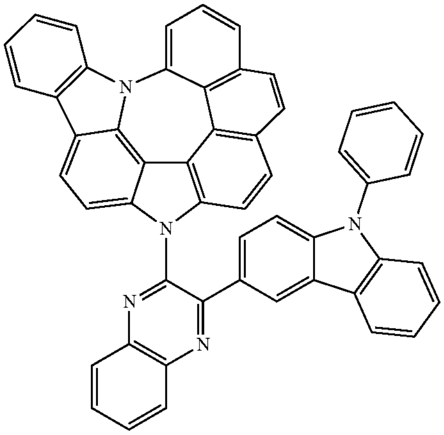
194
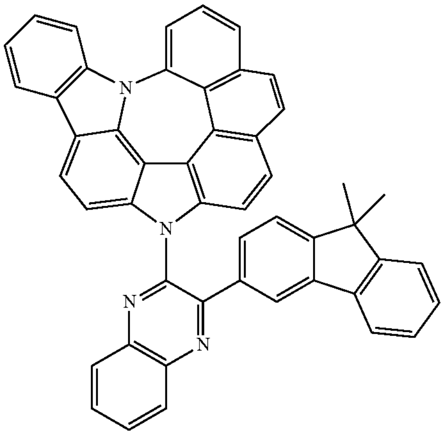

-continued
195
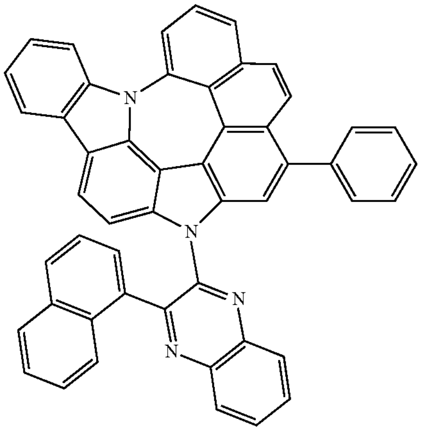
196
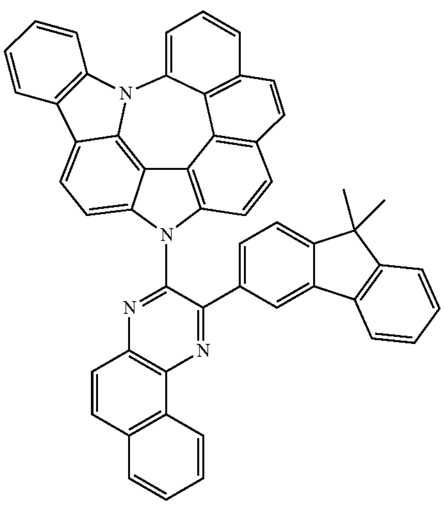
197
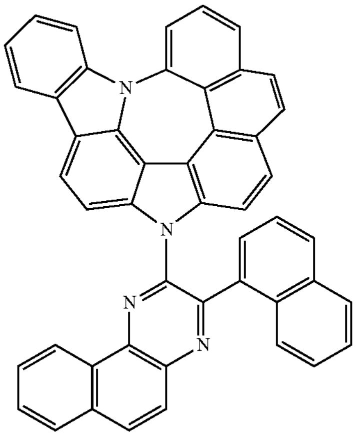
-continued
198
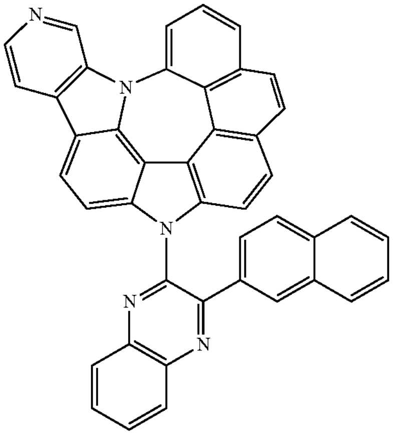
199
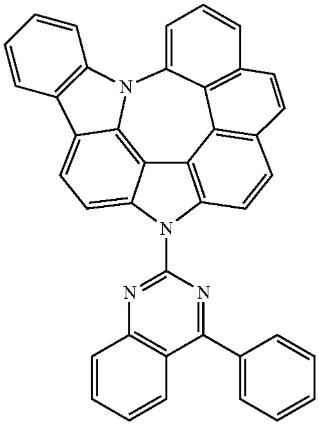
200
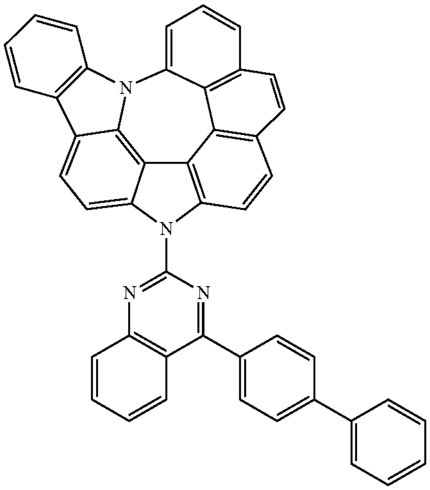

-continued
201
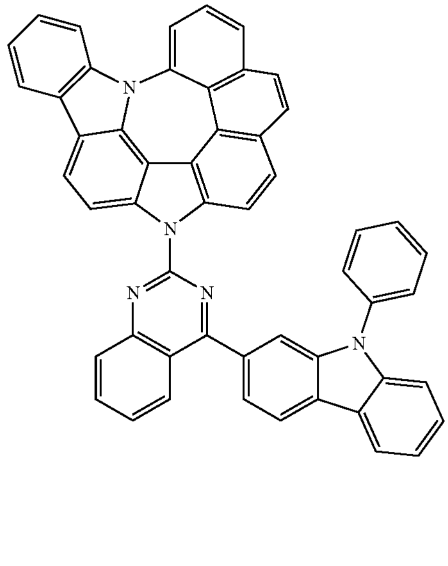
202
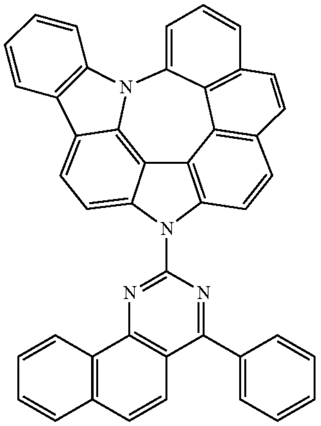
203
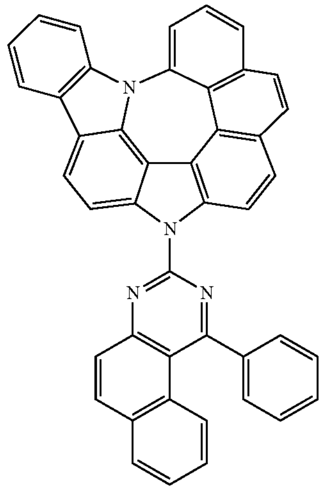
-continued
204
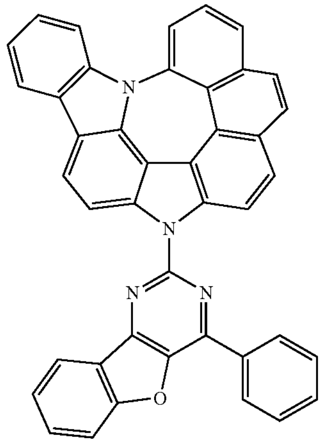
205
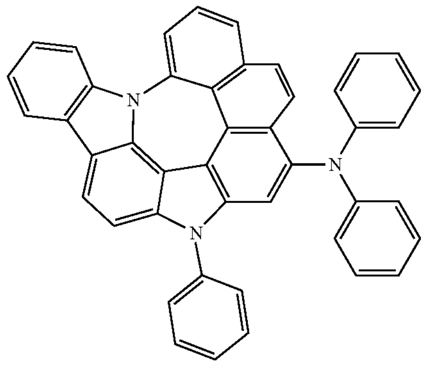
206
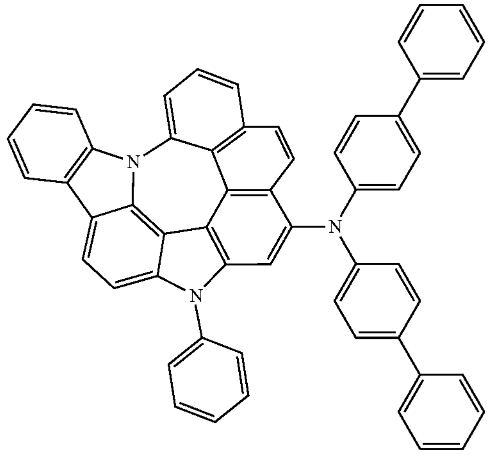

-continued
207
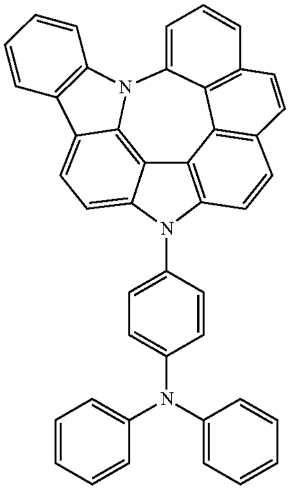
208
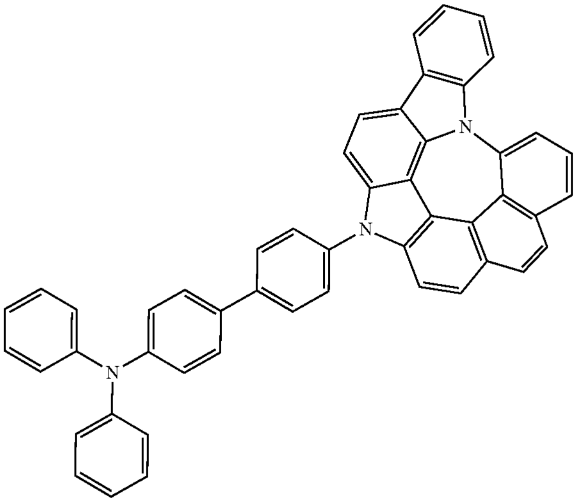
209
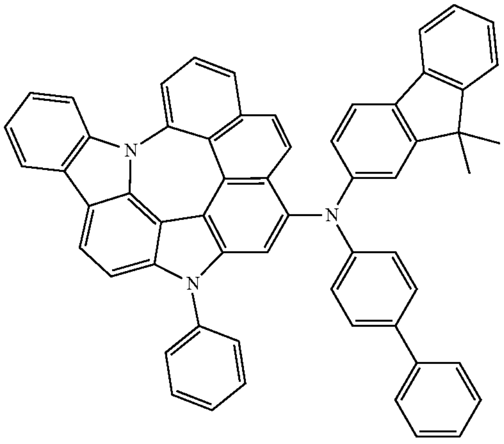
-continued
210
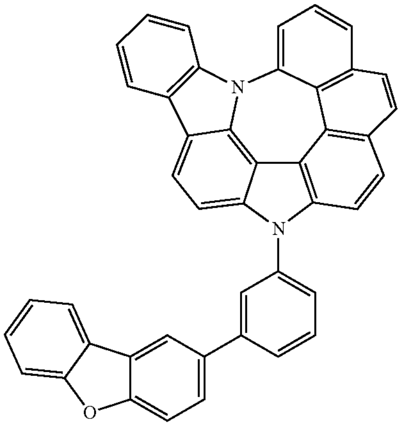
211
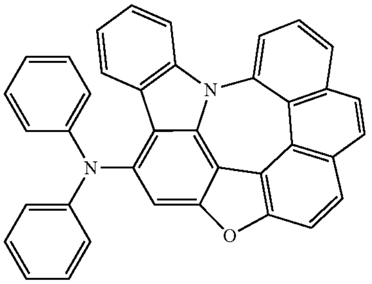
212
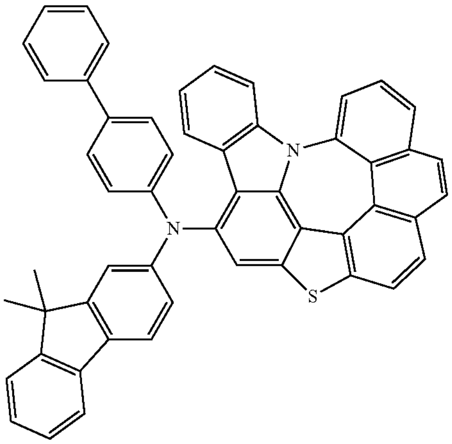
213
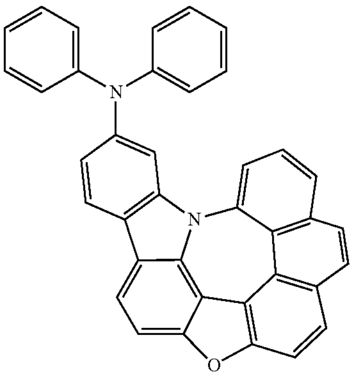

-continued
214
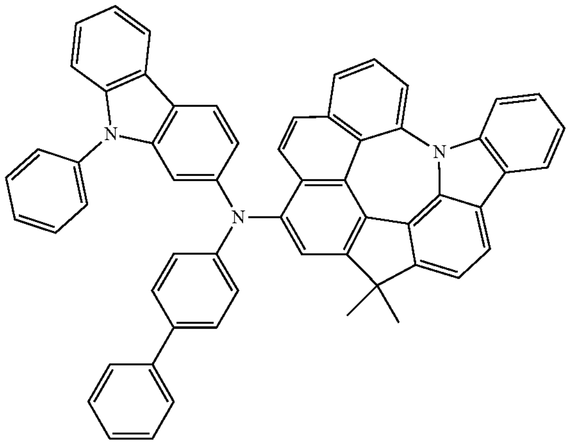
215
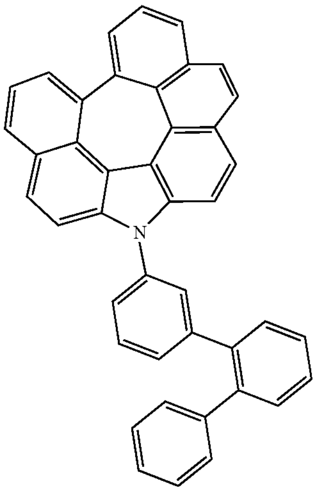
216
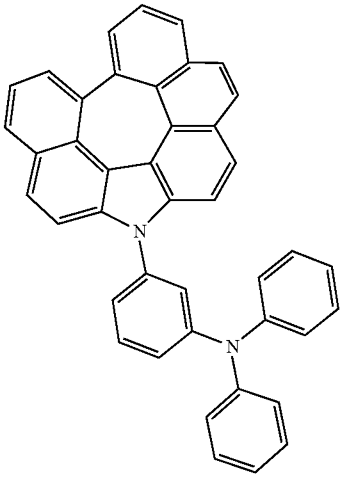
-continued
217
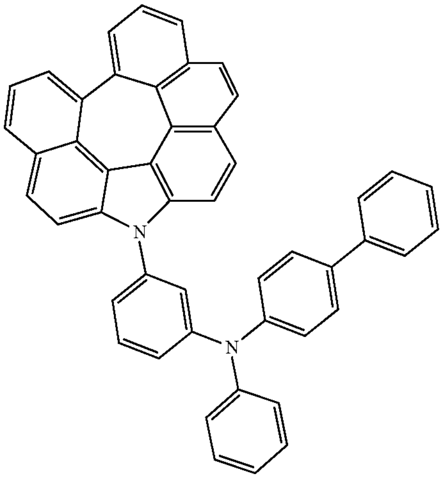
218
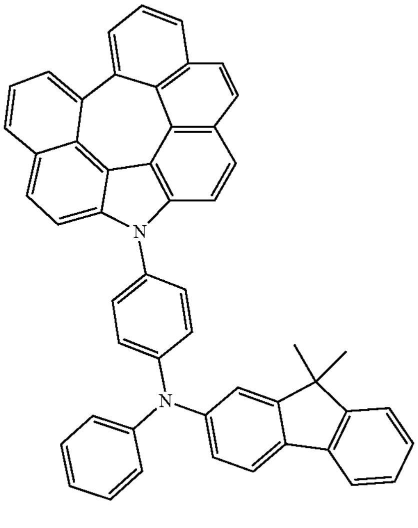
219
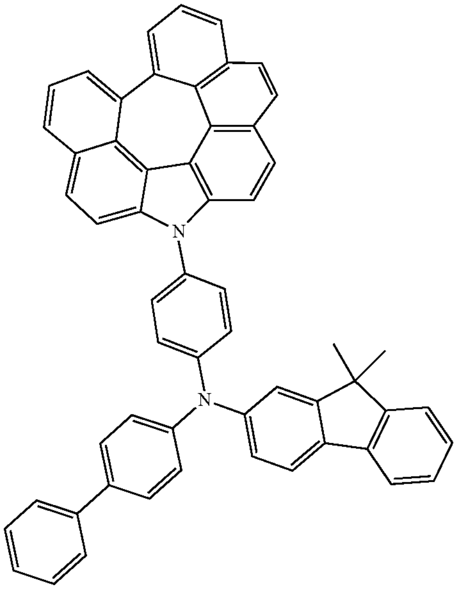

-continued
220
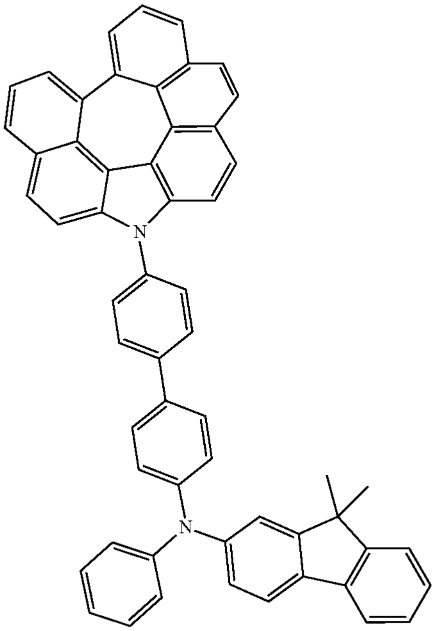
221
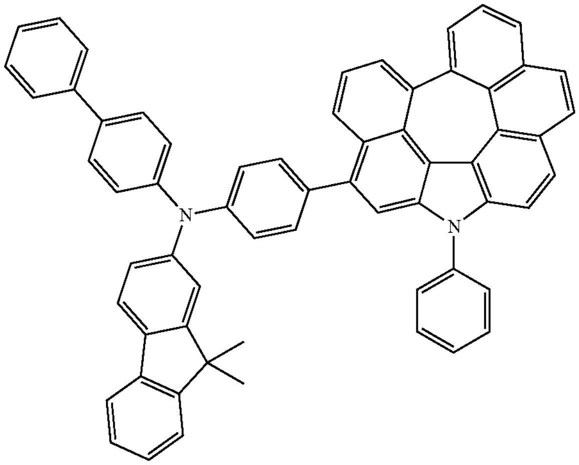
222
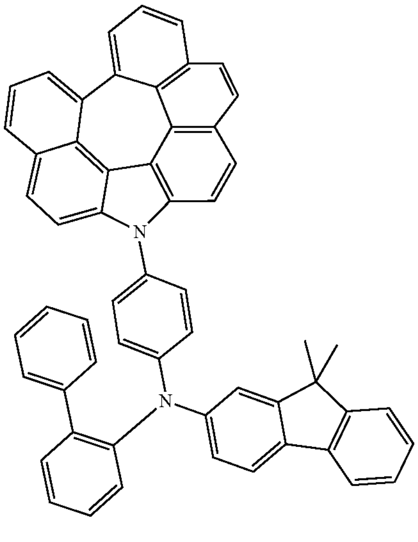
-continued
223
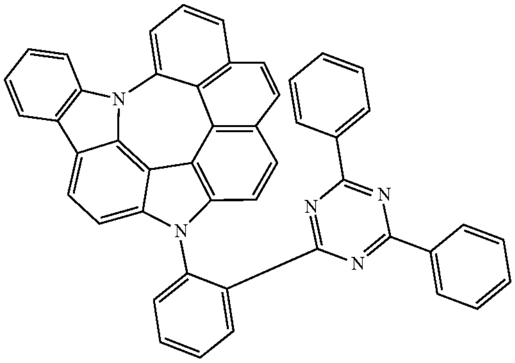
224
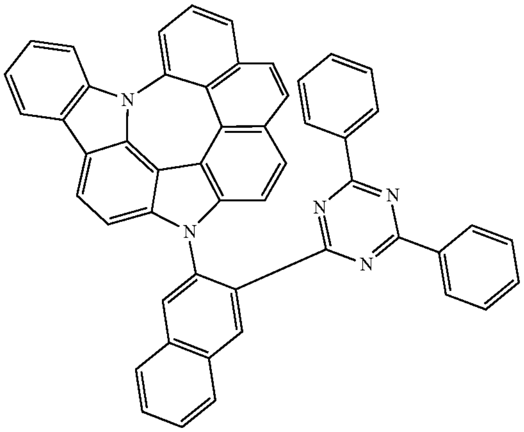
225
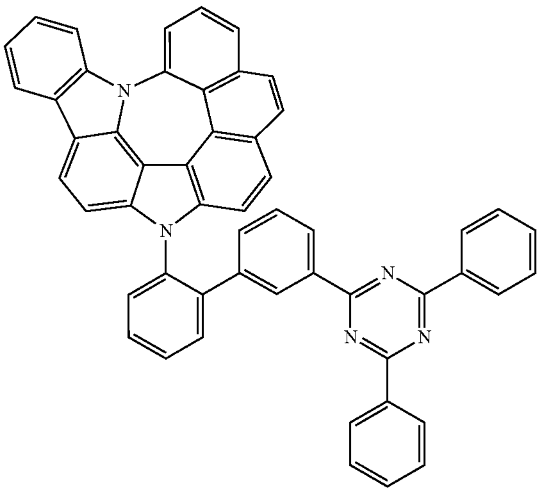

-continued
226
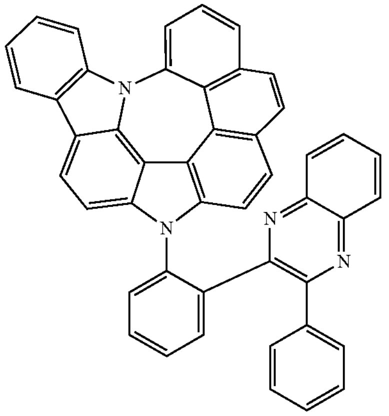
227
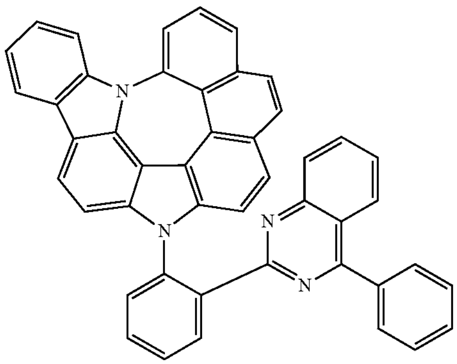
228
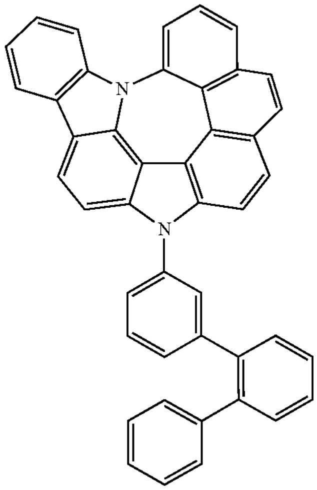
-continued
229
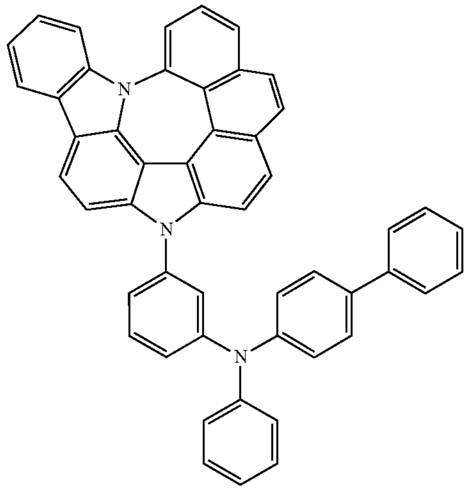
230
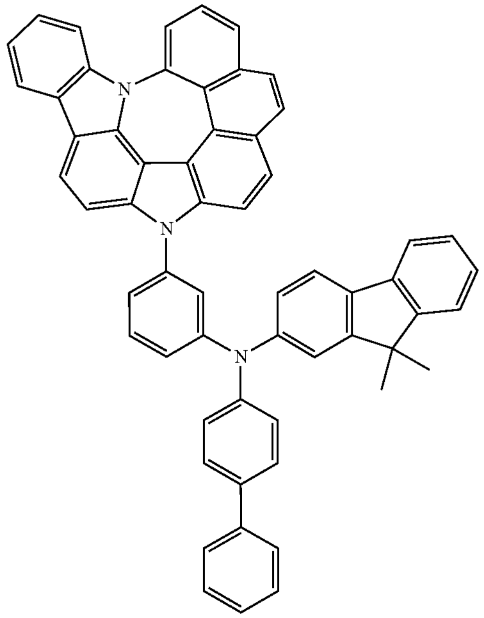
231
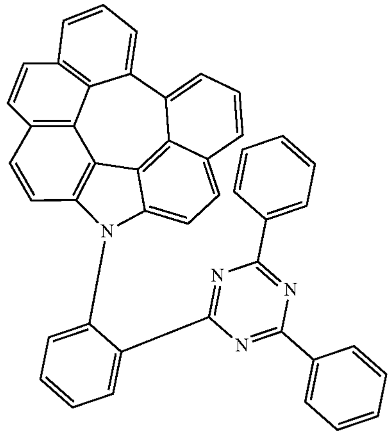

-continued
232
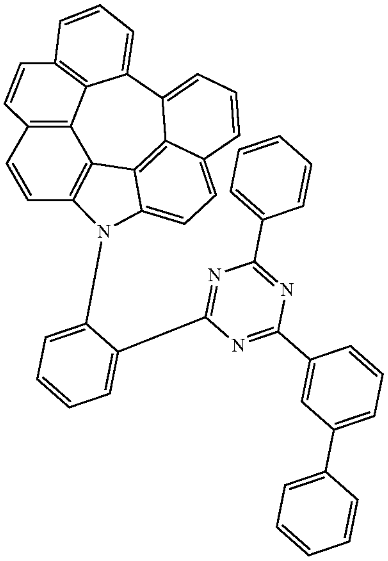
233
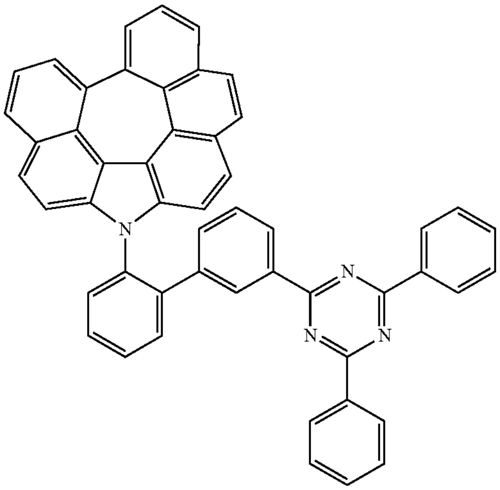
-continued
234
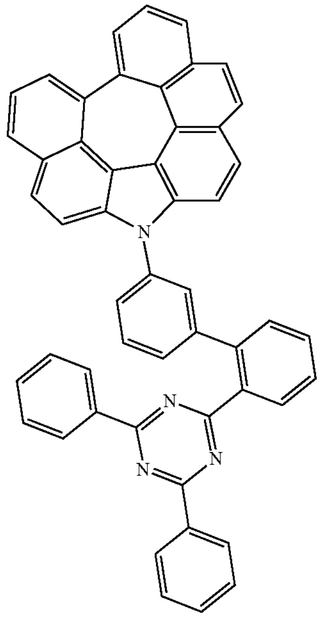
235
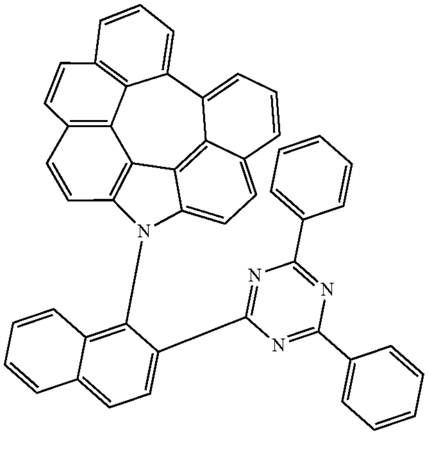
236
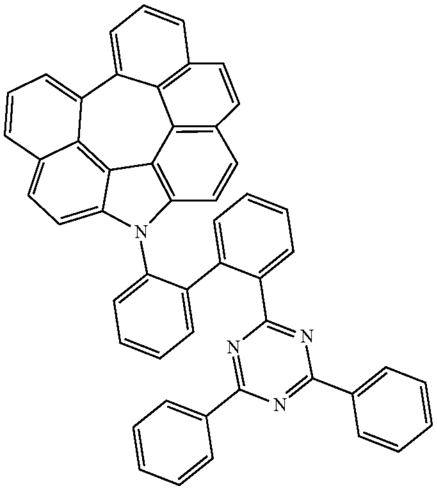

237
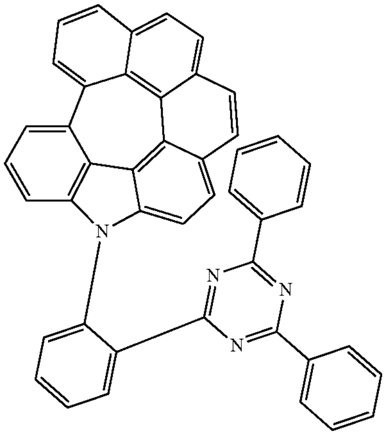
238
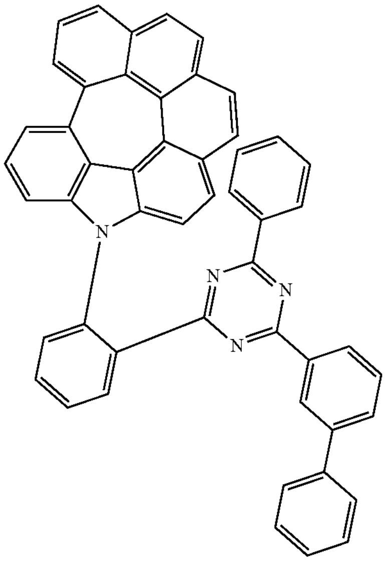
239
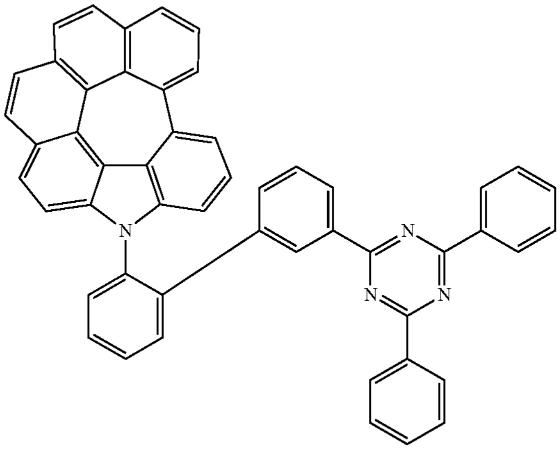
240
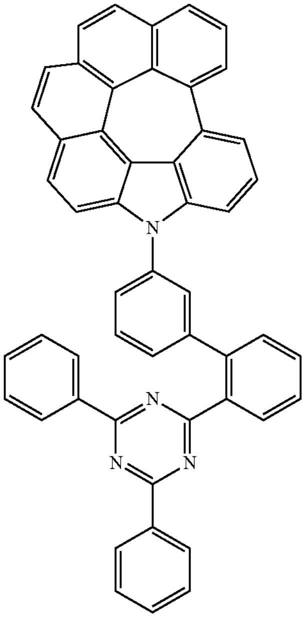
241
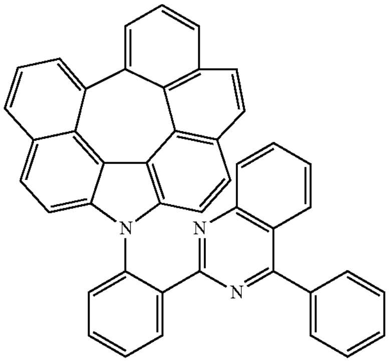
242
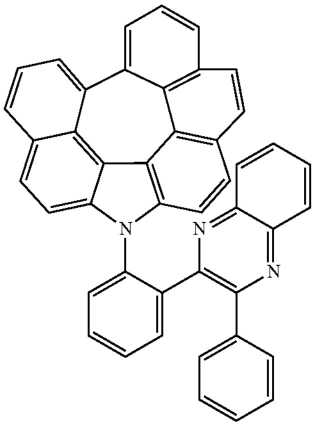

-continued
243
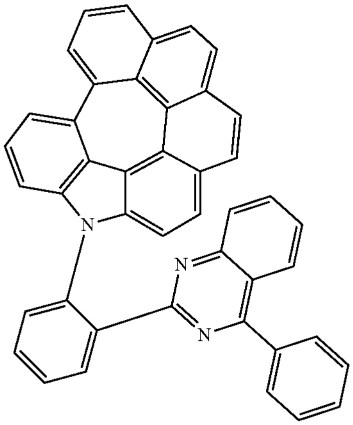
244
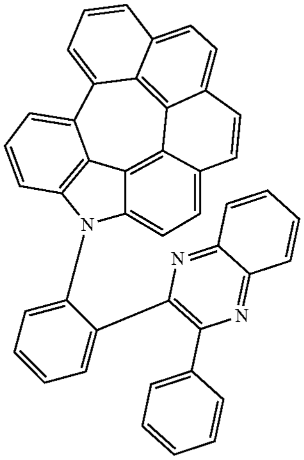
245
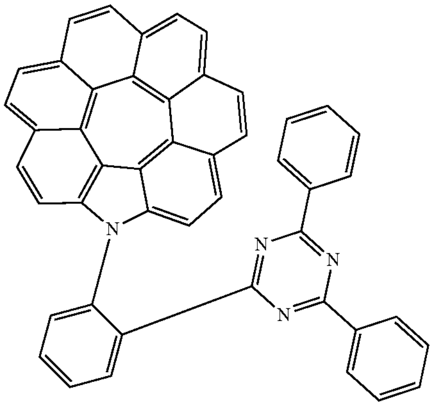
-continued
246
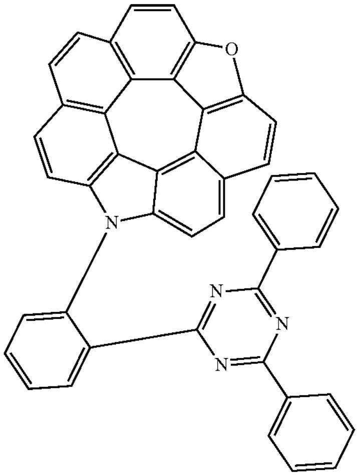
247
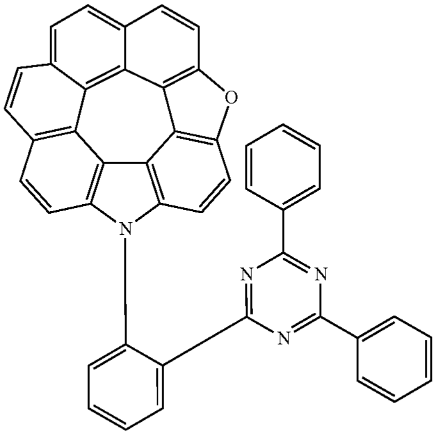
248
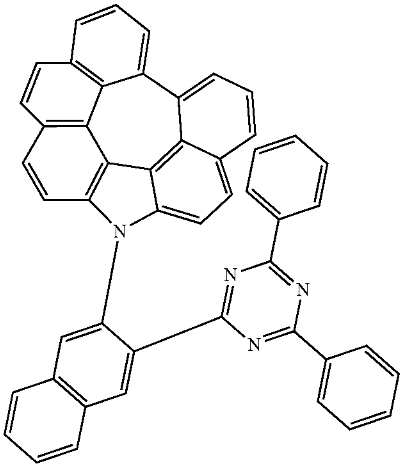

-continued
249
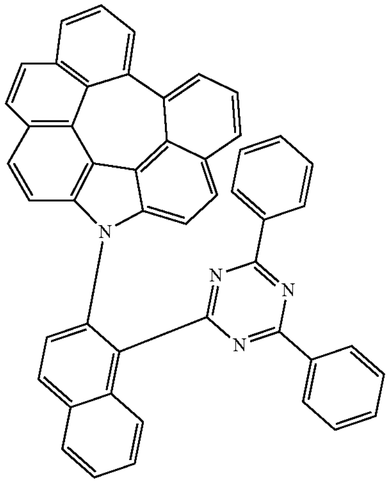
250
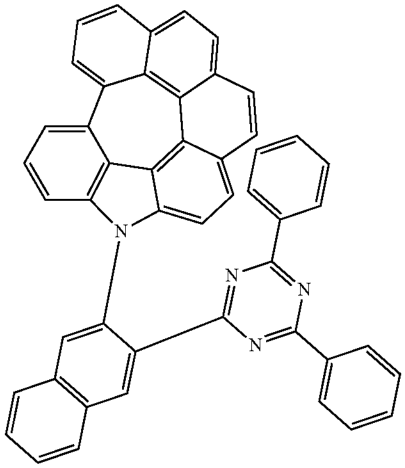
251
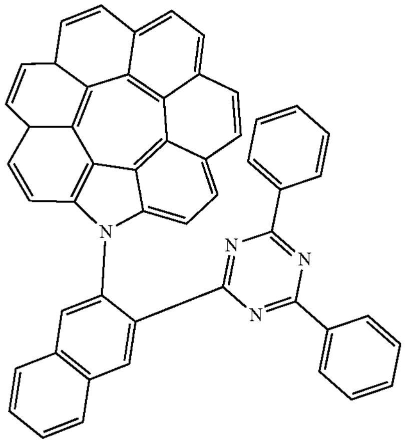
-continued
252
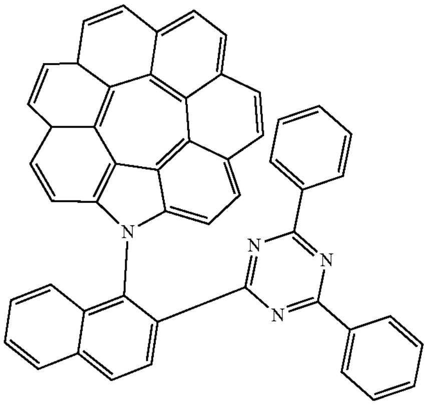
The compound of formula 1 according to the present disclosure may be produced as represented by the following reaction schemes 1 to 6, but is not limited thereto and by a synthetic method known to a person skilled in the art.
[Reaction Scheme 1]
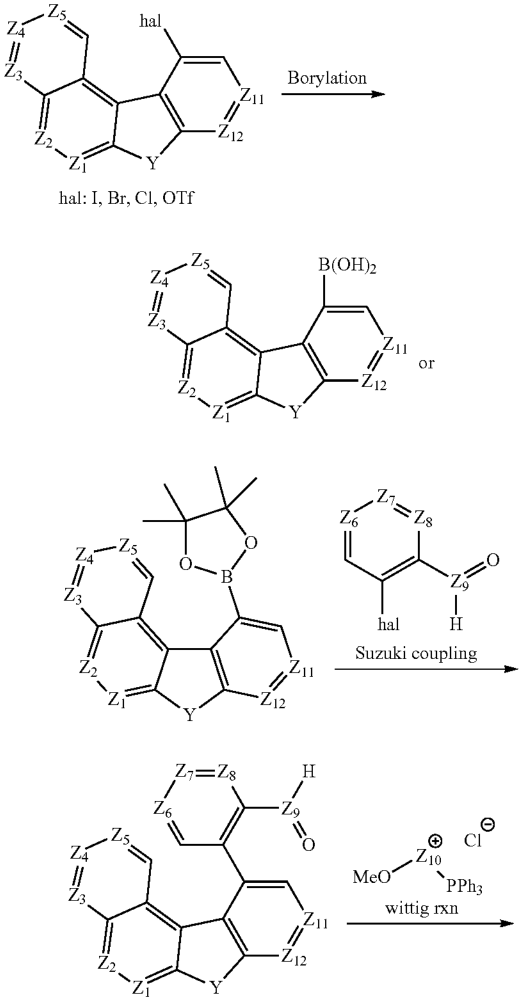

-continued
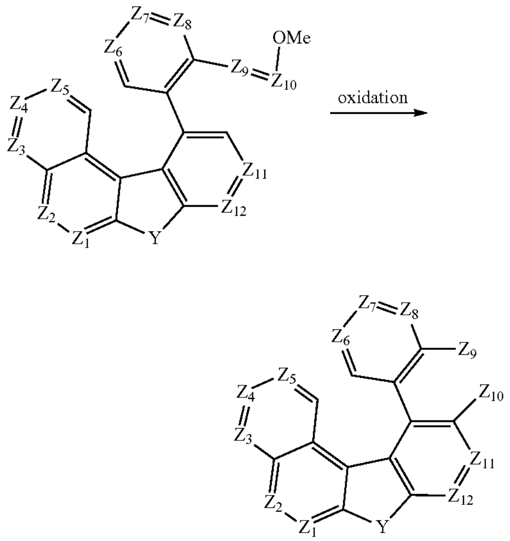
[Reaction Scheme 2]
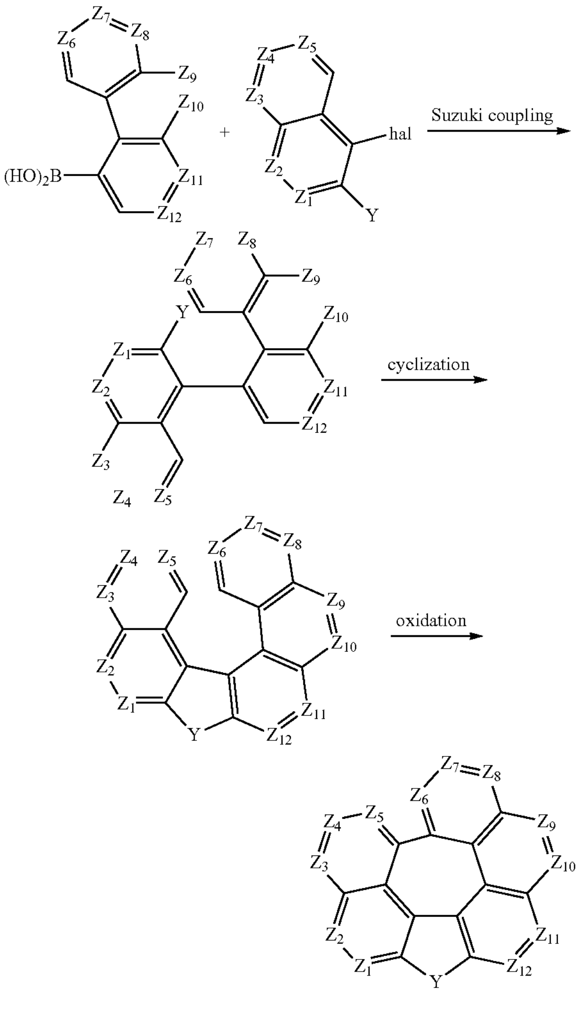
[Reaction Scheme 3]
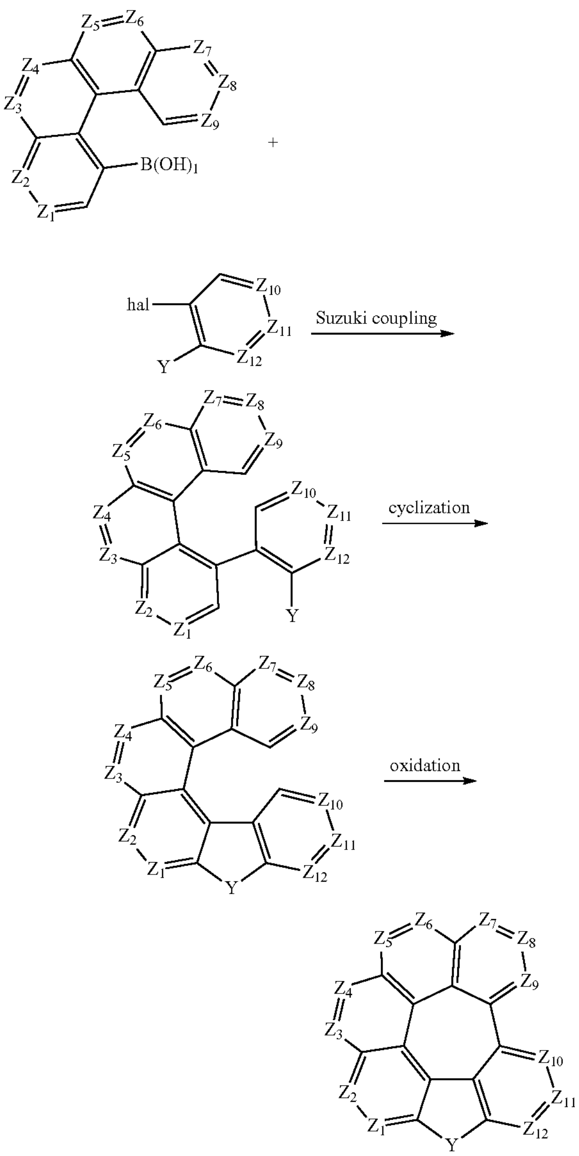
[Reaction Scheme 4]
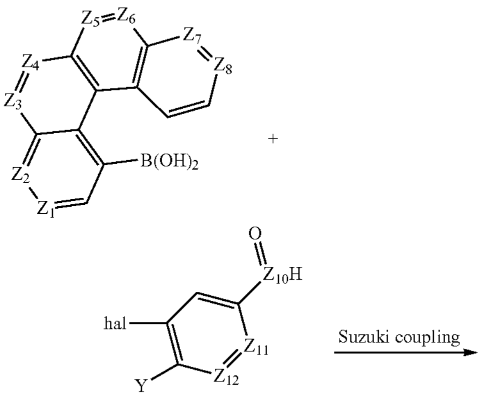

-continued
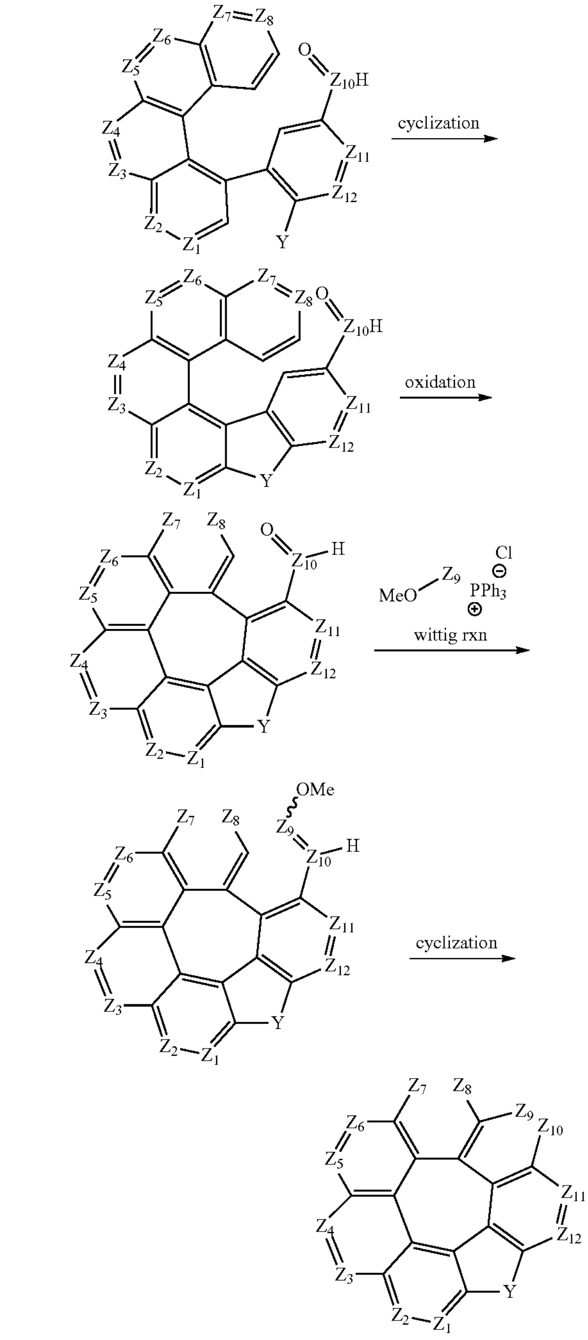
-continued
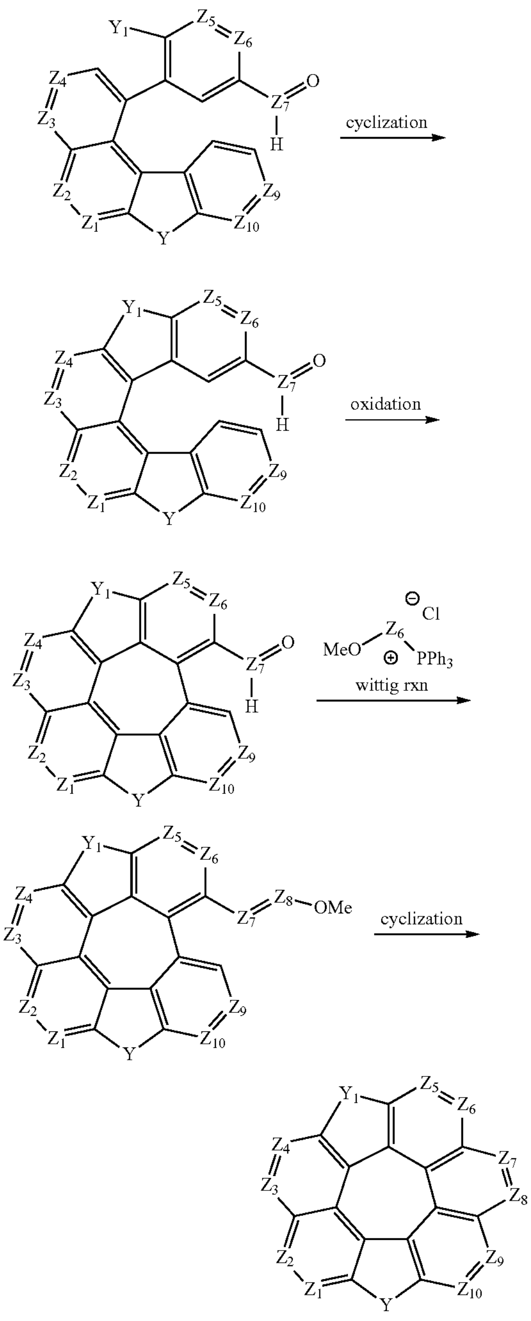
[Reaction Scheme 5]
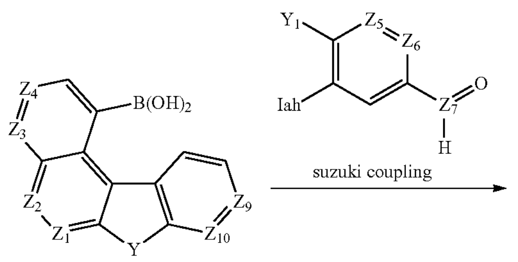
[Reaction Scheme 6]
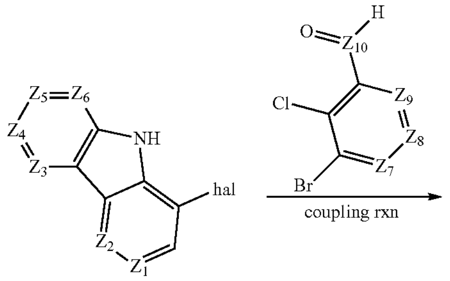

-continued

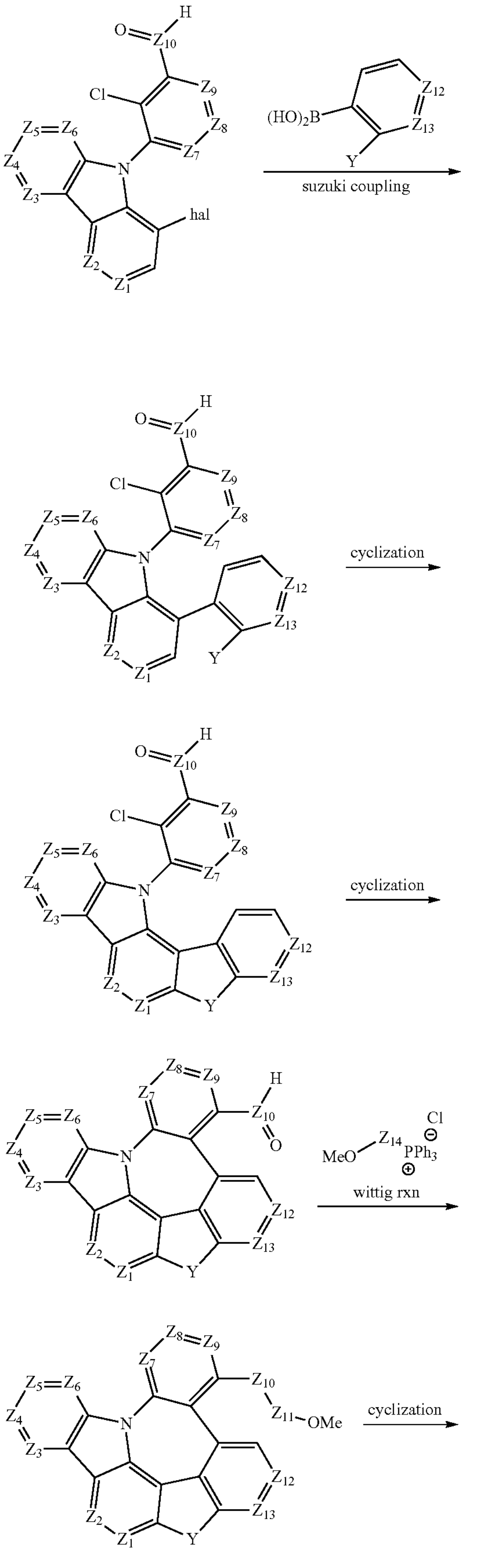

-continued

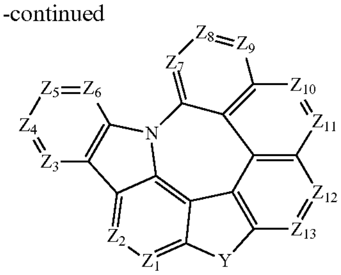

In reaction schemes 1 to 6, Y and $Z_1$ to $Z_{13}$ are as defined in the formulae 2 to 7.

As described above, exemplary synthesis examples of the compounds represented by formulae 2 to 7 according to one embodiment are described, but they are based on Wittig reaction, Suzuki cross-coupling reaction, Ullmann-coupling reaction, Buchwald-Hartwig cross coupling reaction. N-arylation reaction, H-mont-mediated etherification reaction. Miyaura borylation reaction, Intramolecular acid-induced cyclization reaction, Pd(II)-catalyzed oxidative cyclization reaction. Grignard reaction, Heck reaction, Cyclic Dehydration reaction, $SN_1$ substitution reaction, $SN_2$ substitution reaction, Phosphine-mediated reductive cyclization reaction, etc. It will be understood by one skilled in the art that the above reaction proceeds even if other substituents defined in the formulae 2 to 7 other than the substituents described in the specific synthesis examples are bonded.

Hereinafter, the organic electroluminescent device to which the aforementioned organic electroluminescent compound is applied will be described.

The present disclosure may provide an organic electroluminescent material comprising the organic electroluminescent compound of the formula 1, and an organic electroluminescent device comprising the organic electroluminescent material.

The organic electroluminescent material may be comprised solely of the organic electroluminescent compound of the present disclosure, or may further comprise conventional materials included in the organic electroluminescent material.

An organic electroluminescent material according to one embodiment may be used as light-emitting materials for a white organic light-emitting device. The white organic light-emitting device has suggested various structures such as a parallel side-by-side arrangement method, a stacking arrangement method, or CCM (color conversion material) method, etc., according to the arrangement of R (Red), G (Green), B (blue), or YG (yellowish green) light-emitting units. In addition, the organic electroluminescent material according to one embodiment may also be applied to the organic electroluminescent device comprising a QD (quantum dot).

An organic electroluminescent material according to one embodiment may comprise at least one compound represented by the formula 1. For example, the compound of the formula 1 may be contained in a light-emitting layer, and when contained in the light emitting layer, the compound of formula 1 may be contained as a host.

The organic electroluminescent device according to the present disclosure includes a first electrode; a second electrode; and at least one organic layer interposed between the first electrode and the second electrode.

According to one embodiment, the organic layer includes the light-emitting layer containing the organic electroluminescent compound according to the present disclosure. For example, the light-emitting layer is comprised solely of the organic electroluminescent compound of the present disclosure or at least two species of the organic electroluminescent compound of the present disclosure, and may further comprise conventional materials included in the organic electroluminescent material.

Also, the organic layer may further comprise at least one compound selected from the group consisting of an arylamine-based compound and a styryl arylamine-based compound, and may further comprise at least one metal selected from the group consisting of metals of Group 1, metals of Group 2, transition metals of the $4^{th}$ period, transition metals of the $5^{th}$ period, lanthanides, and organic metals of the d-transition elements of the Periodic Table, or at least one complex compound comprising such a metal.

One of the first electrode and the second electrode may be an anode and the other may be a cathode, wherein the first electrode and the second electrode may each be formed as a transmissive conductive material, a transflective conductive material, or a reflective conductive material. The organic electroluminescent device may be a top emission type, a bottom emission type, or a both-sides emission type according to the kinds of the material forming the first electrode and the second electrode. The organic layer may comprise at least one light-emitting layer, and may further comprise at least one layer selected from a hole injection layer, a hole transport layer, a hole auxiliary layer, a light-emitting auxiliary layer, an electron transport layer, an electron injection layer, an interlayer, a hole blocking layer, an electron blocking layer, and an electron buffer layer.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. Also, the hole injection layer may be doped as a p-dopant. The electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. The hole transport layer or the electron blocking layer may be multi-layers, and wherein each layer may use a plurality of compounds.

An electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer or the electron transport layer may also be multi-layers, wherein each layer may use a plurality of compounds. Also, the electron injection layer may be doped as an n-dopant.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes. In addition, the hole auxiliary layer may be placed between the hole transport layer (or hole injection layer) and the light-emitting layer, and may be effective to promote or block the hole transport rate (or the hole injection rate), thereby enabling the charge balance to be controlled. When an organic electroluminescent device includes two or more hole transport layers, the hole transport layer, which is further included, may be used as the hole auxiliary layer or the electron blocking layer. The light-emitting auxiliary layer, the hole auxiliary layer, or the electron blocking layer may have an effect of improving the efficiency and/or the lifespan of the organic electroluminescent device.

In the organic electroluminescent device of the present disclosure, preferably, at least one layer (hereinafter, "a surface layer") selected from a chalcogenide layer, a halogenated metal layer, and a metal oxide layer may be placed on an inner surface(s) of one or both electrode(s). Specifically, a chalcogenide (including oxides) layer of silicon and aluminum is preferably placed on an anode surface of an electroluminescent medium layer, and a halogenated metal layer or a metal oxide layer is preferably placed on a cathode surface of an electroluminescent medium layer. The operation stability for the organic electroluminescent device may be obtained by the surface layer. Preferable examples of the chalcogenide include $SiO_x(1 \leq X \leq 2)$, $AlO_x(1 \leq X \leq 1.5)$, SiON, SiAlON, etc.; the halogenated metal include LiF, $MgF_2$, $CaF_2$, a rare earth metal fluoride, etc.; and the metal oxide include $Cs_2O$, $Li_2O$, MgO, SrO, BaO, CaO, etc.

In addition, in the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferable examples of the oxidative dopant include various Lewis acids and acceptor compounds, and the reductive dopant include alkali metals, alkali metal compounds, alkaline earth metals, rare-earth metals, and mixtures thereof. Also, a reductive dopant layer may be employed as a charge generating layer to prepare an organic electroluminescent device having two or more light-emitting layers and emitting white light.

An organic electroluminescent device of the present disclosure may comprise at least one host compound other than the organic electroluminescent compound of the formula 1, preferably, the light-emitting layer may further comprise at least one dopant.

The dopant comprised in the organic electroluminescent material of the present disclosure may be at least one phosphorescent or fluorescent dopant, preferably a phosphorescent dopant. The phosphorescent dopant material applied to the organic electroluminescent device of the present disclosure is not particularly limited, but may be preferably a metallated complex compound(s) of a metal atom(s) selected from iridium (Ir), osmium (Os), copper (Cu), and platinum (Pt), more preferably an ortho-metallated complex compound(s) of a metal atom(s) selected from iridium (Ir), osmium (Os), copper (Cu), and platinum (Pt), and even more preferably ortho-metallated iridium complex compound(s).

The dopant comprised in the organic electroluminescent device may use the compound represented by the following formula 101, but is not limited thereto:

(101)

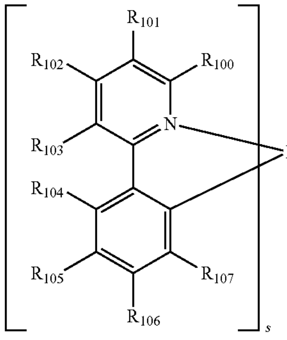

In formula 101,

L is selected from the following structure 1 or 2:

structure (1)

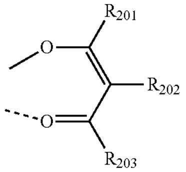

structure (2)

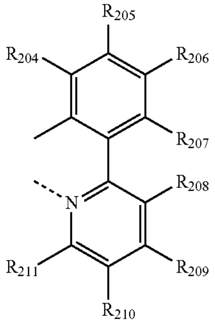

$R_{100}$ to $R_{103}$ each independently represent hydrogen, deuterium, halogen, halogen-substituted or unsubstituted (C1-C30)alkyl, a substituted or unsubstituted (C3-C30) cycloalkyl, a substituted or unsubstituted (C6-C30)aryl, cyano, a substituted or unsubstituted (3- to 30-membered)heteroaryl, or a substituted or unsubstituted (C1-C30)alkoxy; or $R_{100}$ to $R_{103}$ may be linked to an adjacent substituent(s) to form a substituted or unsubstituted fused ring, e.g., a substituted or unsubstituted quinoline, a substituted or unsubstituted benzofuropyridine, a substituted or unsubstituted benzothienopyridine, a substituted or unsubstituted indenopyridine, a substituted or unsubstituted benzofuroquinoline, a substituted or unsubstituted benzothienoquinoline, or a substituted or unsubstituted indenoquinoline;

$R_{104}$ to $R_{107}$ each independently represent hydrogen, deuterium, halogen, halogen-substituted or unsubstituted (C1-C30)alkyl, a substituted or unsubstituted (C3-C30) cycloalkyl, a substituted or unsubstituted (C6-C30)aryl, a substituted or unsubstituted (3- to 30-membered) heteroaryl, cyano, or a substituted or unsubstituted (C1-C30)alkoxy; or $R_{104}$ to $R_{107}$ may be linked to an adjacent substituent(s) to form a substituted or unsubstituted fused ring, e.g., a substituted or unsubstituted naphthyl, a substituted or unsubstituted fluorene, a substituted or unsubstituted dibenzothiophene, a substituted or unsubstituted dibenzofuran, a substituted or unsubstituted indenopyridine, a substituted or unsubstituted benzofuropyridine, or a substituted or unsubstituted benzothienopyridine;

$R_{201}$ to $R_{211}$ each independently represent hydrogen, deuterium, halogen, halogen-substituted or unsubstituted (C1-C30)alkyl, a substituted or unsubstituted (C3-C30) cycloalkyl, or a substituted or unsubstituted (C6-C30) aryl; or may be linked to an adjacent substituent(s) to form a substituted or unsubstituted fused ring; and s represents an integer of 1 to 3.

The specific examples of the dopant compound include the following, but are not limited thereto.

D-1

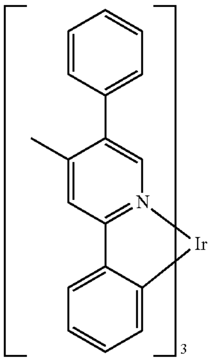

D-2

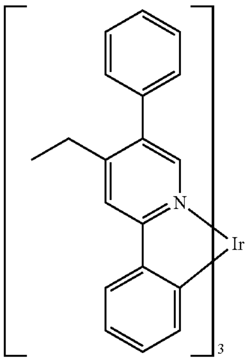

D-3

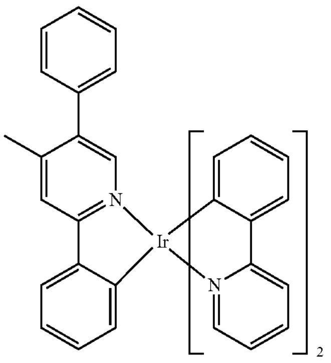

-continued
D-4
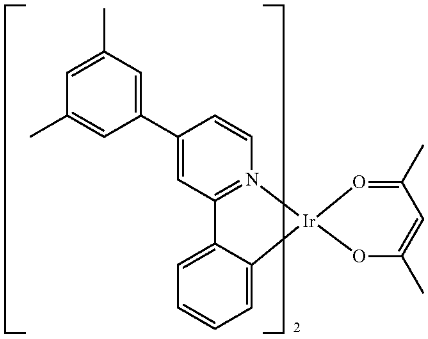
D-5
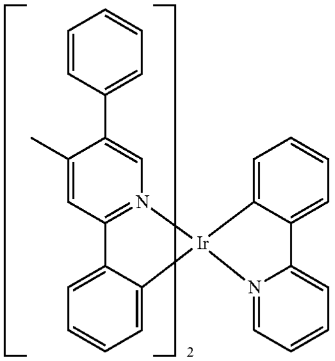
D-6
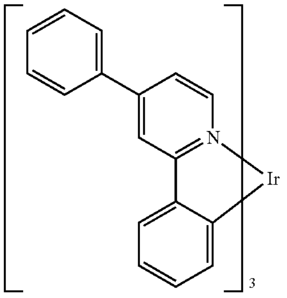
D-7
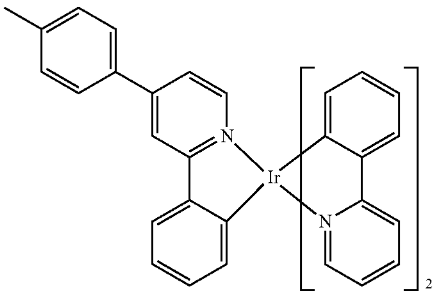
-continued
D-8
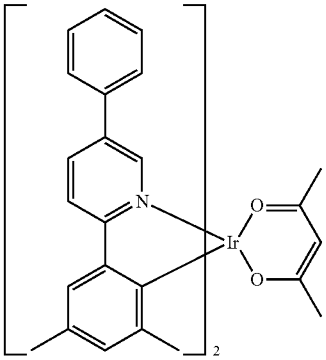
D-9
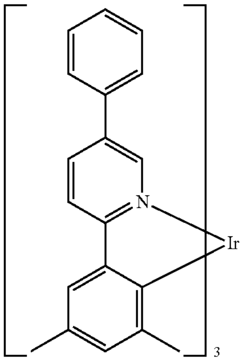
D-10
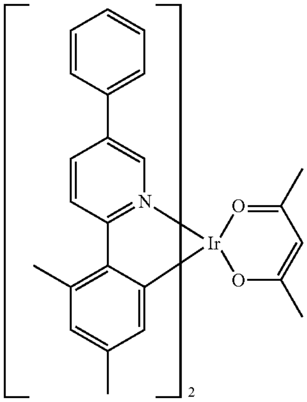
D-11
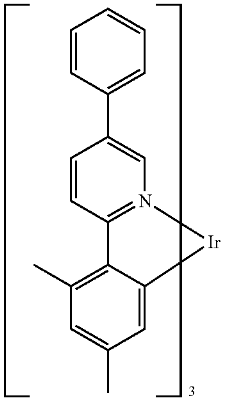

-continued
D-12
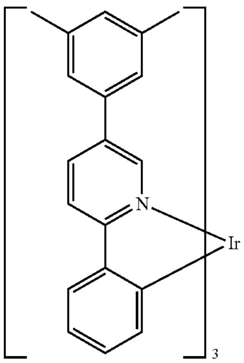
D-13
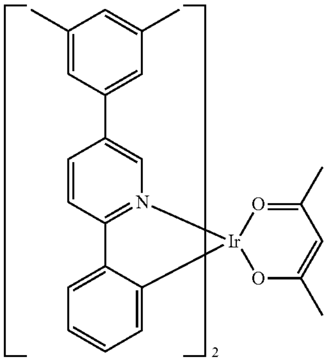
D-14
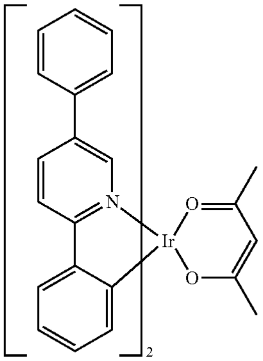
D-15
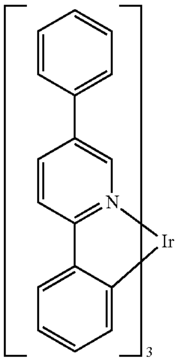
-continued
D-16
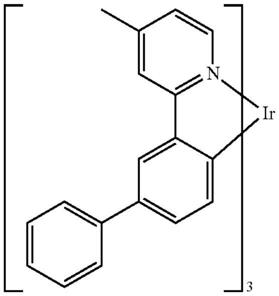
D-17
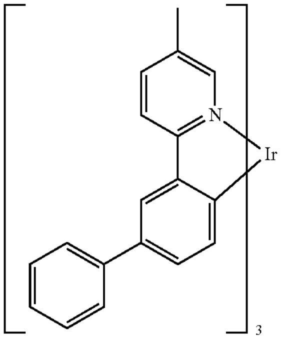
D-18
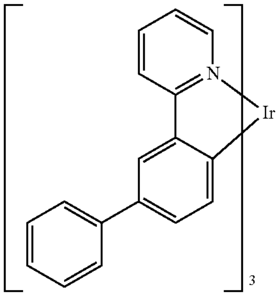
D-19
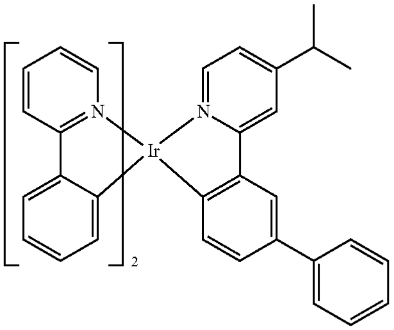
D-20
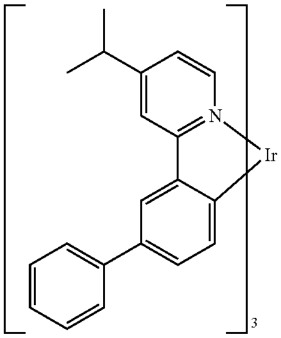

-continued
D-21
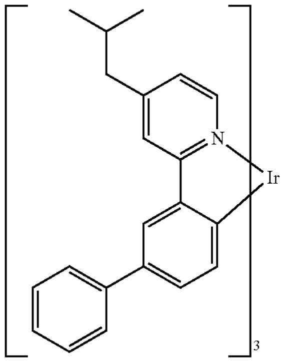
D-22
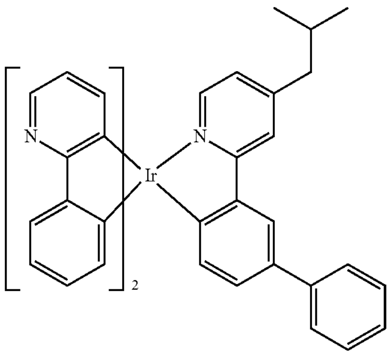
D-23
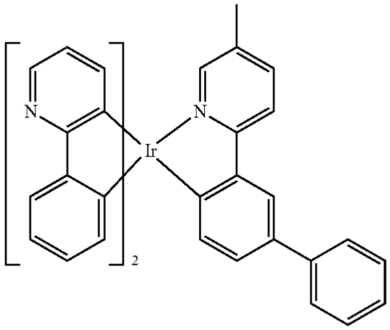
D-24
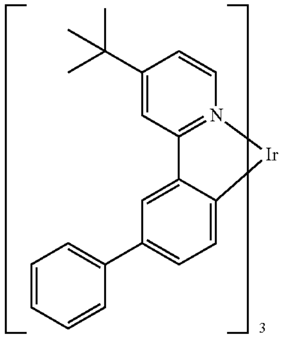
-continued
D-25
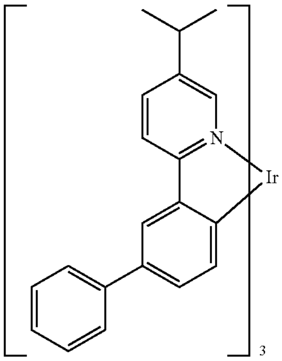
D-26
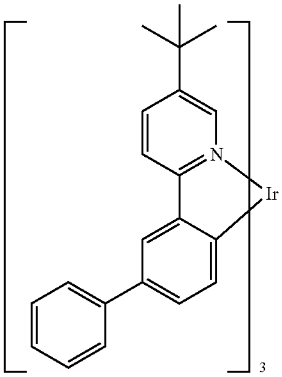
D-27
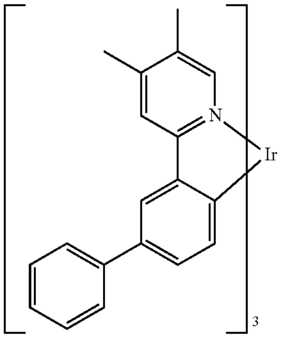
D-28
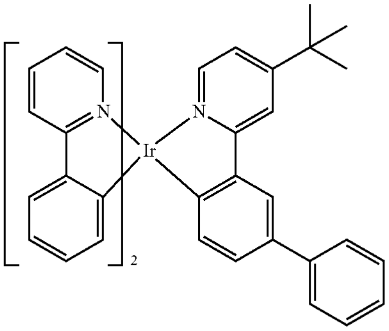

-continued
D-29
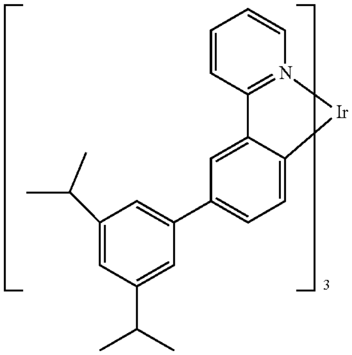
D-30
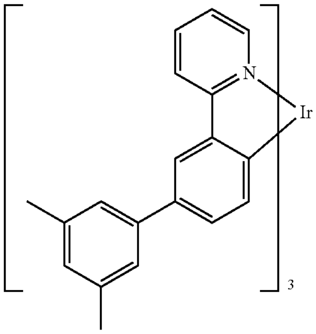
D-31
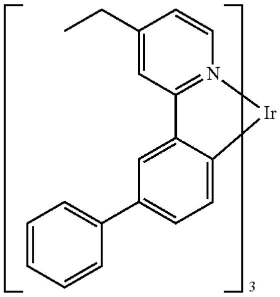
D-32
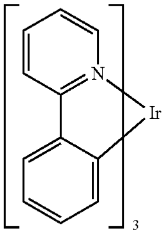
D-33
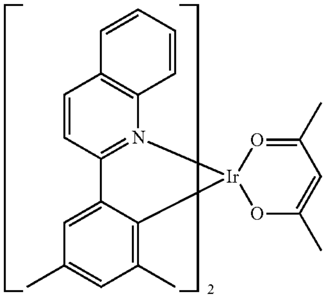
-continued
D-34
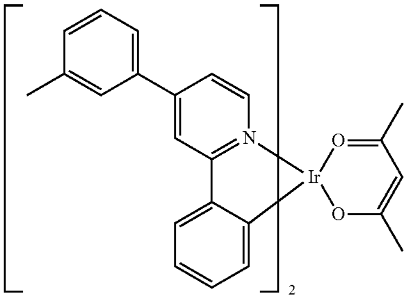
D-35
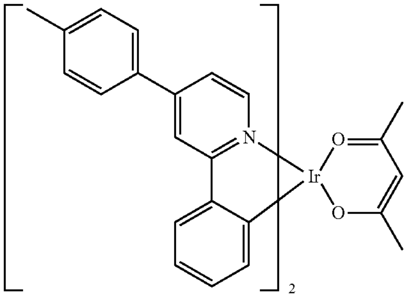
D-36
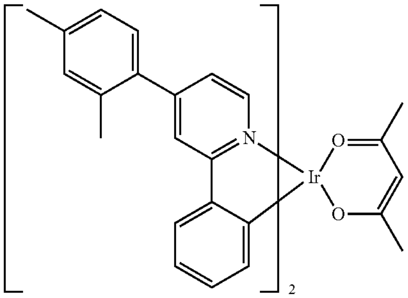
D-37
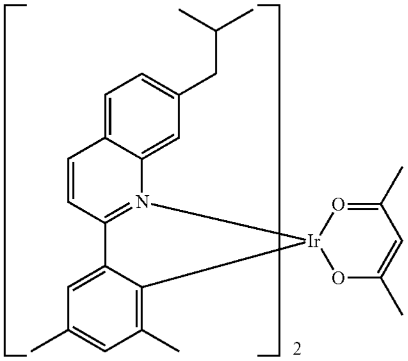
D-38
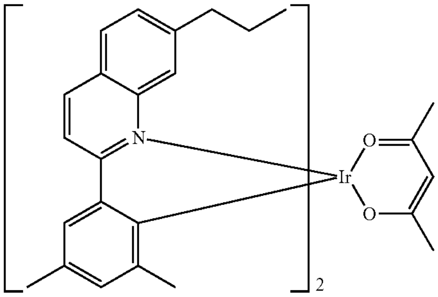

D-39
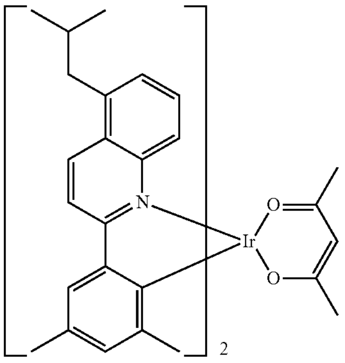
D-40
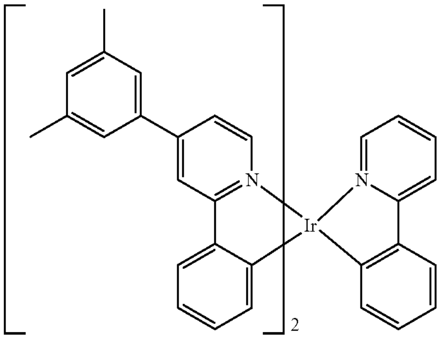
D-41
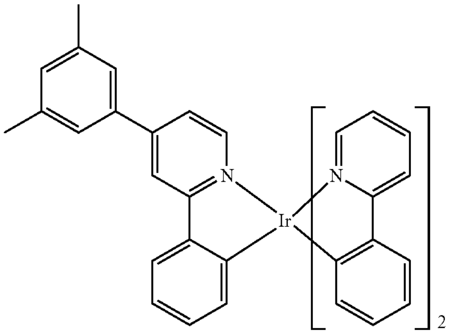
D-42
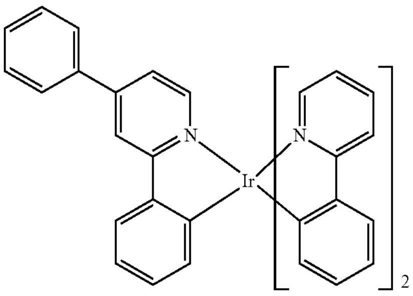
D-43
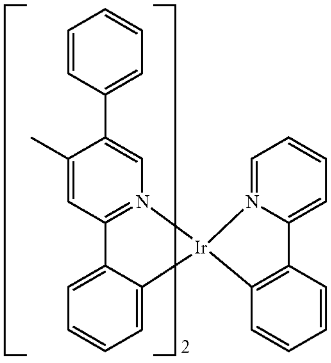
D-44
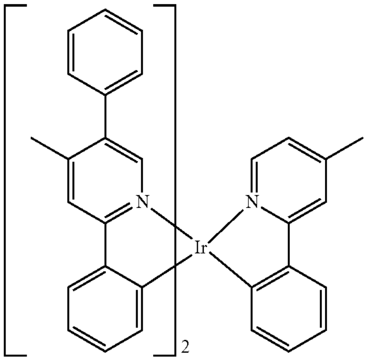
D-45
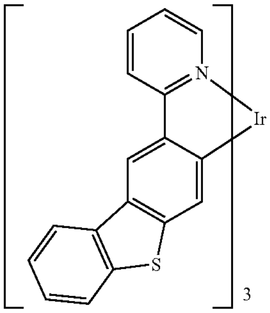
D-46
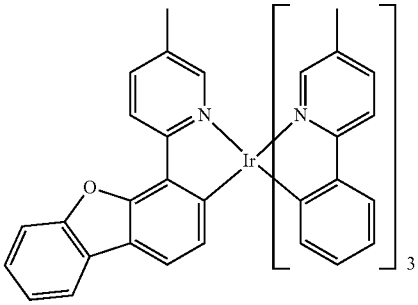

-continued
D-47
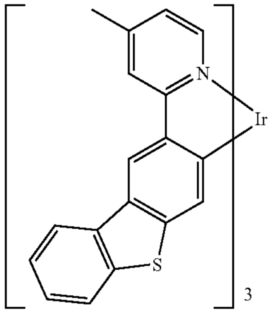
D-48
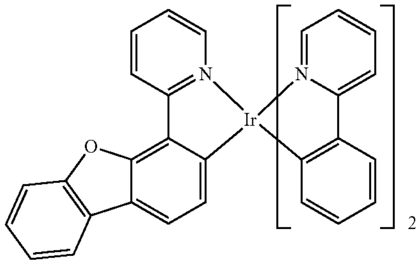
D-49
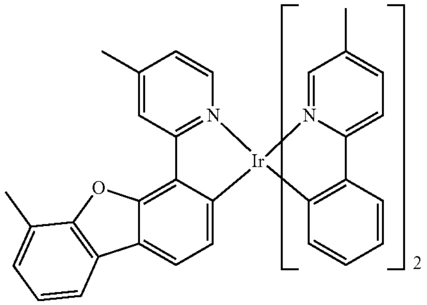
D-50
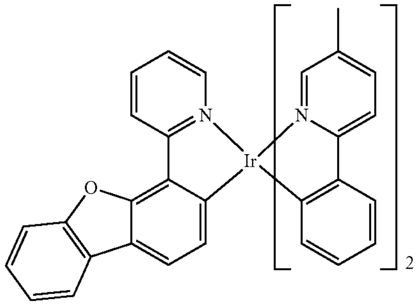
D-51
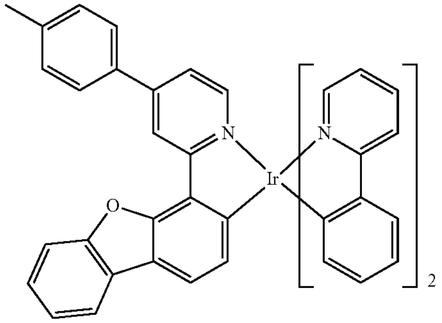
-continued
D-52
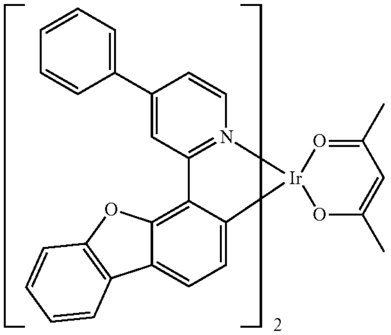
D-53
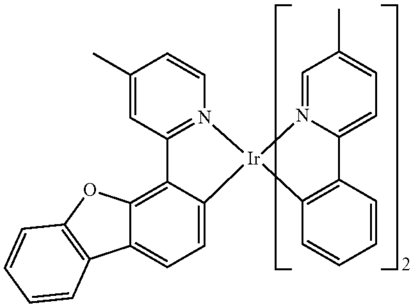
D-54
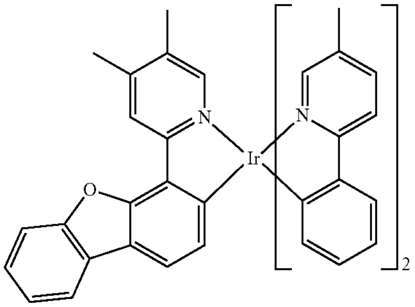
D-55
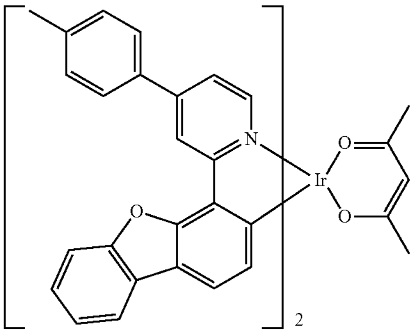
D-56
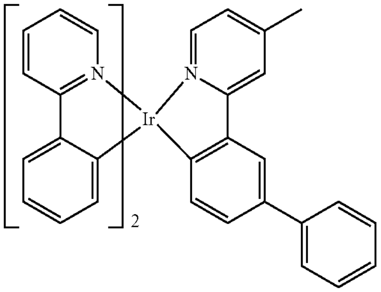

-continued
D-57
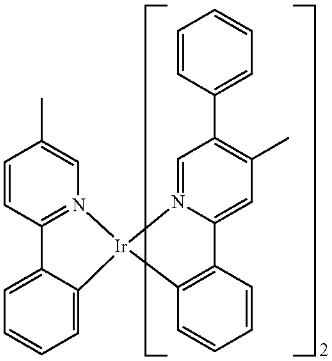
D-58
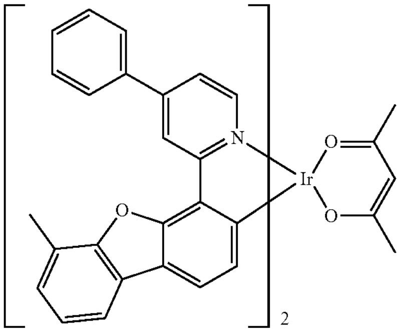
D-59
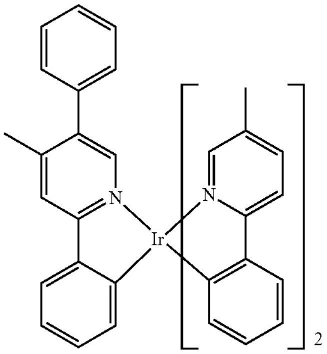
D-60
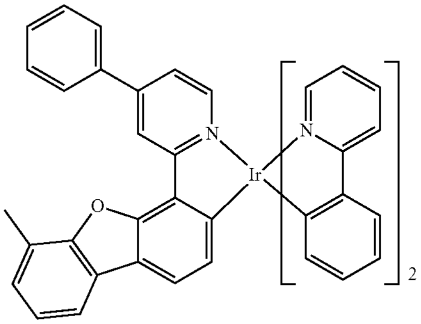
-continued
D-61
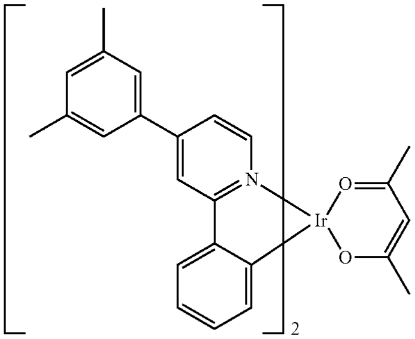
D-62
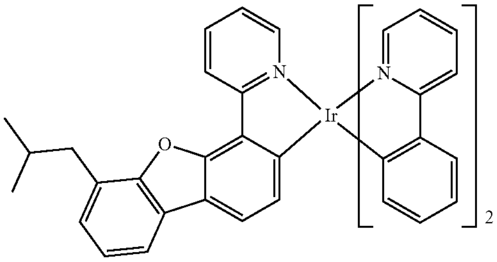
D-63
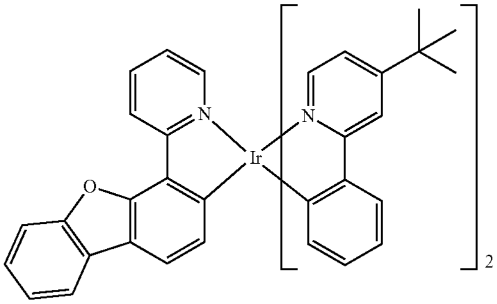
D-64
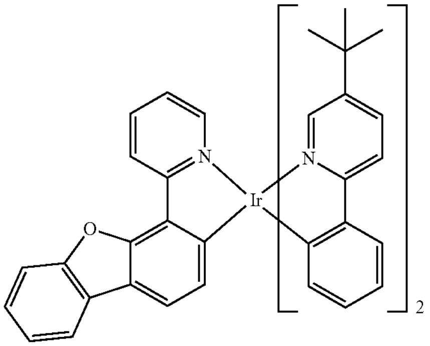

D-65
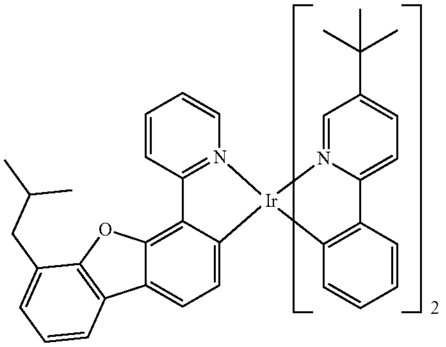
D-66
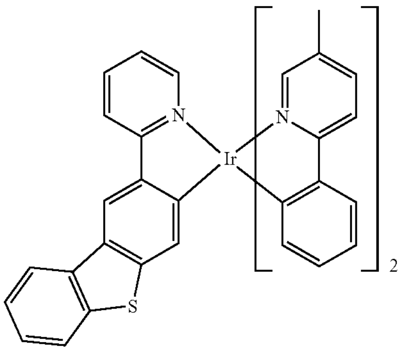
D-67
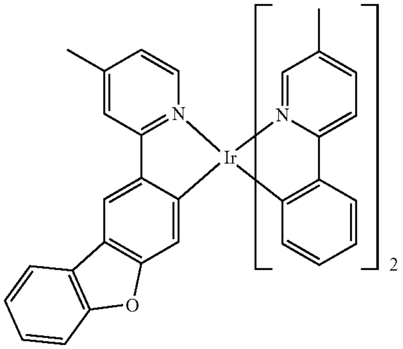
D-68
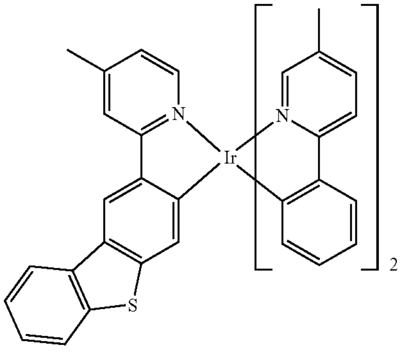
D-69
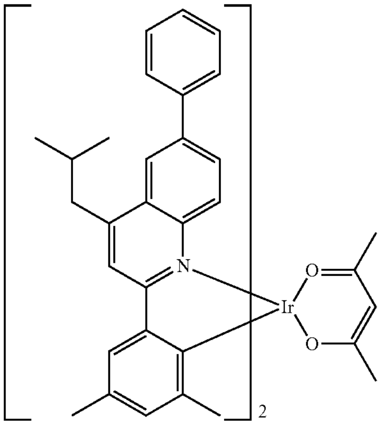
D-70
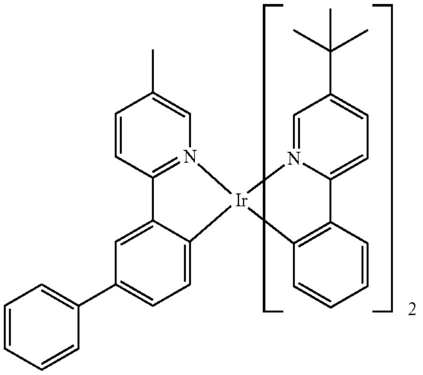
D-71
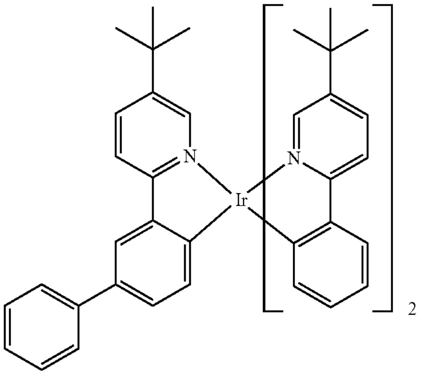
D-72
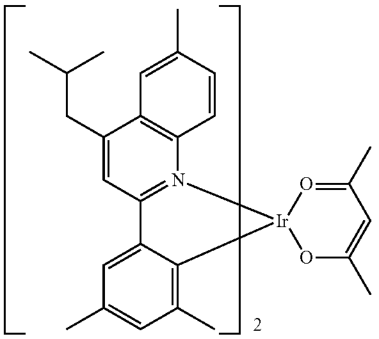

-continued
D-73
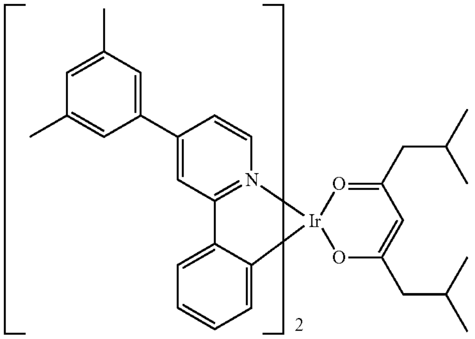
D-74
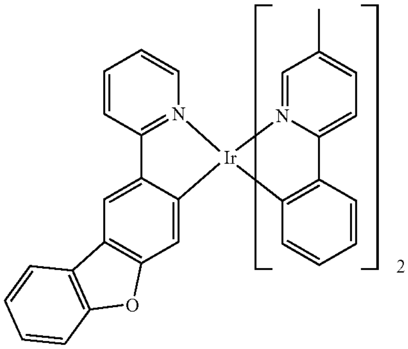
D-75
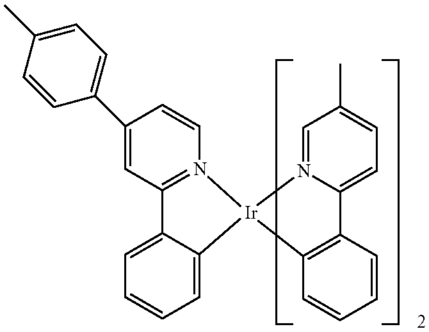
D-76
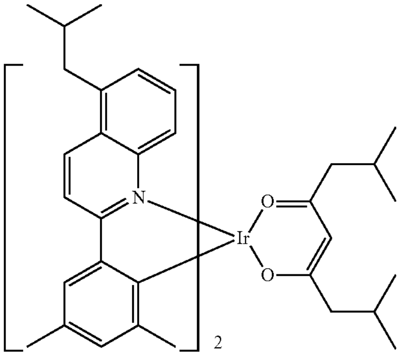
-continued
D-77
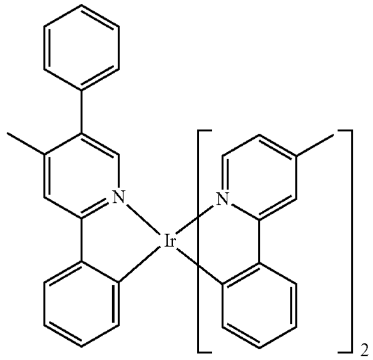
D-78
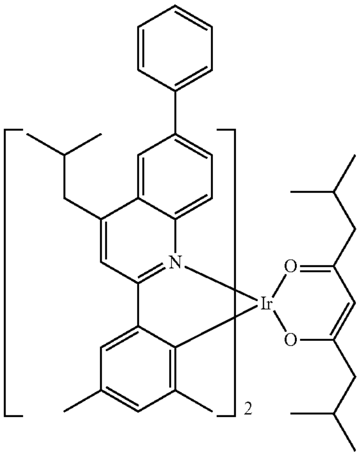
D-79
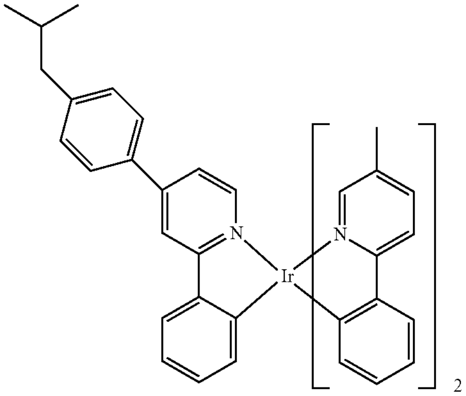
D-80
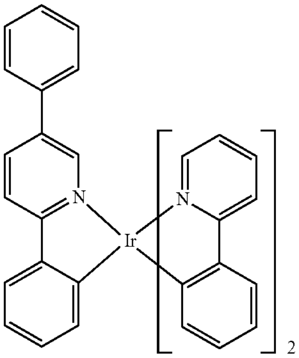

-continued
D-81
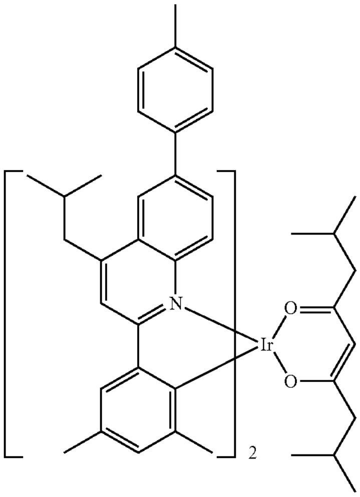
D-82
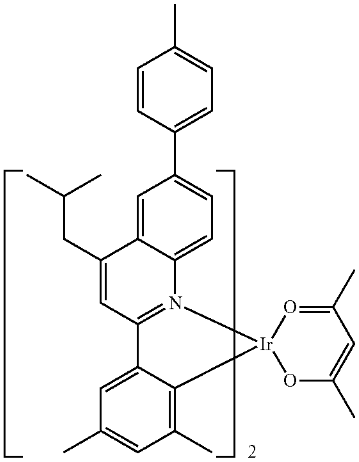
D-83
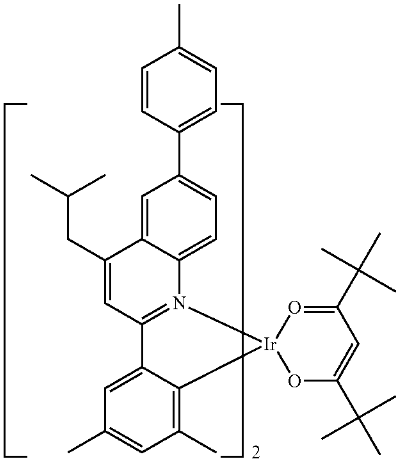
-continued
D-84
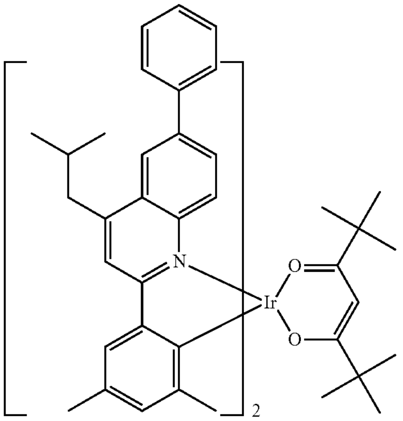
D-85
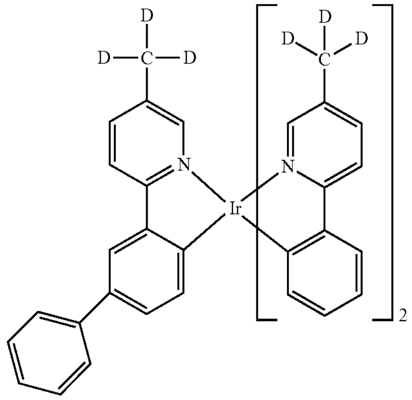
D-86
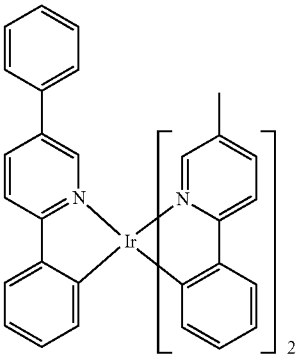
D-87
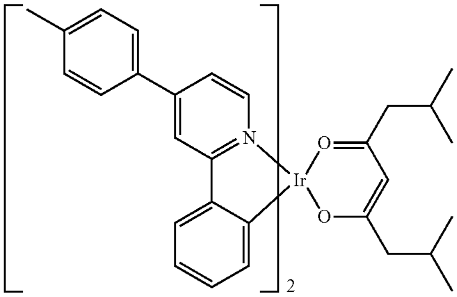

-continued
D-88
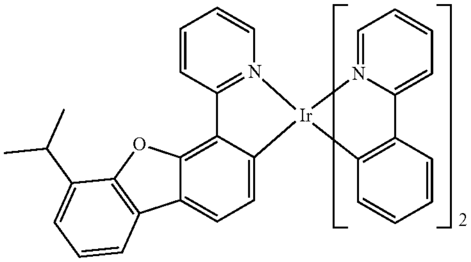
D-89
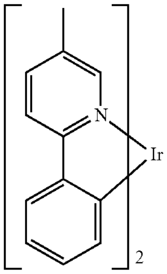
D-90
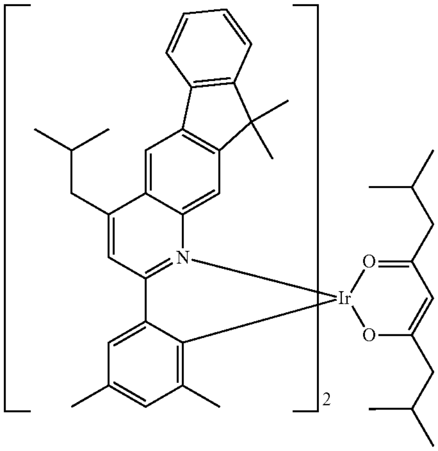
D-91
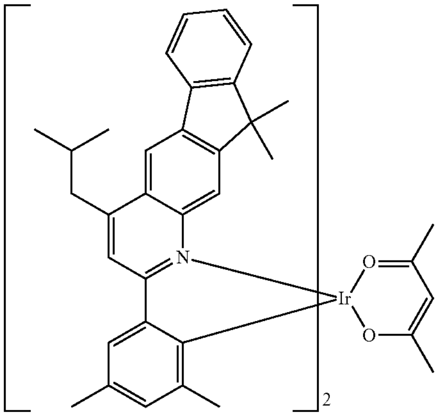
-continued
D-92
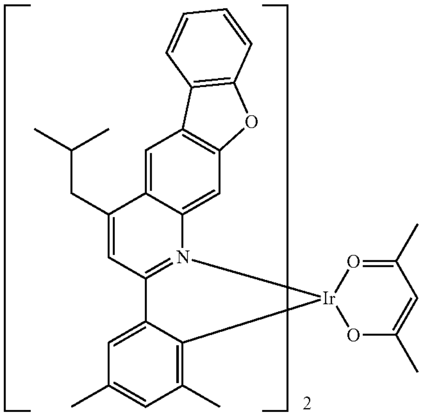
D-93
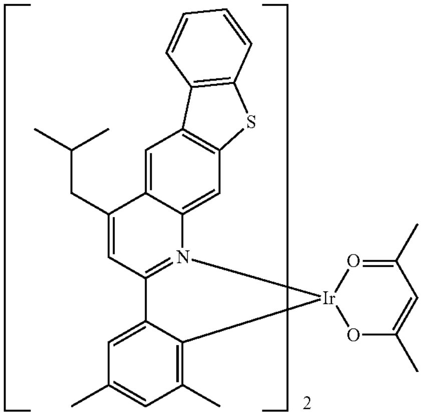
D-94
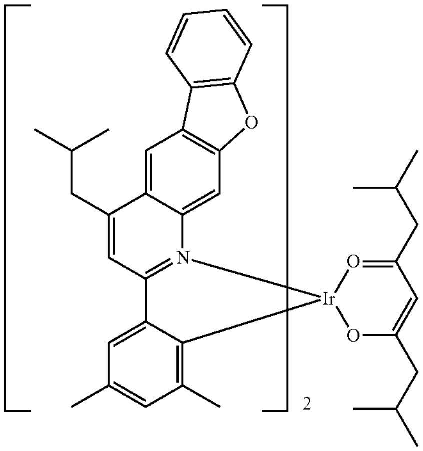

-continued
D-95
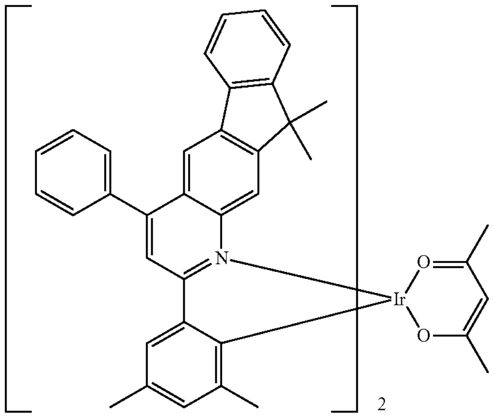
D-96
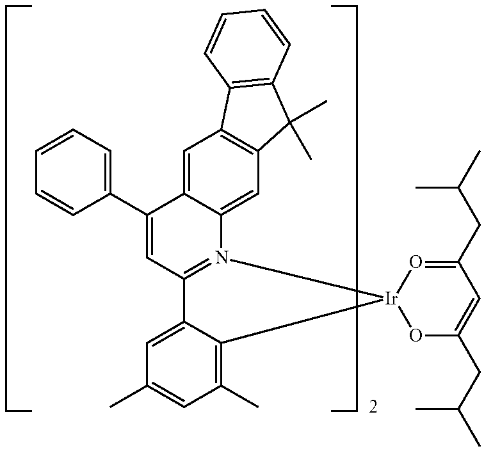
D-97
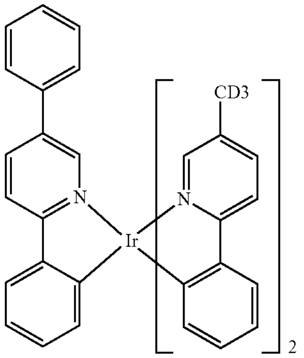
D-98
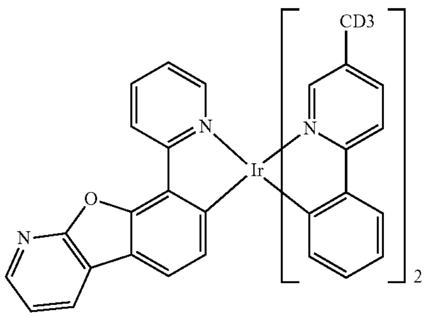
-continued
D-99
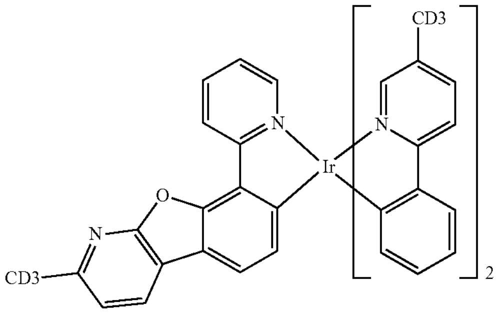
D-100
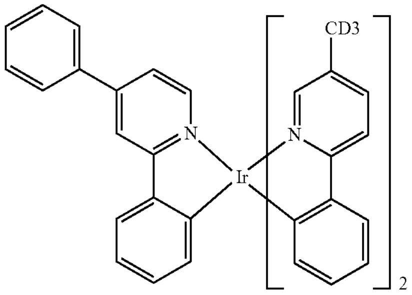
D-101
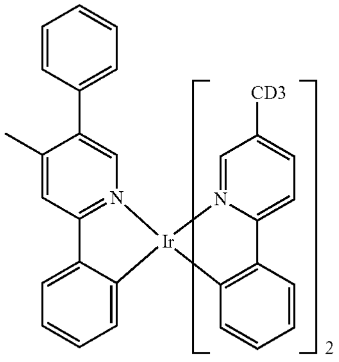
D-102
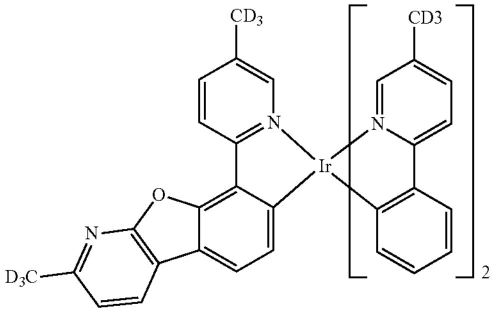

-continued
D-103
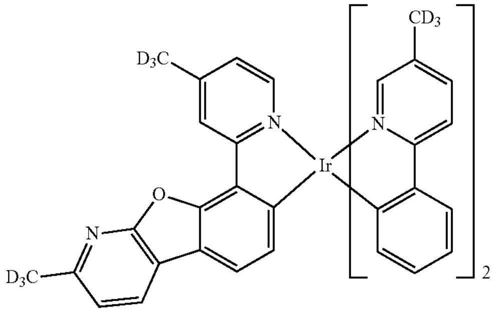
D-104
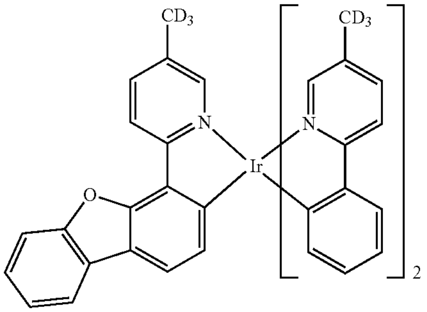
D-105
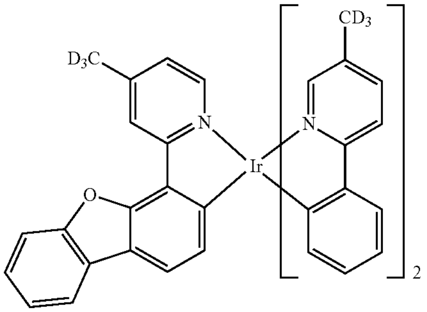
D-106
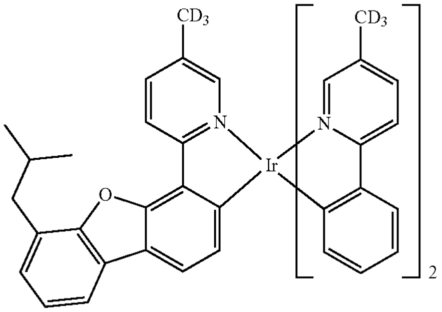
D-107
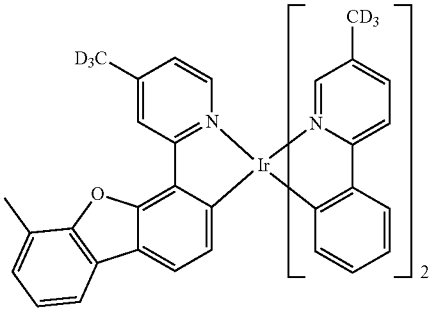
-continued
D-108
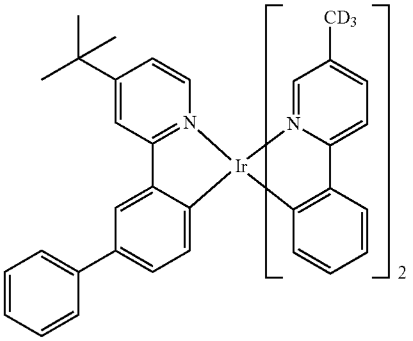
D-109
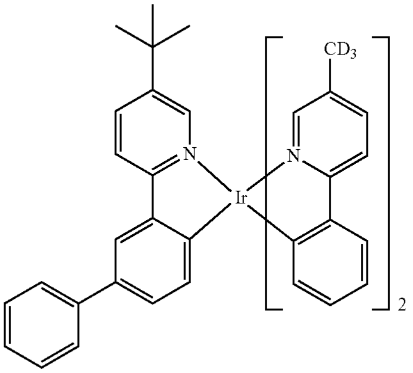
D-110
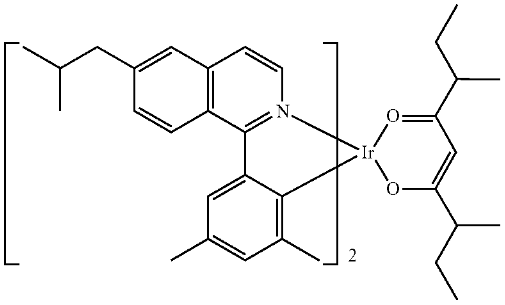
D-111
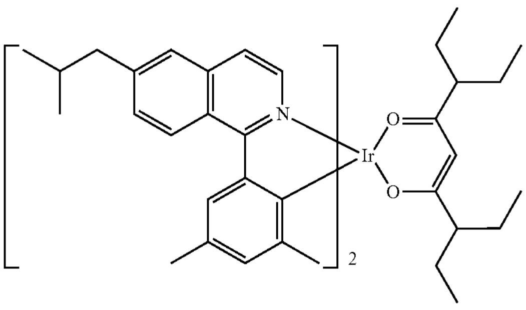

-continued

D-112

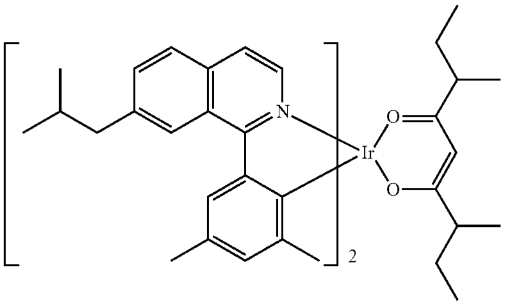

D-113

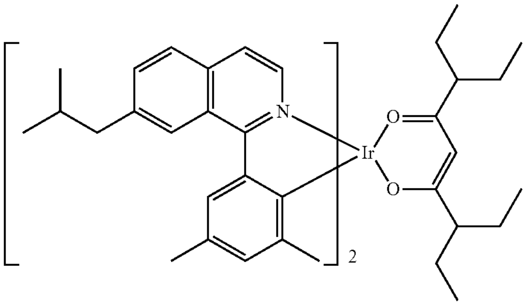

D-114

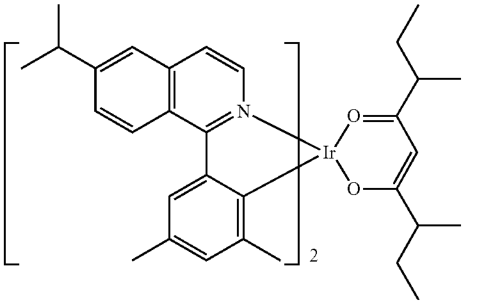

D-115

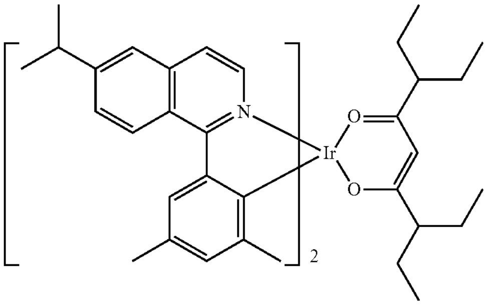

In order to form each layer of the organic electroluminescent device of the present disclosure, dry film-forming methods such as vacuum evaporation, sputtering, plasma, ion plating methods, etc., or wet film-forming methods such as ink jet printing, nozzle printing, slot coating, spin coating, dip coating, flow coating methods, etc., can be used.

When using a wet film-forming method, a thin film may be formed by dissolving or diffusing materials forming each layer into any suitable solvent such as ethanol, chloroform, tetrahydrofuran, dioxane, etc. The solvent may be any solvent where the materials forming each layer can be dissolved or diffused, and where there are no problems in film-formation capability.

Hereinafter, the preparation method of compounds according to the present disclosure will be explained with reference to the representative compound or the intermediate compound of the present disclosure in order to understand the present disclosure in detail.

Example 1 Preparation of Compound 4

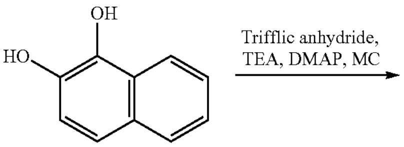

1-1

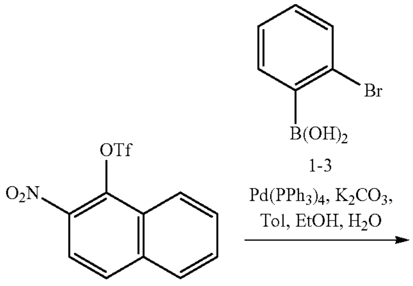

1-3

1-2

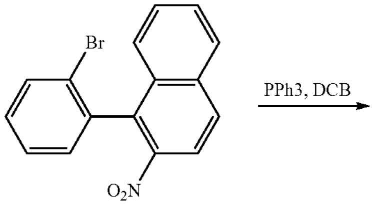

1-4

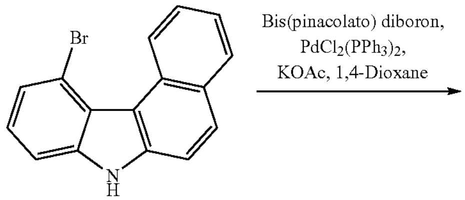

1-5

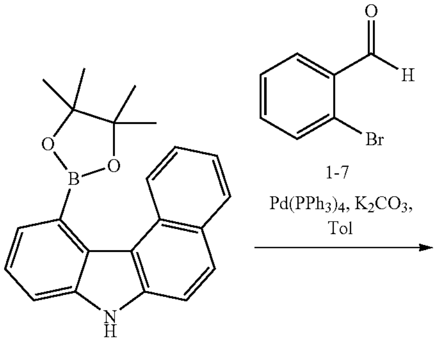

1-7

1-6

-continued

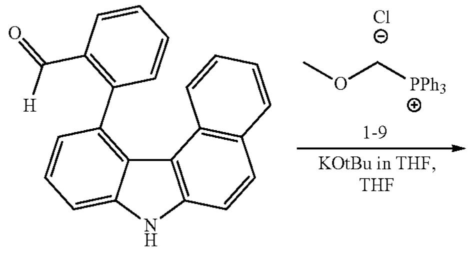

1-8

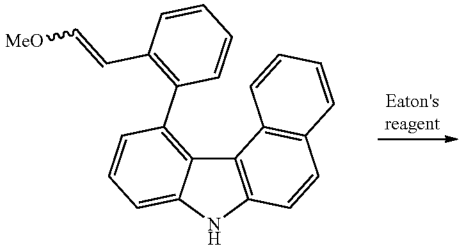

1-10

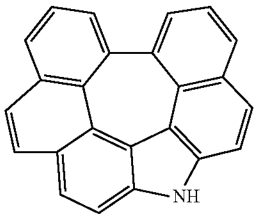

1-11

+

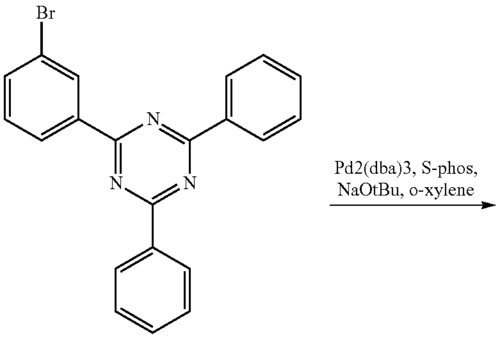

1-12

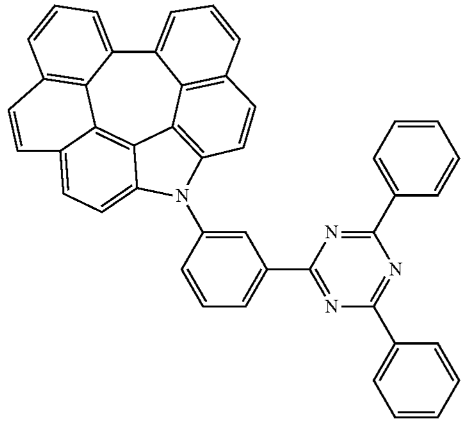

4

1) Synthesis of Compound 1-2

Compound 1-1 (100.0 g, 528.6 mmol) and 4-(dimethylamino)pyridine (DMAP) (6.5 g, 52.9 mmol) were dissolved in 1,000 mL of methylene chloride (MC) in a flask. At 0° C., trifluoromethanesulfonic anhydride (Triflic anhydride) (107.0 mL, 634.4 mmol) and triethylamine (TEA) (89.0 mL, 634.4 mmol) were slowly added dropwise to the flask and the mixture was stirred for 1.5 hours at room temperature. After completion of the reaction by adding distilled water thereto, the organic layer was extracted with MC/$H_2O$, and thereafter separated by column chromatography to obtain compound 1-2 (115.4 g, yield: 68%).

2) Synthesis of Compound 1-4

Compound 1-2 (114.0 g, 354.9 mmol), compound 1-3 (65.0 g, 346.5 mmol), tetrakis(triphenylphosphine) palladium(O)(Pd($PPh_3$)$_4$) (18.6 g, 16.1 mmol), potassium carbonate ($K_2CO_3$) (89.2 g, 645.2 mmol) were dissolved in 1,600 mL of toluene (Tol), 300 mL of ethanol (EtOH), and 400 mL of distilled water ($H_2O$) in a flask and refluxed for 1 hour. After completion of the reaction, the organic layer was extracted with ethylacetate (EA)/$H_2O$, and thereafter separated by column chromatography to obtain compound 1-4 (104 g, yield: 97%).

3) Synthesis of Compound 1-5

Compound 1-4 (104.0 g, 316.8 mmol) and triphenylphosphine ($PPh_3$) (208.0 g, 792.1 mmol) were added to 1,000 mL of 1,2-dichlorobenzene (DCB) in a flask and stirred for 19 hours at 200° C. After completion of the reaction, the mixture was separated by column chromatography to obtain compound 1-5 (22.0 g, yield: 29%).

4) Synthesis of Compound 1-6

Compound 1-5 (21.0 g, 70.9 mmol), bis(pinacolato)diboron (36.0 g, 141.8 mmol), bis(triphenylphosphine)palladiumdichloride(II) ($PdCl_2(PPh_3)_2$) (1.5 g, 2.13 mmol), and potassium acetate (KOAc) (20.9 g, 212.7 mmol) were added to 350 mL of 1,4-dioxane, and dissolved. Thereafter, the mixture was refluxed for 100 minutes. After completion of the reaction, the organic layer was extracted with EA/$H_2O$, and thereafter separated by column chromatography to obtain compound 1-6 (18.9 g, yield: 74%).

5) Synthesis of Compound 1-8

Compound 1-6 (18.9 g, 55.1 mmol), compound 1-7 (10.5 g, 56.7 mmol), $Pd(PPh_3)_4$ (3.2 g, 2.76 mmol), and $K_2CO_3$ (19.0 g, 137.8 mmol) were dissolved in 280 mL of Tol in a flask and refluxed for 24 hours. After completion of the reaction, the organic layer was extracted with EA/$H_2O$, and thereafter separated by column chromatography to obtain compound 1-8 (13.2 g, yield: 77%).

6) Synthesis of Compound 1-10

Compound 1-8 (13.2 g, 41.0 mmol) and compound 1-9 (21.1 g, 61.6 mmol) were dissolved in 200 mL of tetrahydrofuran (THF) in a flask, and then potassium tert-butoxide (KOtBu, in THF) (62.0 mL, 61.6 mmol) were added dropwise to the flask and the mixture was stirred for 2 hours. After completion of the reaction, the organic layer was extracted with EA/$H_2O$, and thereafter separated by column chromatography to obtain compound 1-10 (14.3 g, yield: 100%).

7) Synthesis of Compound 1-11

Compound 1-10 (14.3 g, 41.0 mmol) was dissolved in 200 mL of chlorobenzene in a flask, and then 7.0 mL of Eaton's reagent was added to the mixture and refluxed for 7 hours. After completion of the reaction, the organic layer was extracted with EA/$H_2O$, and thereafter separated by column chromatography to obtain compound 1-11 (4.3 g, yield: 33%).

8) Synthesis of Compound 4

Compound 1-11 (4.2 g, 13.3 mmol), compound 1-12 (5.0 g, 13.0 mmol), tris (dibenzylideneacetone)dipalladium(O) ($Pd_2(dba)_3$) (609 mg, 0.67 mmol), 2-dicyclohexylphosphino-2',6'-dimethoxybiphenyl (S-phos) (546 mg, 1.33 mmol), and sodium tert-butoxide (NaOtBu) (3.2 g, 33.3 mmol) were added to 89 mL of o-xylene in a flask and refluxed for 3 hours. After completion of the reaction, the organic layer was extracted with EA/$H_2O$, and thereafter separated by column chromatography to obtain compound 4 (3.8 g, yield: 46%)

| | MW | M.P |
|---|---|---|
| 4 | 622.17 | 305° C. |

Example 2 Preparation of Compound 215

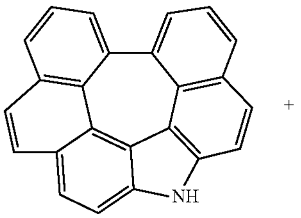

1-11

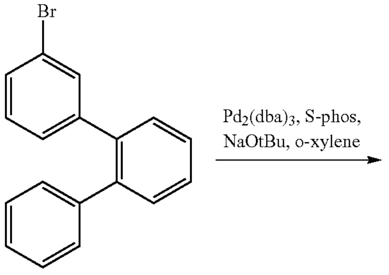

1-13

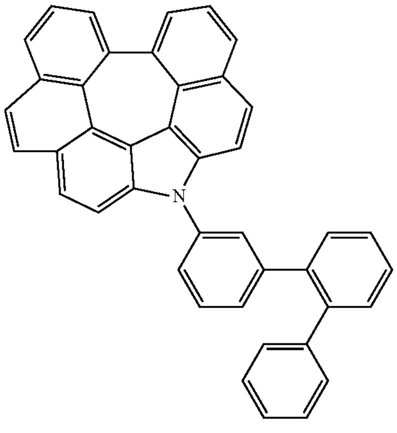

215

Compound 1-11 (4.0 g, 12.7 mmol), compound 1-13 (4.3 g, 13.9 mmol), tris (dibenzylideneacetone)dipalladium(O) ($Pd_2(dba)_3$) (581 mg, 0.63 mmol), 2-dicyclohexylphosphino-2',6'-dimethoxybiphenyl (S-phos) (520 mg, 1.26 mmol), and sodium tert-butoxide (NaOtBu) (3.0 g, 31.7 mmol) were added to 63 mL of o-xylene in a flask and refluxed for 5 hours. After completion of the reaction, the organic layer was extracted with EA/$H_2O$, and thereafter separated by column chromatography to obtain compound 215 (2.2 g, yield: 32%).

| | MW | M.P |
|---|---|---|
| 215 | 543.65 | 154° C. |

Example 3 Preparation of Compound 217

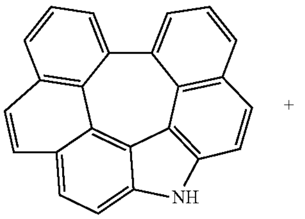

1-11

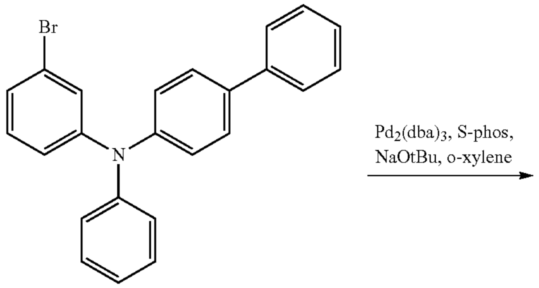

1-14

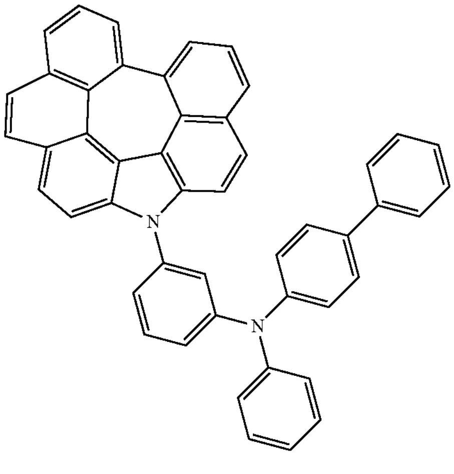

217

Compound 1-11 (4.7 g, 14.9 mmol), compound 1-14 (6.6 g, 16.4 mmol), tris (dibenzylideneacetone)dipalladium(O) ($Pd_2(dba)_3$) (682 mg, 0.75 mmol), 2-dicyclohexylphosphino-2',6'-dimethoxybiphenyl (S-phos) (612 mg, 1.50 mmol), and sodium tert-butoxide (NaOtBu) (3.6 g, 37.3 mmol) were added to 75 mL of o-xylene in a flask and refluxed for 7 hours After completion of the reaction, the organic layer was extracted with EA/$H_2O$, and thereafter separated by column chromatography to obtain compound 217 (4.3 g, yield: 45%).

| | MW | M.P |
|---|---|---|
| 217 | 634.77 | 139° C. |

Hereinafter, the light-emitting properties of an organic electroluminescent device comprising an organic electroluminescent compound will be explained in order to understand the present disclosure in detail.

Device Example 1 Producing an OLED in which the Organic Electroluminescent Compound According to the Present Disclosure is Deposited as a Host An OLED device comprising the compound according to the present disclosure was produced. First, a transparent electrode indium tin oxide (ITO) thin film (10 Ω/sq) on a glass substrate for an OLED device (GEOMATEC CO., LTD., Japan) was subjected to an ultrasonic washing with acetone, ethanol, and distilled water, sequentially, and then was stored in isopropanol. The ITO substrate was then mounted on a substrate holder of a vacuum vapor deposition apparatus. Compound HI-1 was introduced into a cell of the vacuum vapor deposition apparatus, and then the pressure in the chamber of the apparatus was controlled to $10^{-6}$ torr. Thereafter, an electric current was applied to the cell to evaporate the above-introduced material, thereby forming a first hole injection layer having a thickness of 80 nm on the ITO substrate. Next, compound HI-2 was introduced into another cell of the vacuum vapor deposition apparatus, and was evaporated by applying an electric current to the cell, thereby forming a second hole injection layer having a thickness of 5 nm on the first hole injection layer. Compound HT-1 was then introduced into another cell of the vacuum vapor deposition apparatus, and was evaporated by applying an electric current to the cell, thereby forming a first hole transport layer having a thickness of 10 nm on the second hole injection layer. Compound HT-2 was then introduced into another cell of the vacuum vapor deposition apparatus, and was evaporated by applying an electric current to the cell, thereby forming a second hole transport layer having a thickness of 60 nm on the first hole transport layer. After forming the hole injection layers and the hole transport layers, a light-emitting layer was formed thereon as follows:

Compound 4 was introduced into one cell of the vacuum vapor depositing apparatus as a host, and compound D-39 was introduced into another cell as a dopant. The two materials were evaporated at a different rate and deposited in a doping amount of 3 wt %, to form a light-emitting layer having a thickness of 40 nm on the hole transport layer. Next, compounds ET-1 and EI-1 were evaporated at a rate of 1:1, and were deposited to form an electron transport layer having a thickness of 35 nm on the light-emitting layer. After depositing compound EI-1 as an electron injection layer having a thickness of 2 nm on the electron transport layer, an Al cathode having a thickness of 80 nm was deposited on the electron injection layer by another vacuum vapor deposition apparatus. Thus, an OLED was produced.

Comparative Example 1 Producing an OLED Comprising the Comparative Compound as a Host An OLED was produced in the same manner as in Device Example 1, except that compound CBP was used as the host of the light-emitting layer.

The results of the driving voltage and the efficiency at a luminance of 1,000 nits, and the time taken to reduce from 100% to 95% at a luminance of 5,000 nit (lifespan; T95), of the organic electroluminescent device of Device Example 1 and Comparative Example 1 produced as described above, are shown in the following Table 1.

TABLE 1

| | Host Material | Driving Voltage (V) | Efficiency (cd/A) | Lifespan (T95, hr) |
|---|---|---|---|---|
| Comparative Example 1 | CBP | 9.2 | 9.2 | 0.25 |
| Device Example 1 | 4 | 2.8 | 23.4 | 142.0 |

Referring to Table 1 above, it can be confirmed that the organic electroluminescent device comprising the organic electroluminescent compound according to one embodiment as a host material can significantly reduce the driving voltage and improve the efficiency and lifespan compared to the organic electroluminescent device comprising a conventional host material.

The compounds used in Device Example 1 and Comparative Example 1 are shown specifically in Table 2 below.

TABLE 2
| | | |
|---|---|---|
| Hole Injection Layer/ Hole Transport Layer | 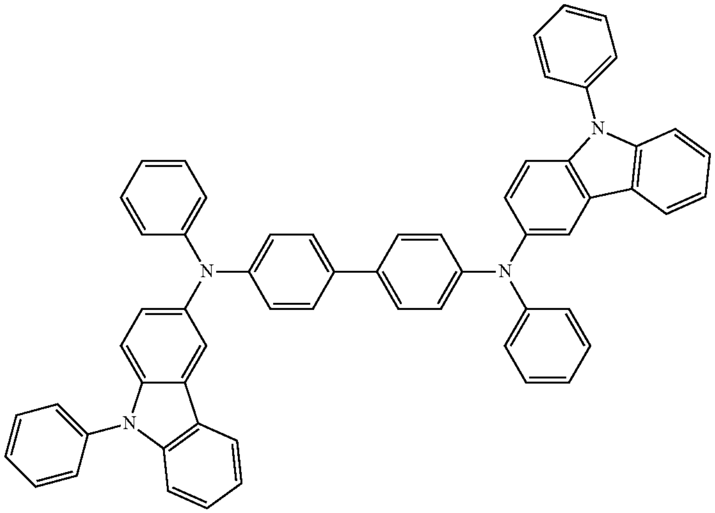 HI-1 | 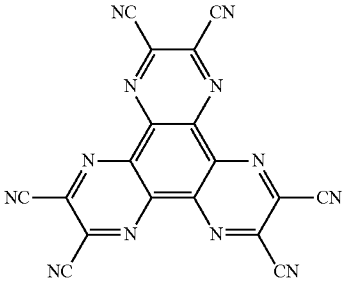 HI-2 |
| | 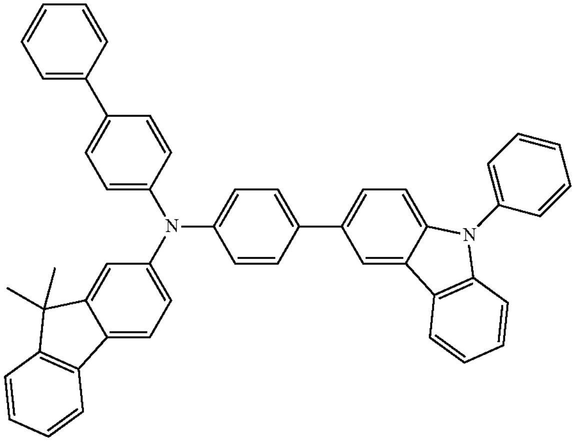 HT-1 | 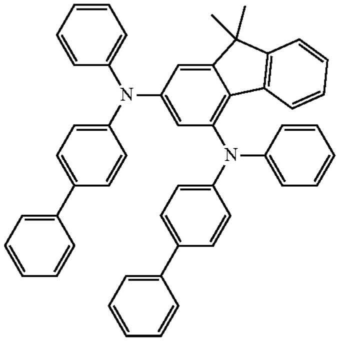 HT-2 |

TABLE 2-continued
| | | | |
|---|---|---|---|
| Light-Emitting Layer | 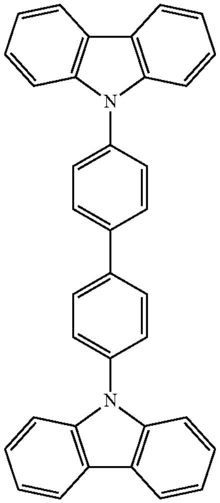 CBP | 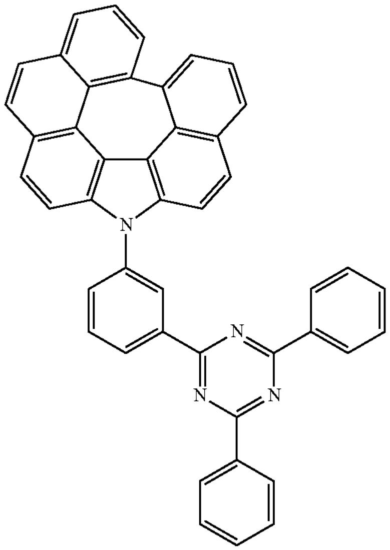 4 | 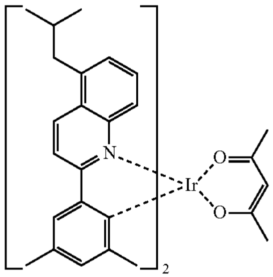 D-39 |
| Electron Transport Layer/ Electron Injection Layer | | 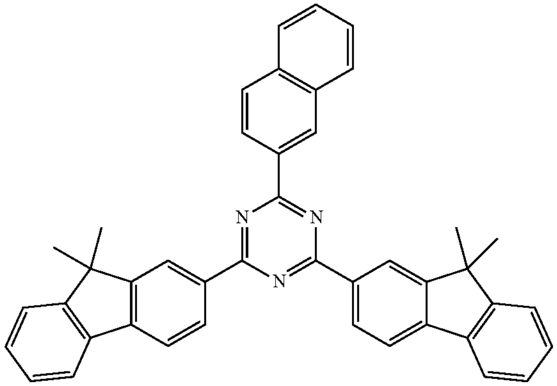 ET-1 | 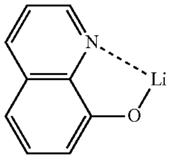 EI-1 |

The invention claimed is:

1. An organic electroluminescent compound represented by any one of the following formulae 2, 3, and 5:

(2)

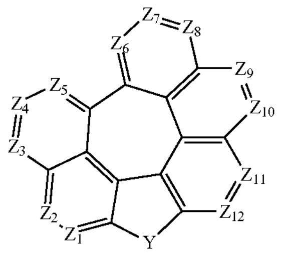

(3)

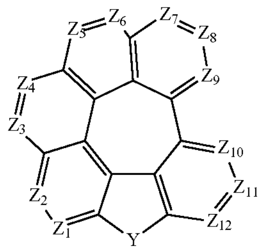

(5)

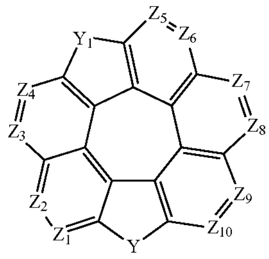

Wherein,

Y and $Y_1$ each independently represent —N-$L_1$-$Ar_1$, —O—, —S—, or —$CR_1R_2$;

$L_1$ represents a single bond, a substituted or unsubstituted (C1-C30)alkylene, a substituted or unsubstituted (C6-C30)arylene, a substituted or unsubstituted (3-to 30-membered) heteroarylene, or a substituted or unsubstituted (C3-C30)cycloalkylene;

$Ar_1$ represents a substituted or unsubstituted (C6-C30) aryl, a substituted or unsubstituted (3-to 30-membered) heteroaryl, or —$NR_3R_4$;

$R_1$ to $R_4$ each independently represent hydrogen, deuterium, halogen, cyano, a substituted or unsubstituted (C1-C30)alkyl, a substituted or unsubstituted (C6-C30) aryl, a substituted or unsubstituted (3-to 30-membered) heteroaryl, or a substituted or unsubstituted (C3-C30) cycloalkyl; or may be linked to an adjacent substituent to form a substituted or unsubstituted ring;

$Z_1$ to $Z_{12}$ each independently represent N or $CR_a$; and $R_a$ each independently represent hydrogen, deuterium, halogen, cyano, a substituted or unsubstituted (C1-C30)alkyl, a substituted or unsubstituted (C6-C30)aryl, a substituted or unsubstituted (3-to 30-membered) heteroaryl, a substituted or unsubstituted (C3-C30)cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, a substituted or unsubstituted (C1-C30)alkyl (C6-30)arylamino, a substituted or unsubstituted mono- or di-(3-to 30-membered)heteroarylamino, or a substituted or unsubstituted (C6-C30)aryl (3-to 30-membered)heteroarylamino.

2. The organic electroluminescent compound according to claim 1, wherein the substituents of the substituted (C1-C30)alkyl(ene), the substituted (C6-C30)aryl(ene), the substituted (3-to 30-membered)heteroaryl(ene), the substituted (C3-C30)cycloalkyl(ene), the substituted (C1-C30)alkoxy, the substituted tri(C1-C30)alkylsilyl, the substituted di(C1-C30)alkyl(C6-C30)arylsilyl, the substituted (C1-C30)alkyldi(C6-C30)arylsilyl, the substituted tri(C6-C30)arylsilyl, the substituted mono- or di-(C1-C30)alkylamino, the substituted mono- or di-(C6-C30)arylamino, the substituted (C1-C30)alkyl(C6-30)arylamino, and the substituted ring in $Ar_1$, $L_1$, $R_1$ to $R_4$, and $R_a$ each independently represent at least one selected from the group consisting of deuterium, halogen, cyano, carboxyl, nitro, hydroxyl, (C1-C30)alkyl, halo(C1-C30)alkyl, (C2-C30)alkenyl, (C2-C30)alkynyl, (C1-C30)alkoxy, (C1-C30)alkylthio, (C3-C30)cycloalkyl, (C3-C30)cycloalkenyl, (3-to 7-membered)heterocycloalkyl, (C6-C30)aryloxy, (C6-C30)arylthio, (C6-C30)aryl, (3-to 30-membered) heteroaryl, tri(C1-C30)alkylsilyl, tri(C6-C30)arylsilyl, di(C1-C30)alkyl(C6-C30)arylsilyl, (C1-C30) alkyldi(C6-C30)arylsilyl, amino, mono- or di-(C1-C30)alkylamino, (C1-C30)alkyl-substituted or unsubstituted mono- or di-(C6-C30)arylamino, (C1-C30)alkyl(C6-C30) arylamino, (C1-C30)alkylcarbonyl, (C1-C30)alkoxycarbonyl, (C6-C30)arylcarbonyl, di(C6-C30)arylboronyl, di(C1-C30)alkylboronyl, (C1-C30)alkyl(C6-C30)arylboronyl, (C6-C30)ar(C1-C30)alkyl, and (C1-C30)alkyl(C6-C30) aryl.

3. The organic electroluminescent compound according to claim 1, wherein $Ar_1$ and $R_a$ each independently represent any one of the substituents selected from the following Group 1:

[Group 1]

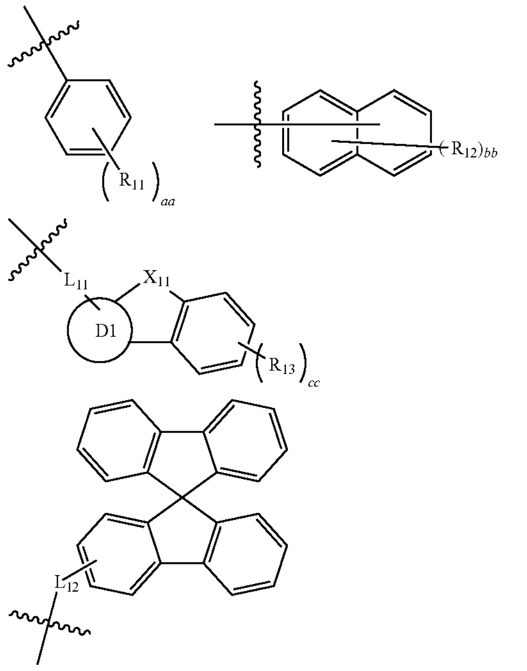

-continued

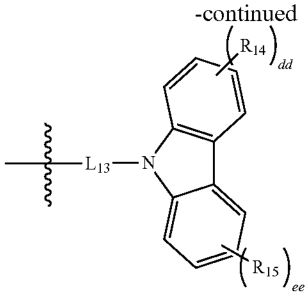

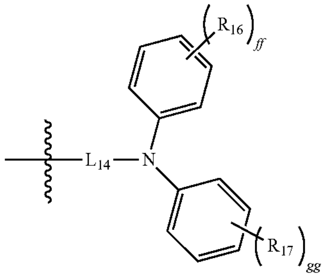

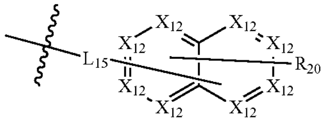

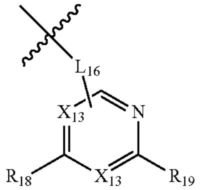

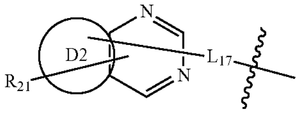

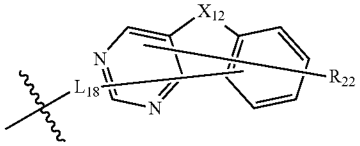

wherein,

D1 and D2 each independently represent a benzene ring or a naphthalene ring;

$X_{11}$ represents O, S, $NR_{11}$, or $CR_{12}R_{13}$;

$X_{12}$ each independently represent $CR_{31}$ or N; provided that at least one $X_{12}$ is N;

$X_{13}$ each independently represent $CR_{32}$ or N;

$L_{11}$ to $L_{18}$ each independently represent a single bond, a substituted or unsubstituted (C6-C30)arylene, or a substituted or unsubstituted (3-to 30-membered)heteroarylene;

$R_{11}$ to $R_{22}$, $R_{31}$, and $R_{32}$ each independently represent hydrogen, deuterium, halogen, cyano, a substituted or unsubstituted (C1-C30)alkyl, a substituted or unsubstituted (C6-C30)aryl, a substituted or unsubstituted (3-to 30-membered)heteroaryl, or a substituted or unsubstituted (C3-C30)cycloalkyl; or may be linked to an adjacent substituent to form a substituted or unsubstituted ring;

aa, ff, and gg each independently represent an integer of 1 to 5, bb represents an integer of 1 to 7, cc to ee represent an integer of 1 to 4; and when aa to gg are 2 or more, each of $R_{11}$ to $R_{17}$ may be the same or different.

4. The organic electroluminescent compound according to claim 1, wherein $Ar_1$ and $R_a$ each independently represent any one of the substituents selected from the following Group 2:

[Group 2]

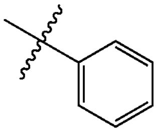

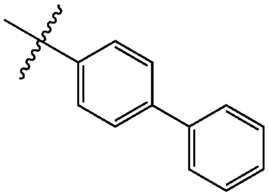

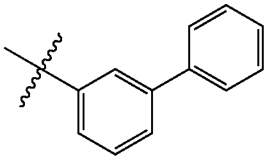

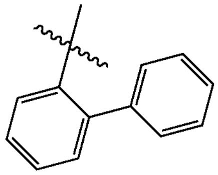

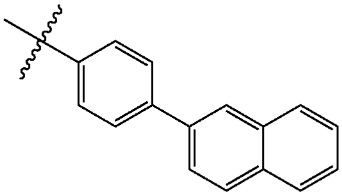

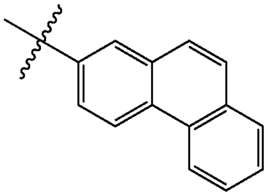

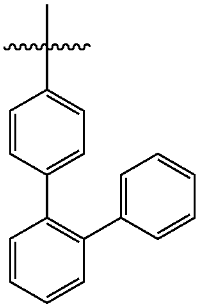

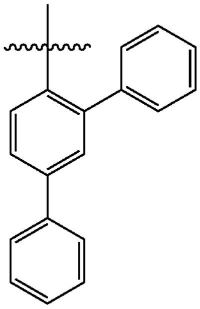

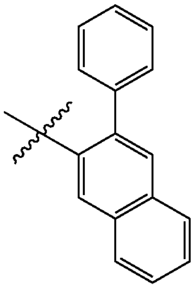

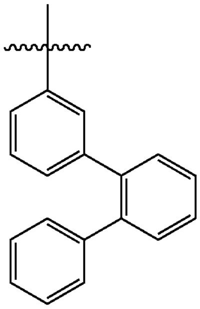

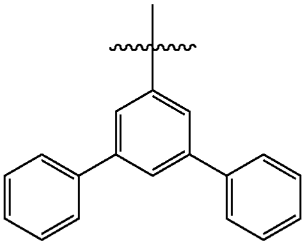

-continued
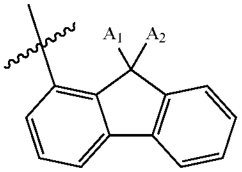
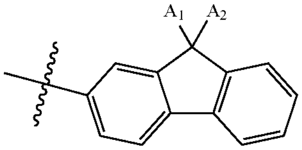
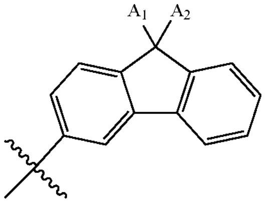
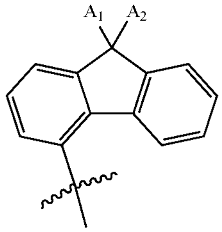
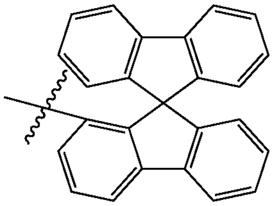
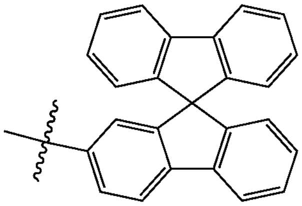
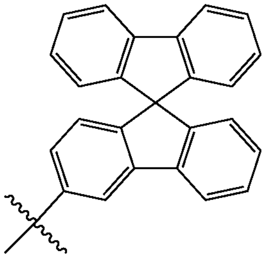
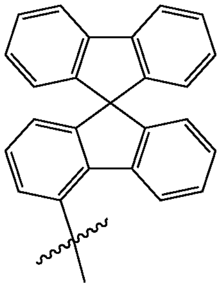
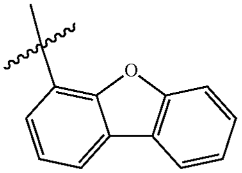
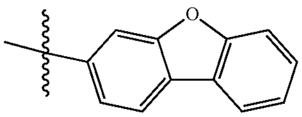
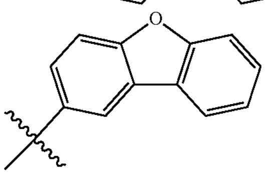
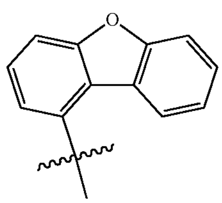
-continued
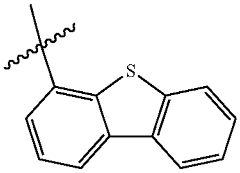
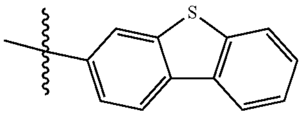
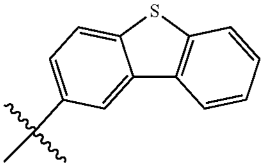
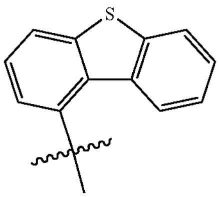
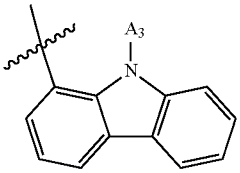
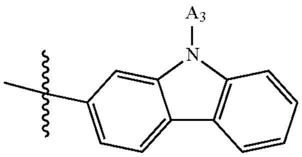
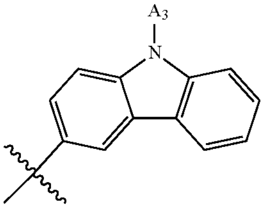
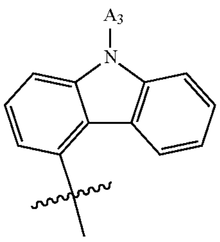
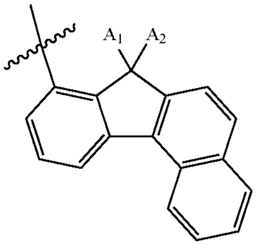
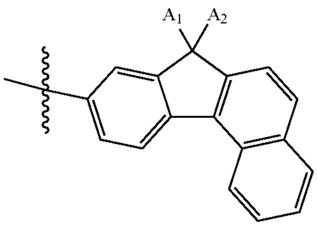

-continued
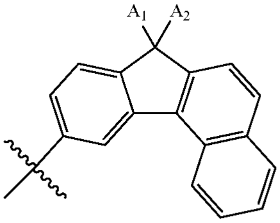
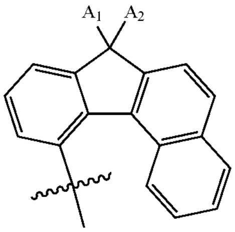
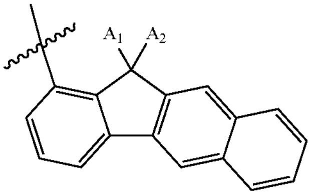
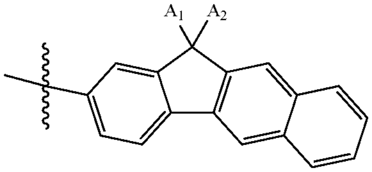
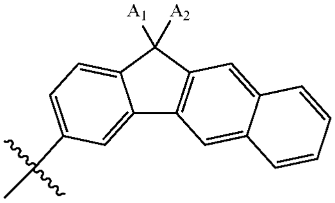
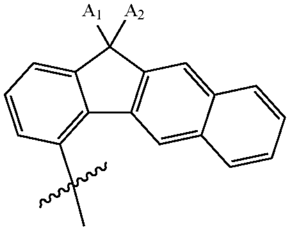
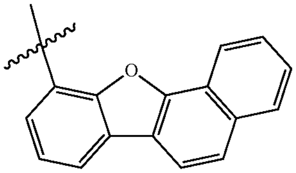
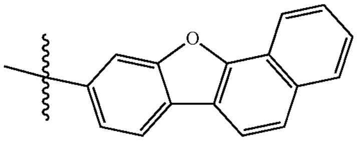
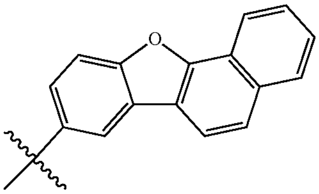
-continued
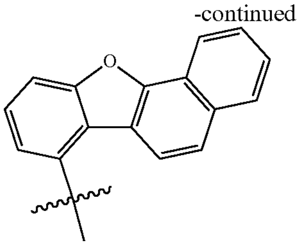
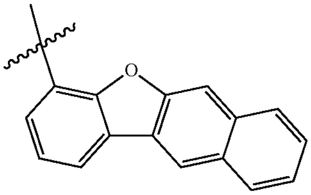
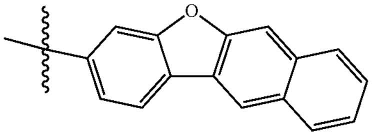
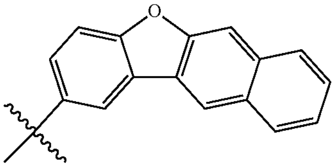
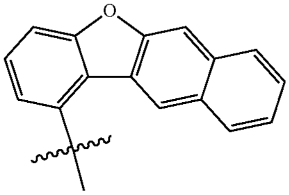
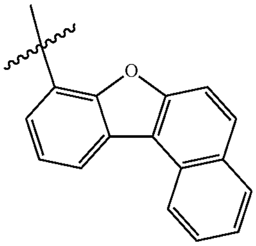
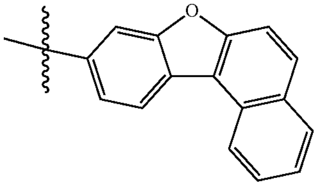
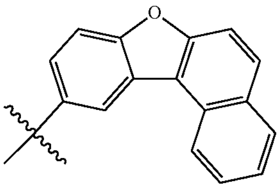
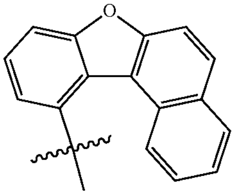
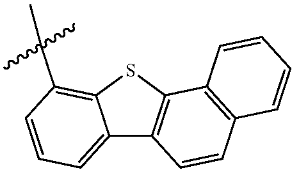

-continued
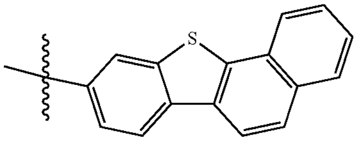
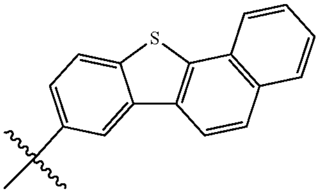
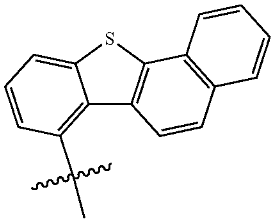
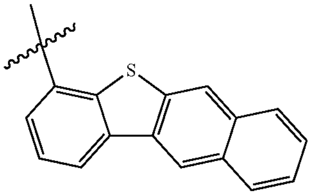
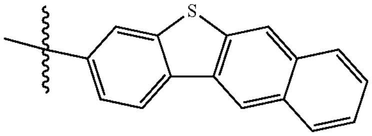
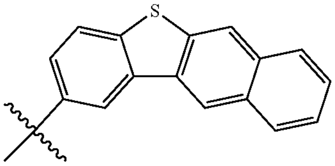
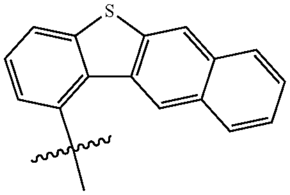
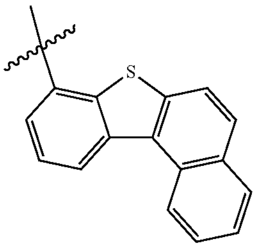
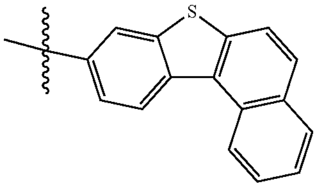
-continued
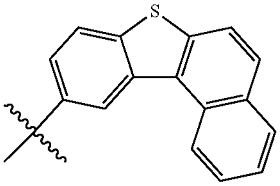
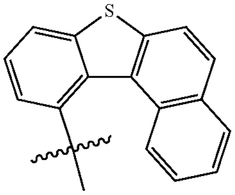
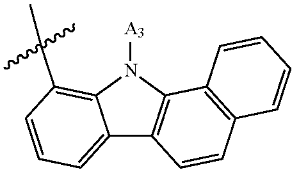
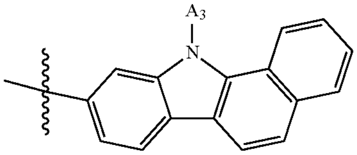
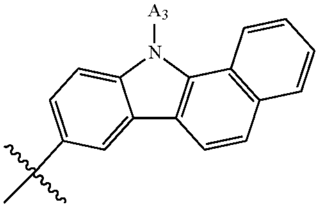
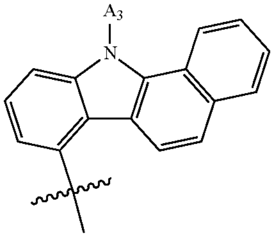
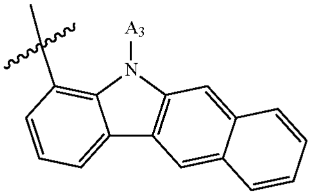
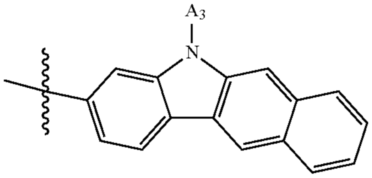
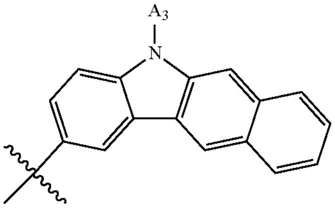

-continued
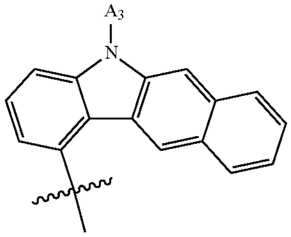
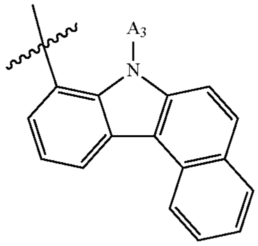
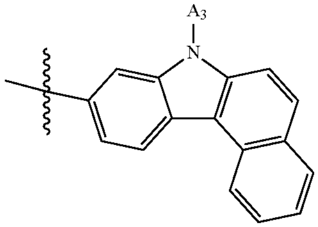
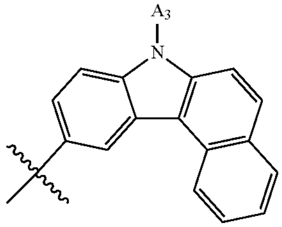
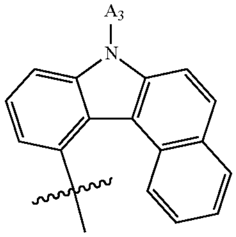
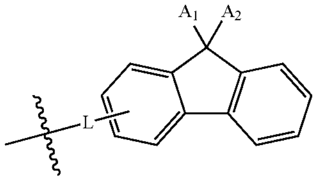
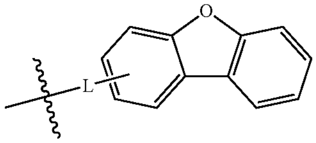
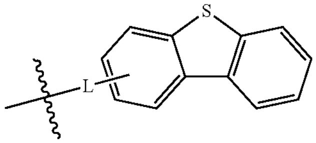
-continued
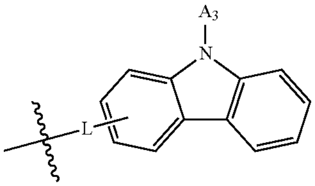
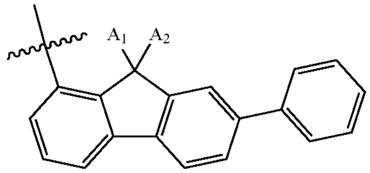
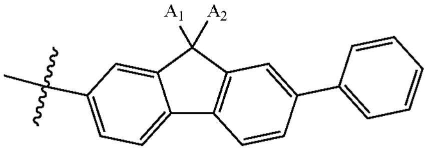
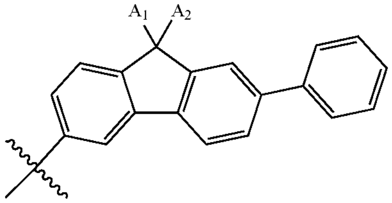
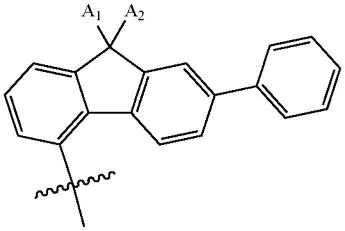
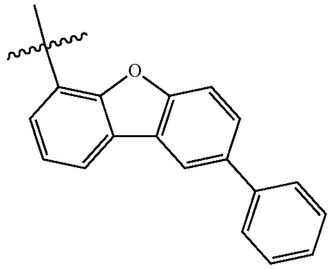
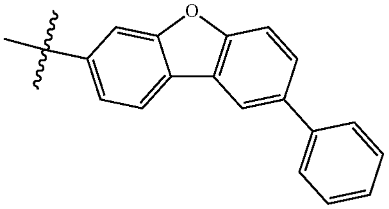
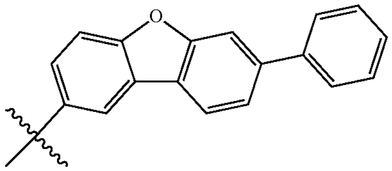

-continued
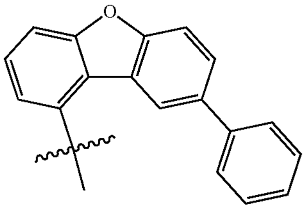
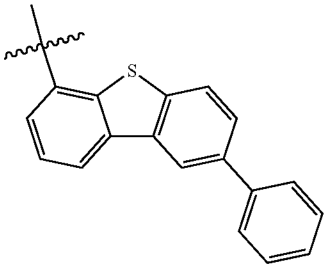
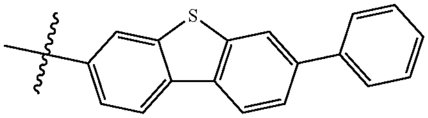
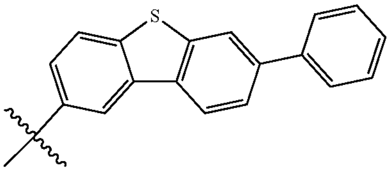
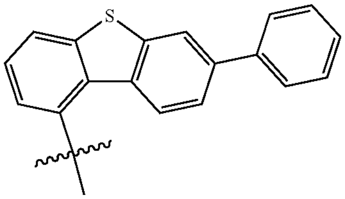
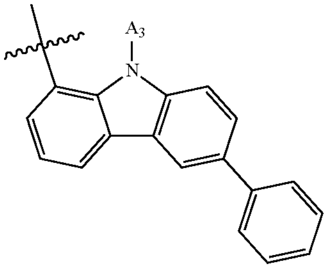
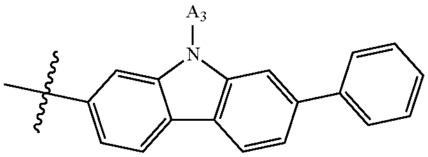
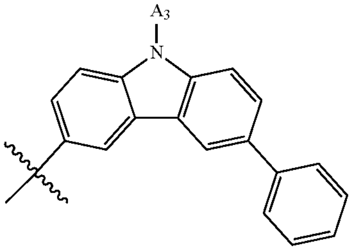
-continued
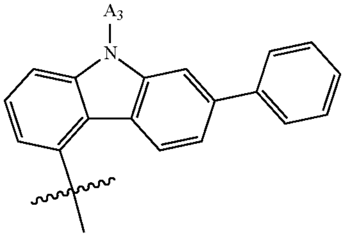
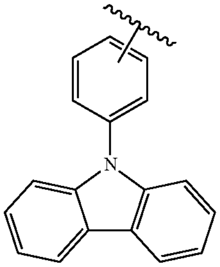
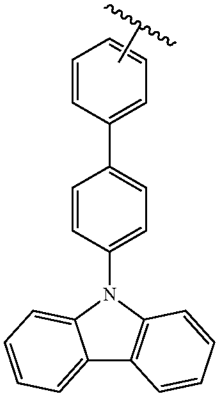
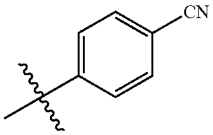
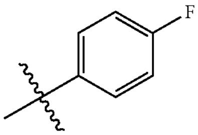
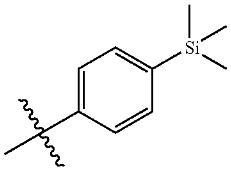
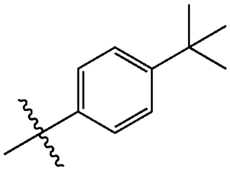
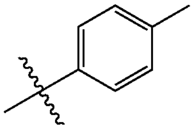
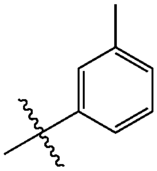
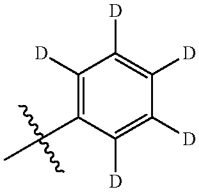
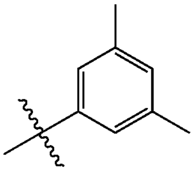
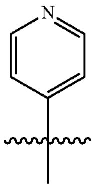
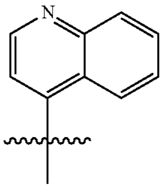
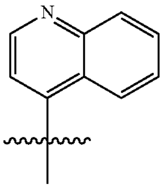
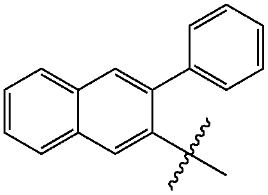
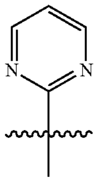

-continued

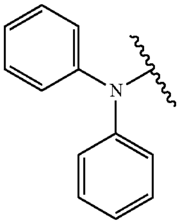

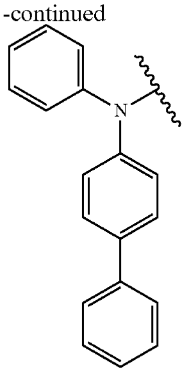

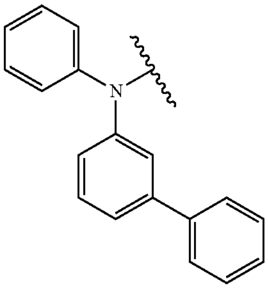

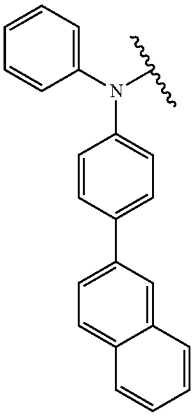

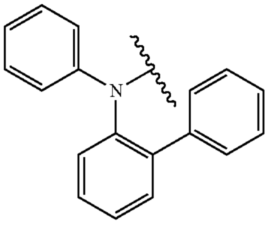

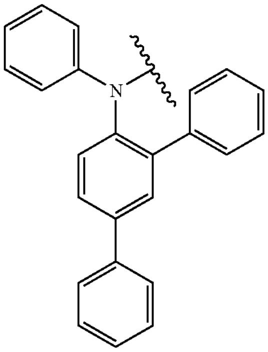

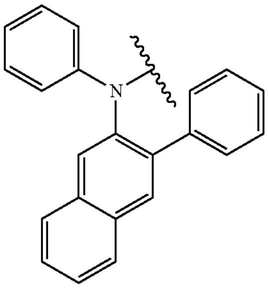

-continued

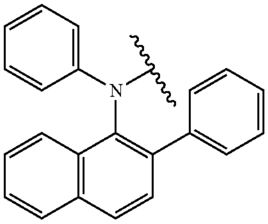

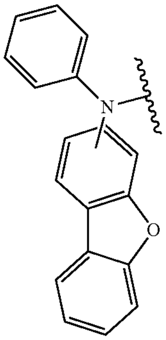

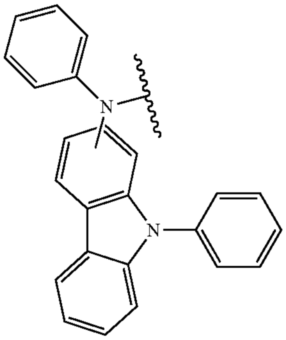

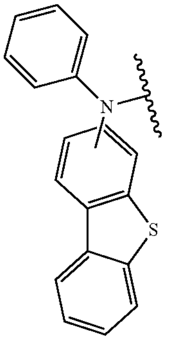

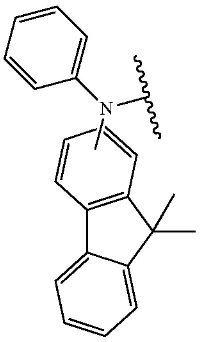

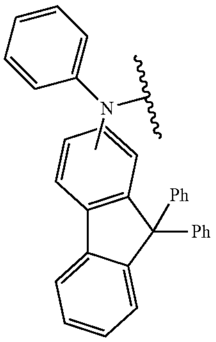

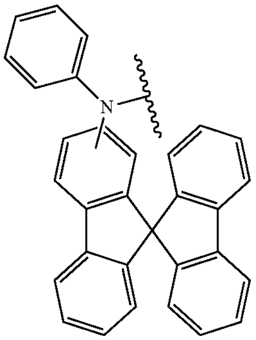

wherein,

L is as defined of $L_1$ in claim 1; and $A_1$ to $A_3$ each independently represent a substituted or unsubstituted (C1-C30)alkyl or a substituted or unsubstituted (C6-C30)aryl.

5. The organic electroluminescent compound according to claim 1, wherein, $Ar_1$, $R_1$ to $R_4$, and $R_a$ each independently represent any one of the substituents selected from the following Group 3.

[Group 3]
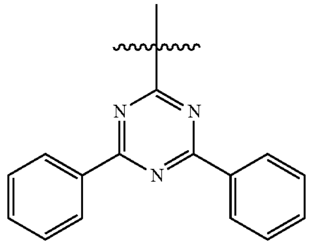
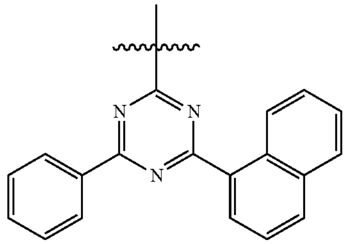
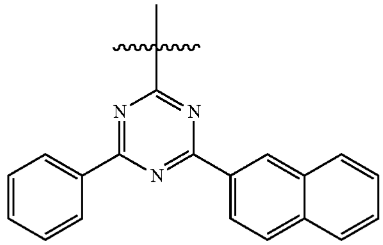
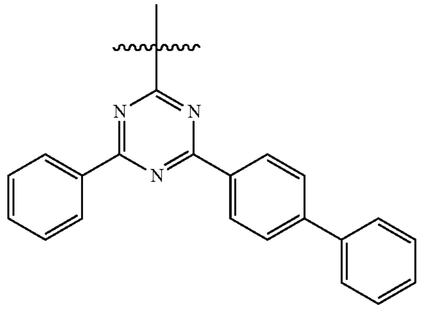
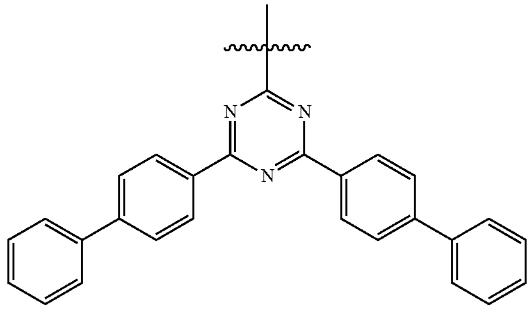
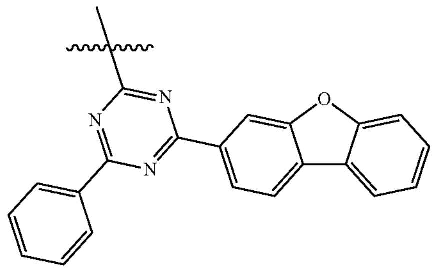
-continued
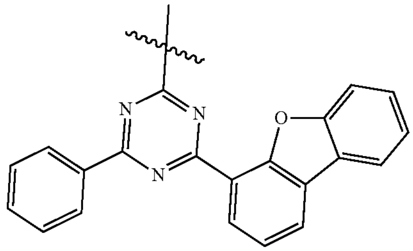
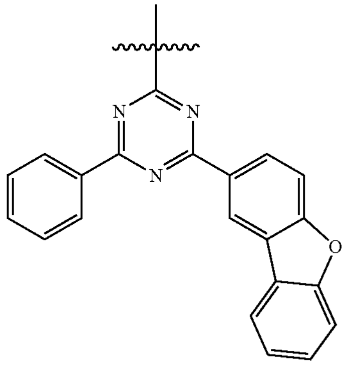
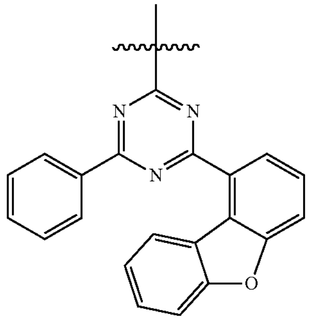
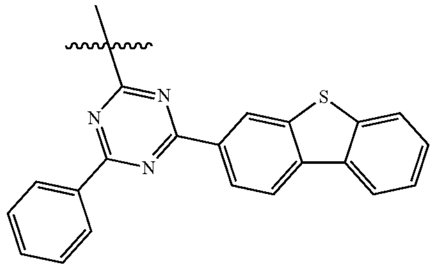
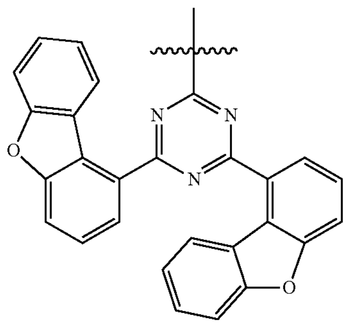

-continued
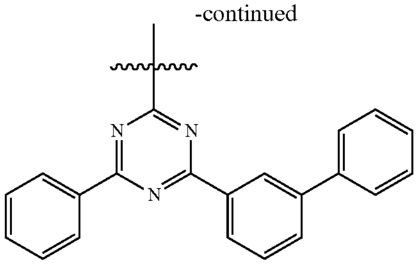
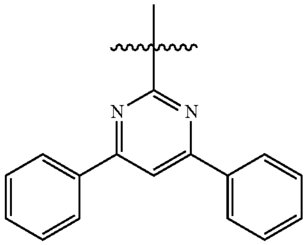
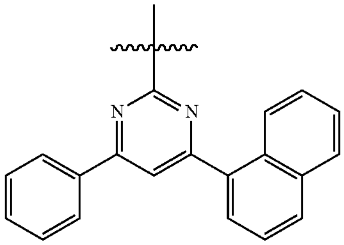
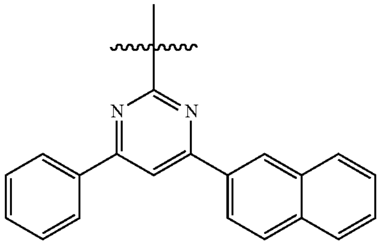
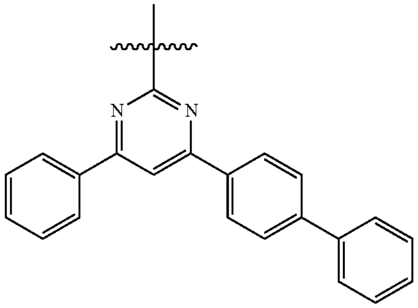
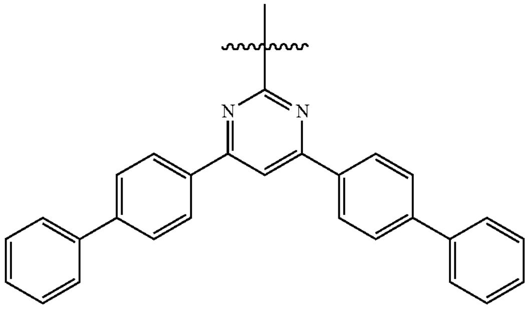
-continued
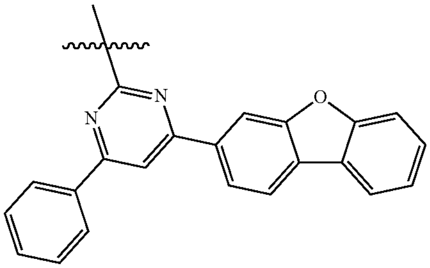
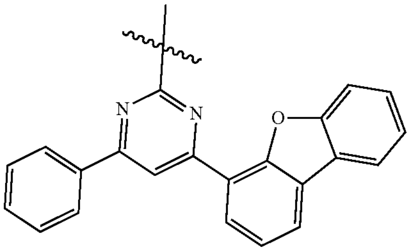
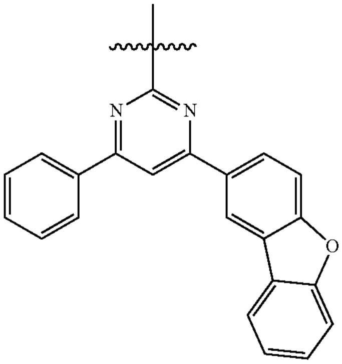
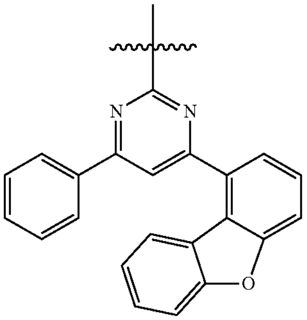
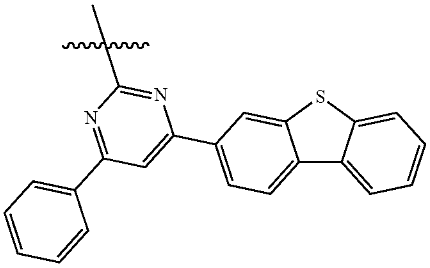

-continued
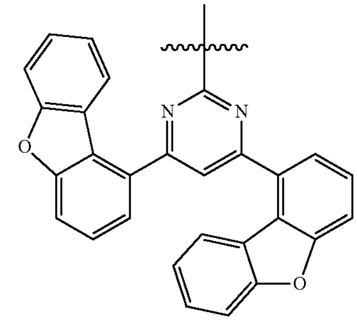
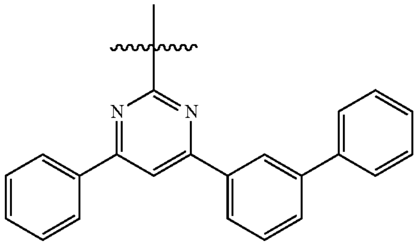
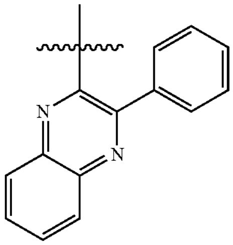
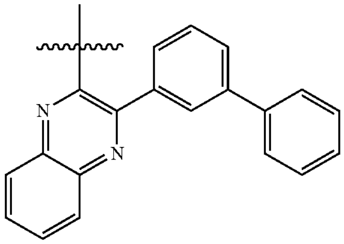
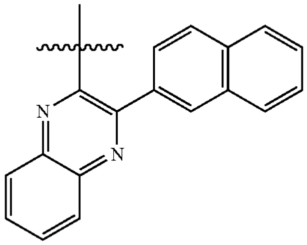
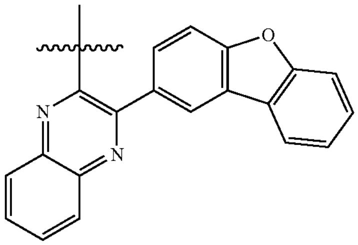
-continued
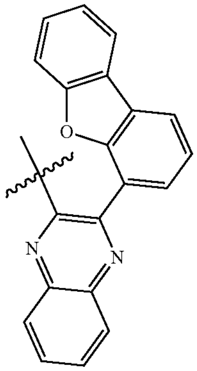
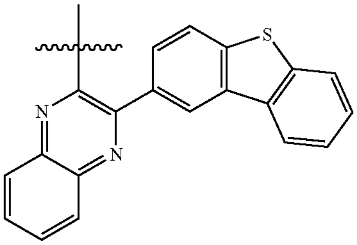
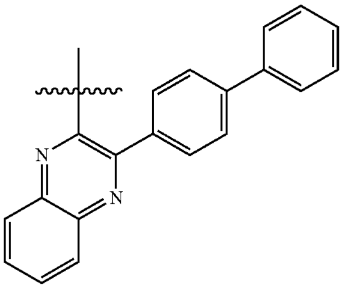
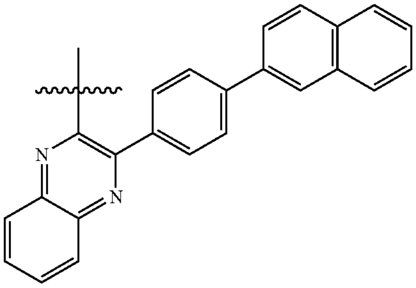
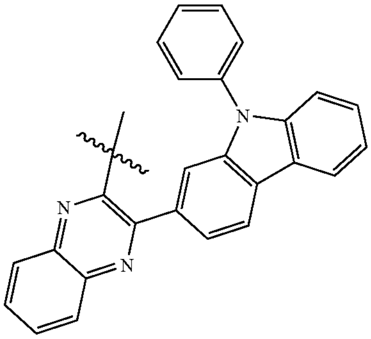

-continued
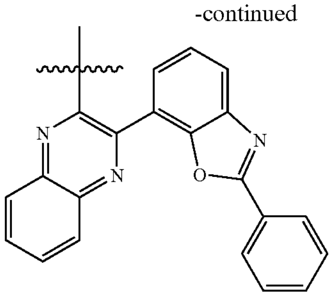
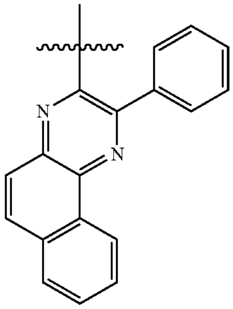
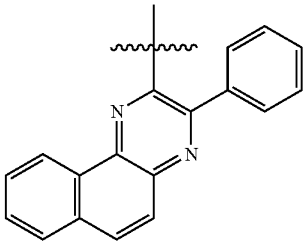
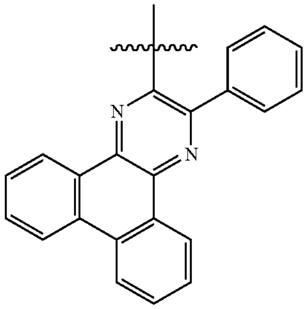
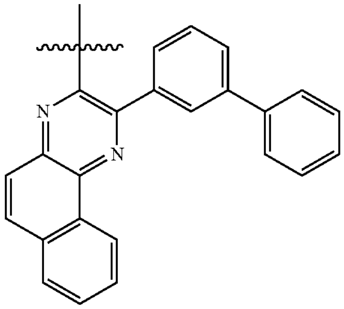
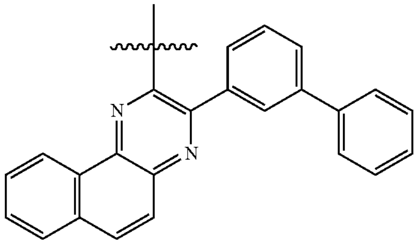
-continued
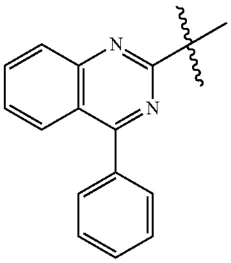
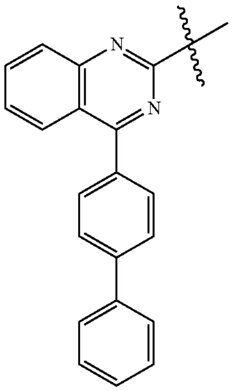
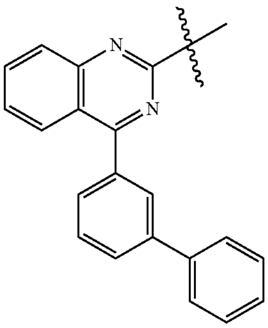
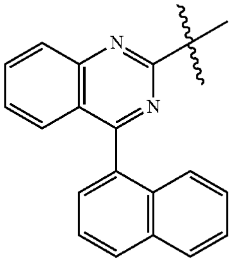
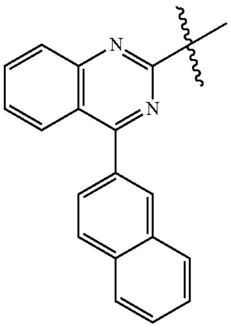
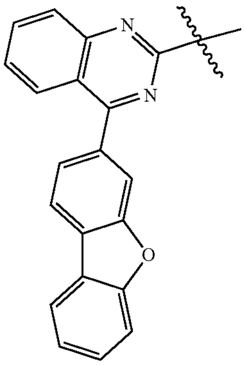
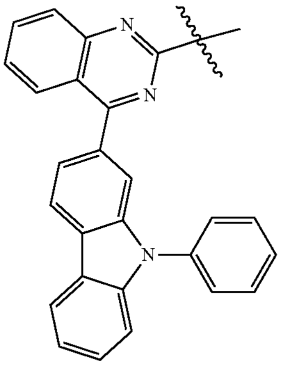

-continued
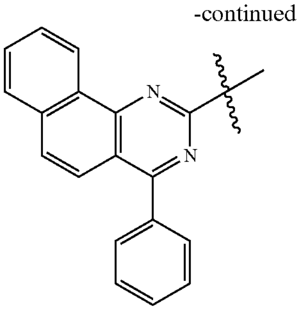
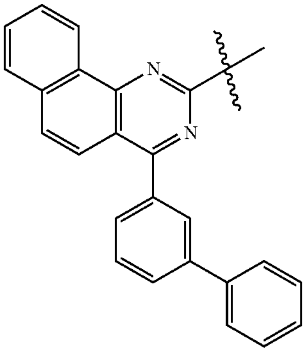
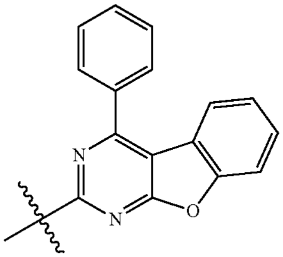
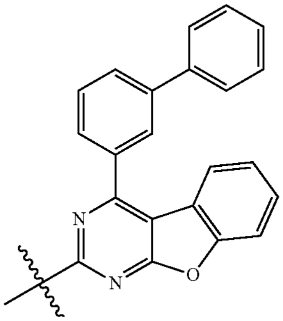
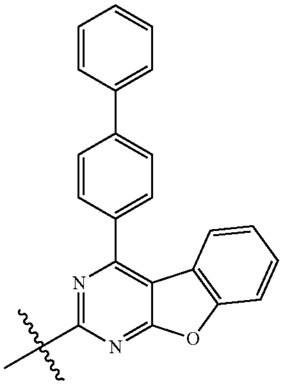
-continued
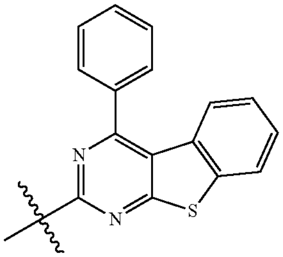
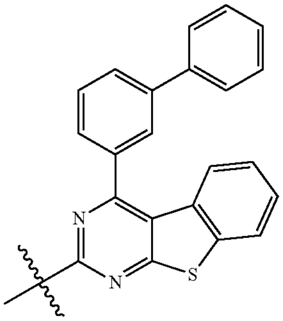
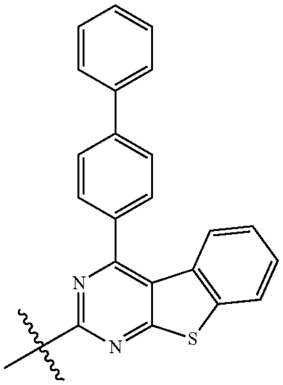
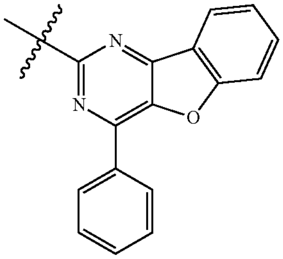
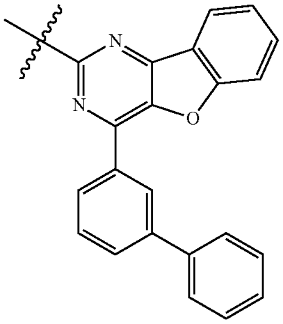

-continued
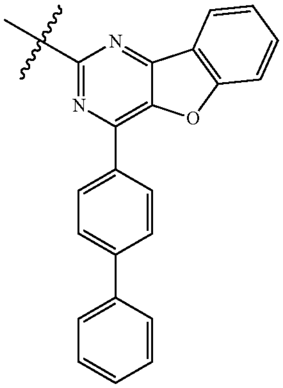
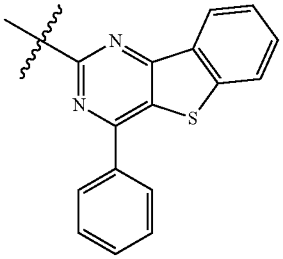
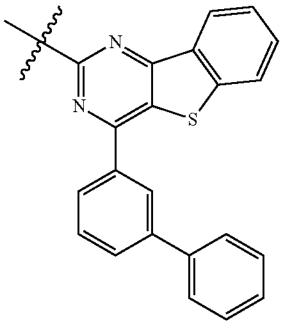
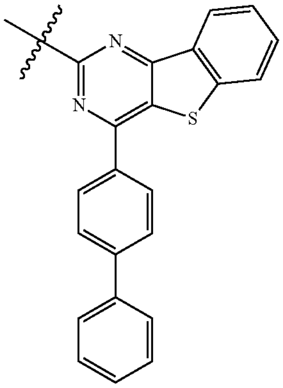
-continued
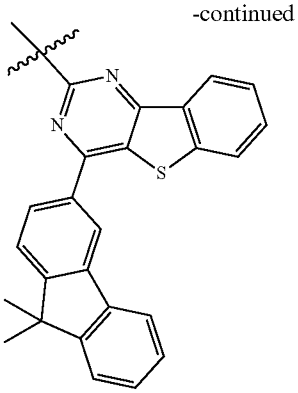
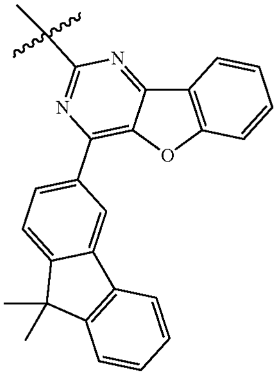
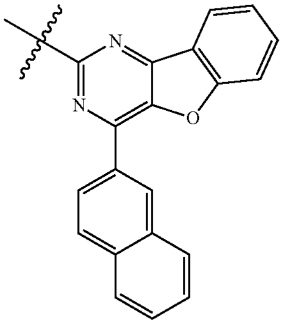
.
6. The organic electroluminescent compound according to claim 1, wherein the compound represented by formulae 2, 3, and 5 is selected from the group consisting of:
1
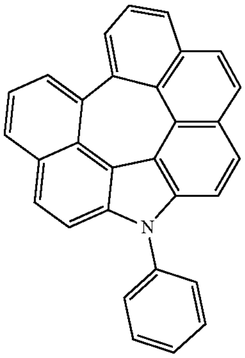

-continued
2
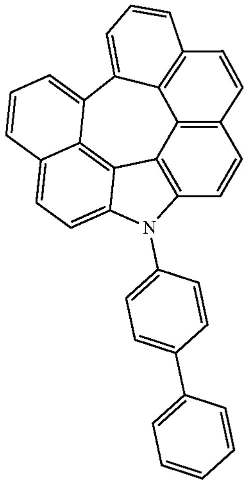
3
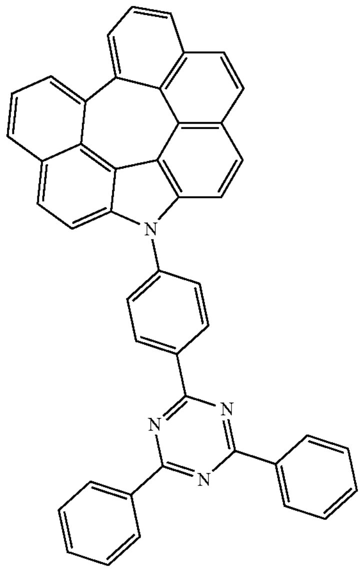
4
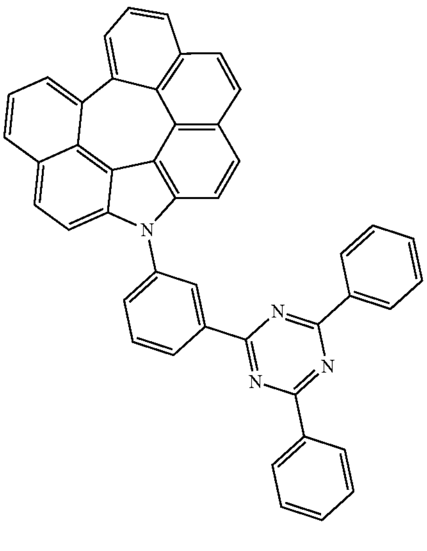
-continued
5
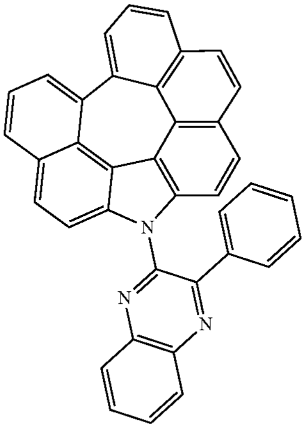
6
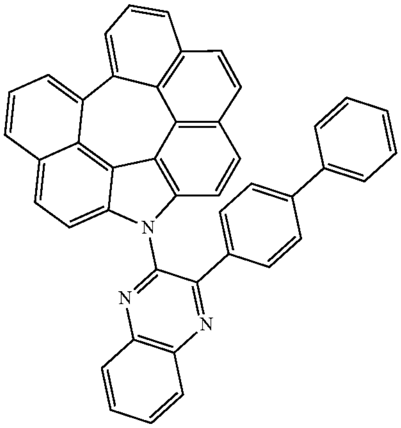
7
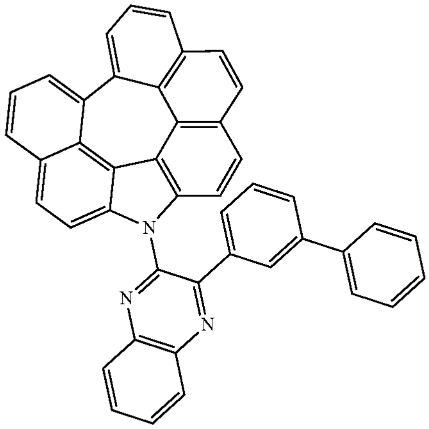

-continued
8
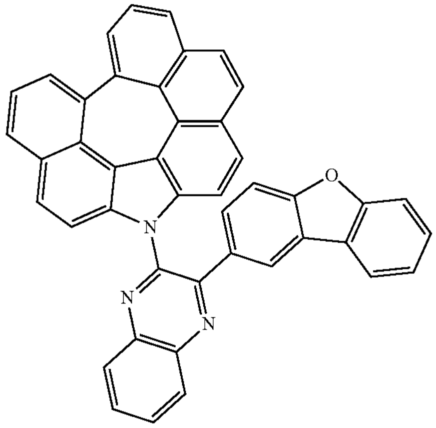
11
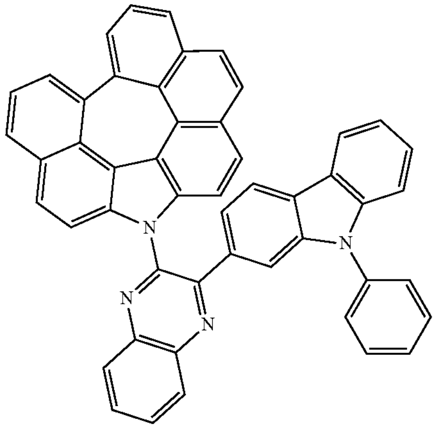
9
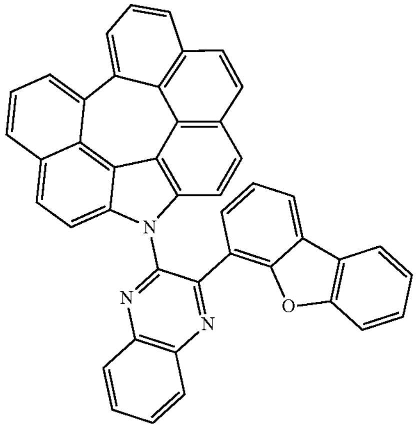
12
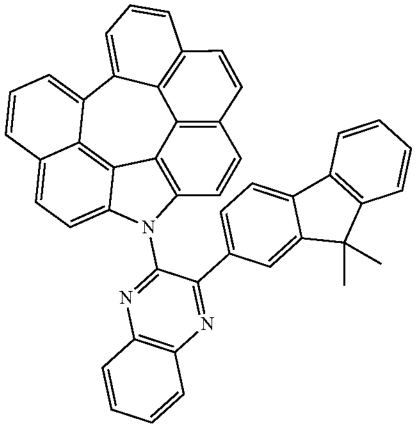
10
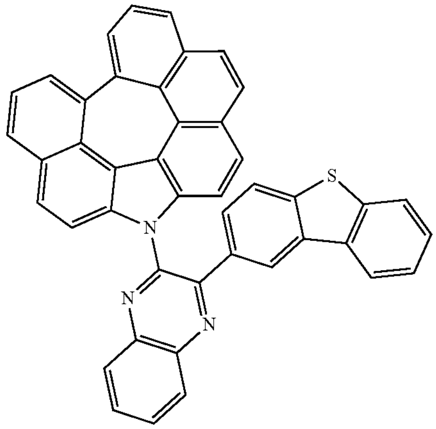
13
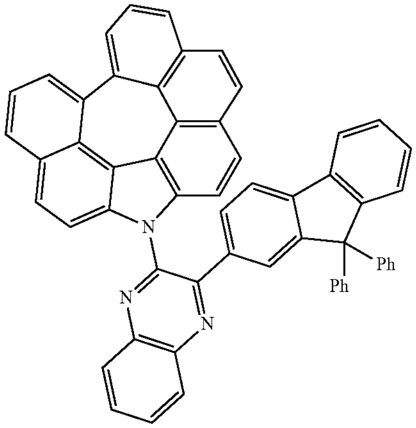

-continued
14
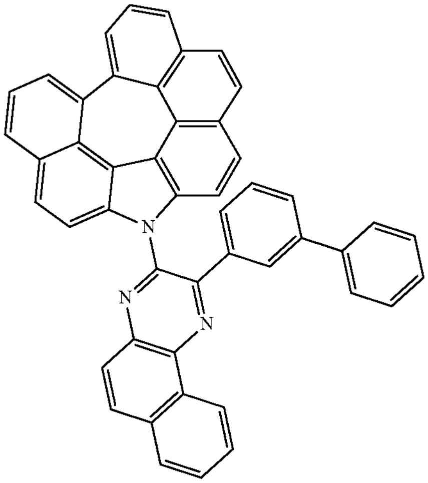
15
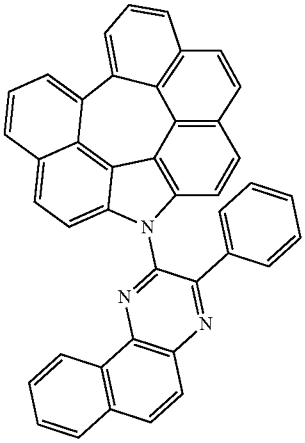
16
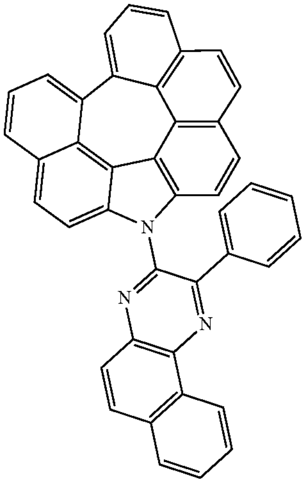
-continued
17
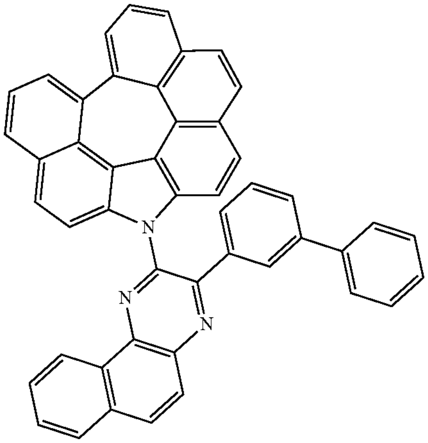
18
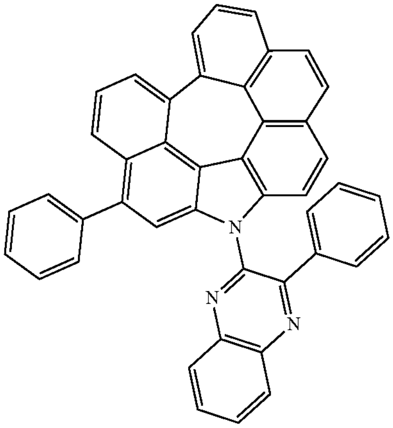
19
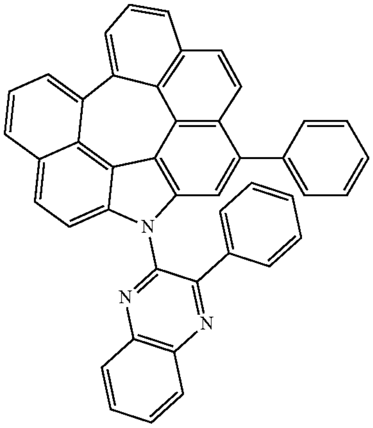

-continued
20
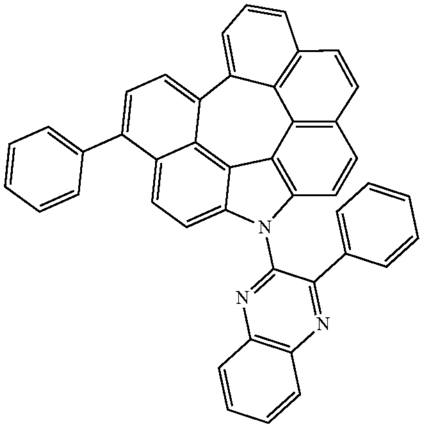
21
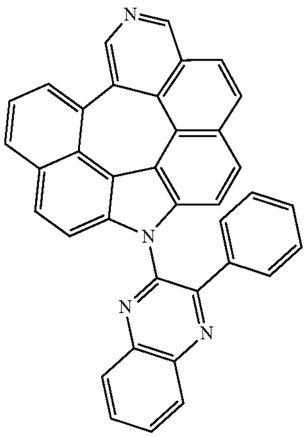
22
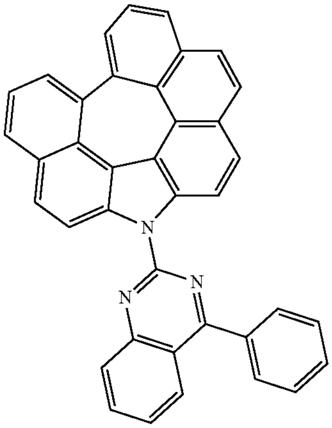
-continued
23
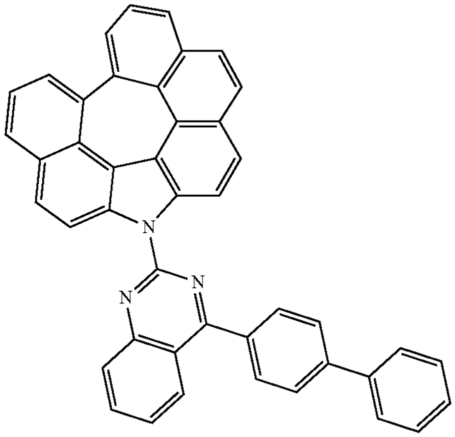
24
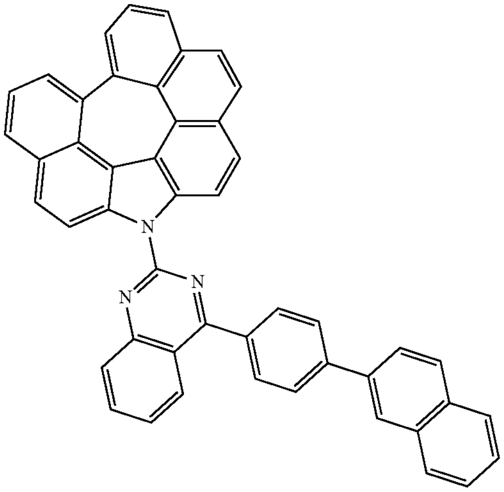
25
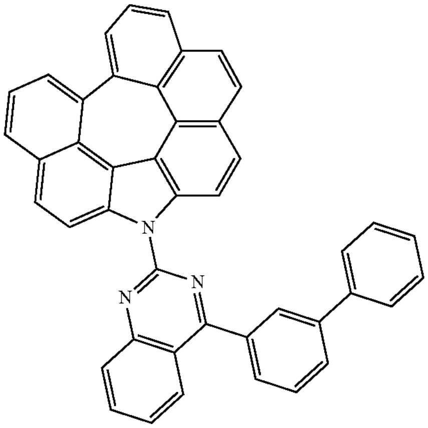

26
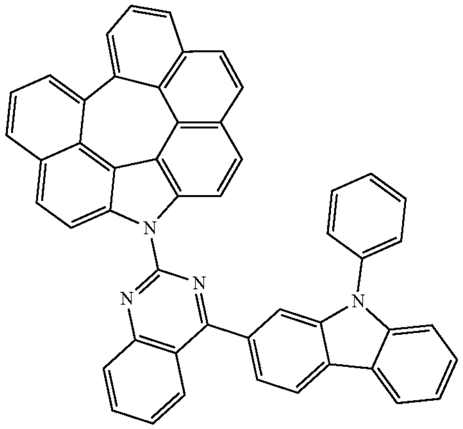
27
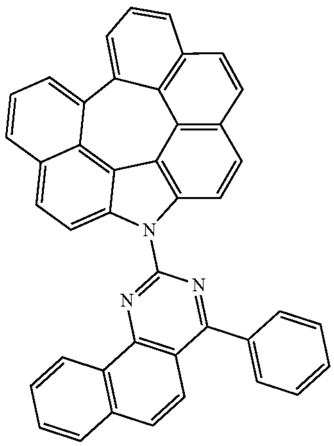
28
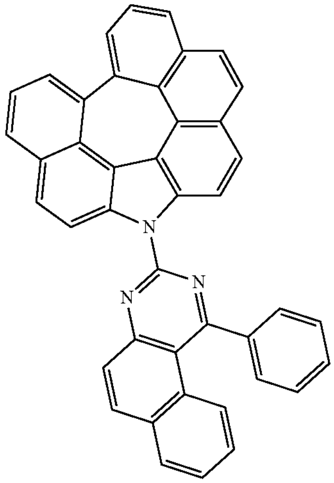
29
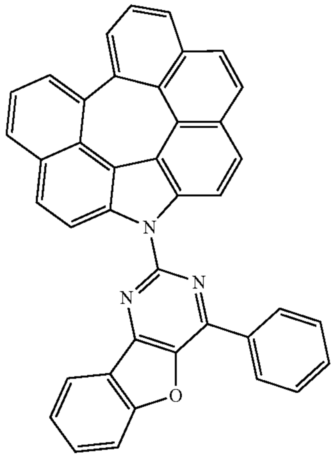
30
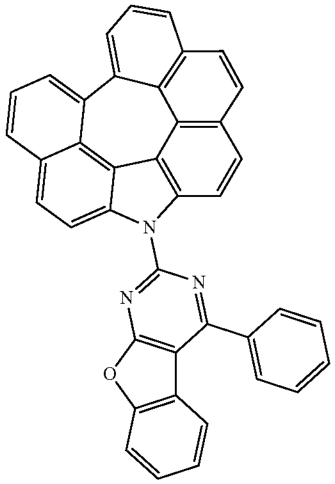
31
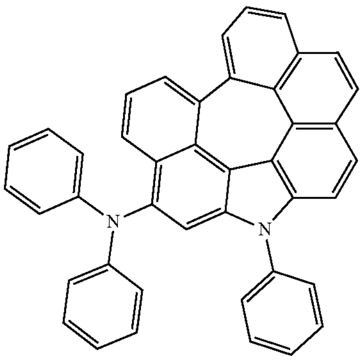

-continued
32
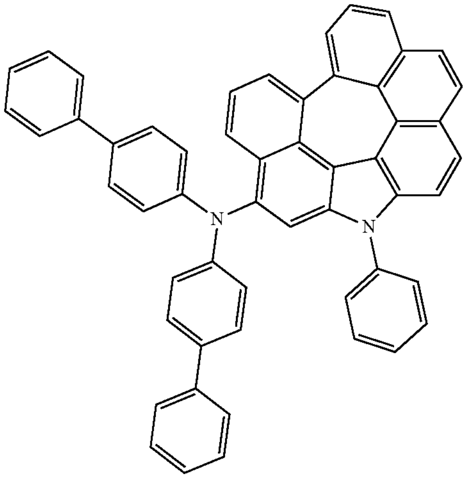
33
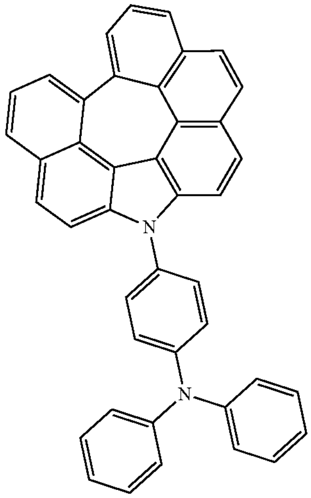
34
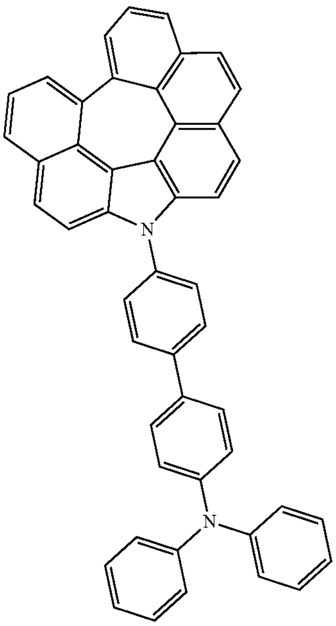
-continued
35
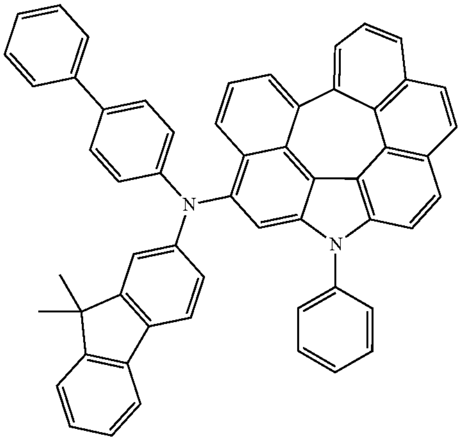
36
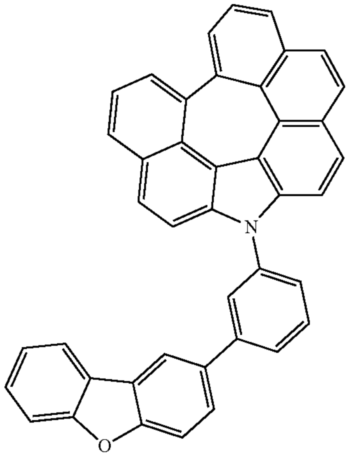
37
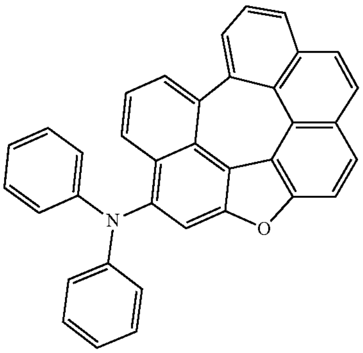

38
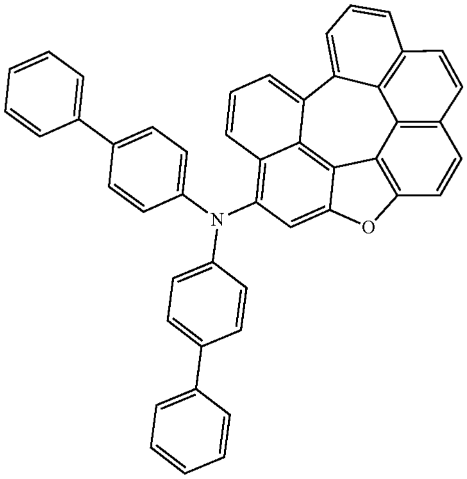
39
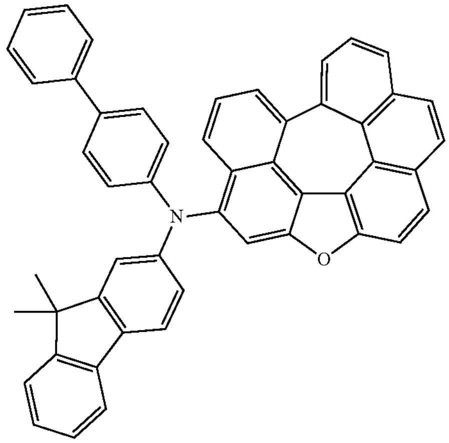
40
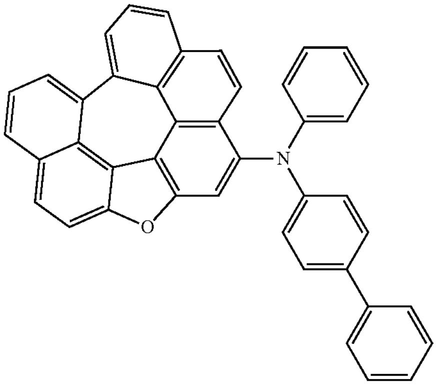
41
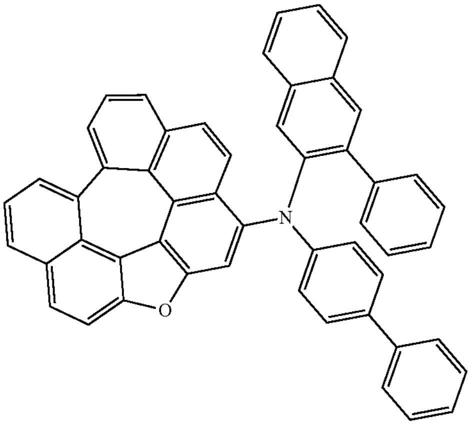
42
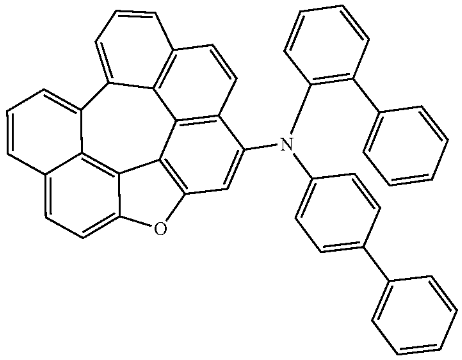
43
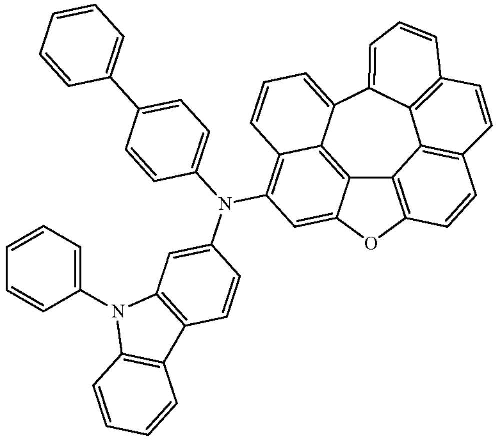

-continued
44
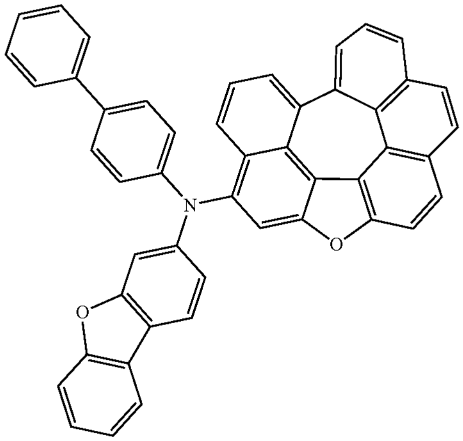
45
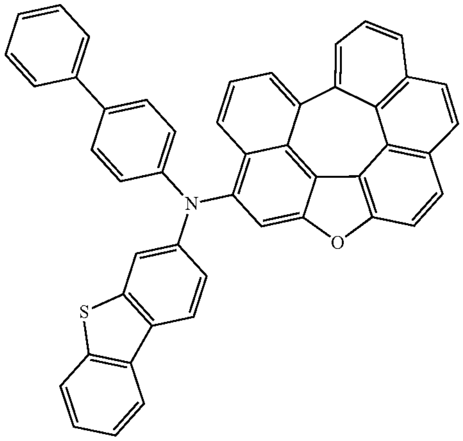
46
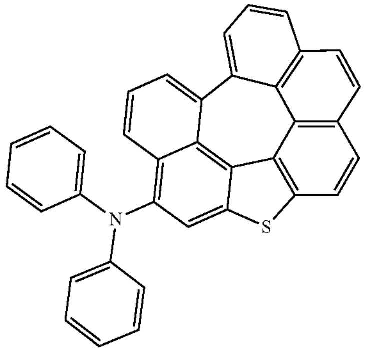
-continued
47
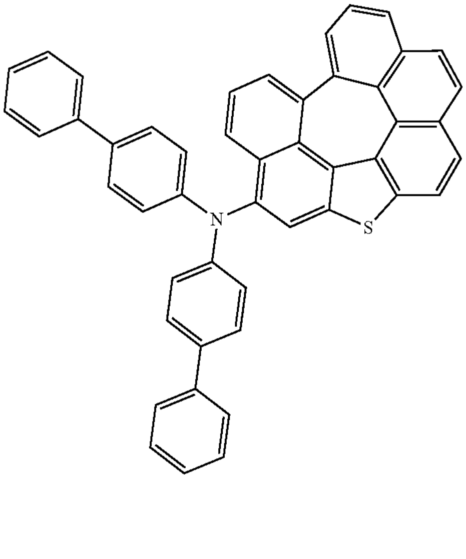
48
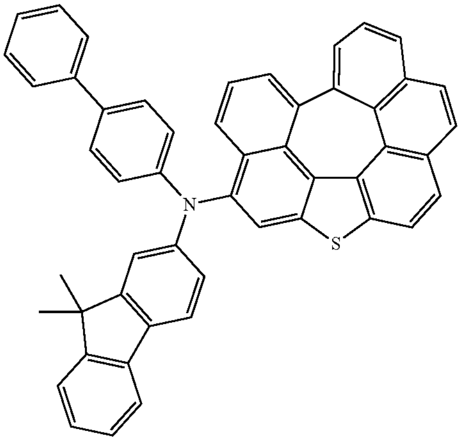
49
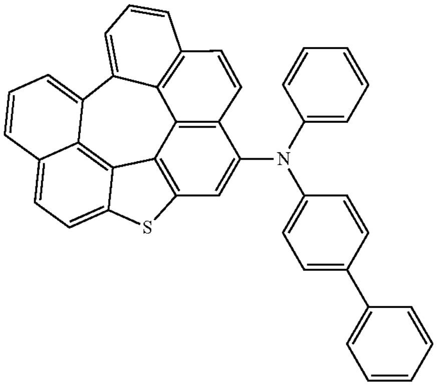

-continued
50
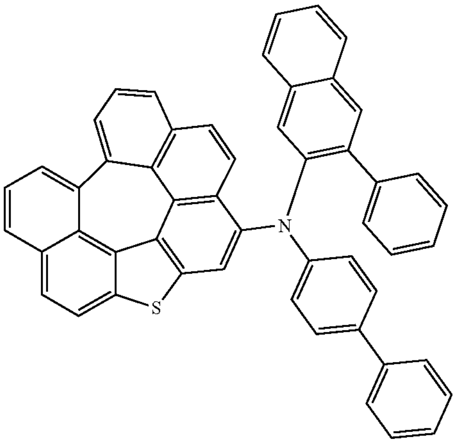
51
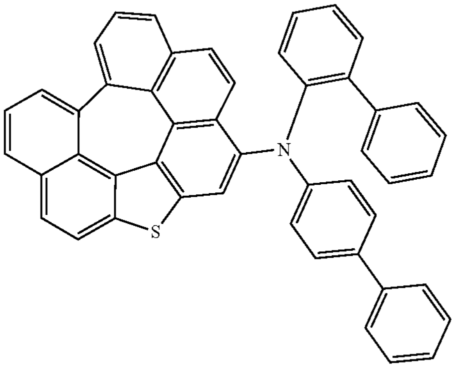
52
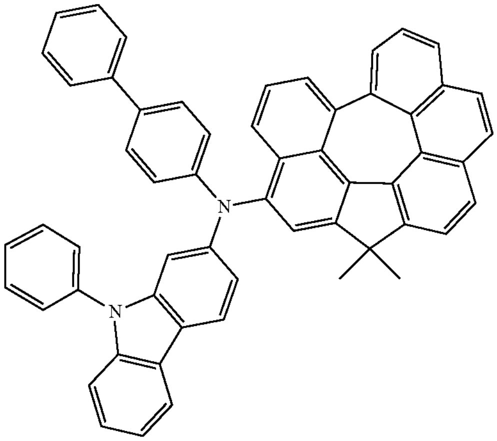
-continued
53
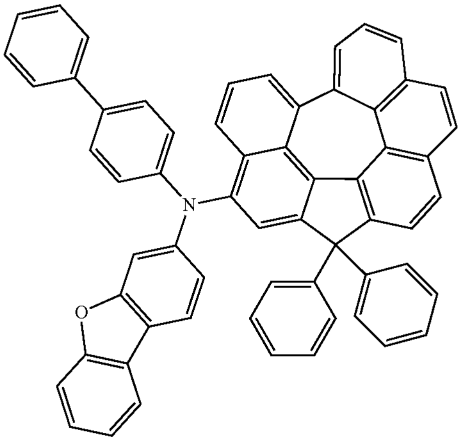
54
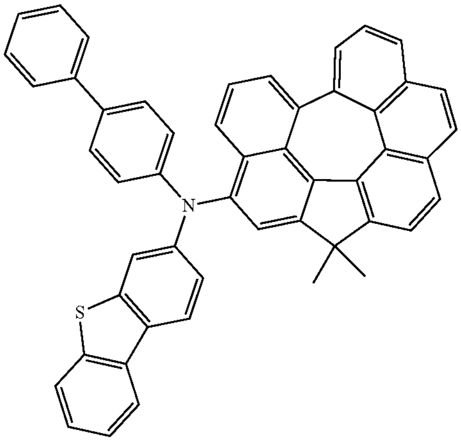
55
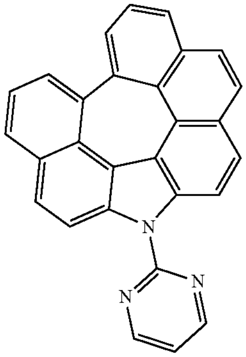

-continued
56
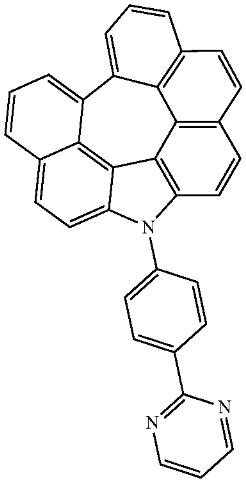
57
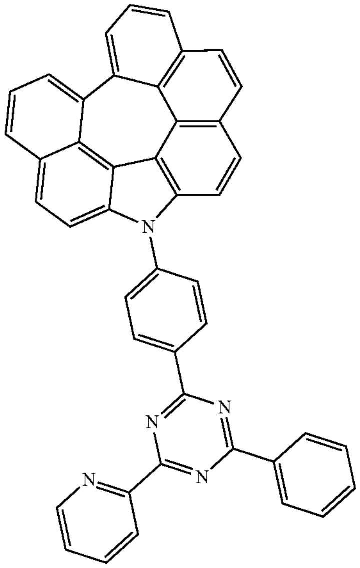
58
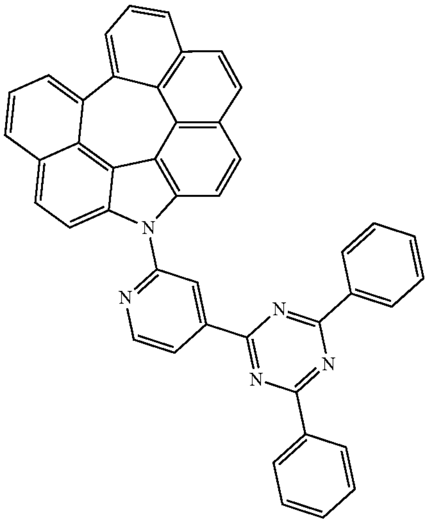
-continued
59
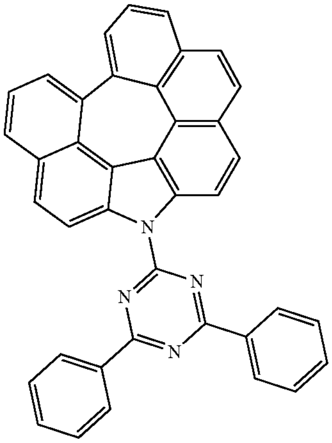
60
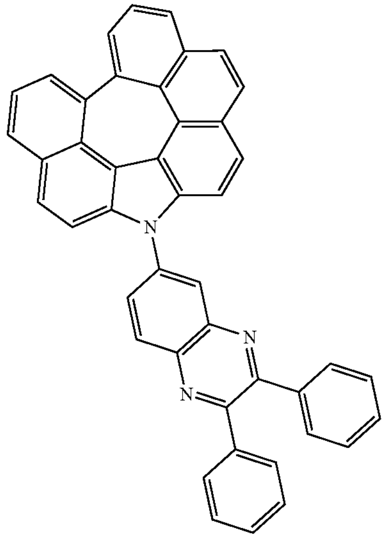
61
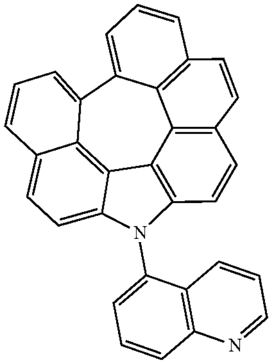

-continued
62
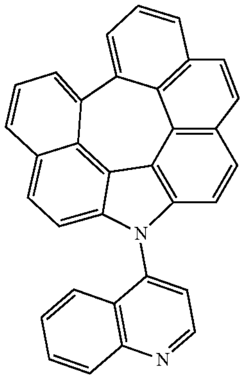
63
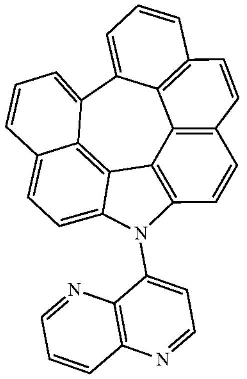
64
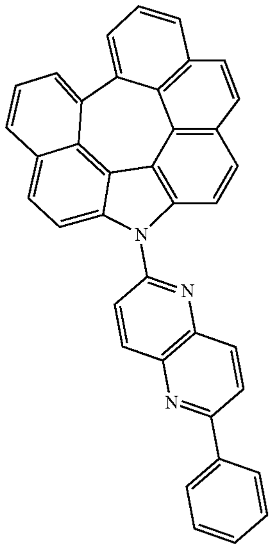
-continued
65
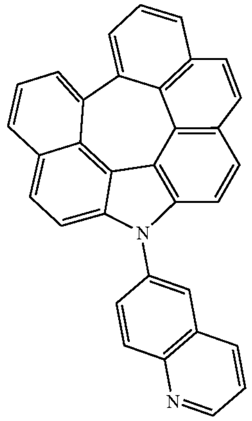
66
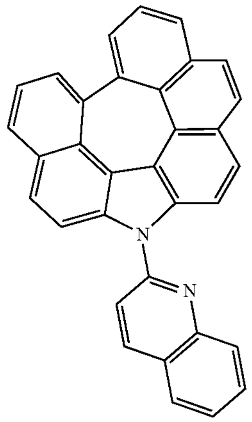
67
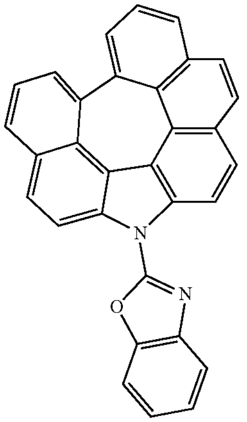

-continued
68
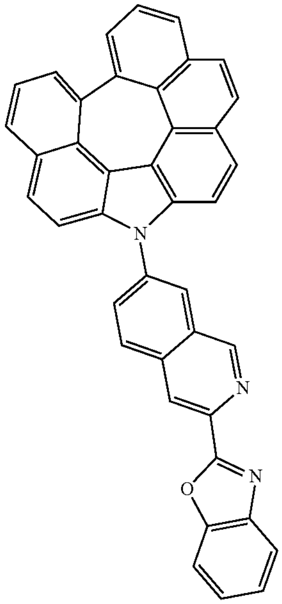
69
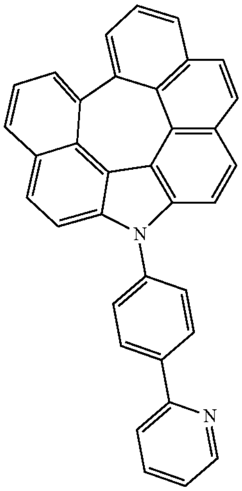
70
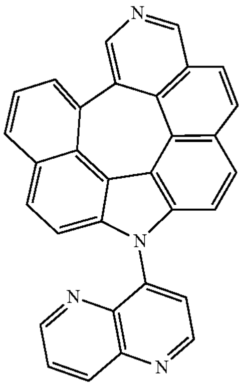
-continued
71
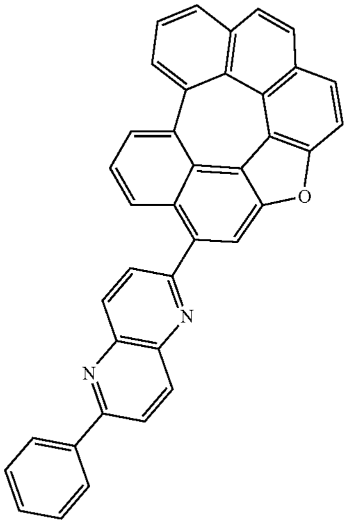
72
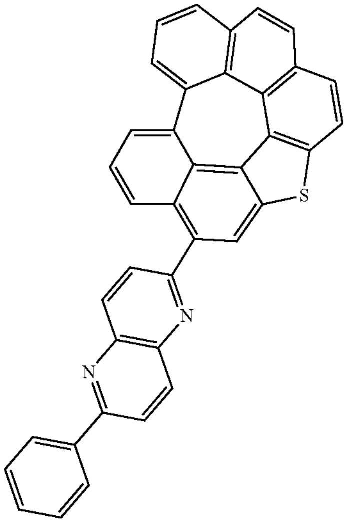
73
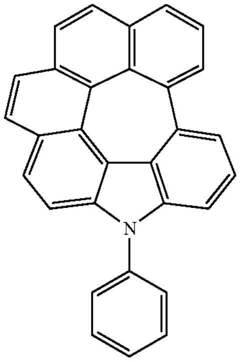

74
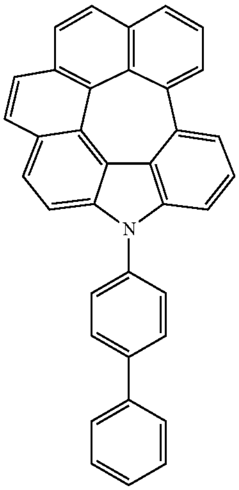
75
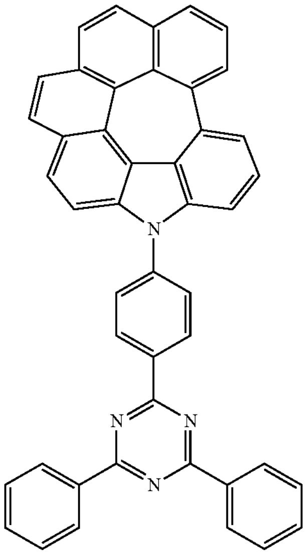
76
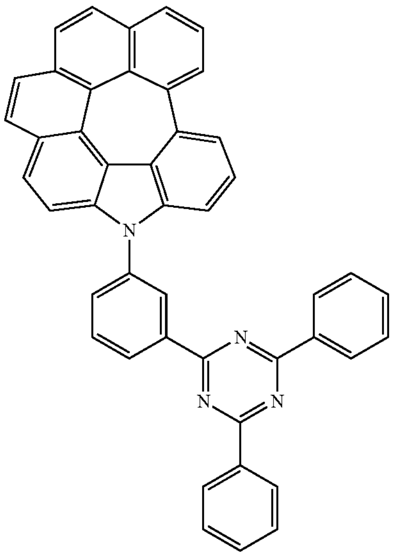
77
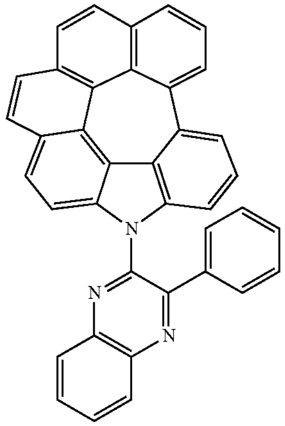
78
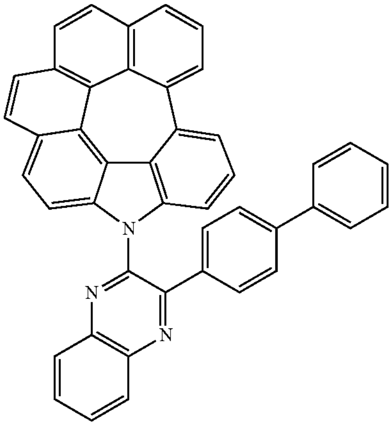
79
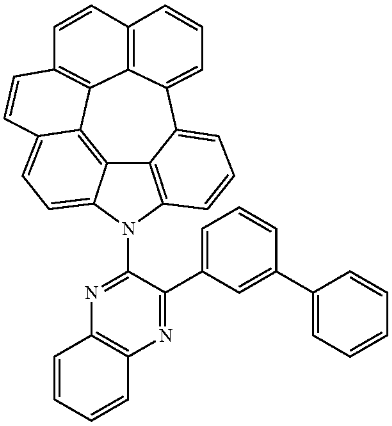

-continued
80
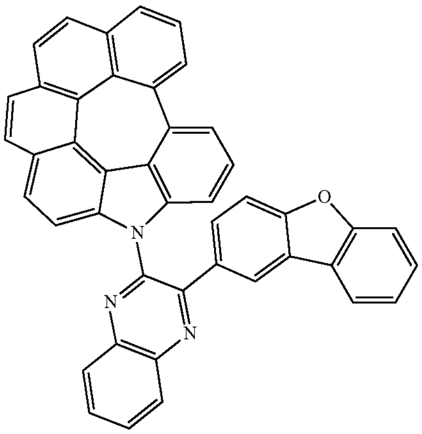
81
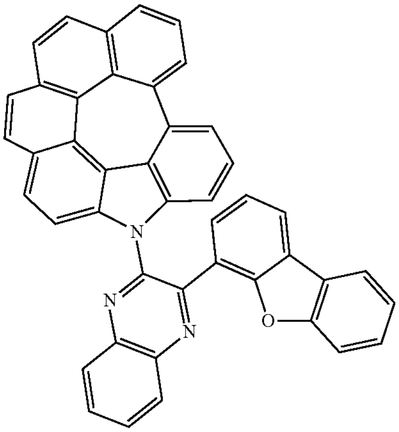
82
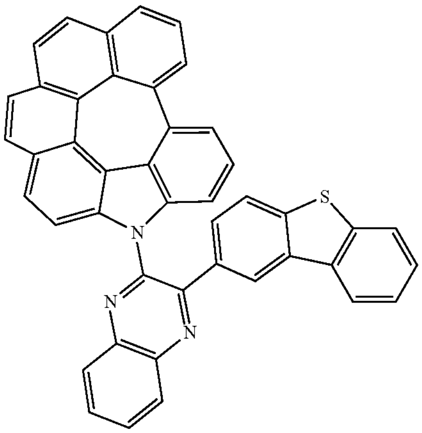
-continued
83
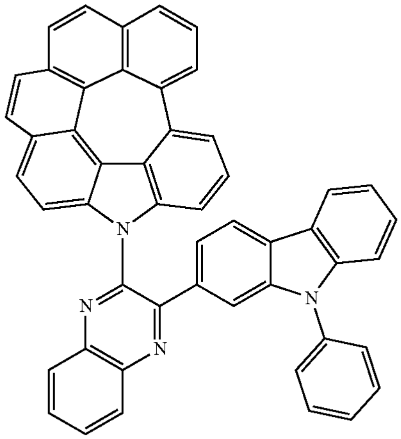
84
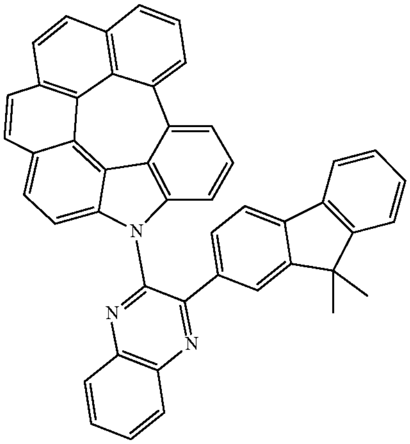
85
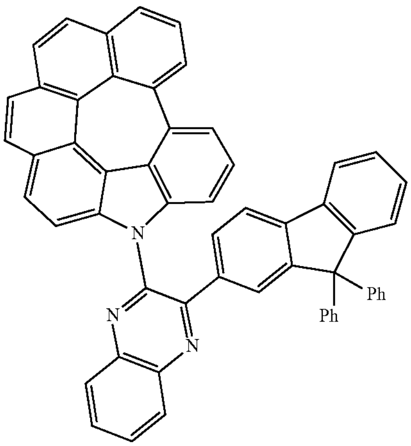

-continued
86
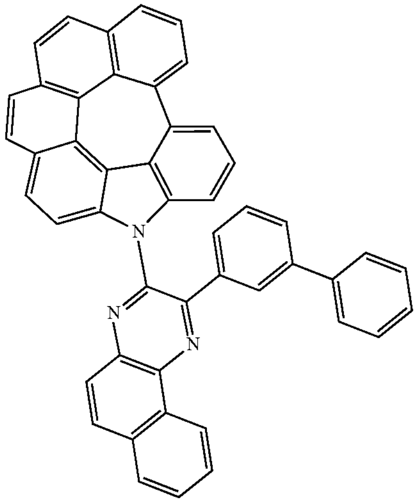
87
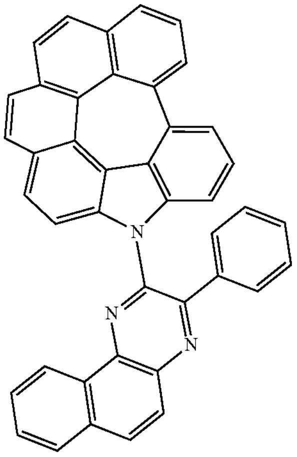
88
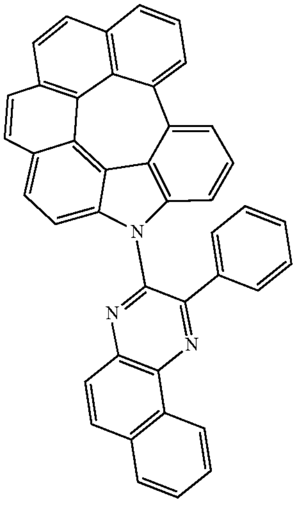
-continued
89
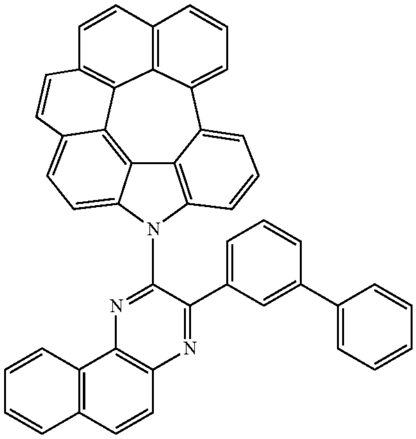
90
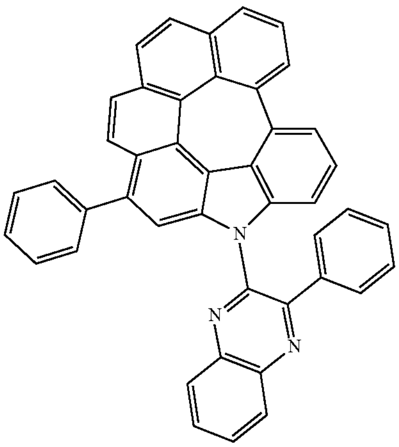
91
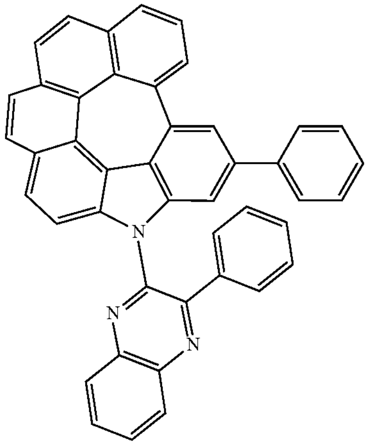

-continued
92
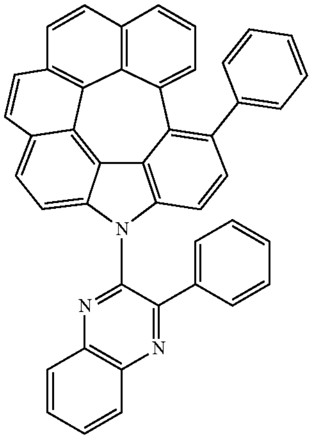
93
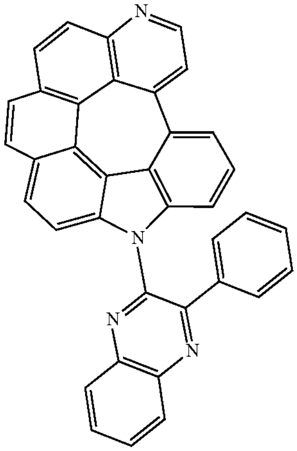
94
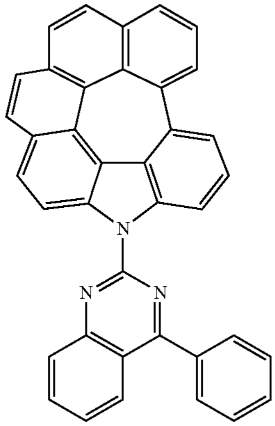
-continued
95
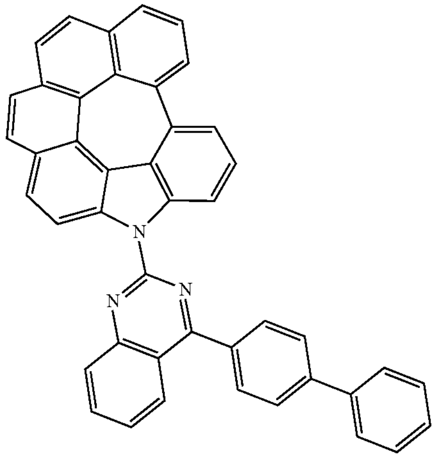
96
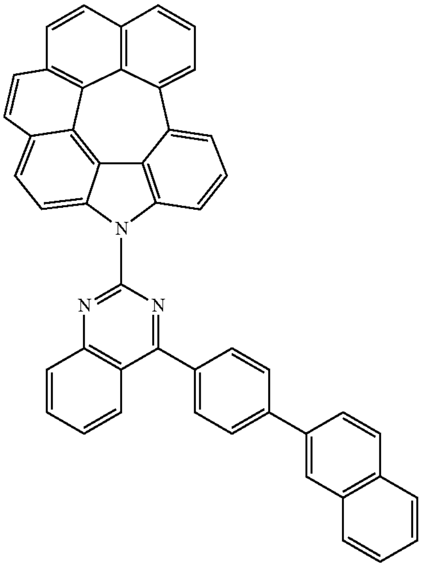
97
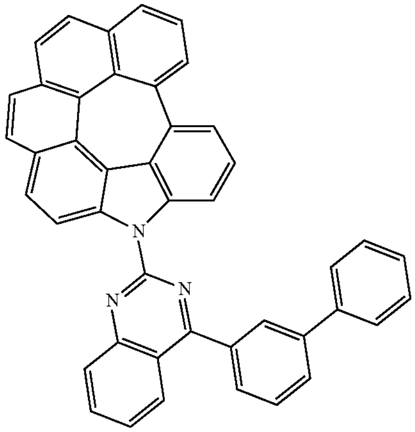

-continued
98
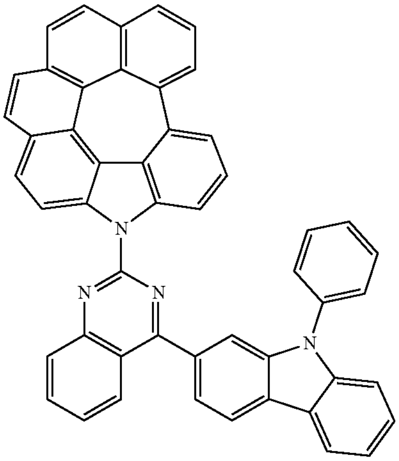
99
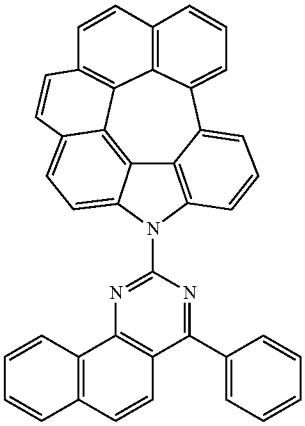
100
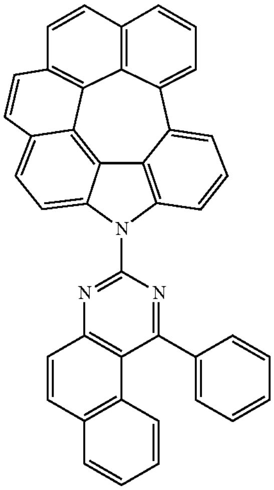
-continued
101
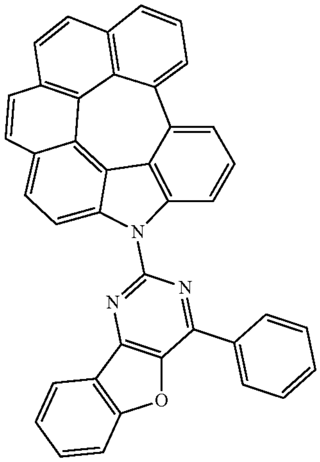
102
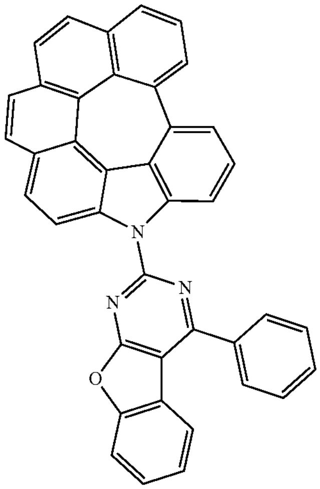
103
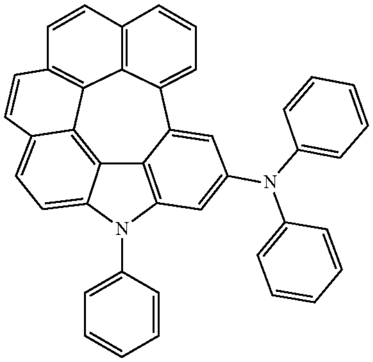

-continued
104
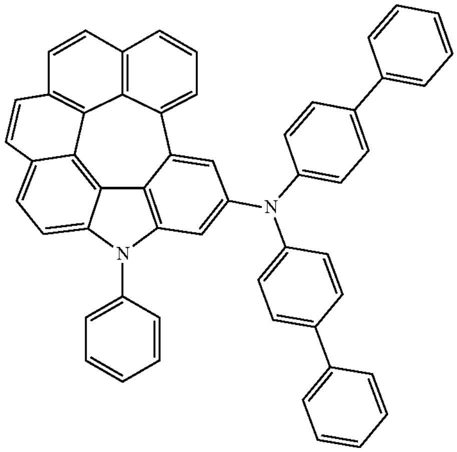
105
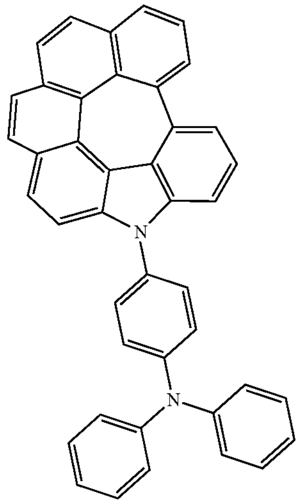
106
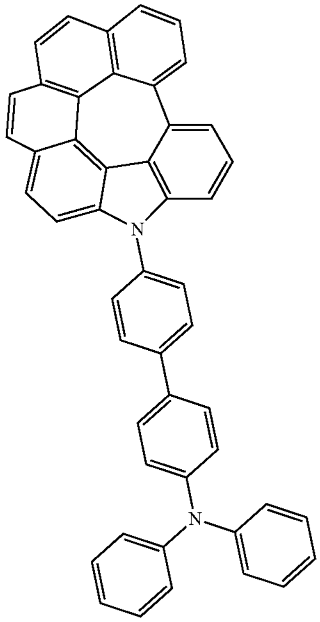
-continued
107
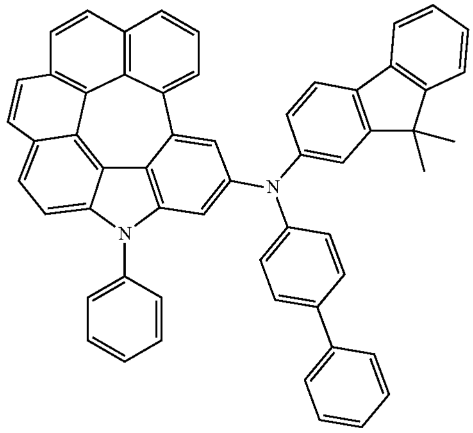
108
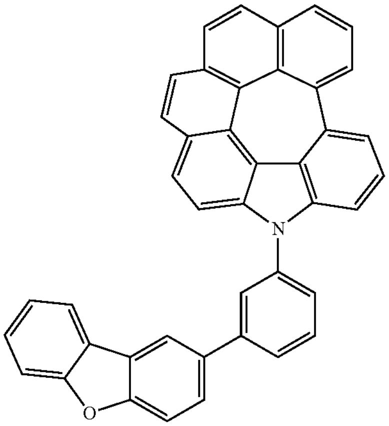
109
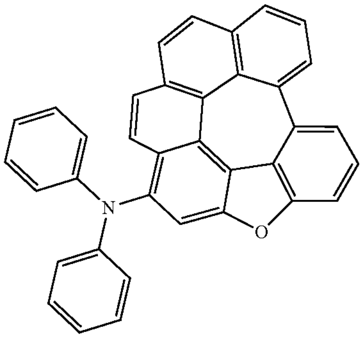

110
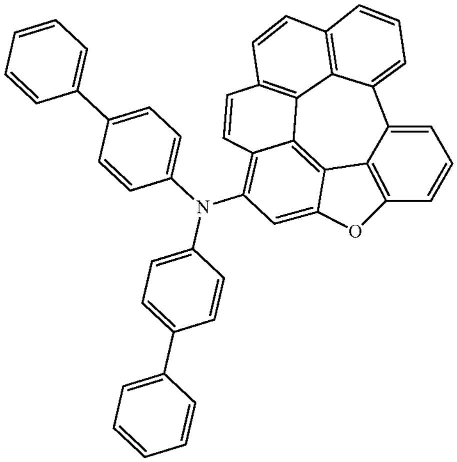
111
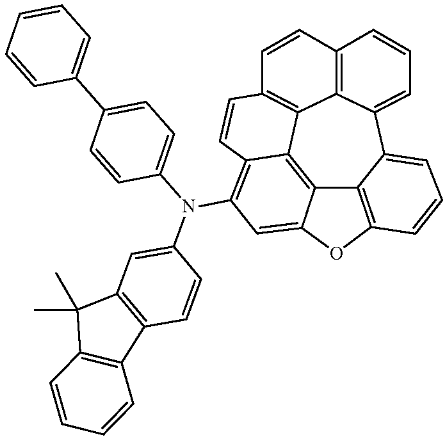
112
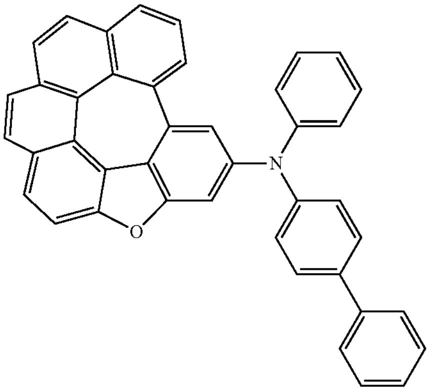
113
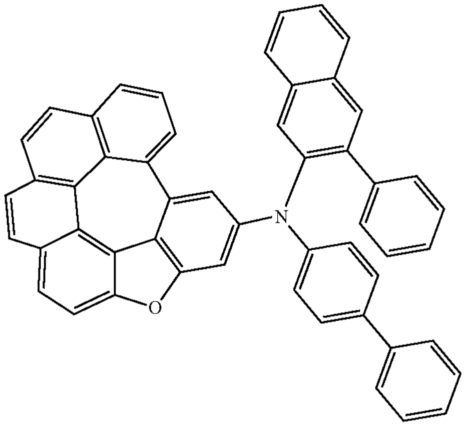
114
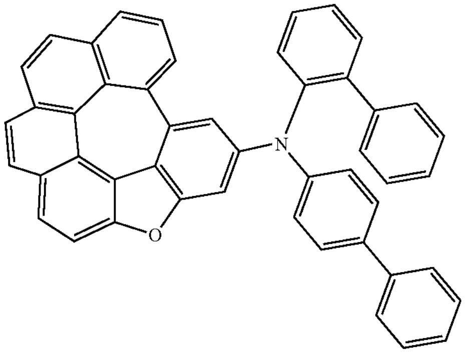
115
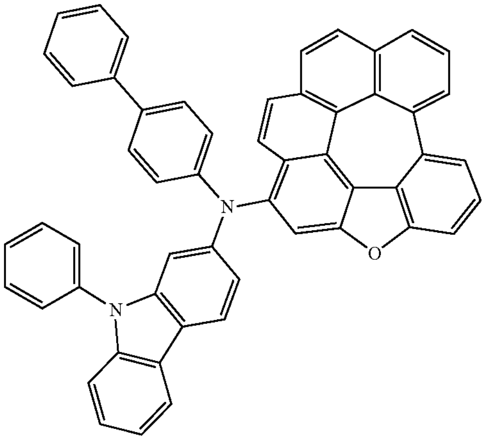

-continued
116
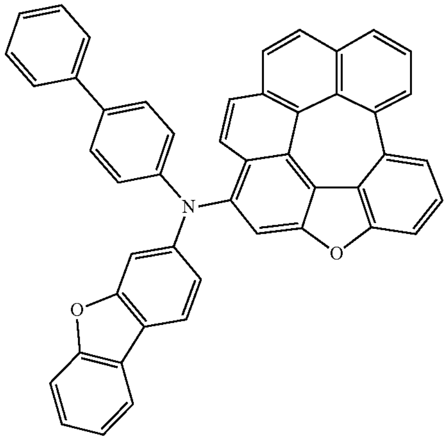
117
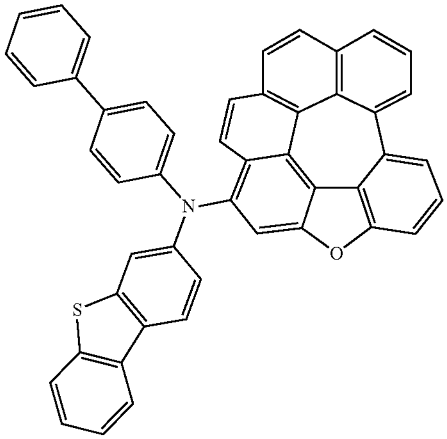
118
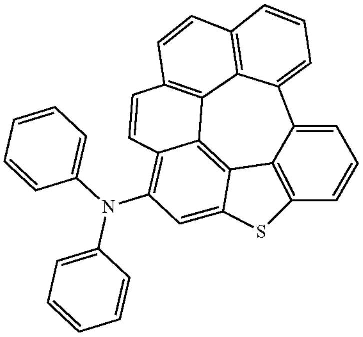
-continued
119
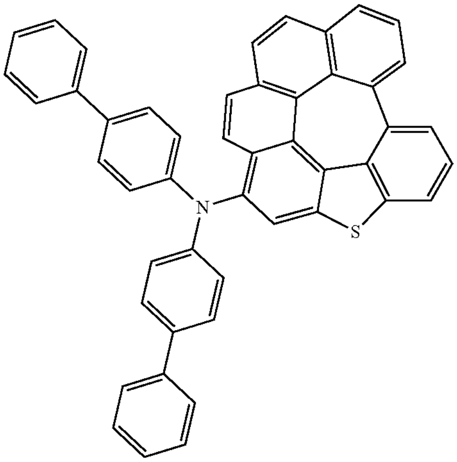
120
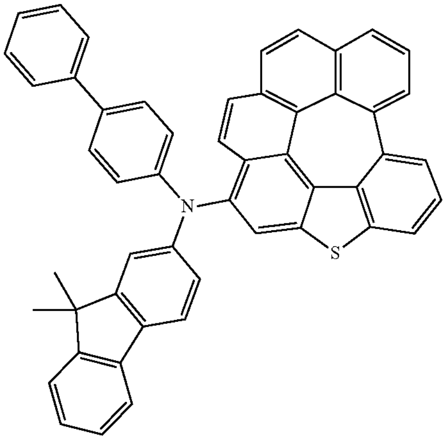
121
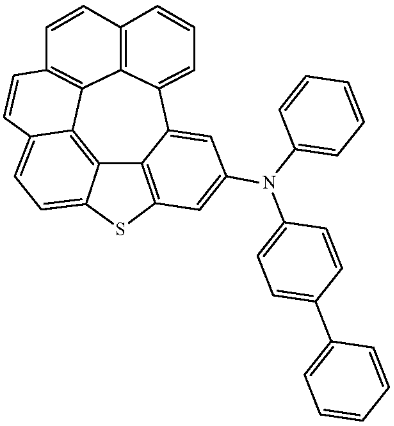

-continued
122
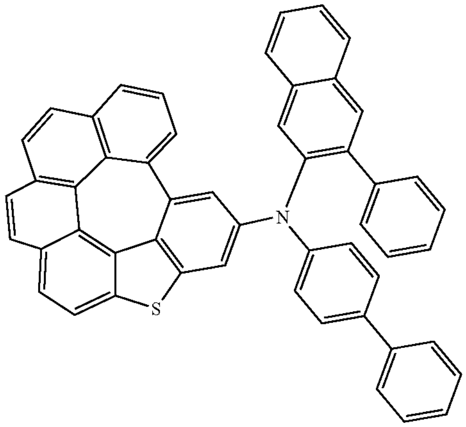
123
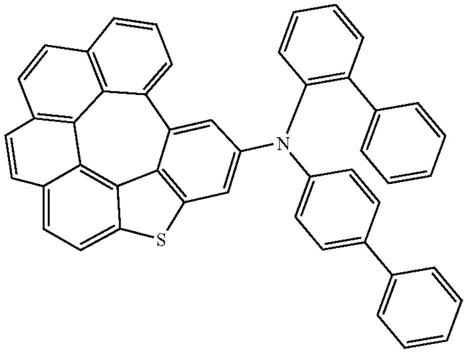
124
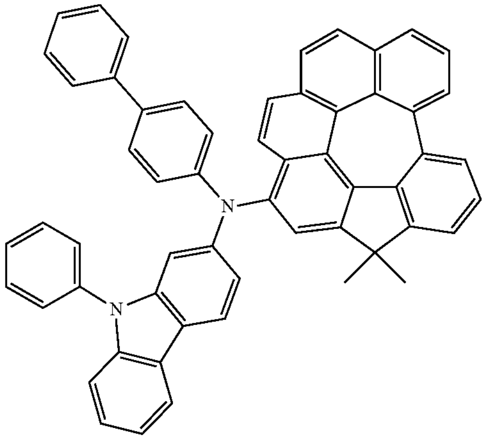
-continued
125
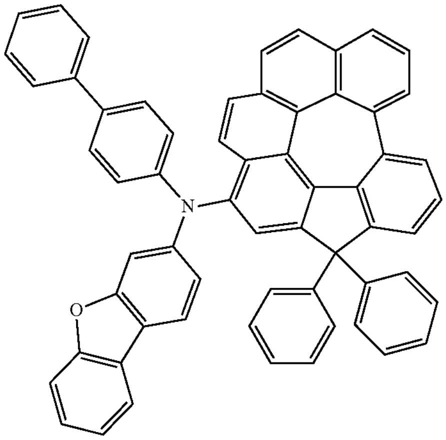
126
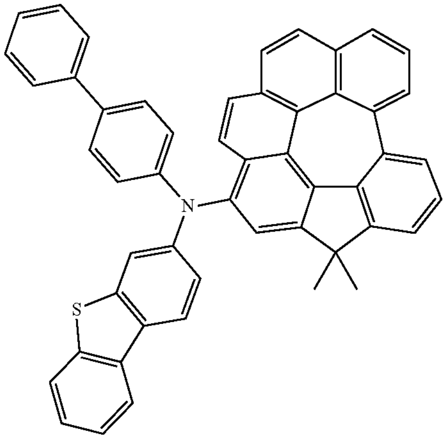
127
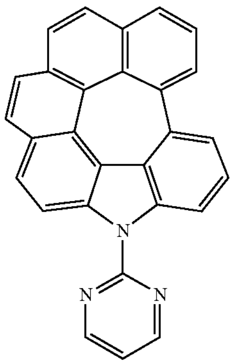

-continued
128
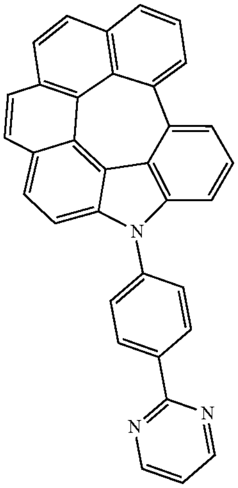
129
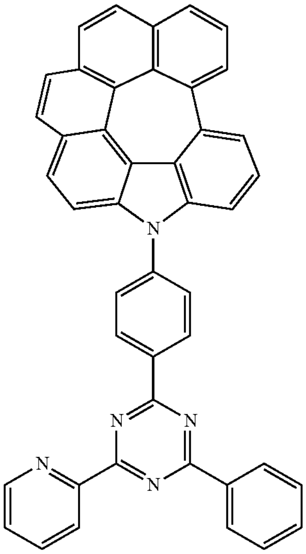
130
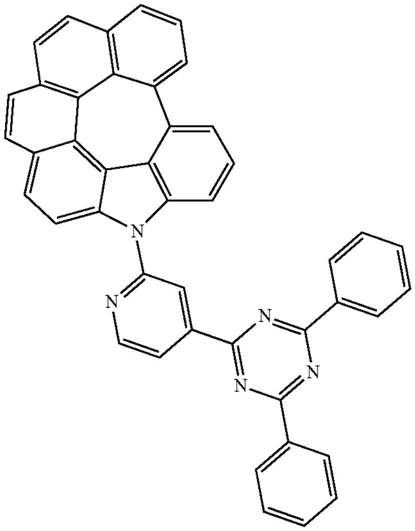
-continued
131
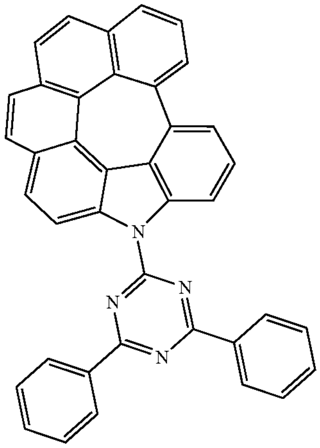
132
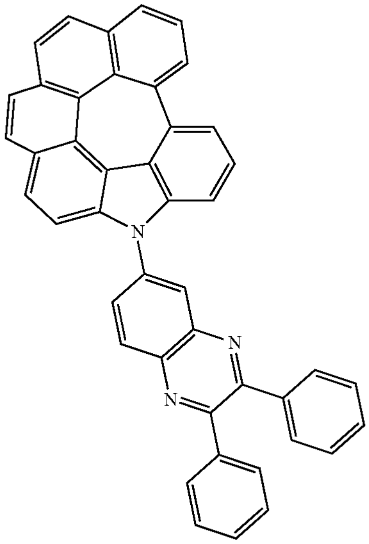
133
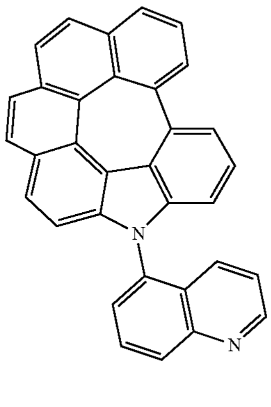

-continued
134
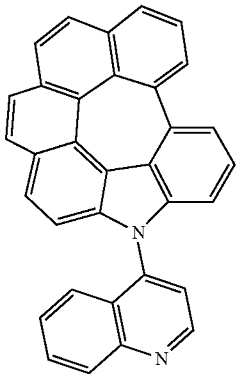
135
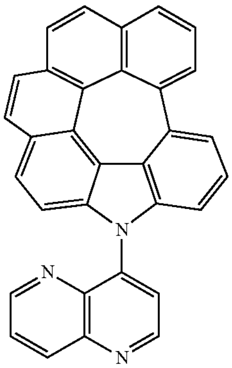
136
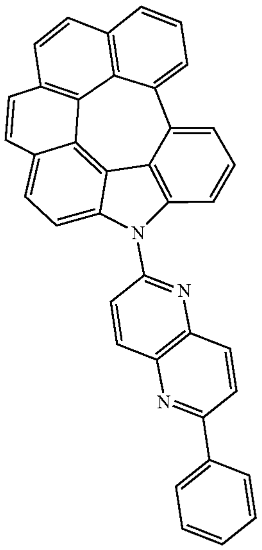
-continued
137
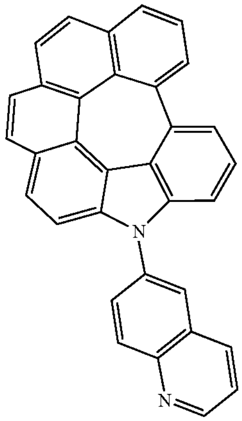
138
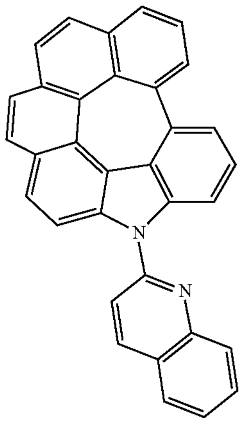
139
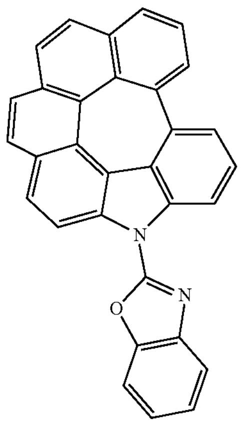

-continued
140
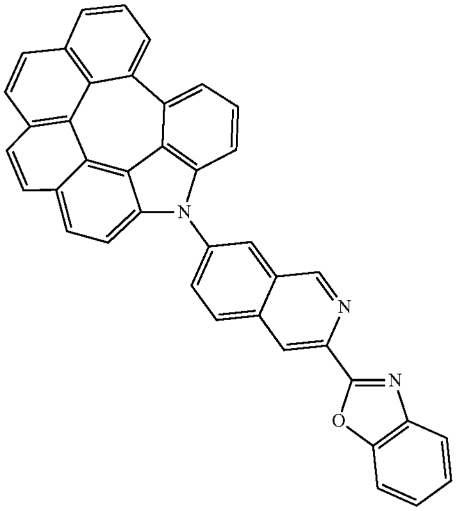
141
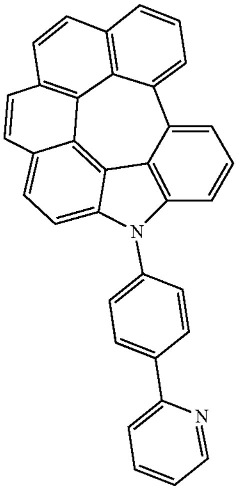
142
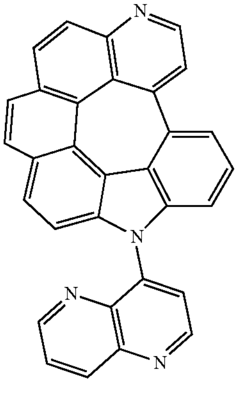
-continued
143
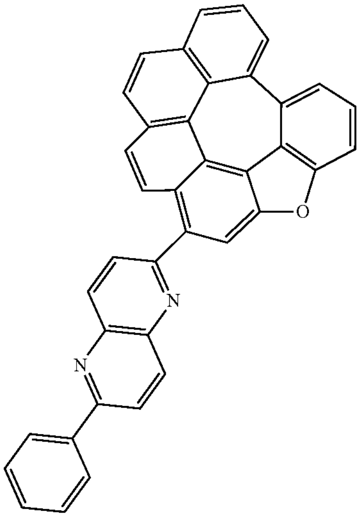
144
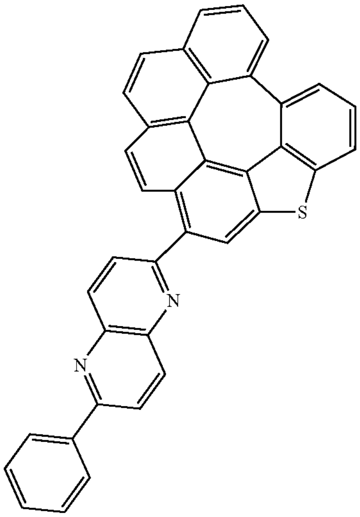
152
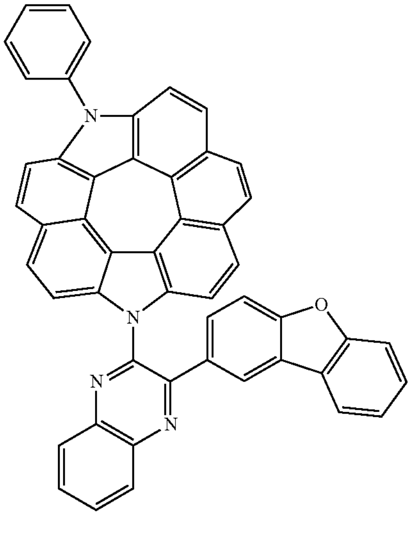

-continued
159
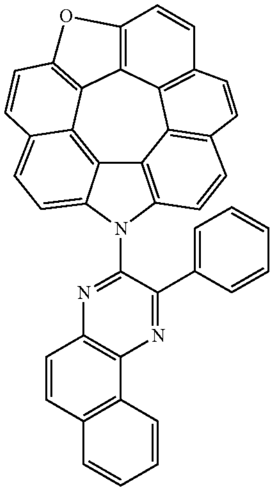
166
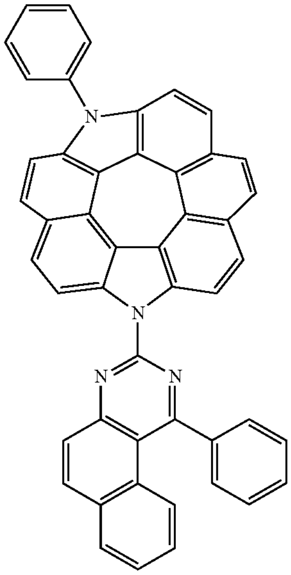
169
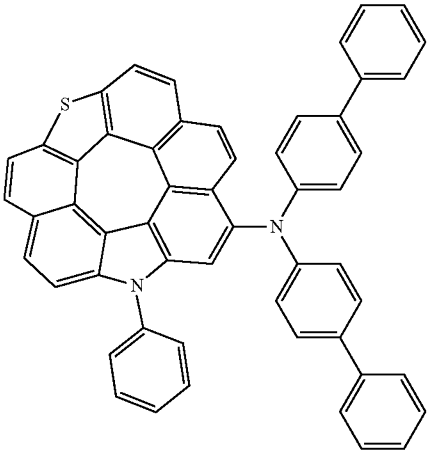
-continued
177
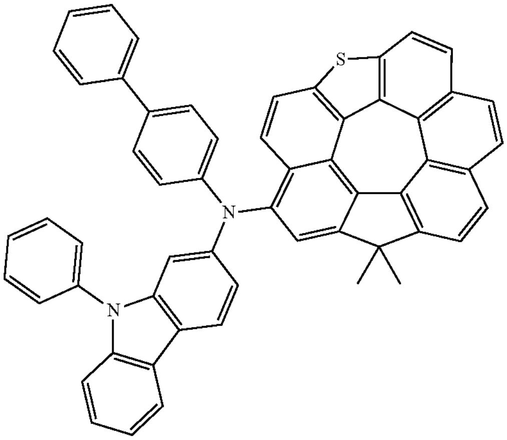
215
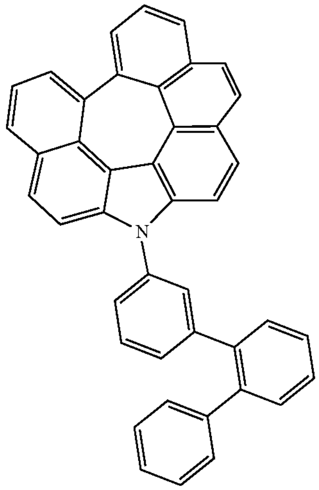
216
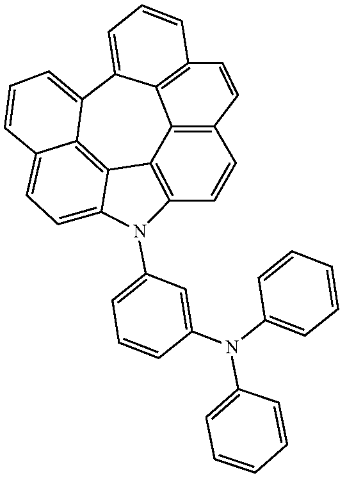

-continued
217
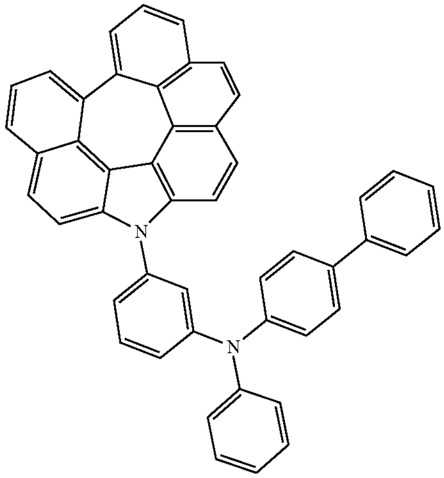
218
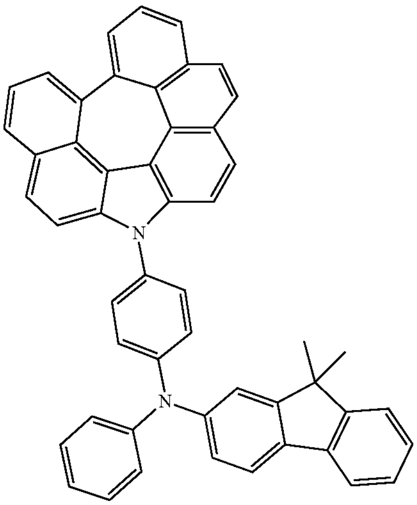
219
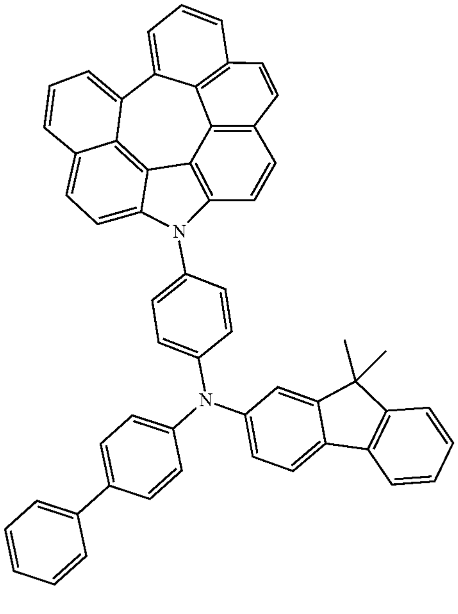
-continued
220
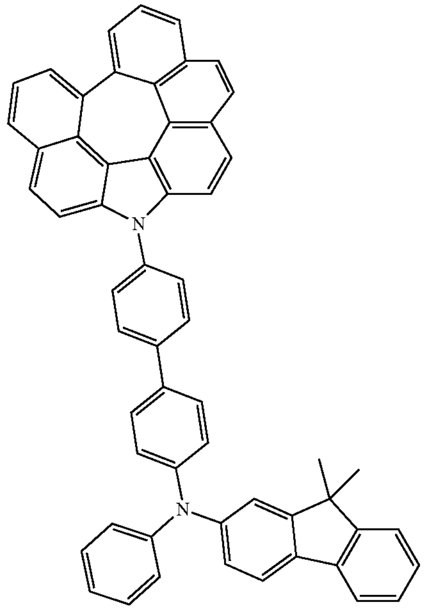
221
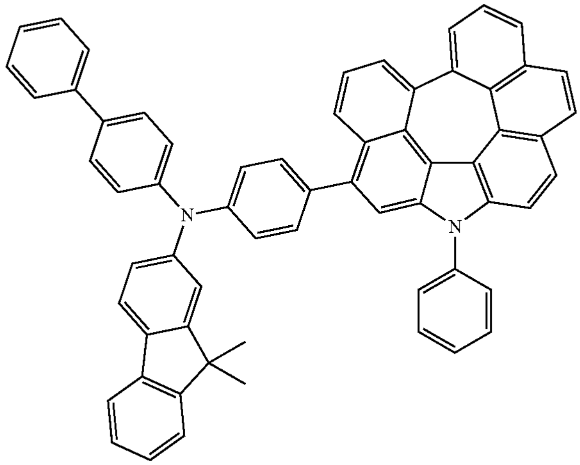
222
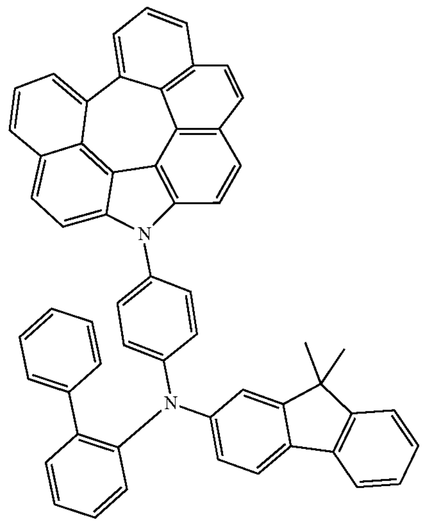

-continued
231
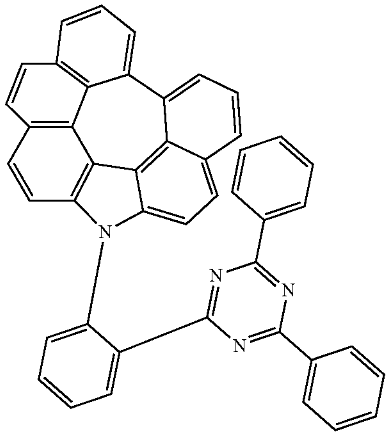
232
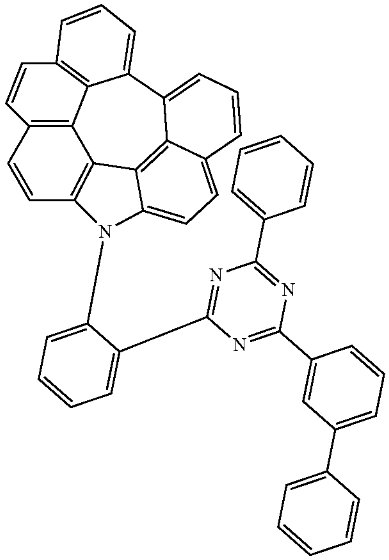
233
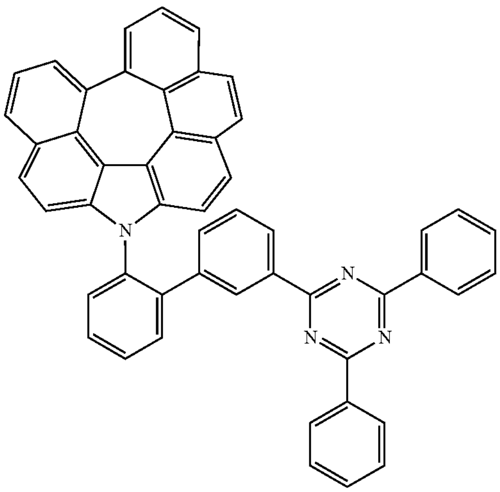
234
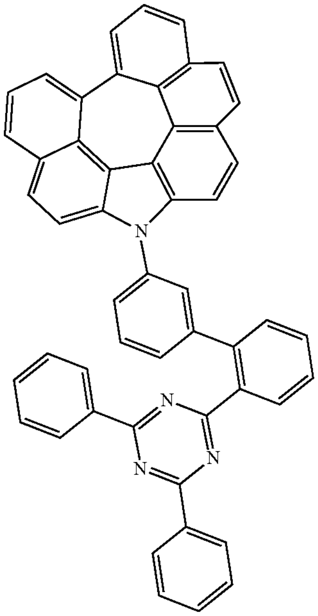
235
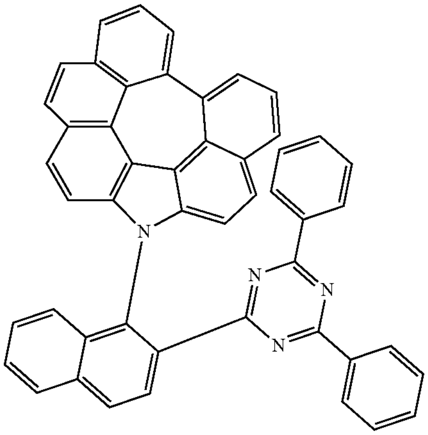
236
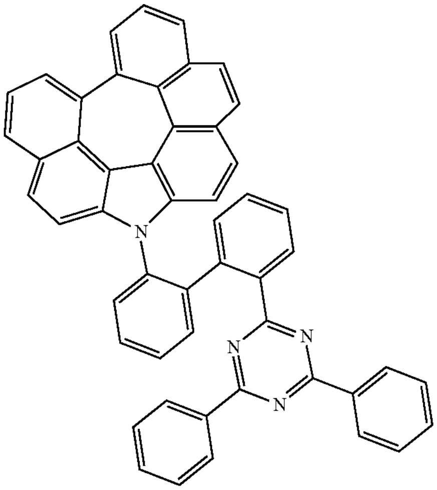

-continued
237
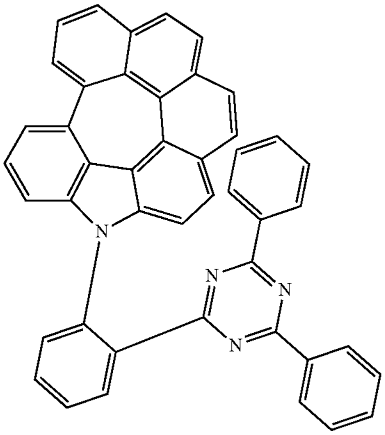
238
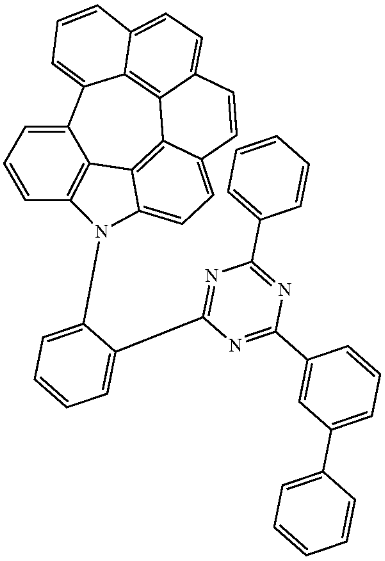
239
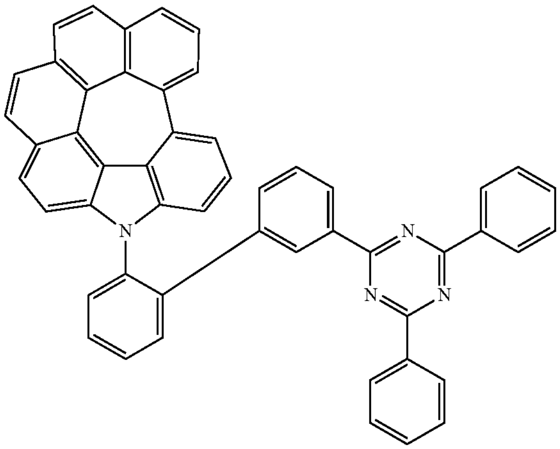
-continued
240
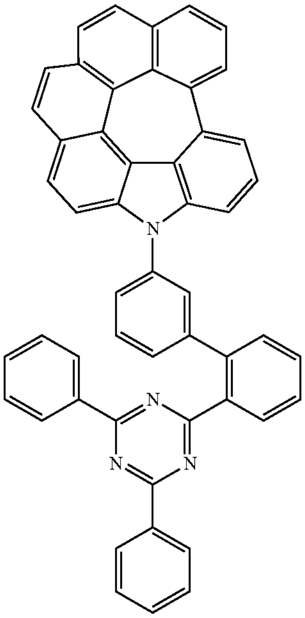
241
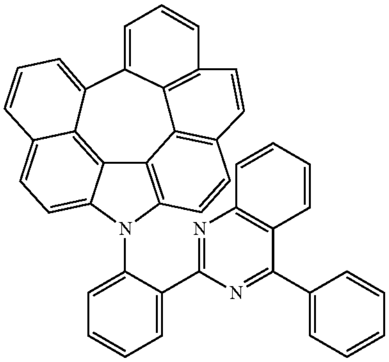
242
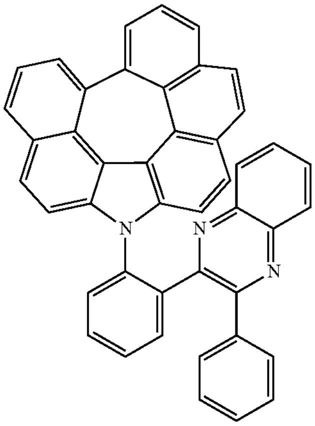

-continued
243
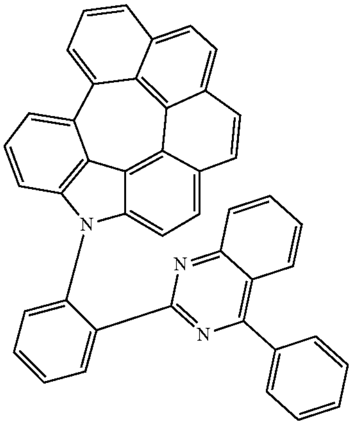
244
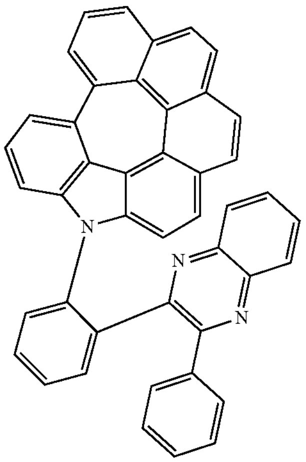
246
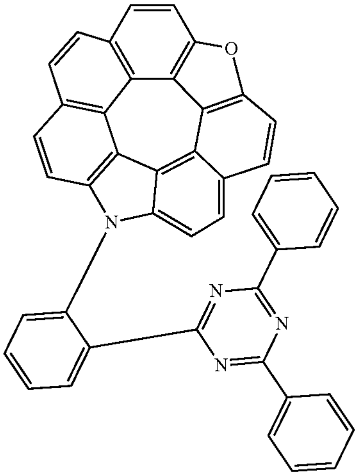
-continued
248
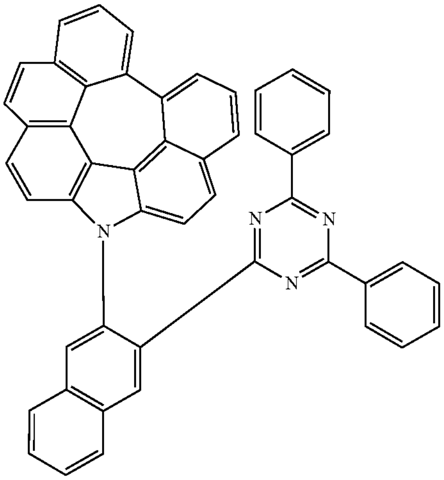
249
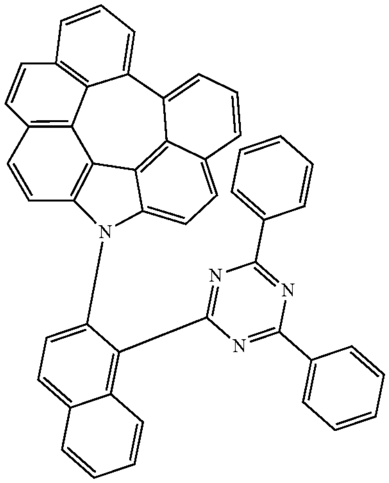
and
250
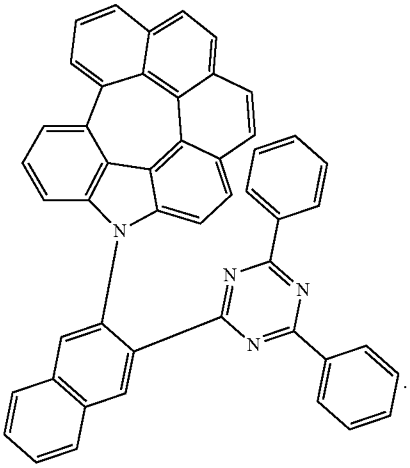
.
7. An organic electroluminescent device comprising the organic electroluminescent compound according to claim 1 as host materials.
* * * * *